United States Patent
Kim et al.

(10) Patent No.: US 11,588,110 B2
(45) Date of Patent: Feb. 21, 2023

(54) HETEROCYCLIC COMPOUND AND ORGANIC LIGHT EMITTING DEVICE COMPRISING THE SAME

(71) Applicant: LT MATERIALS CO., LTD., Yongin-Si (KR)

(72) Inventors: Ji-Young Kim, Yongin-Si (KR); Juntae Mo, Yongin-Si (KR); Dong-Jun Kim, Yongin-Si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 363 days.

(21) Appl. No.: 16/876,300

(22) Filed: May 18, 2020

(65) Prior Publication Data

US 2020/0373499 A1    Nov. 26, 2020

(30) Foreign Application Priority Data

May 20, 2019  (KR) .......... 10-2019-0058711

(51) Int. Cl.
| | |
|---|---|
| *H01L 51/00* | (2006.01) |
| *C07D 491/048* | (2006.01) |
| *C07D 495/04* | (2006.01) |
| *H01L 51/50* | (2006.01) |

(52) U.S. Cl.
CPC ...... *H01L 51/0067* (2013.01); *C07D 491/048* (2013.01); *C07D 495/04* (2013.01); *H01L 51/0071* (2013.01); *H01L 51/0072* (2013.01); *H01L 51/0073* (2013.01); *H01L 51/0074* (2013.01); *H01L 51/0085* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC ............. H01L 51/0067; H01L 51/0071–0074; C07D 49/048; C07D 495/04
USPC ........................................................ 428/690
See application file for complete search history.

(56) References Cited

U.S. PATENT DOCUMENTS

| | | | |
|---|---|---|---|
| 4,356,429 A | 10/1982 | Tang | |
| 2014/0374711 A1* | 12/2014 | Cho ................... | H01L 51/0067 257/40 |
| 2015/0349272 A1 | 12/2015 | Park et al. | |

(Continued)

FOREIGN PATENT DOCUMENTS

| | | |
|---|---|---|
| CN | 105131020 A | 12/2015 |
| CN | 106795166 A | 5/2017 |

(Continued)

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)tripbenylamine (m-MTDATA), as Hole-Transport Materials", Advanced Material, 1994, vol. 6, No. 9, pp. 677-679.

*Primary Examiner* — Sheng-Bai Zhu
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device including the same.

12 Claims, 2 Drawing Sheets

(56) References Cited

U.S. PATENT DOCUMENTS

| | | | |
|---|---|---|---|
| 2016/0190477 A1* | 6/2016 | Kawakami | C07D 471/14 |
| | | | 252/500 |
| 2016/0233433 A1 | 8/2016 | Park et al. | |
| 2017/0309841 A1 | 10/2017 | Kim et al. | |
| 2018/0182970 A1 | 6/2018 | Lee et al. | |
| 2019/0135730 A1 | 5/2019 | Mun et al. | |
| 2019/0296256 A1* | 9/2019 | Kim | H01L 51/0085 |
| 2020/0343455 A1 | 10/2020 | Wei et al. | |
| 2020/0343456 A1 | 10/2020 | Wei et al. | |

FOREIGN PATENT DOCUMENTS

| | | |
|---|---|---|
| CN | 106967021 A | 7/2017 |
| CN | 108232021 A | 6/2018 |
| CN | 110330506 A | 10/2019 |
| KR | 10-2013-0083817 A | 7/2013 |
| KR | 10-2014-0145888 A | 12/2014 |
| KR | 10-2016-0126792 A | 11/2016 |
| KR | 10-2017-0122115 A | 11/2017 |

\* cited by examiner

[FIG. 1]
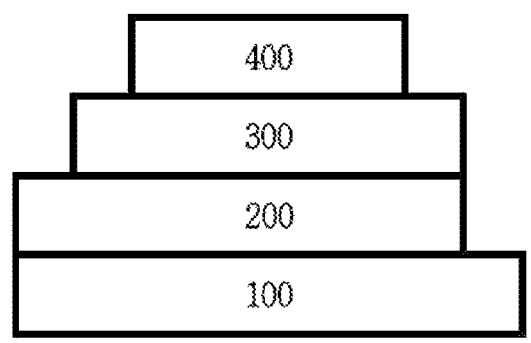
[FIG. 2]

【FIG. 3】
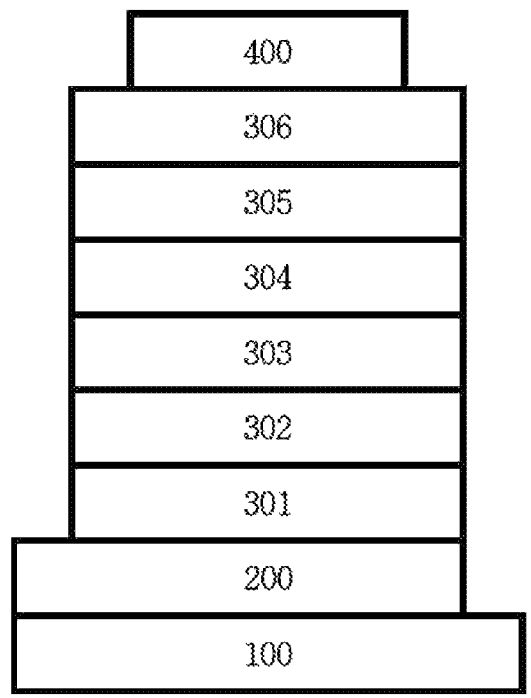

HETEROCYCLIC COMPOUND AND ORGANIC LIGHT EMITTING DEVICE COMPRISING THE SAME

TECHNICAL FIELD

The present specification relates to a heterocyclic compound, and an organic light emitting device including the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

A material of the organic thin film can have a light emitting function as necessary. For example, as a material of the organic thin film, compounds capable of forming a light emitting layer themselves alone can be used, or compounds capable of performing a role of a host or a dopant of a host-dopant-based light emitting layer can also be used. In addition thereto, compounds capable of performing roles of hole injection, hole transfer, electron blocking, hole blocking, electron transfer, electron injection and the like can also be used as a material of the organic thin film.

Development of an organic thin film material has been continuously required for enhancing performance, lifetime or efficiency of an organic light emitting device.

PRIOR ART DOCUMENT

Patent Document (Patent Document 1) U.S. Pat. No. 4,356,429

DISCLOSURE

Technical Problem

The present specification is directed to providing a heterocyclic compound, and an organic light emitting device including the same.

Technical Solution

One embodiment of the present specification provides a heterocyclic compound represented by the following Chemical Formula 1.

[Chemical Formula 1]

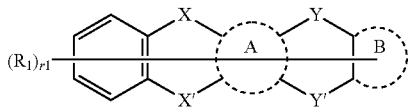

In Chemical Formula 1, one of X and X' is O; S; or $NR_{21}$, and the other one is a direct bond, one of Y and Y' is O; S; or $NR_{22}$, and the other one is a direct bond, A and B are each independently a C6 to C60 aryl ring, and at least one thereof is a C10 to C60 aryl ring, $R_1$ is selected from the group consisting of a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, $R_{21}$ and $R_{22}$ are each independently a substituted or unsubstituted aryl group; or a substituted or unsubstituted heteroaryl group, r1 is an integer of 1 to 12, and when r1 is an integer of 2 or greater, substituents in the parentheses are the same as or different from each other.

Another embodiment of the present specification provides an organic light emitting device including a first electrode; a second electrode provided opposite to the first electrode; and an organic material layer provided between the first electrode and the second electrode, wherein the organic material layer includes one or more types of the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in an organic light emitting device. Particularly, the compound can be used as a light emitting layer material of an organic light emitting device. For example, the compound can be used alone as a light emitting material, or can be used as a host material of a light emitting layer.

Chemical Formula 1 has a form in which 6 aromatic rings are fused, and has a wide conjugated structure. This increases interactions between molecules due to an increase in planarity and aromaticity of the compound, which allows an even and solid packing structure of the compound. This accelerates hole and electron injections as a host material, and facilitates a dopant energy transfer of formed excitons.

Specifically, when using the compound represented by Chemical Formula 1 in an organic material layer, a device driving voltage can be lowered, light efficiency can be enhanced, and device lifetime properties can be enhanced.

DESCRIPTION OF DRAWINGS

FIG. 1 to FIG. 3 are diagrams each illustrating a lamination structure of an organic light emitting device according to one embodiment of the present specification.

MODE FOR DISCLOSURE

Hereinafter, the present specification will be described in more detail.

In the present specification, a certain part "including" certain constituents means capable of further including other constituents, and does not exclude other constituents unless particularly stated on the contrary.

A term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification,

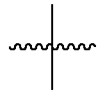

means a substituted position.

In the present specification, "substituted or unsubstituted" means being substituted with one or more substituents selected from the group consisting of a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; a silyl group; a phosphine oxide group; and an amine group, or being unsubstituted, or being substituted with a substituent linking two or more substituents selected from among the substituents illustrated above, or being unsubstituted.

In the present specification, the halogen can be fluorine, chlorine, bromine or iodine.

In the present specification, the alkyl group includes linear or branched having 1 to 60 carbon atoms, and can be further substituted with other substituents. The number of carbon atoms of the alkyl group can be from 1 to 60, specifically from 1 to 40 and more specifically from 1 to 20. Specific examples thereof can include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and can be further substituted with other substituents. The number of carbon atoms of the alkenyl group can be from 2 to 60, specifically from 2 to 40 and more specifically from 2 to 20. Specific examples thereof can include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and can be further substituted with other substituents. The number of carbon atoms of the alkynyl group can be from 2 to 60, specifically from 2 to 40 and more specifically from 2 to 20.

In the present specification, the alkoxy group can be linear, branched or cyclic. The number of carbon atoms of the alkoxy group is not particularly limited, but is preferably from 1 to 20. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and can be further substituted with other substituents. Herein, the polycyclic means a group in which the cycloalkyl group is directly linked to or fused with other cyclic groups. Herein, the other cyclic groups can be a cycloalkyl group, but can also be different types of cyclic groups such as a heterocycloalkyl group, an aryl group and a heteroaryl group. The number of carbon groups of the cycloalkyl group can be from 3 to 60, specifically from 3 to 40 and more specifically from 5 to 20. Specific examples thereof can include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and can be further substituted with other substituents. Herein, the polycyclic means a group in which the heterocycloalkyl group is directly linked to or fused with other cyclic groups. Herein, the other cyclic groups can be a heterocycloalkyl group, but can also be different types of cyclic groups such as a cycloalkyl group, an aryl group and a heteroaryl group. The number of carbon atoms of the heterocycloalkyl group can be from 2 to 60, specifically from 2 to 40 and more specifically from 3 to 20.

In the present specification, the aryl group includes monocyclic or polycyclic having 6 to 60 carbon atoms, and can be further substituted with other substituents. Herein, the polycyclic means a group in which the aryl group is directly linked to or fused with other cyclic groups. Herein, the other cyclic groups can be an aryl group, but can also be different types of cyclic groups such as a cycloalkyl group, a heterocycloalkyl group and a heteroaryl group. The aryl group includes a spiro group. The number of carbon atoms of the aryl group can be from 6 to 60, specifically from 6 to 40 and more specifically from 6 to 25. Specific examples of the aryl group can include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent including Si, having the Si atom directly linked as a radical, and is represented by —SiR$_{104}$R$_{105}$R$_{106}$. R$_{104}$ to R$_{106}$ are the same as or different from each other, and can be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group can be substituted, and adjacent substituents can bond to each other to form a ring.

When the fluorenyl group is substituted,

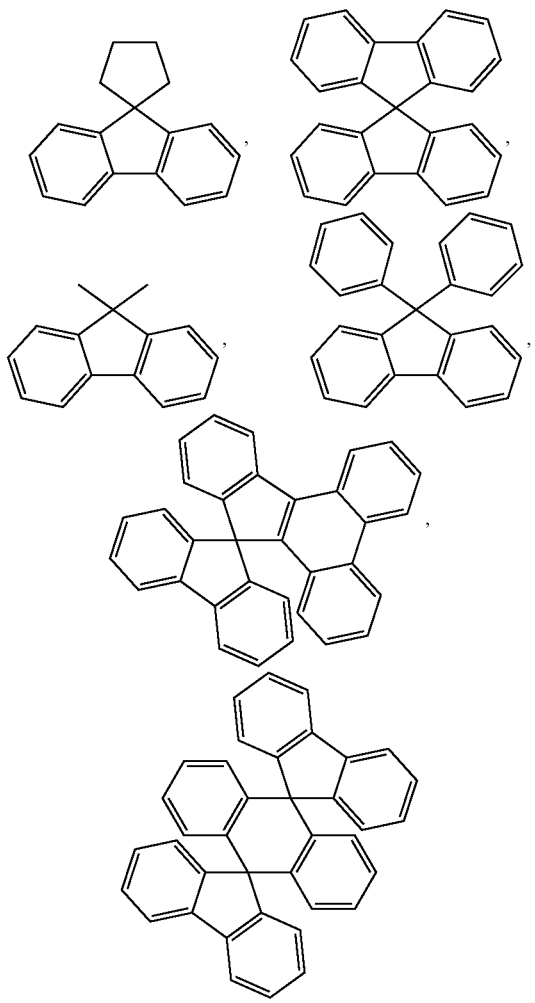

and the like can be included, however, the structure is not limited thereto.

In the present specification, the heteroaryl group includes O, S, Se, N or Si as a heteroatom, includes monocyclic or polycyclic having 2 to 60 carbon atoms, and can be further substituted with other substituents. Herein, the polycyclic means a group in which the heteroaryl group is directly linked to or fused with other cyclic groups. Herein, the other cyclic groups can be a heteroaryl group, but can also be different types of cyclic groups such as a cycloalkyl group, a heterocycloalkyl group and an aryl group. The number of carbon atoms of the heteroaryl group can be from 2 to 60, specifically from 2 to 40 and more specifically from 3 to 25. Specific examples of the heteroaryl group can include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the phosphine oxide group can be specifically substituted with an aryl group, and as the aryl group, examples described above can be used. Examples of the phosphine oxide group can include a diphenylphosphine oxide group, a dinaphthylphosphine oxide group and the like, but are not limited thereto.

In the present specification, the amine group can be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group can include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

As the aliphatic or aromatic hydrocarbon ring or heteroring that the adjacent groups can form, the structures illustrated as the cycloalkyl group, the heterocycloalkyl group, the aryl group and the heteroaryl group can be used except for those that are not monovalent.

One embodiment of the present specification provides a heterocyclic compound represented by Chemical Formula 1.

By introducing various substituents to the central fused ring of Chemical Formula 1, a hole transfer ability of the central structure can be increased, and the expanded conjugated structure can stabilize homo energy. This allows formation of proper energy level and band gap as a host material, which resultantly leads to effects of enhancing driving voltage and efficiency of a device by increasing excitons in the light emitting region.

In one embodiment of the present specification, X is $NR_{21}$, Y' is O, and X' and Y are a direct bond.

In another embodiment of the present specification, X is $NR_{21}$, Y is O, and X' and Y' are a direct bond.

In another embodiment of the present specification, X is $NR_{21}$, Y is S, and X' and Y' are a direct bond.

In another embodiment of the present specification, X is $NR_{21}$, Y is $NR_{22}$, and X' and Y' are a direct bond.

In another embodiment of the present specification, X is O, Y is $NR_{22}$, and X' and Y' are a direct bond.

In another embodiment of the present specification, X' is O, Y is $NR_{22}$, and X and Y' are a direct bond.

In another embodiment of the present specification, X is S, Y is $NR_{22}$, and X' and Y' are a direct bond.

In another embodiment of the present specification, X' is S, Y is $NR_{22}$, and X and Y' are a direct bond.

In one embodiment of the present specification, A and B are each independently a C6 to C60 aryl ring, and at least one thereof is a C10 to C60 aryl ring.

In one embodiment of the present specification, A is a C6 to C60 aryl ring, and B is a C10 to C60 aryl ring.

In one embodiment of the present specification, A is a C10 to C60 aryl ring, and B is a C6 to C60 aryl ring.

In one embodiment of the present specification, A is benzene, and B is naphthalene.

In another embodiment of the present specification, A is naphthalene, and B is benzene.

In the heterocyclic compound provided in one embodiment of the present specification, Chemical Formula 1 is represented by the following Chemical Formula 2 or Chemical Formula 3.

[Chemical Formula 2]

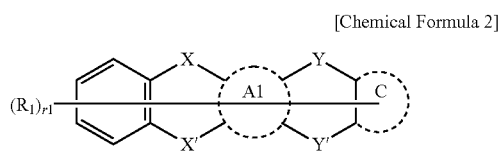

-continued

[Chemical Formula 3]

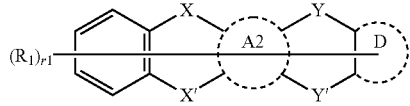

In Chemical Formulae 2 and 3,
X, X', Y, Y', $R_1$ and r1 have the same definitions as in Chemical Formula 1,
A1 is benzene,
A2 is naphthalene,
C is a C10 to C60 aryl ring, and
D is a C6 to C60 aryl ring.

In one embodiment of the present specification, Chemical Formula 2 can be represented by the following Chemical Formula 2-1 or Chemical Formula 2-2.

[Chemical Formula 2-1]

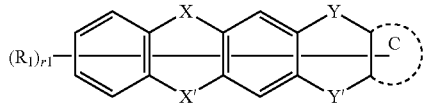

[Chemical Formula 2-2]

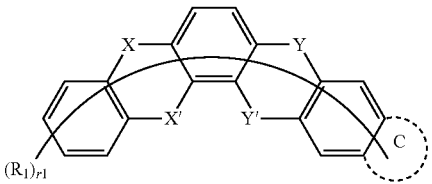

In Chemical Formulae 2-1 and 2-2,
X, X', Y, Y', $R_1$, r1 and C have the same definitions as in Chemical Formula 2.

In one embodiment of the present specification, Chemical Formula 3 can be represented by the following Chemical Formula 3-1.

[Chemical Formula 3-1]

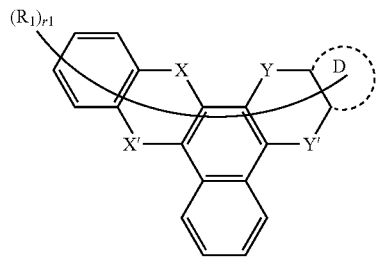

In Chemical Formula 3-1,
X, X', Y, Y', $R_1$, r1 and D have the same definitions as in Chemical Formula 3.

In one embodiment of the present specification, $R_1$ is selected from the group consisting of a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

In one embodiment of the present specification, $R_1$ is a substituted or unsubstituted aryl group; a substituted or unsubstituted heteroaryl group; or a substituted or unsubstituted amine group, or two or more groups adjacent to each other bond to each other to form a substituted or unsubstituted aliphatic or aromatic hydrocarbon ring or heteroring.

In one embodiment of the present specification, $R_1$ is a substituted or unsubstituted C6 to C60 aryl group; a substituted or unsubstituted C2 to C60 heteroaryl group; or a substituted or unsubstituted amine group, or two or more groups adjacent to each other bond to each other to form a substituted or unsubstituted aliphatic or aromatic hydrocarbon ring or heteroring.

In one embodiment of the present specification, $R_1$ is a substituted or unsubstituted C6 to C30 aryl group; a substituted or unsubstituted C2 to C30 heteroaryl group; or a substituted or unsubstituted amine group, or two or more groups adjacent to each other bond to each other to form a substituted or unsubstituted aliphatic or aromatic hydrocarbon ring or heteroring.

In one embodiment of the present specification, $R_1$ is a substituted or unsubstituted phenyl group; a substituted or unsubstituted carbazole group; a substituted or unsubstituted dibenzofuran group; a substituted or unsubstituted dibenzothiophene group; or an amine group unsubstituted or substituted with an aryl group, or two or more groups adjacent to each other bond to each other to form a substituted or unsubstituted aliphatic or aromatic hydrocarbon ring or heteroring.

In one embodiment of the present specification, $R_1$ is a phenyl group; a carbazole group unsubstituted or substituted with a phenyl group; a benzocarbazole group; a dibenzofuran group; a dibenzothiophene group; or an amine group unsubstituted or substituted with one or more substituents selected from the group consisting of a phenyl group, a biphenyl group, a naphthyl group and a 9,9-dimethyl-9H-fluorenyl group.

In one embodiment of the present specification, r1 is 1 or 2.

In one embodiment of the present specification, r1 is 2, and $R_1$s are all a phenyl group.

In one embodiment of the present specification, r1 is 2, and $R_1$s are a phenyl group, and an amine group substituted with a phenyl group.

In one embodiment of the present specification, r1 is 2, and $R_1$s are a phenyl group and a carbazole group.

In one embodiment of the present specification, Chemical Formula 1 is represented by any one of the following Chemical Formula 4 to Chemical Formula 10.

[Chemical Formula 4]

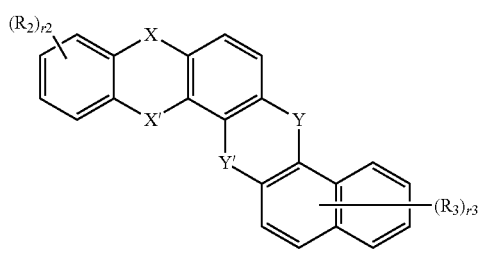

[Chemical Formula 5]

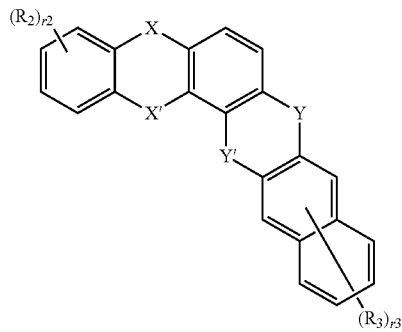

[Chemical Formula 6]

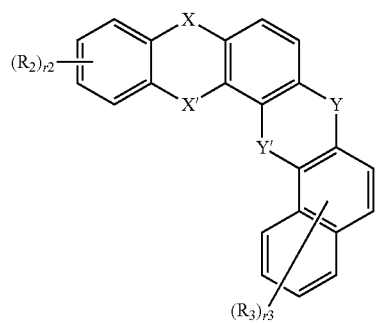

[Chemical Formula 7]

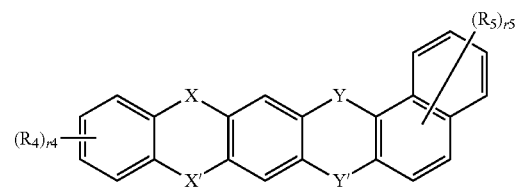

[Chemical Formula 8]

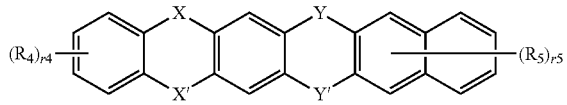

[Chemical Formula 9]

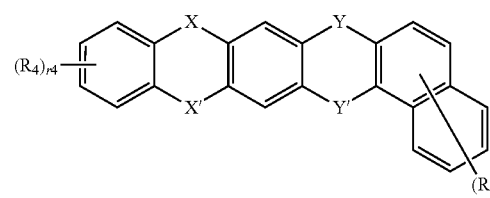

[Chemical Formula 10]

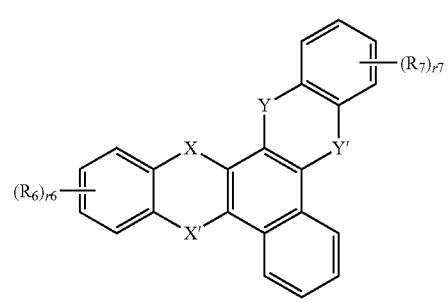

In Chemical Formulae 4 to 10,

X, X', Y and Y' have the same definitions as in Chemical Formula 1, $R_2$ to $R_7$ are each independently selected from the group consisting of hydrogen; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, and at least one of $R_2$ and $R_3$, at least one of $R_4$ and $R_5$ and at least one of $R_6$ and $R_7$ are a substituted or unsubstituted aryl group; a substituted or unsubstituted heteroaryl group; or a substituted or unsubstituted amine group, r2, r4, r6 and r7 are each an integer of 1 to 4, r3 and r5 are each an integer of 1 to 6, and when r2 to r7 are each an integer of 2 or greater, substituents in the parentheses are the same as or different from each other.

In one embodiment of the present specification, $R_2$ to $R_7$ are each independently hydrogen; deuterium; a substituted or unsubstituted aryl group; a substituted or unsubstituted heteroaryl group; or a substituted or unsubstituted amine group, or two or more groups adjacent to each other bond to each other to form a substituted or unsubstituted aliphatic or aromatic hydrocarbon ring or heteroring, and at least one of $R_2$ and $R_3$, at least one of $R_4$ and $R_5$ and at least one of $R_6$ and $R_7$ are a substituted or unsubstituted aryl group; a substituted or unsubstituted heteroaryl group; or a substituted or unsubstituted amine group.

In one embodiment of the present specification, $R_2$ to $R_7$ are each independently hydrogen; deuterium; a substituted or unsubstituted C6 to C60 aryl group; a substituted or unsubstituted C2 to C60 heteroaryl group; or a substituted or unsubstituted amine group, and at least one of $R_2$ and $R_3$, at least one of $R_4$ and $R_5$ and at least one of $R_6$ and $R_7$ are a substituted or unsubstituted C6 to C60 aryl group; a substituted or unsubstituted C2 to C60 heteroaryl group; or a substituted or unsubstituted amine group.

In one embodiment of the present specification, $R_2$ to $R_7$ are each independently hydrogen; deuterium; a substituted or unsubstituted C6 to C30 aryl group; a substituted or unsubstituted C2 to C30 heteroaryl group; or a substituted or unsubstituted amine group, and at least one of $R_2$ and $R_3$, at least one of $R_4$ and $R_5$ and at least one of $R_6$ and $R_7$ are a substituted or unsubstituted C6 to C30 aryl group; a substituted or unsubstituted C2 to C30 heteroaryl group; or a substituted or unsubstituted amine group.

In one embodiment of the present specification, $R_2$ to $R_7$ are each independently hydrogen; deuterium; a substituted or unsubstituted phenyl group; a substituted or unsubstituted carbazole group; a substituted or unsubstituted benzocarbazole group; a substituted or unsubstituted dibenzofuran group; a substituted or unsubstituted dibenzothiophene group; or an amine group unsubstituted or substituted with an aryl group, and at least one of $R_2$ and $R_3$, at least one of $R_4$ and $R_5$ and at least one of $R_6$ and $R_7$ are a substituted or unsubstituted phenyl group; a substituted or unsubstituted carbazole group; a substituted or unsubstituted benzocarbazole group; a substituted or unsubstituted dibenzofuran group; a substituted or unsubstituted dibenzothiophene group; or an amine group unsubstituted or substituted with an aryl group.

In one embodiment of the present specification, $R_2$ to $R_7$ are each independently hydrogen; deuterium; a phenyl group; a carbazole group unsubstituted or substituted with a phenyl group; a benzocarbazole group; a dibenzofuran group; a dibenzothiophene group; or an amine group unsubstituted or substituted with one or more substituents selected from the group consisting of a phenyl group, a biphenyl group, a naphthyl group and a 9,9-dimethyl-9H-fluorenyl group, and at least one of $R_2$ and $R_3$, at least one of $R_4$ and $R_5$ and at least one of $R_6$ and $R_7$ are a phenyl group; a carbazole group unsubstituted or substituted with a phenyl group; a benzocarbazole group; a dibenzofuran group; a dibenzothiophene group; or an amine group unsubstituted or substituted with one or more substituents selected from the group consisting of a phenyl group, a biphenyl group, a naphthyl group and a 9,9-dimethyl-9H-fluorenyl group.

In one embodiment of the present specification, $R_{21}$ and $R_{22}$ are each independently a substituted or unsubstituted aryl group; or a substituted or unsubstituted heteroaryl group.

In one embodiment of the present specification, $R_{21}$ and $R_{22}$ can be each independently any one selected from among the following structural formulae.

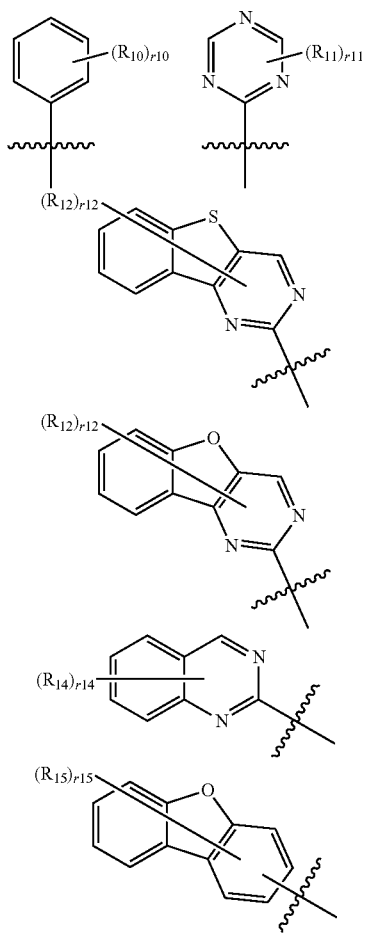

In the structural formulae,

R₁₀ to R₁₅ are each independently hydrogen; a substituted or unsubstituted aryl group; or a substituted or unsubstituted heteroaryl group, r11 is 1 or 2, r10 and r12 to r14 are each independently an integer of 1 to 5, r15 is an integer of 1 to 7, and when r10 to r15 are each an integer of 2 or greater, substituents in the parentheses are the same as or different from each other.

In one embodiment of the present specification, R₁₀ is hydrogen.

In one embodiment of the present specification, R₁₁ to R₁₅ are each independently a substituted or unsubstituted aryl group; or a substituted or unsubstituted heteroaryl group.

In one embodiment of the present specification, R₁₁ to R₁₅ are each independently a substituted or unsubstituted C6 to C60 aryl group; or a substituted or unsubstituted C2 to C60 heteroaryl group.

In one embodiment of the present specification, R₁₁ to R₁₅ are each independently a substituted or unsubstituted C6 to C30 aryl group; or a substituted or unsubstituted C2 to C30 heteroaryl group.

In one embodiment of the present specification, R₁₁ to R₁₅ are each independently a substituted or unsubstituted phenyl group; a substituted or unsubstituted biphenyl group; a substituted or unsubstituted naphthyl group; a substituted or unsubstituted fluorenyl group; a substituted or unsubstituted triazine group; a substituted or unsubstituted carbazole group; a substituted or unsubstituted dibenzothiophene group; a substituted or unsubstituted dibenzofuran group; a substituted or unsubstituted benzonaphthothiophene group; or a substituted or unsubstituted benzonaphthofuran group.

In one embodiment of the present specification, R₁₁ to R₁₅ are each independently a phenyl group; a biphenyl group; a 9,9-dimethyl-9H-fluorenyl group; a naphthyl group; a triazine group unsubstituted or substituted with a phenyl group; a carbazole group unsubstituted or substituted with a phenyl group; a dibenzothiophene group; a dibenzofuran group; a benzonaphthothiophene group; or a benzonaphthofuran group.

In one embodiment of the present specification, Chemical Formula 1 can be represented by any one of the following compounds, but is not limited thereto.

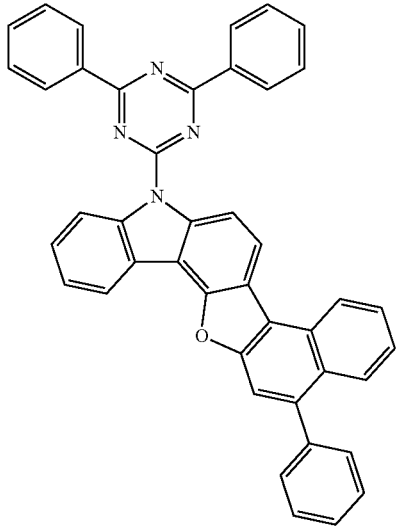

a-1

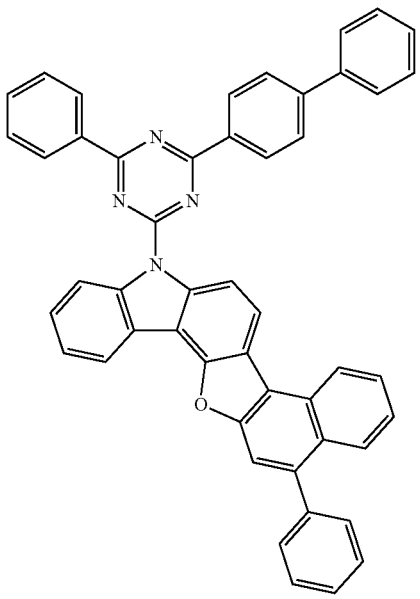

a-2

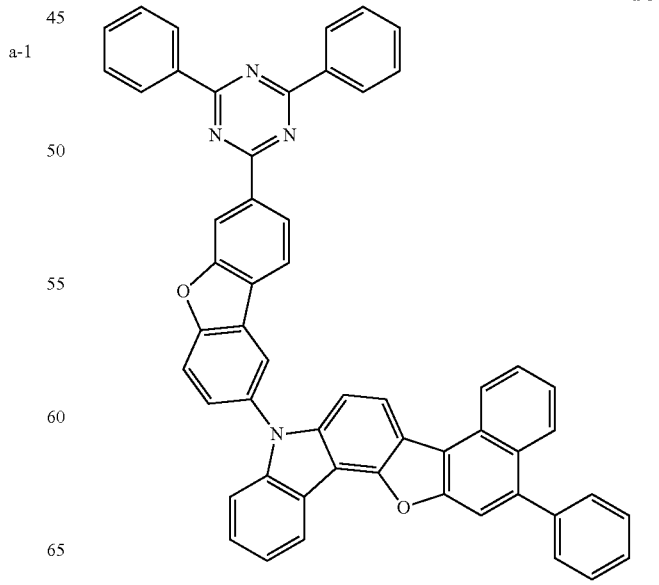

a-3 a-4
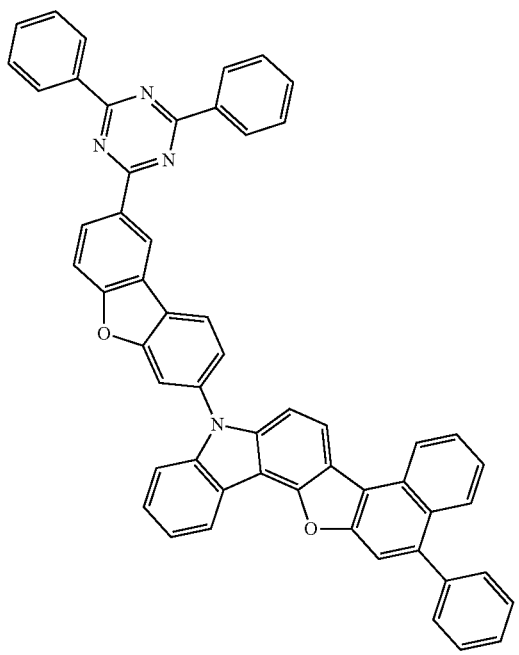
a-6
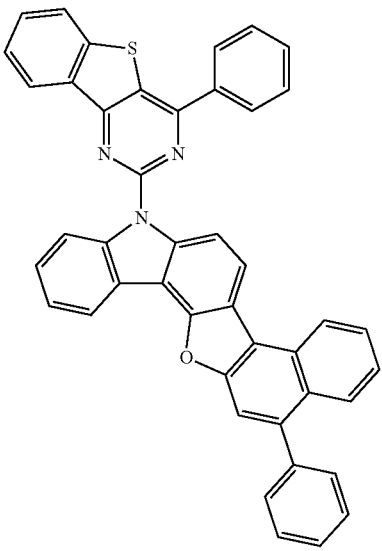
a-5
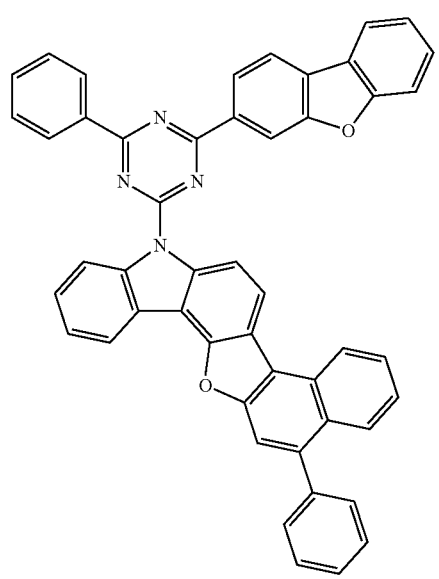
a-7
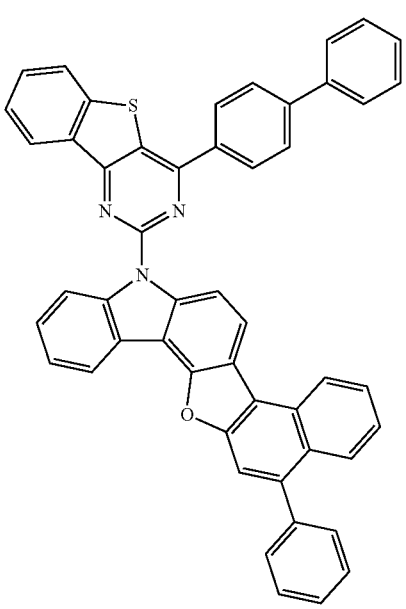

a-8
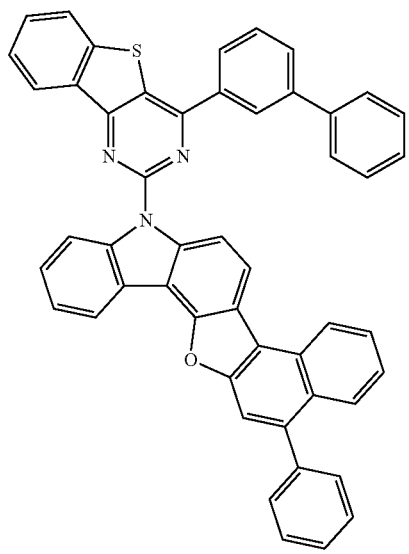
a-9
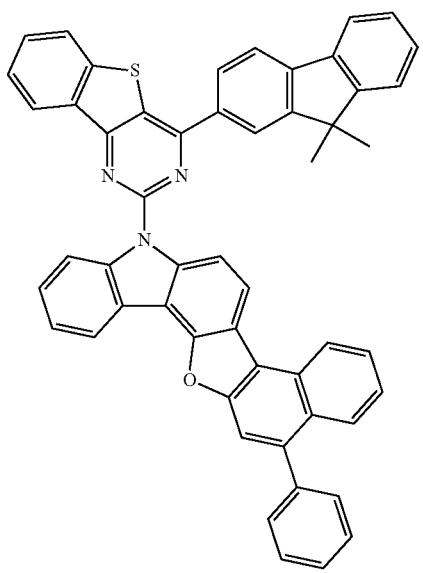
a-10
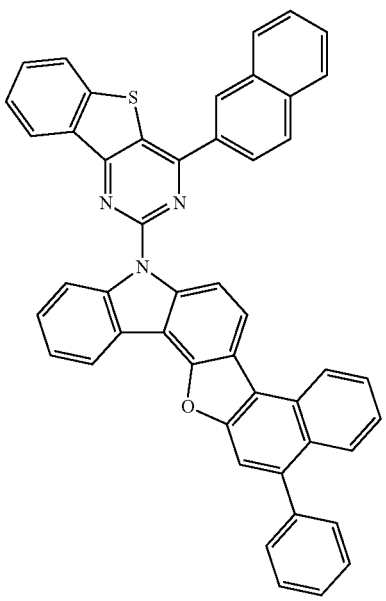
a-11
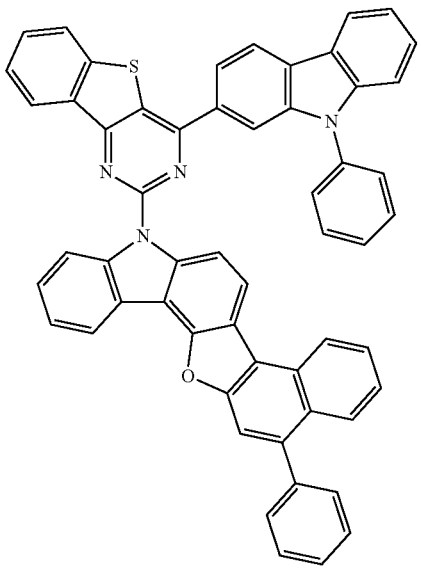

a-12
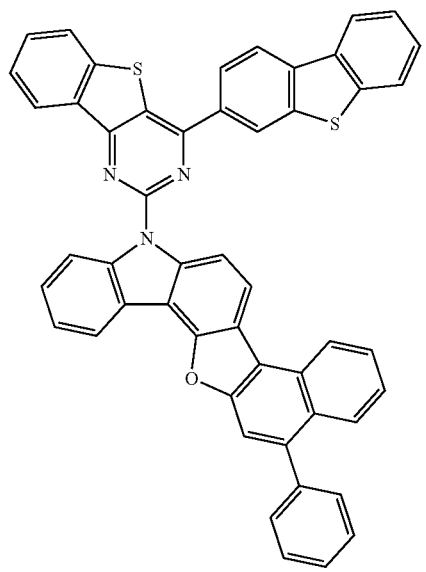
a-13
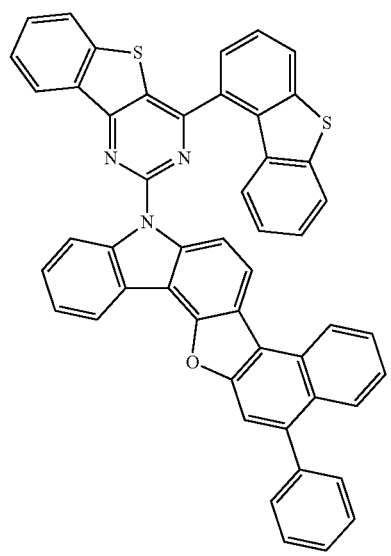
a-14
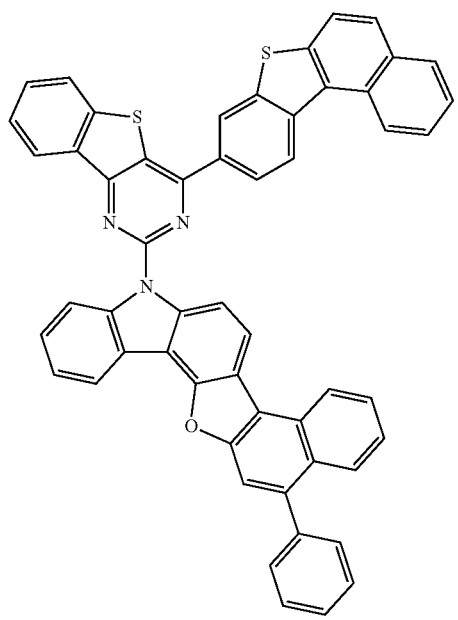
a-15
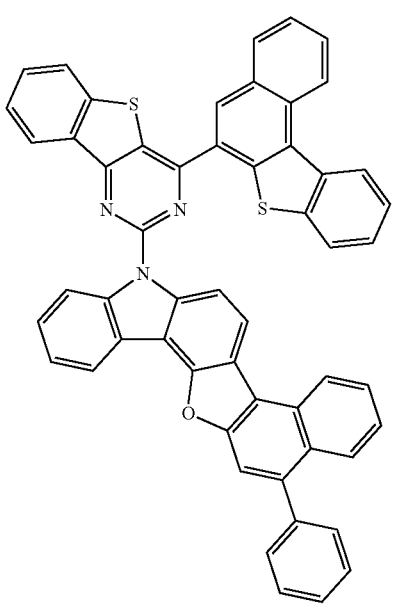

a-16
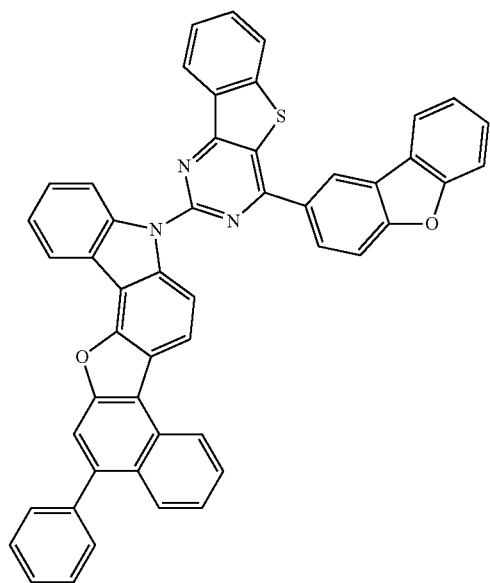
a-17
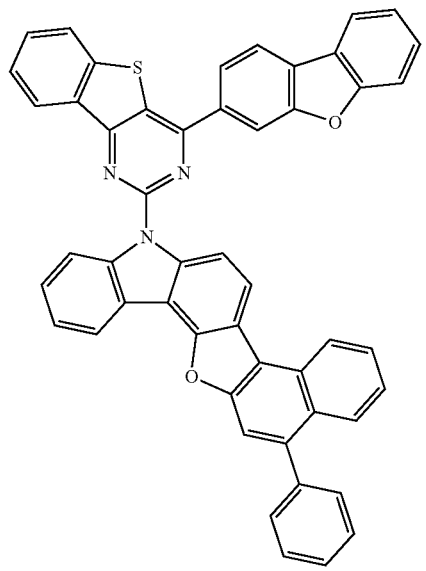
a-18
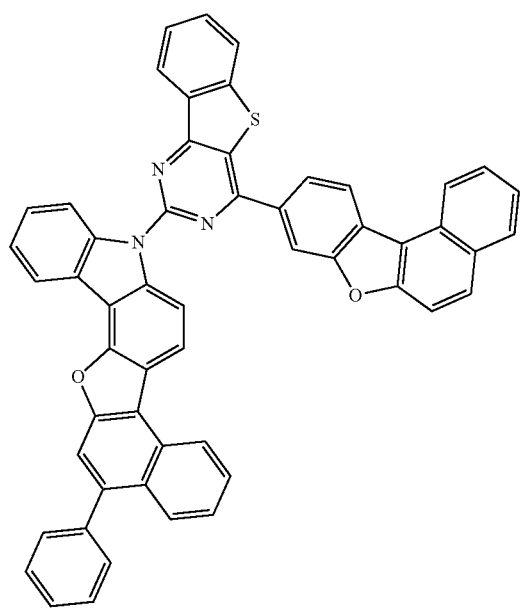
a-19
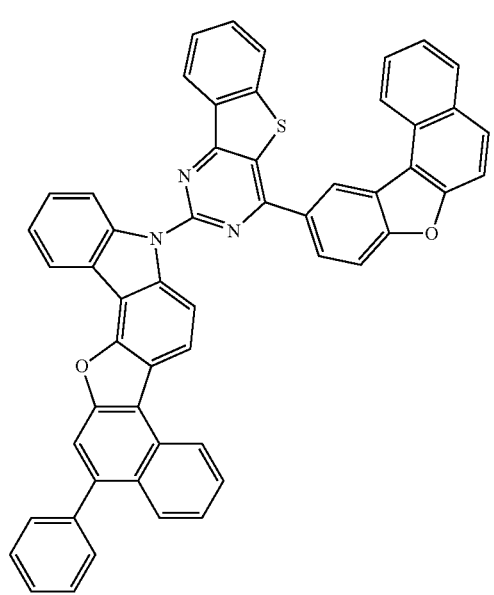

-continued
a-20
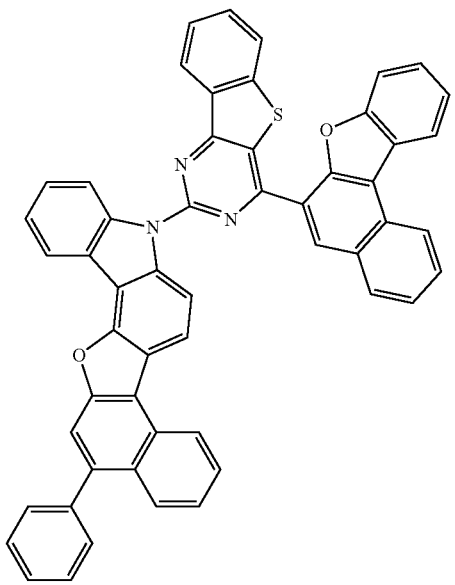
a-22
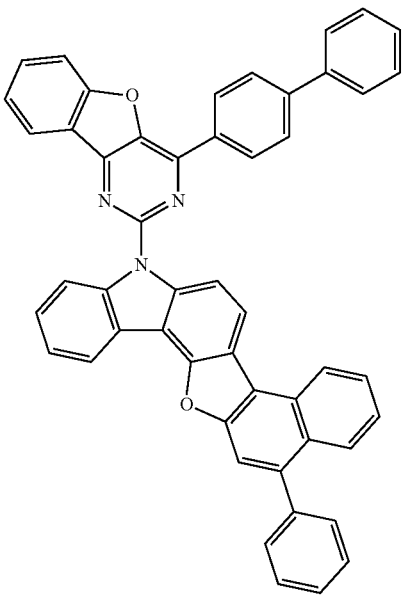
a-21
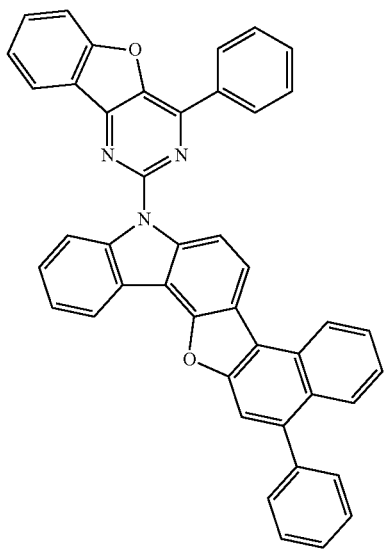
a-23
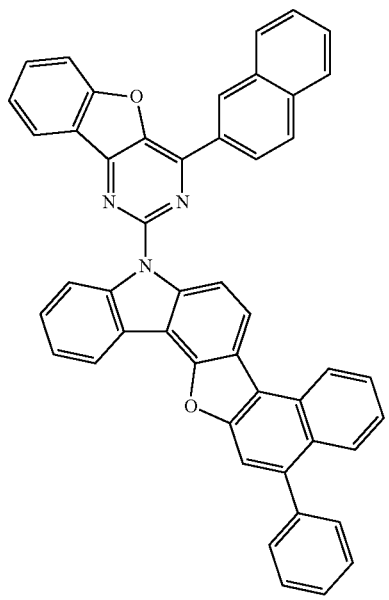

a-24
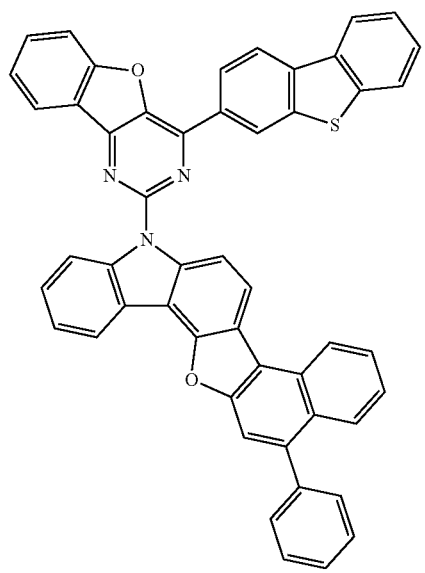
a-25
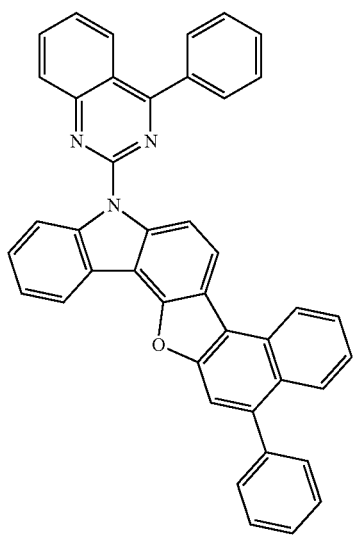
a-26
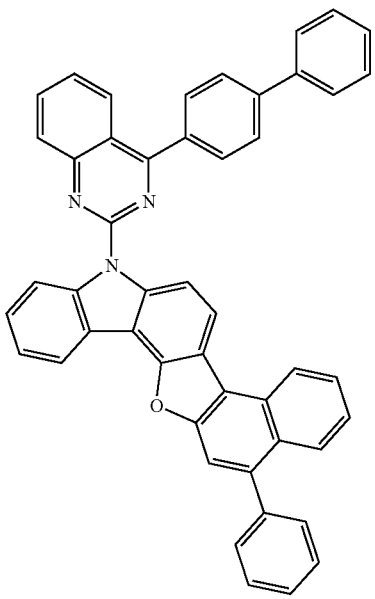
a-27
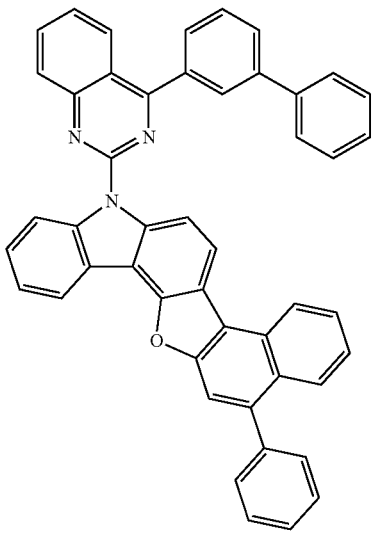

a-28
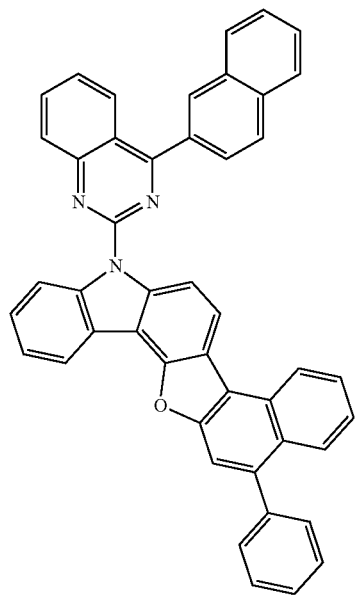
a-30
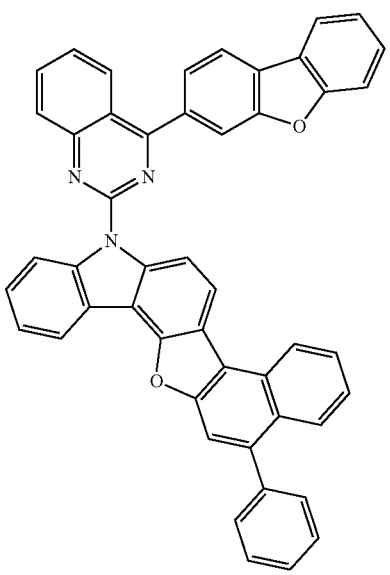
a-31
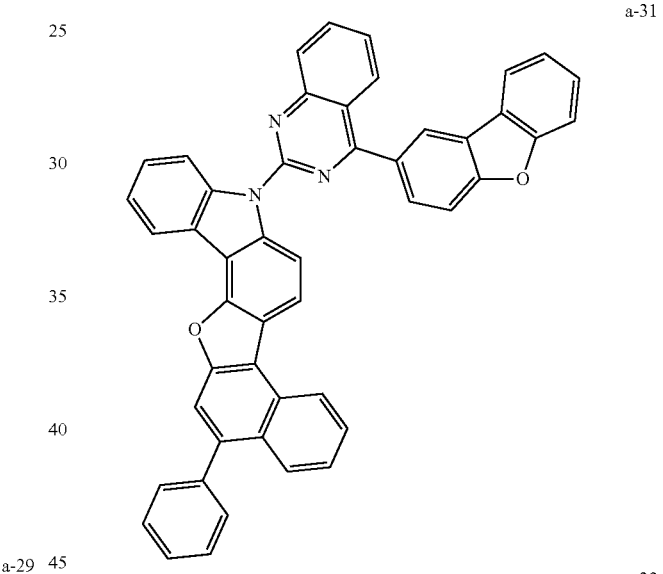
a-29
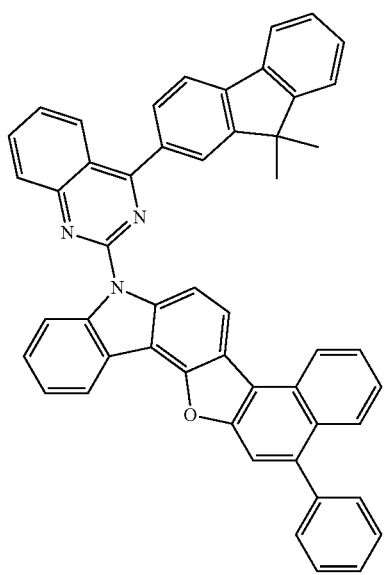
a-32
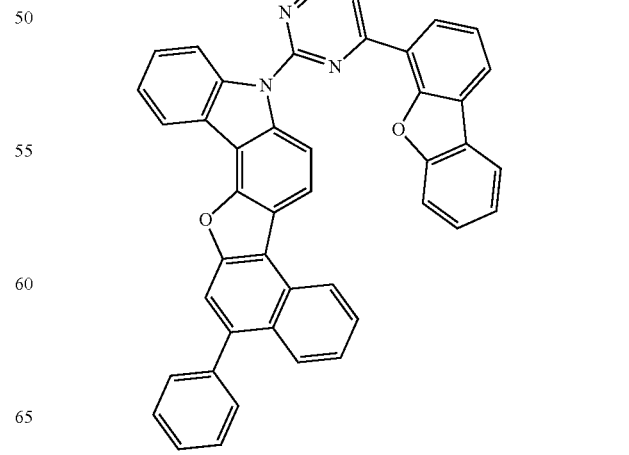

a-33
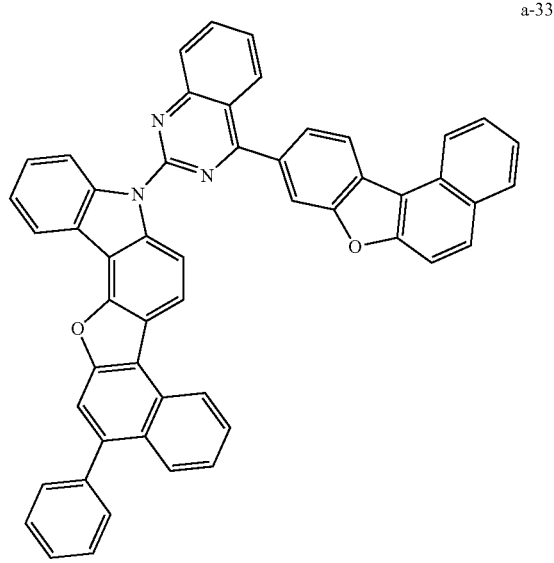
a-36
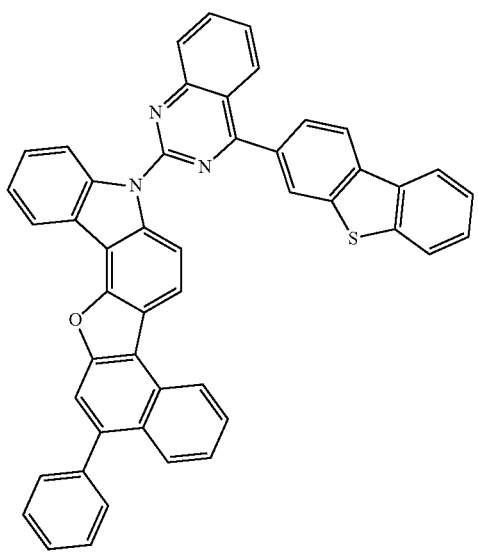
a-34
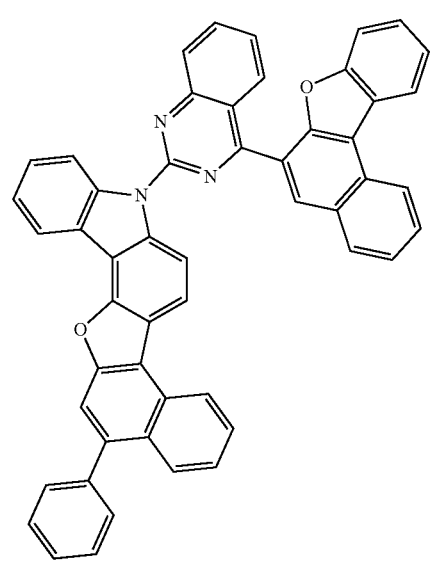
a-35
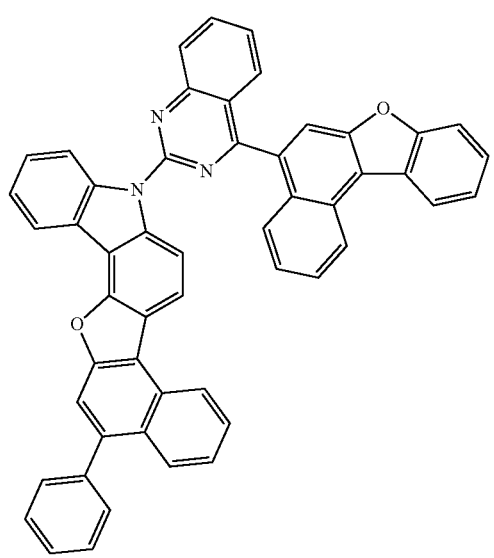
a-37
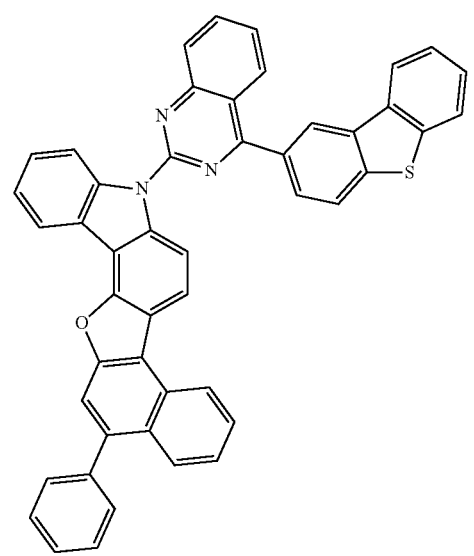

a-38
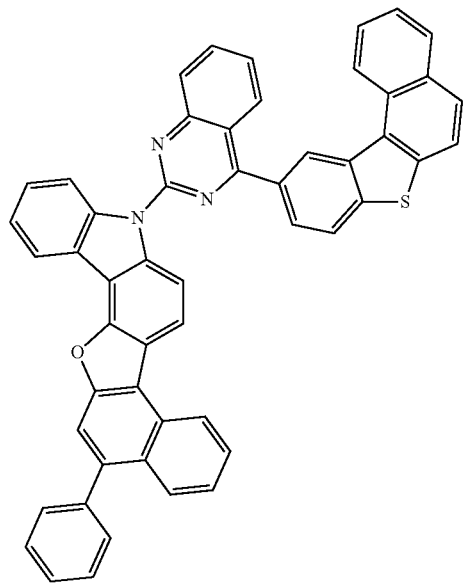
a-40
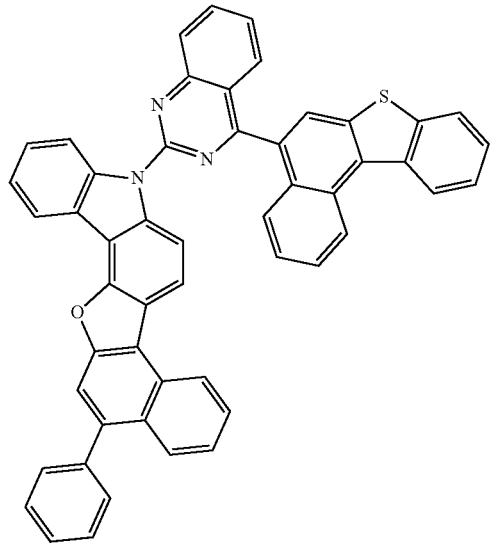
a-41
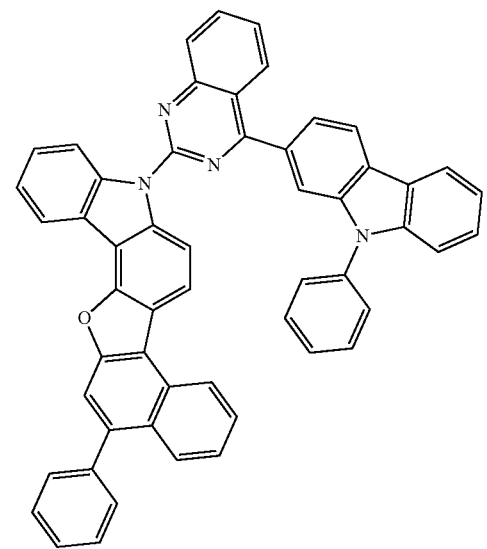
a-39
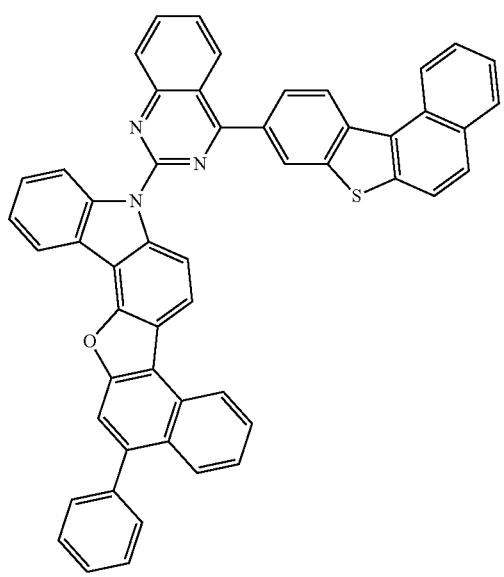
a-42
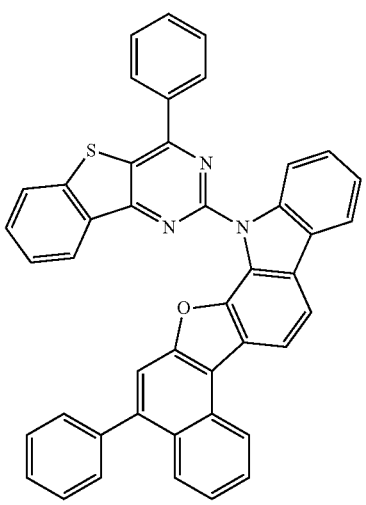

a-43
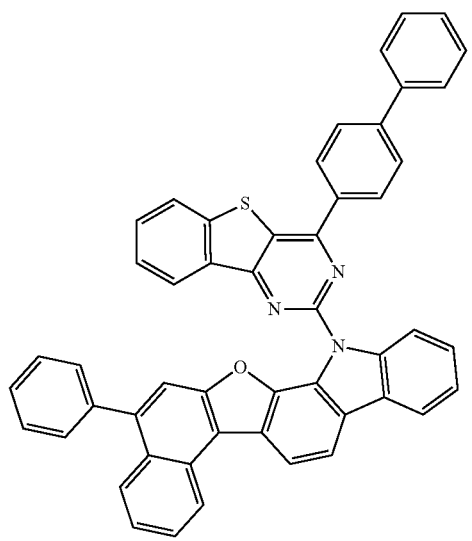
a-44
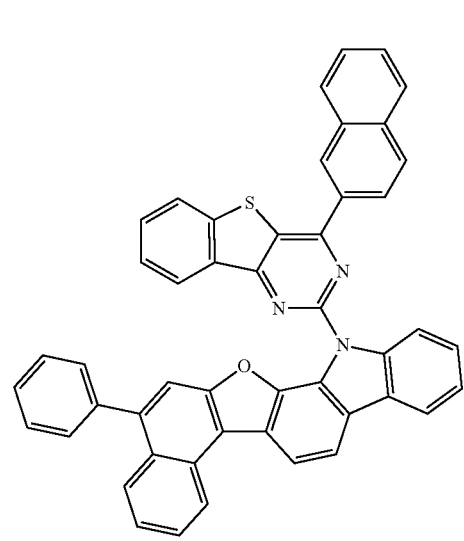
a-45
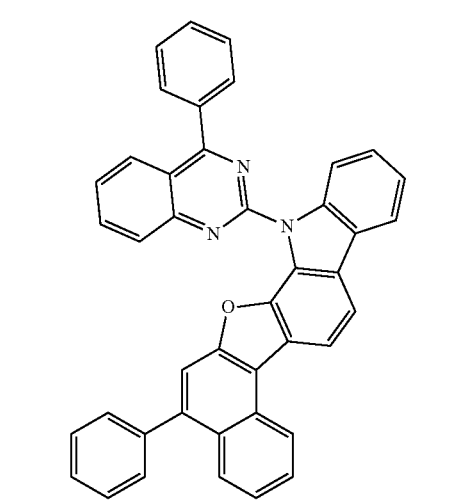
a-46
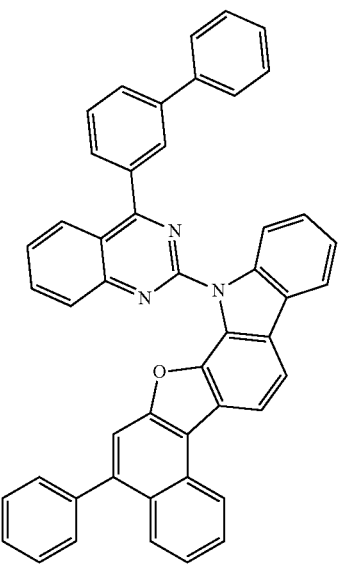
a-47
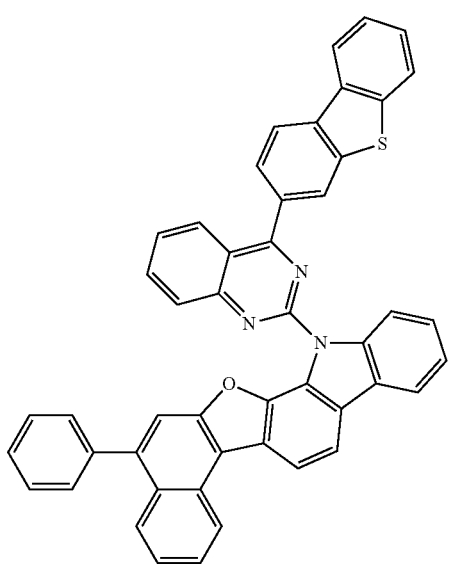
a-48
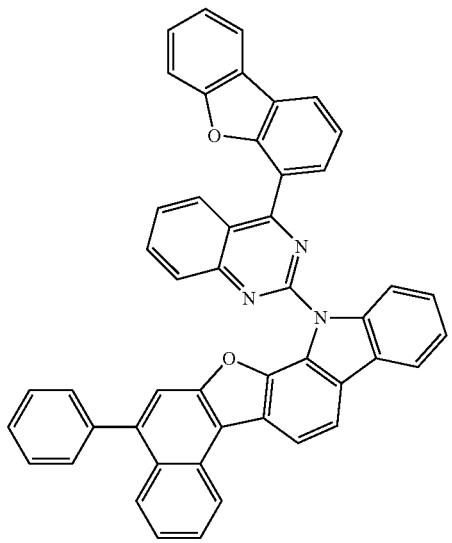

a-49
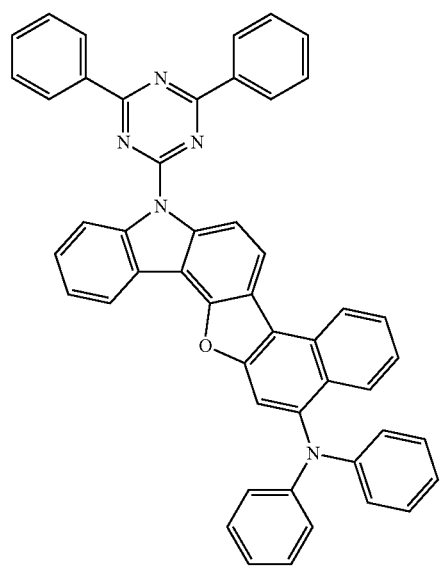
a-50
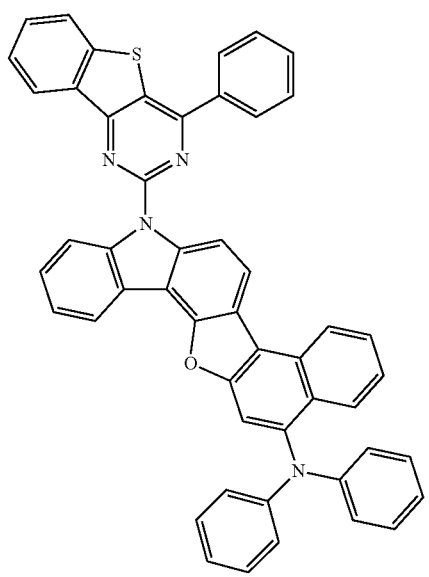
a-51
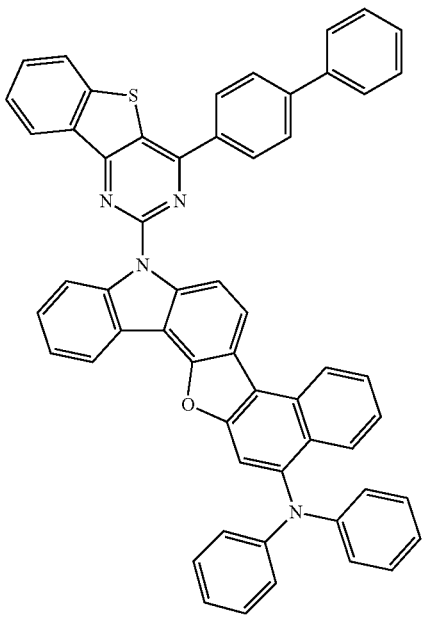
a-52
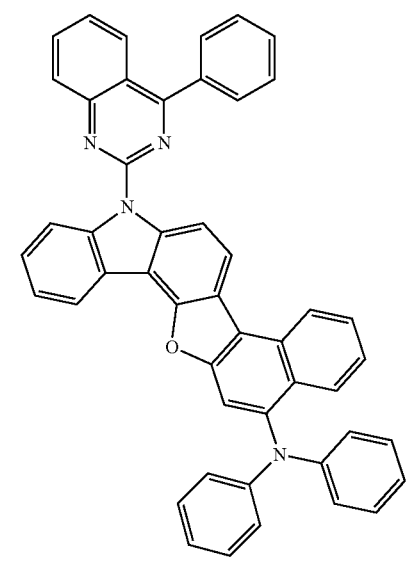

a-53
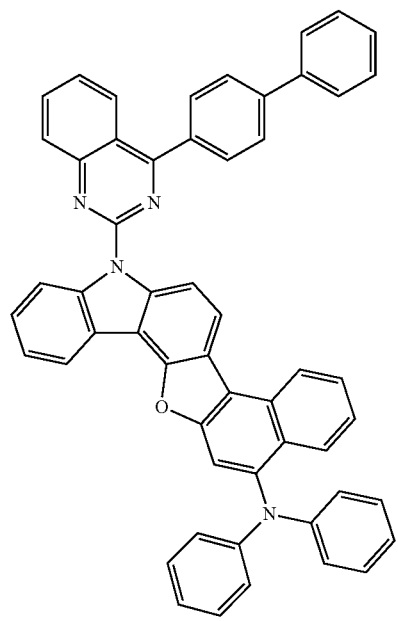
a-55
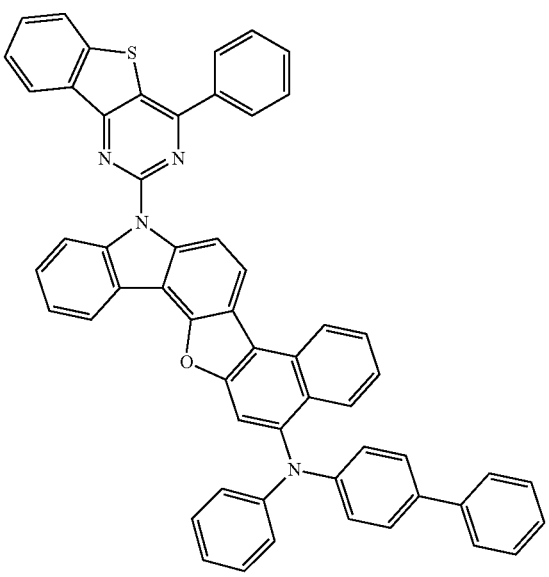
a-54
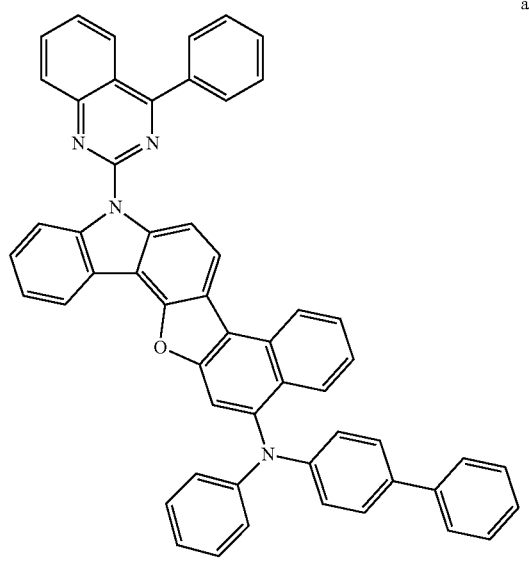
a-56
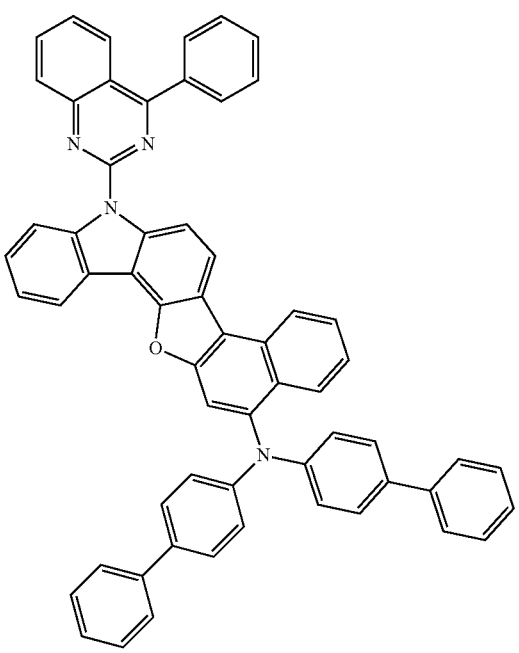

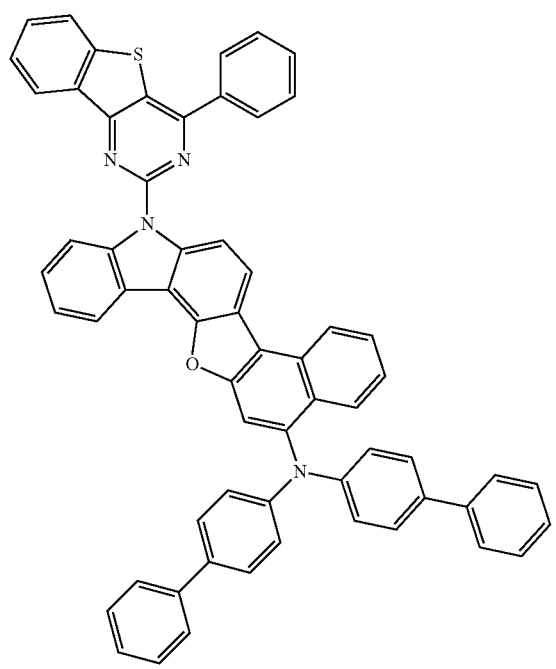
a-57
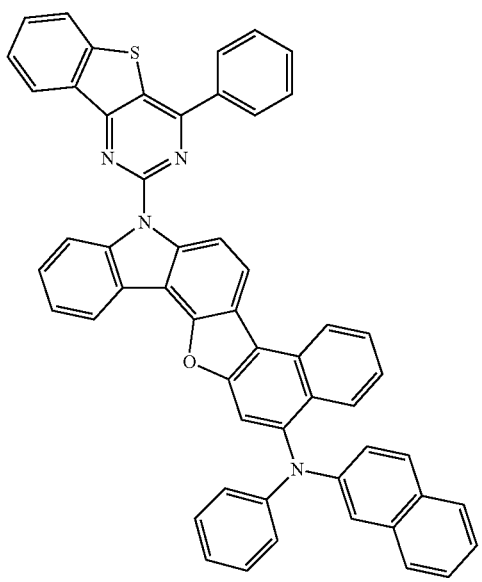
a-59
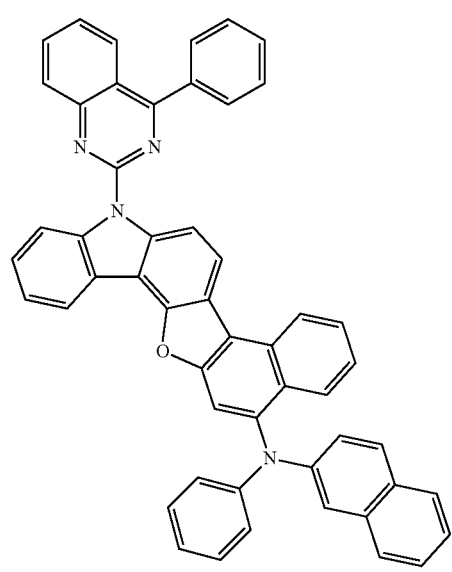
a-58
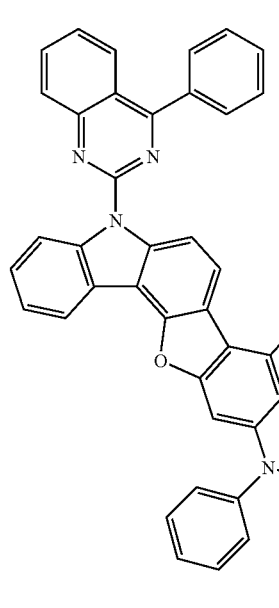
a-60 a-61
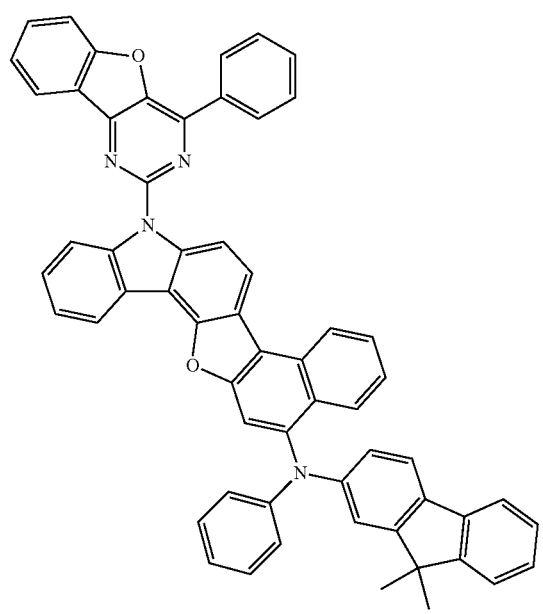
a-63
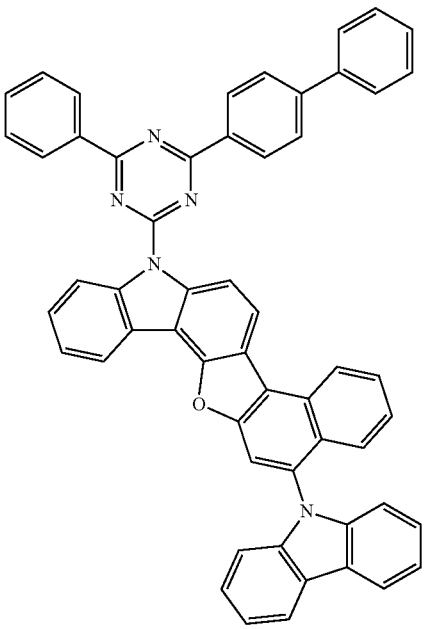
a-62
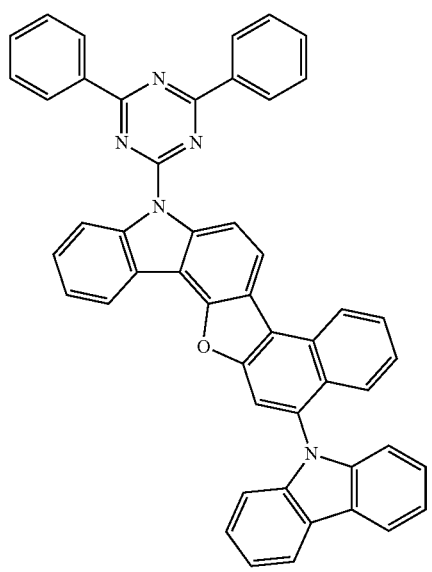
a-64
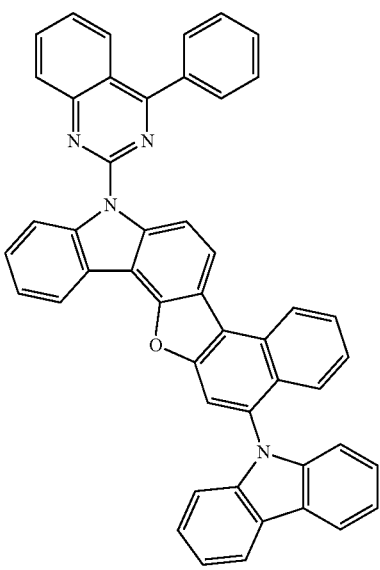

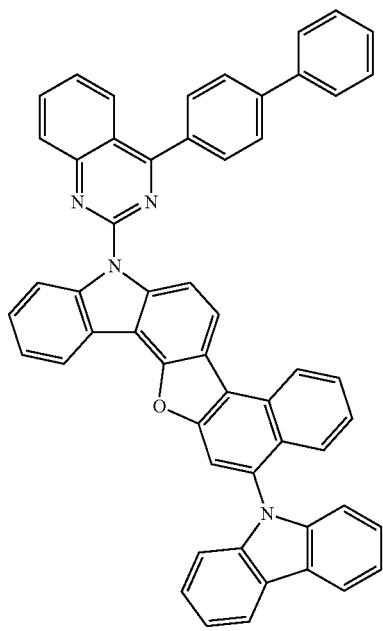
a-65
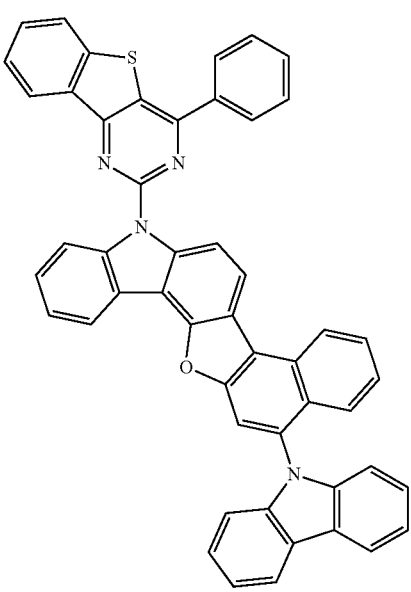
a-67
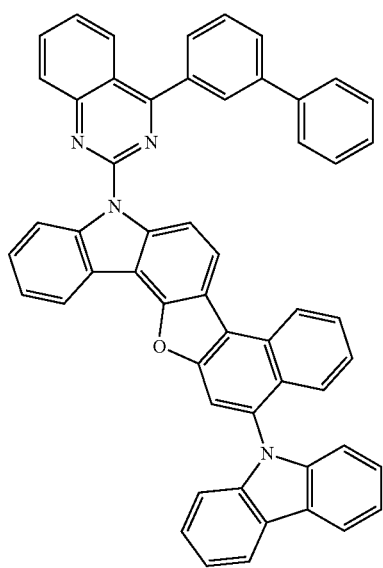
a-66
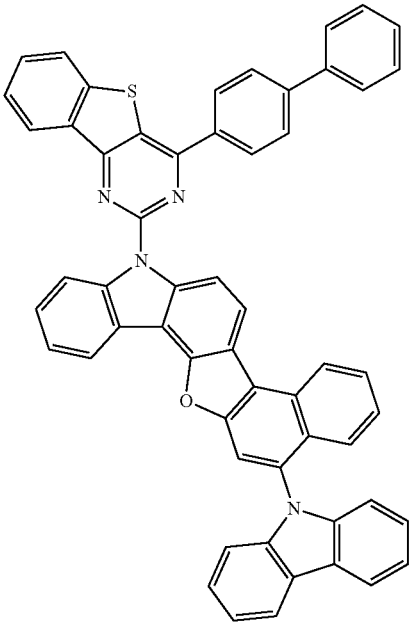
a-68

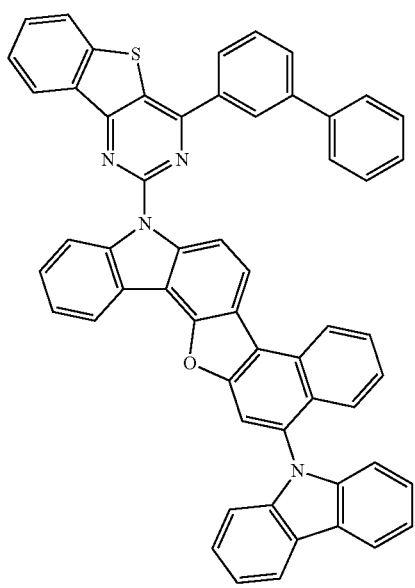
a-69
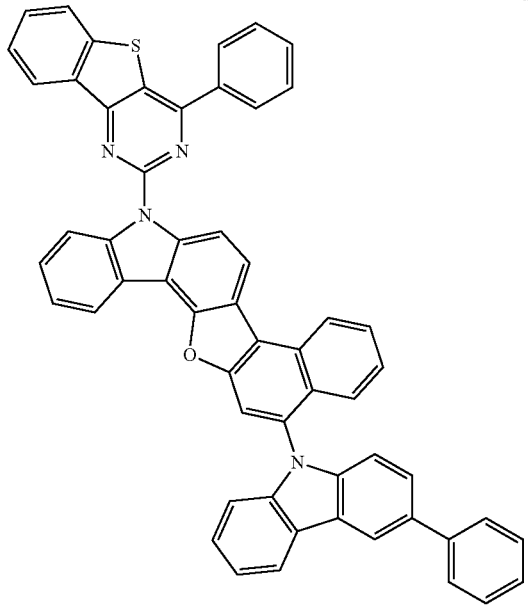
a-71
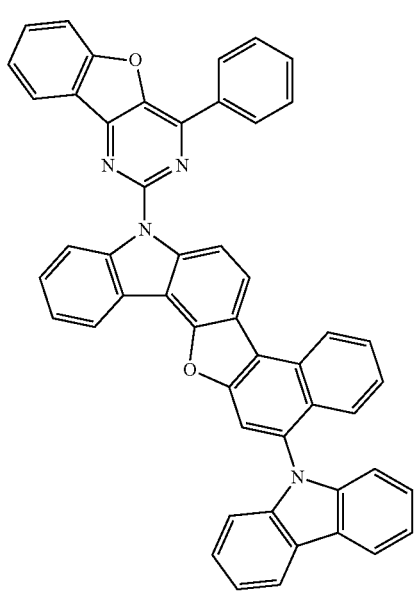
a-70
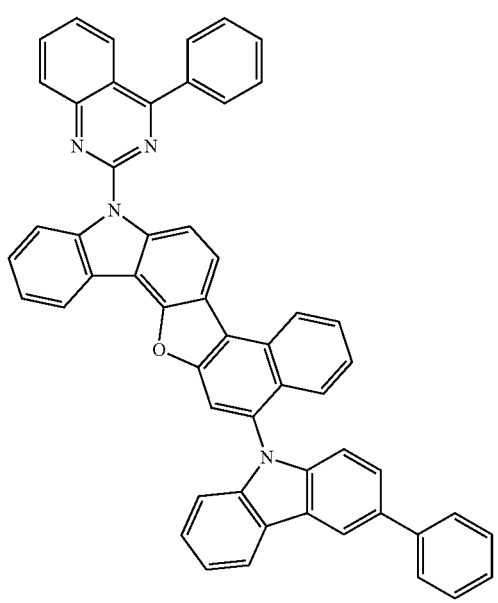
a-72 a-73
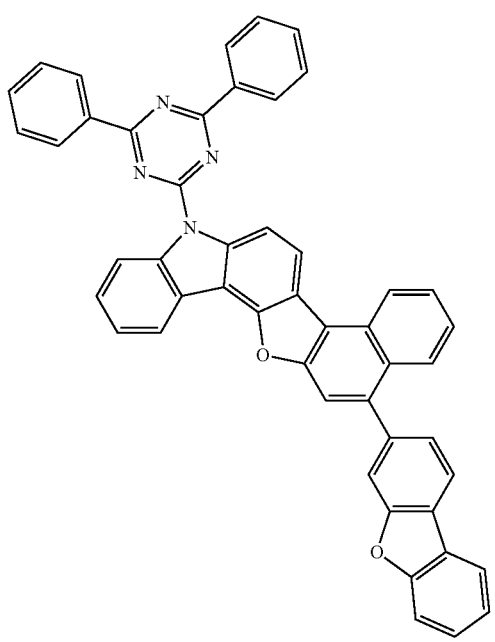
a-74
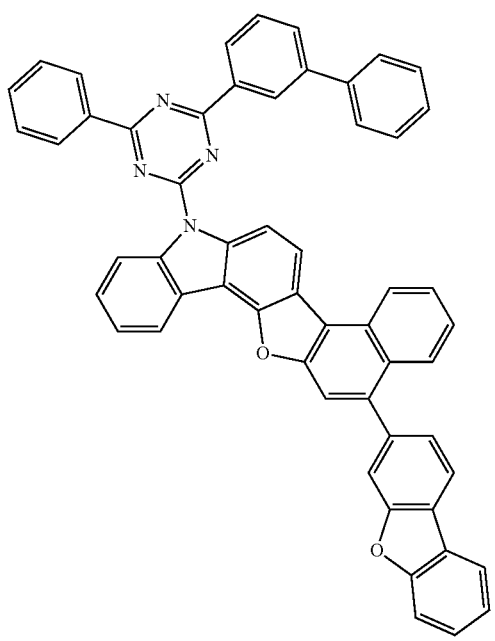
a-75
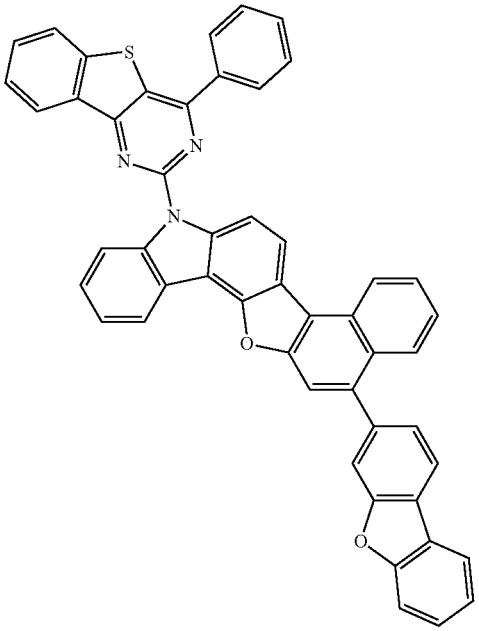
a-76
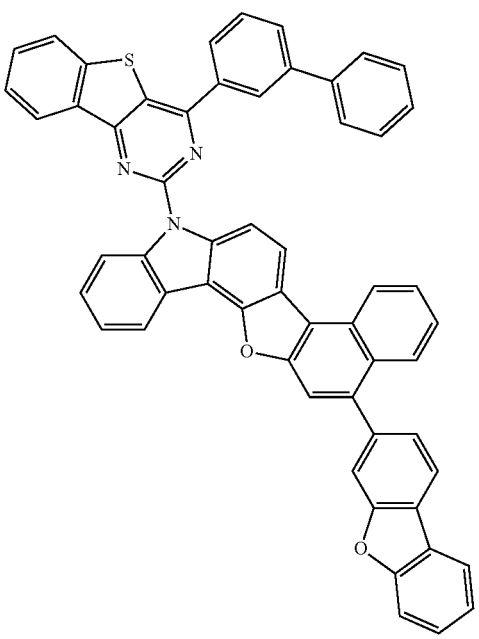

a-77
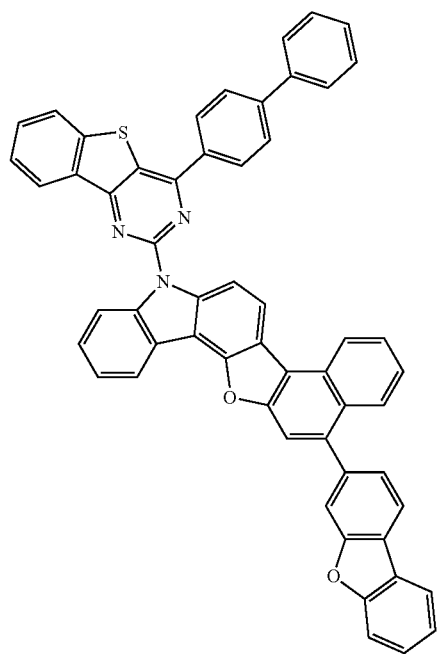
a-78
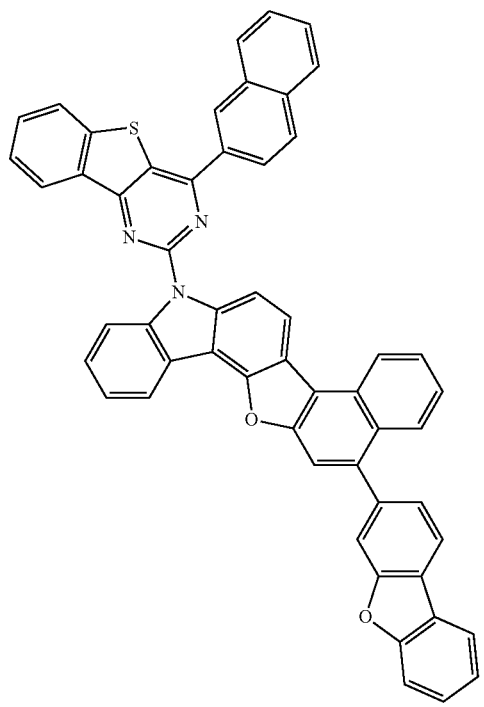
a-79
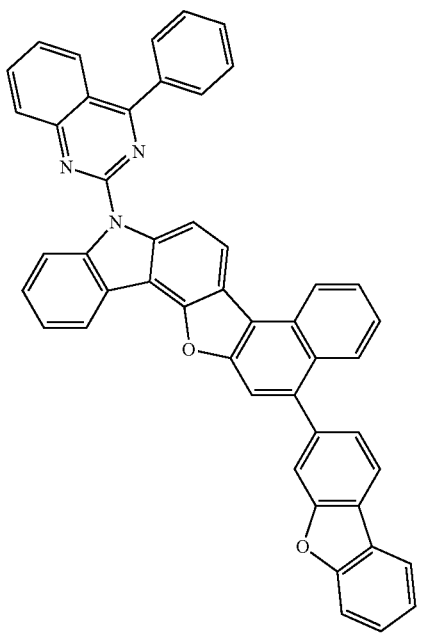
a-80 a-81
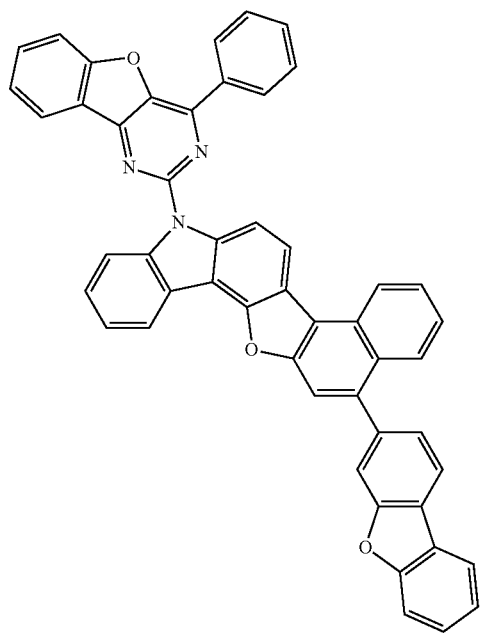
a-83
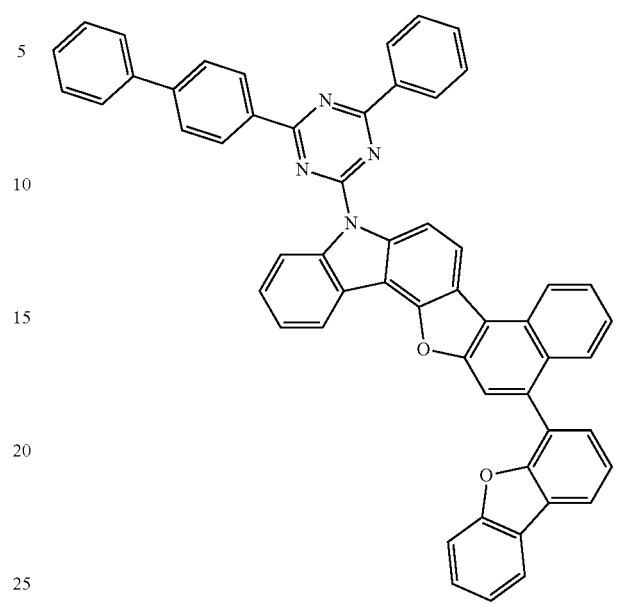
a-82
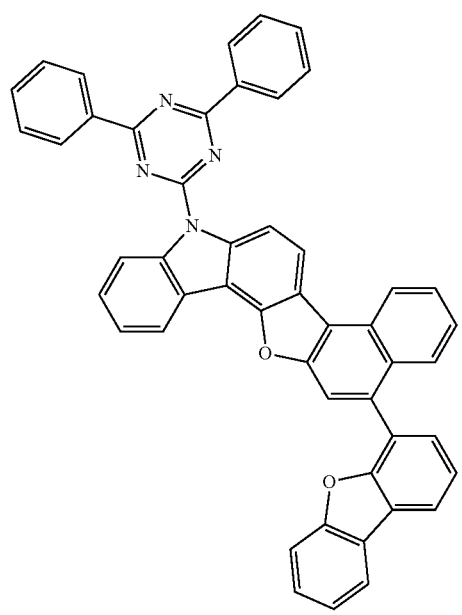
a-84
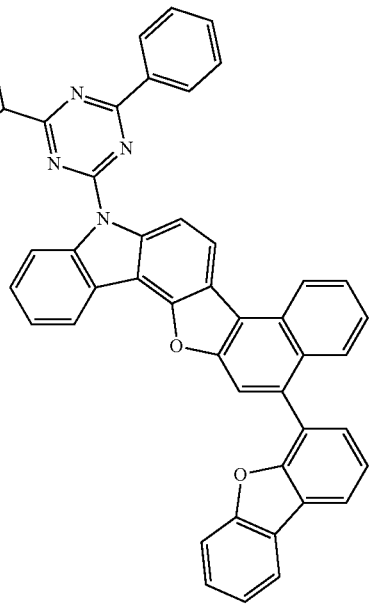

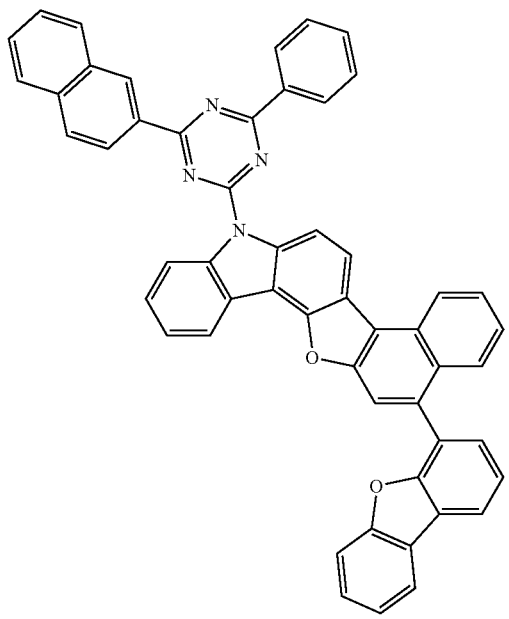
a-85
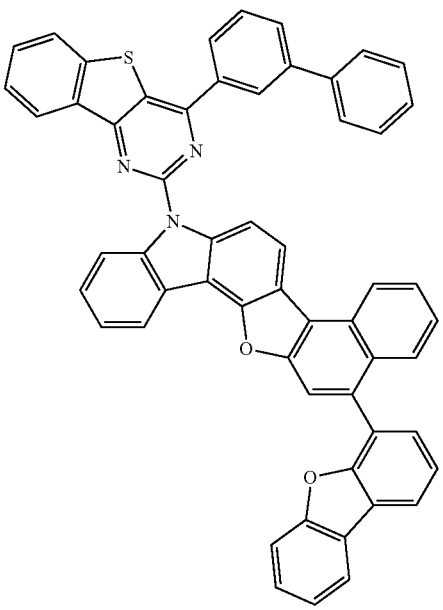
a-87
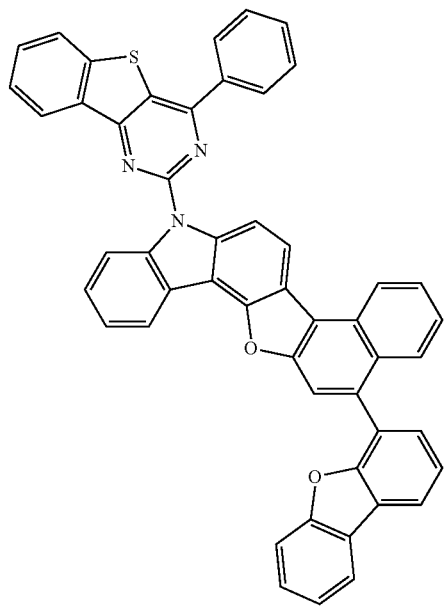
a-86
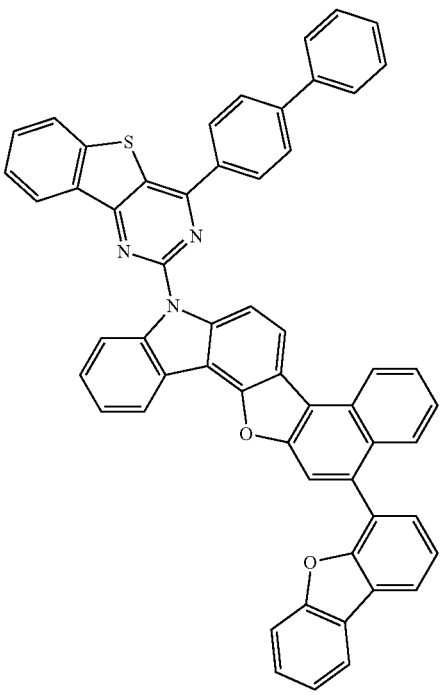
a-88 a-89
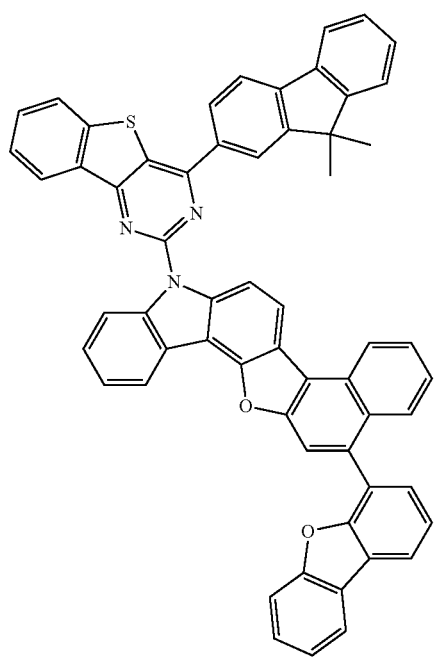
a-91
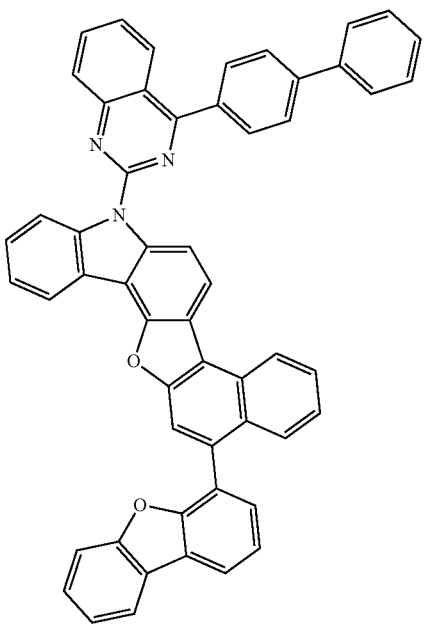
a-90
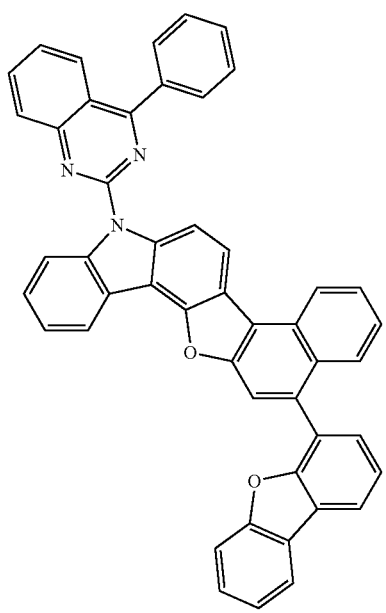
a-92
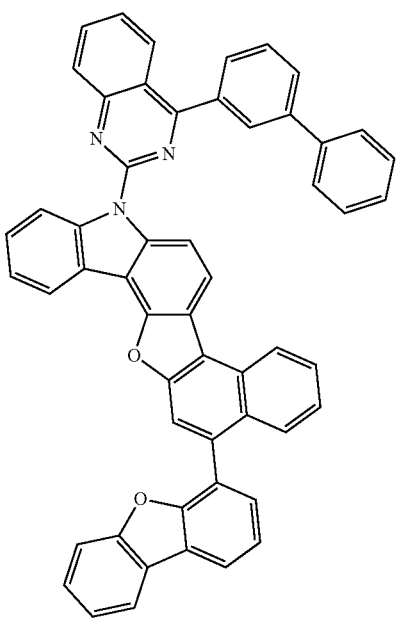

a-93
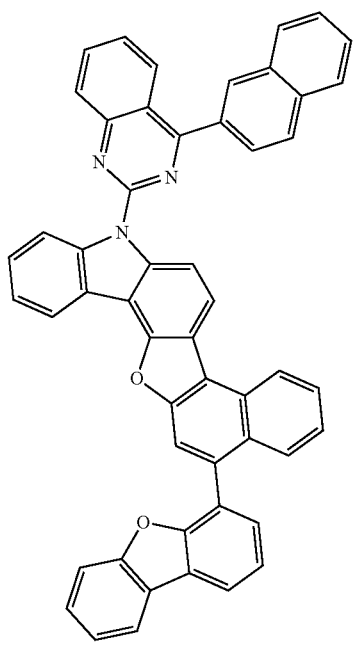
a-94
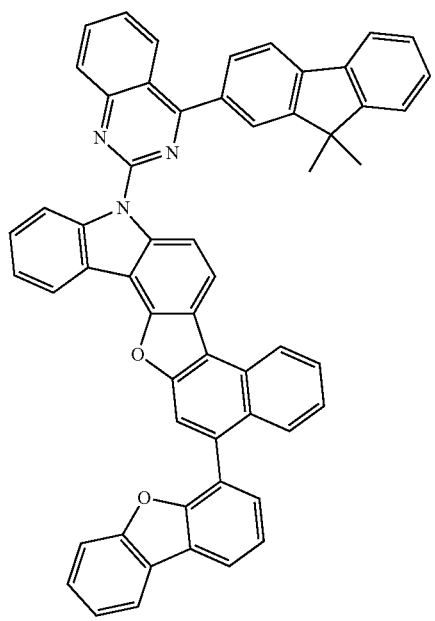
a-95
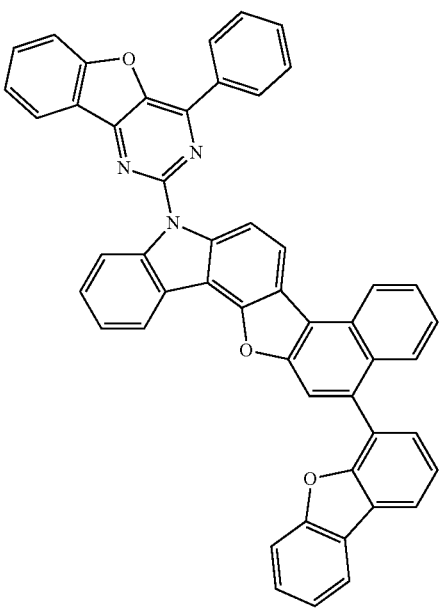
a-96
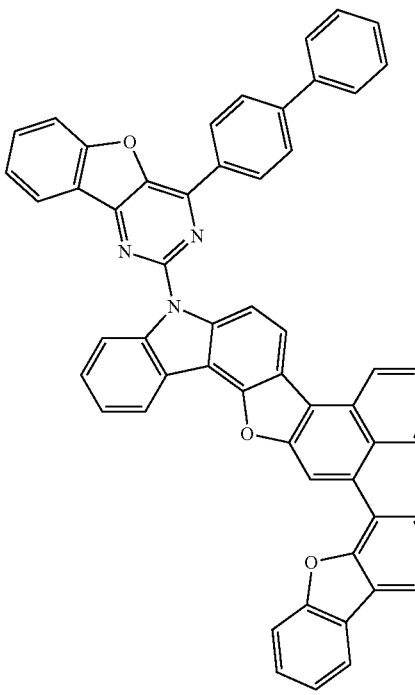

a-97
a-99
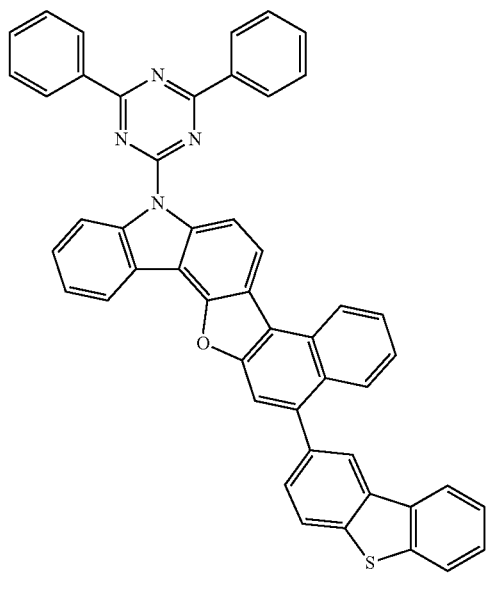
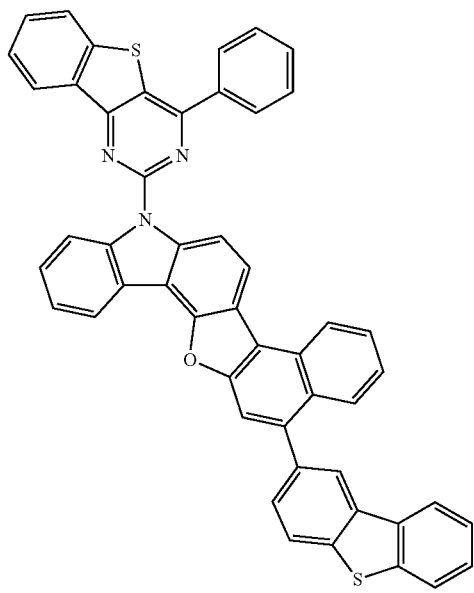
a-98
a-100

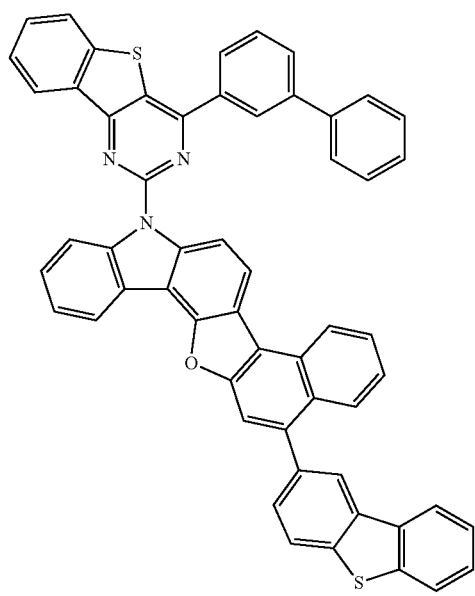
a-101
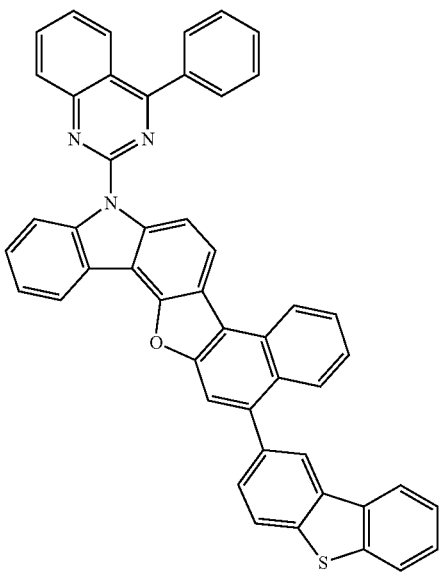
a-103
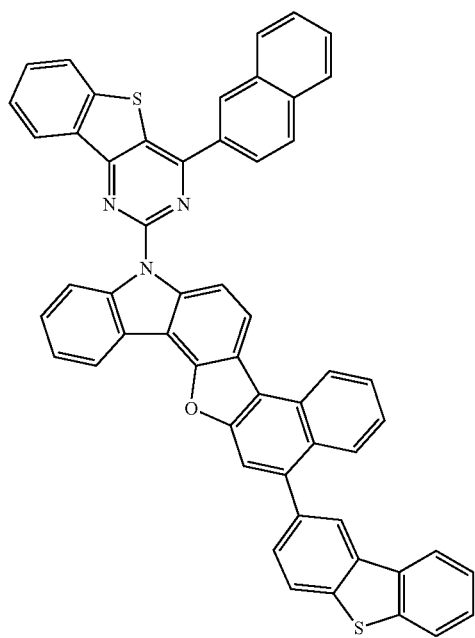
a-102
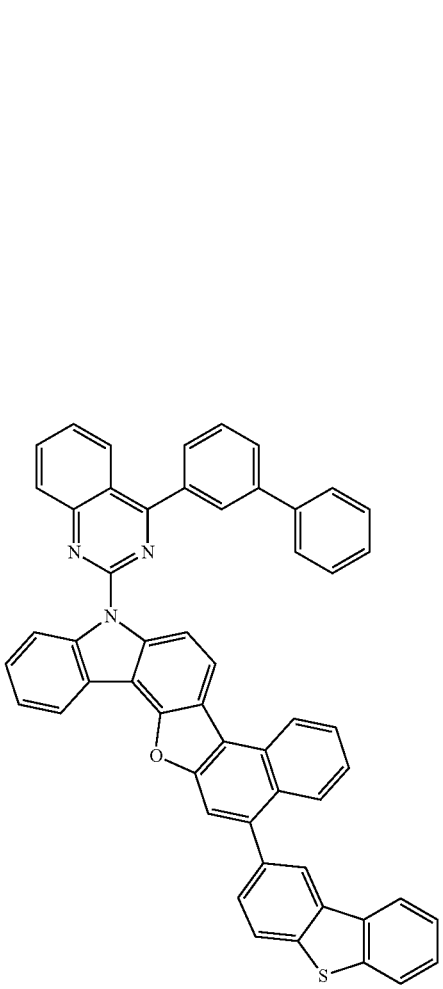
a-104 a-105
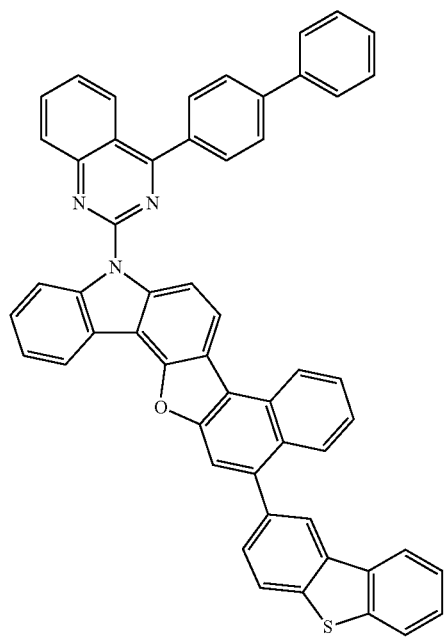
a-106
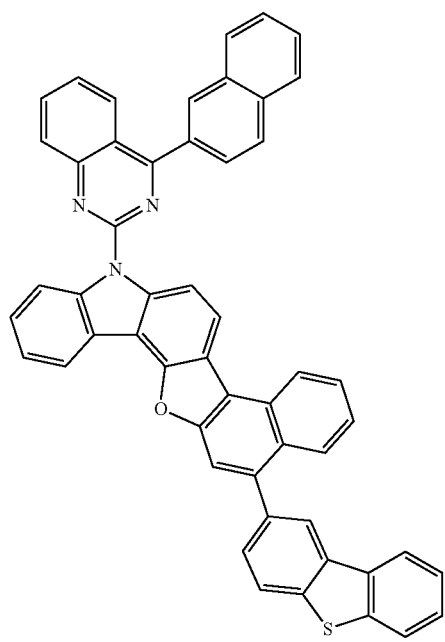
a-107
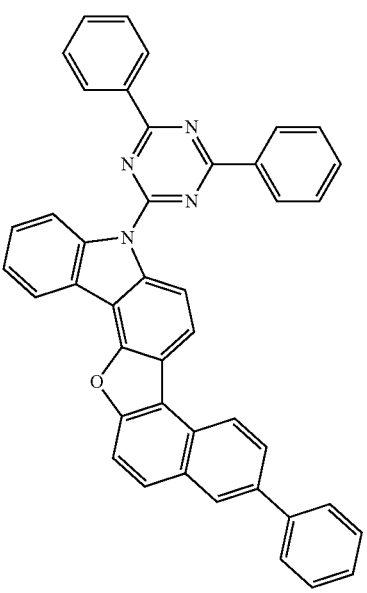
a-108
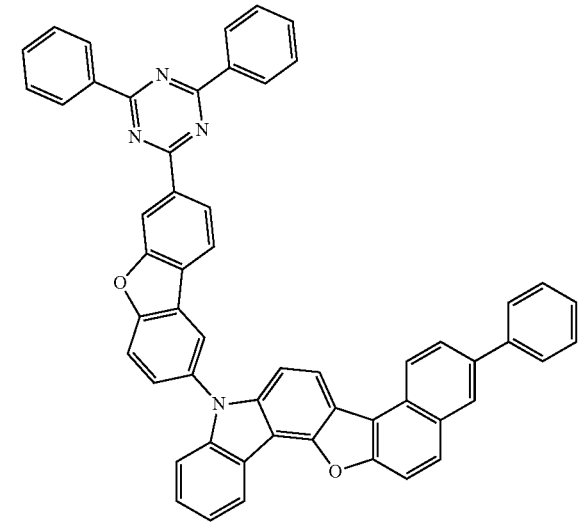

a-109
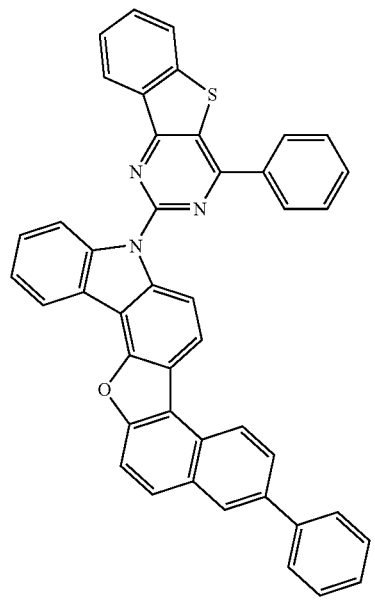
a-111
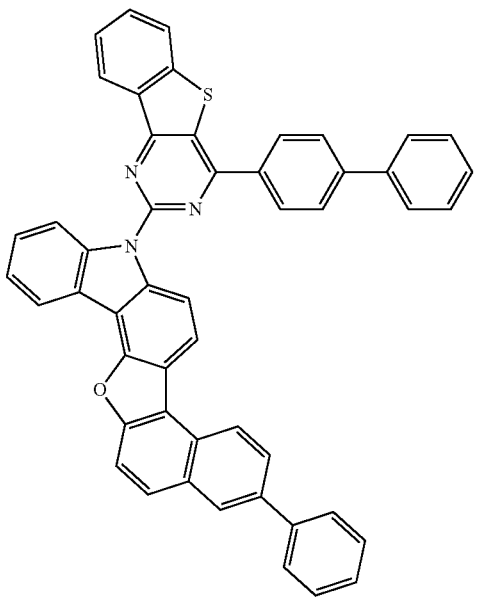
a-110
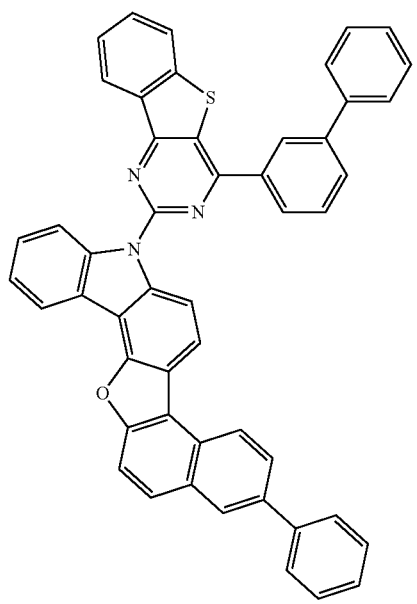
a-112
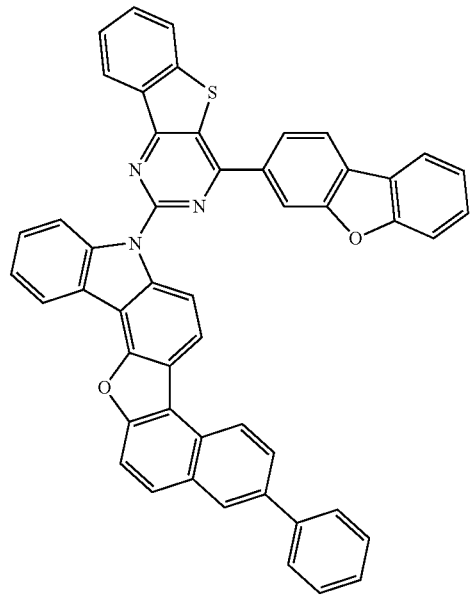

a-113
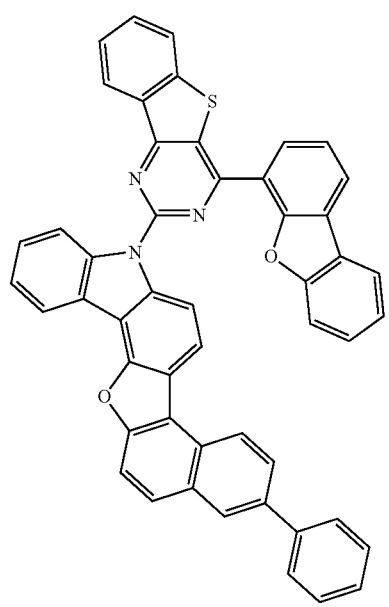
a-114
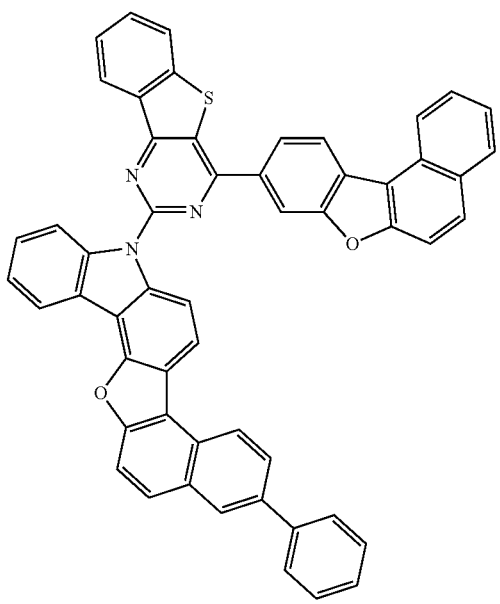
a-115
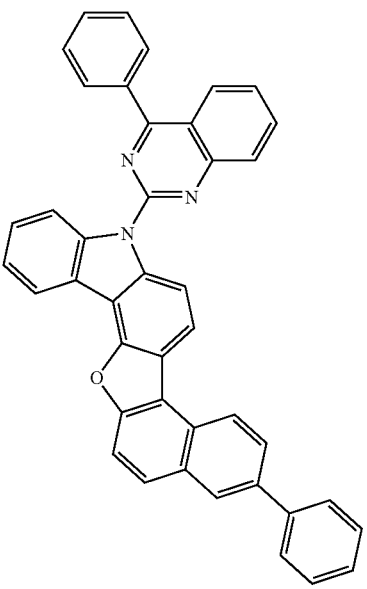
a-116
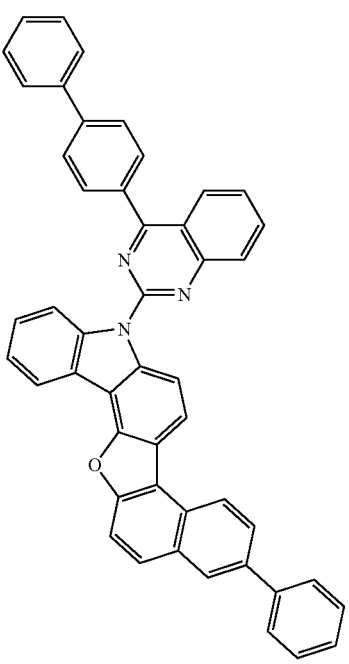

a-117
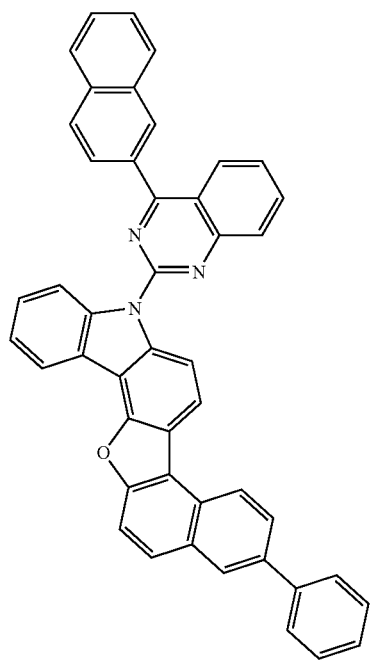
a-118
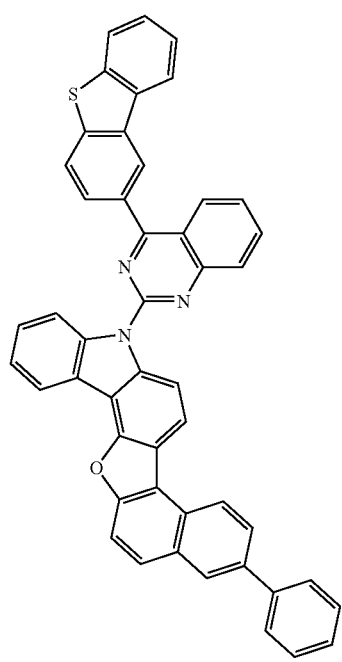
a-119
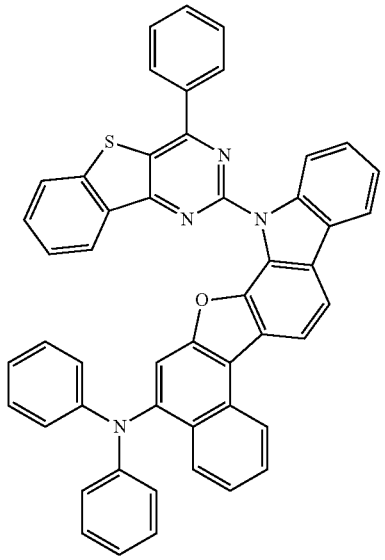
a-120
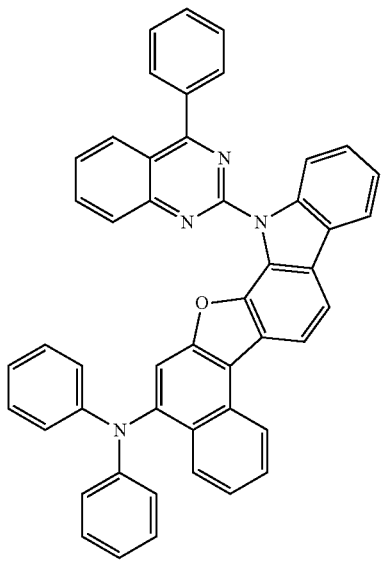

a-121
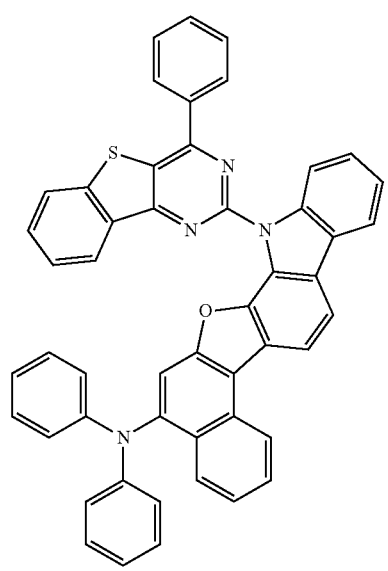
a-123
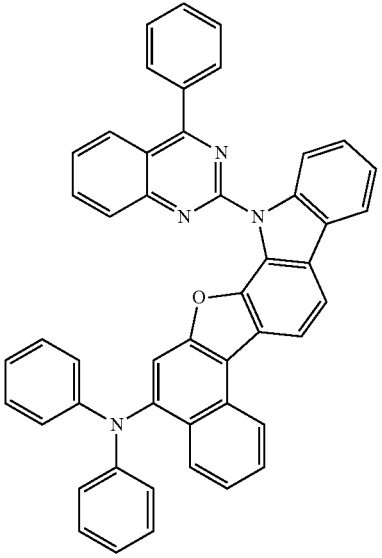
a-122
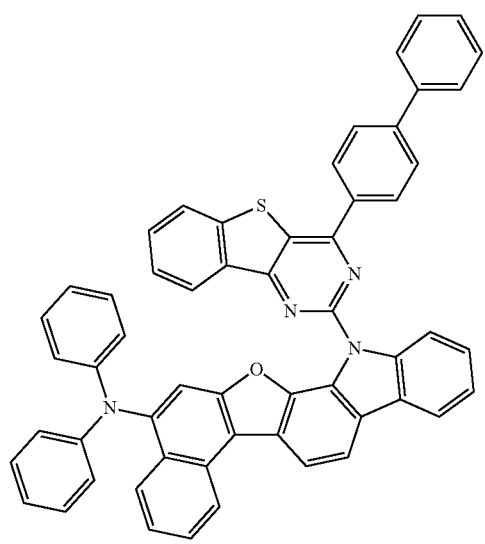
a-124
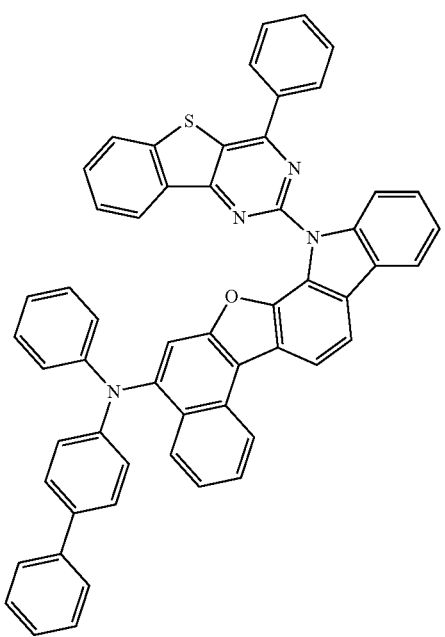

a-125
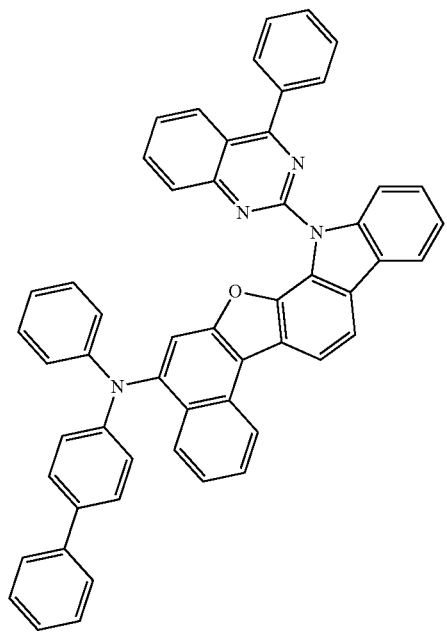
a-126
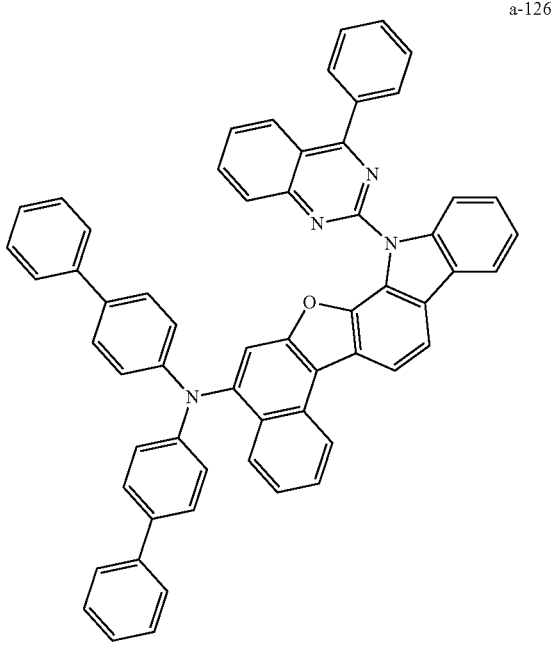
a-127
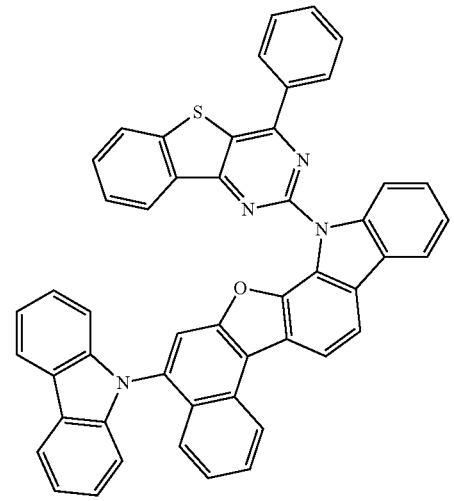
a-128
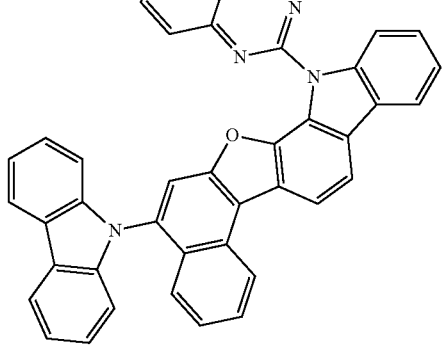
a-129
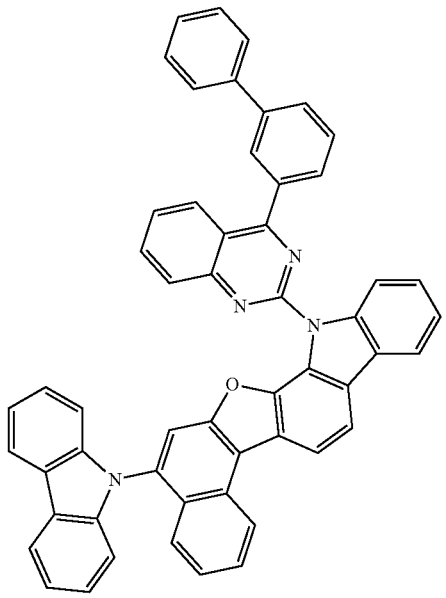

a-130
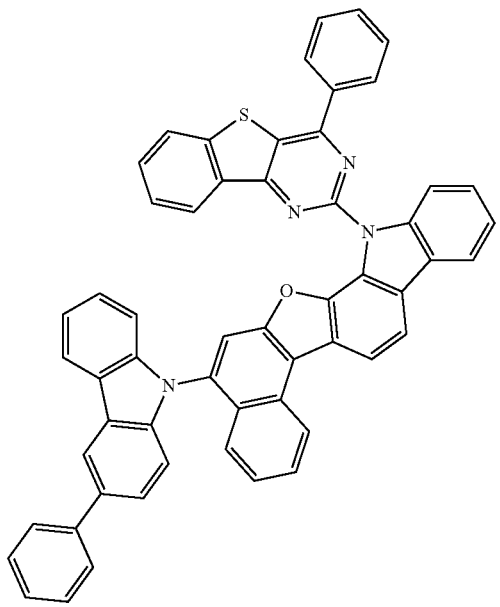
a-131
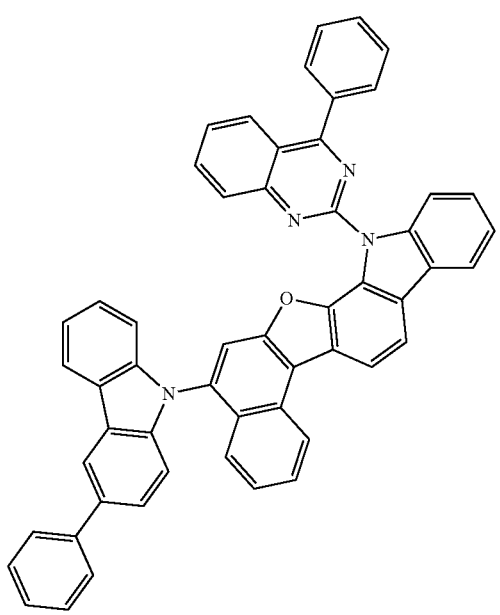
a-132
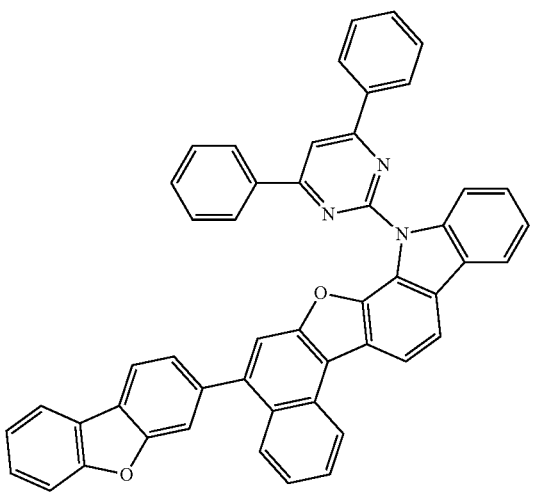
a-133
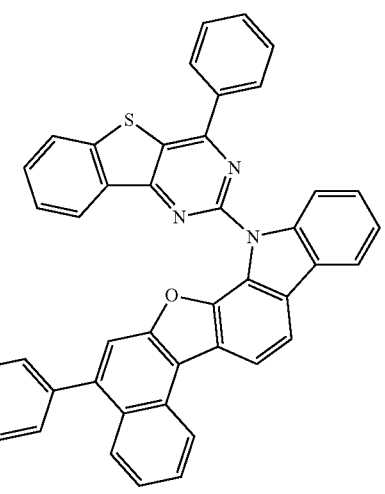
a-134
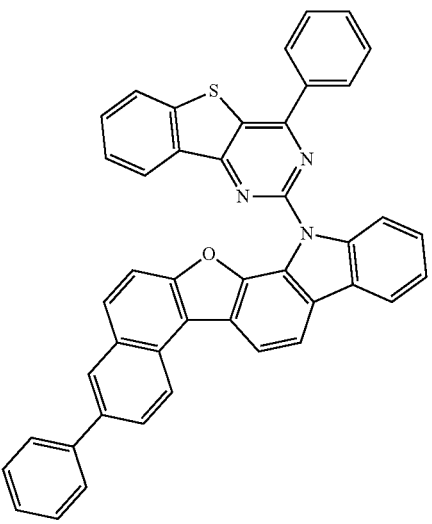

a-135
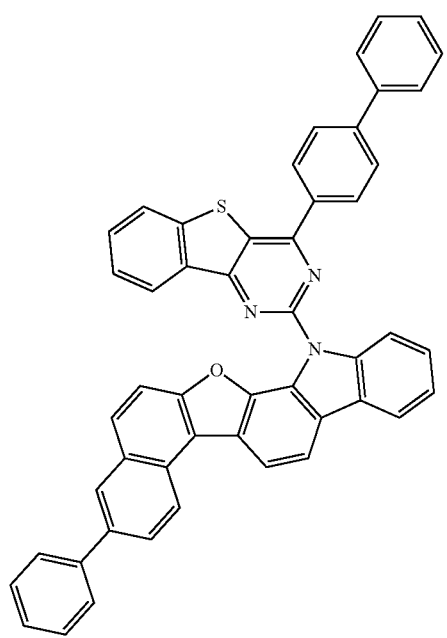
a-136
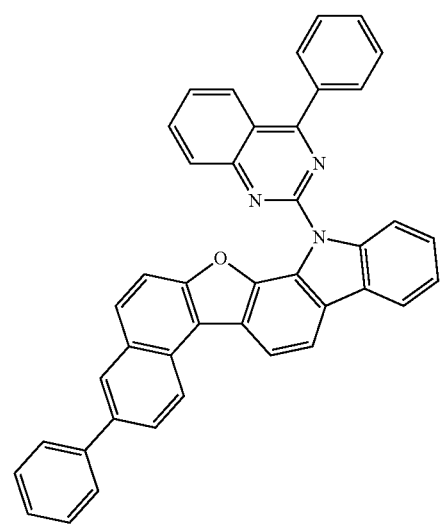
a-137
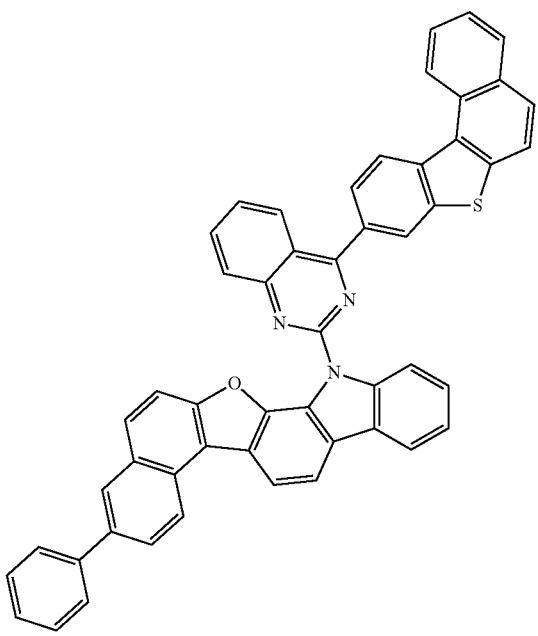
a-138
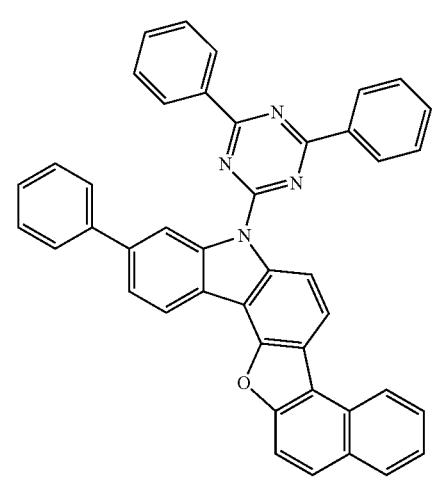
a-139
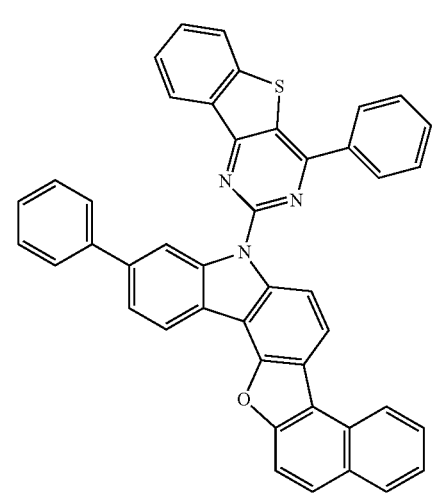

a-140
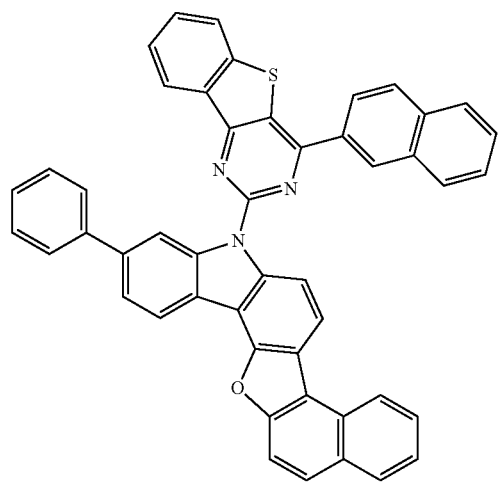
a-141
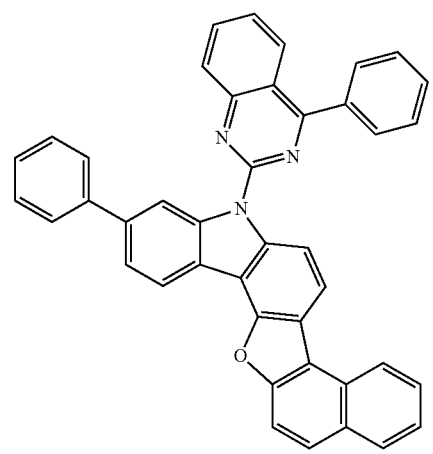
a-142
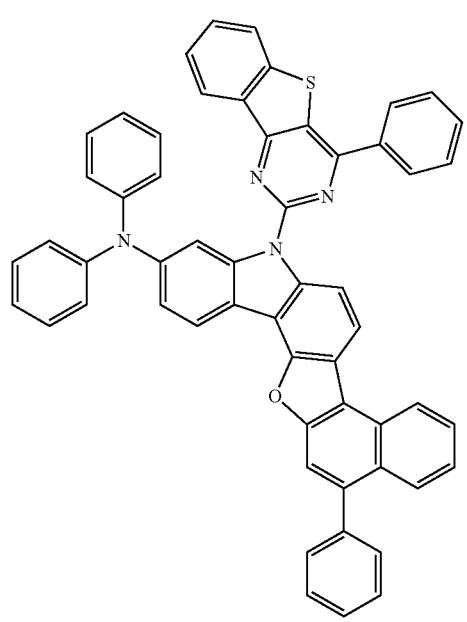
a-143
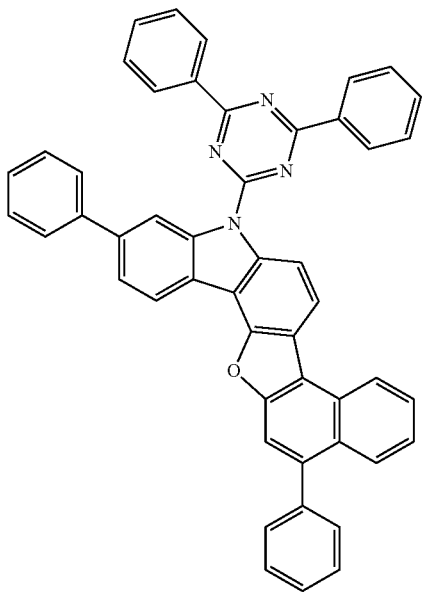
a-144
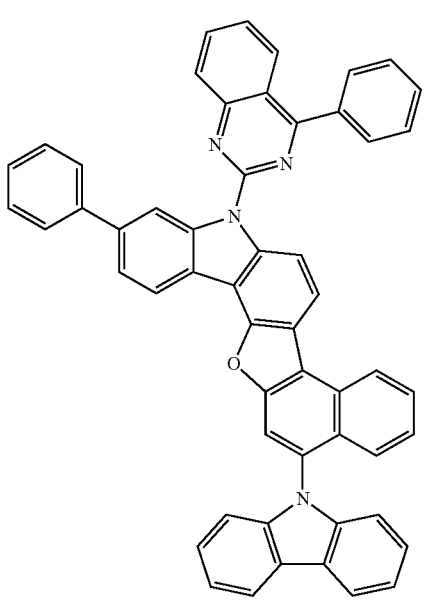

a-145
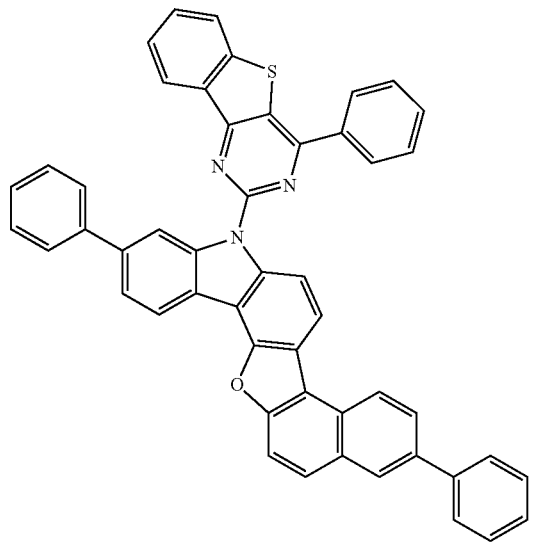
a-146
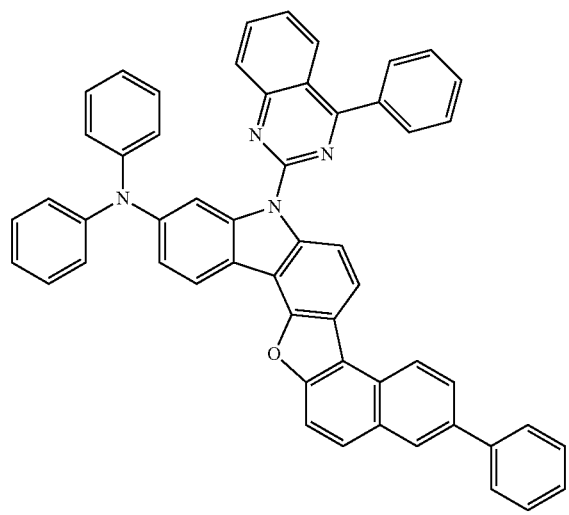
a-147
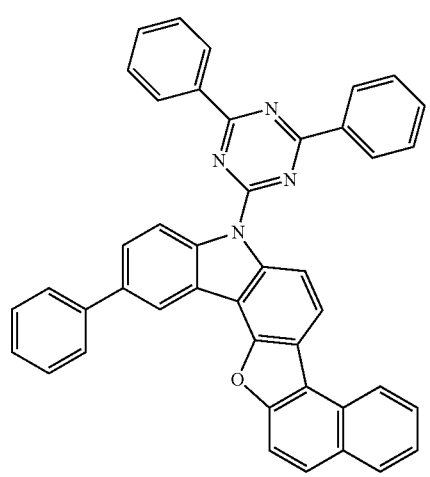
a-148
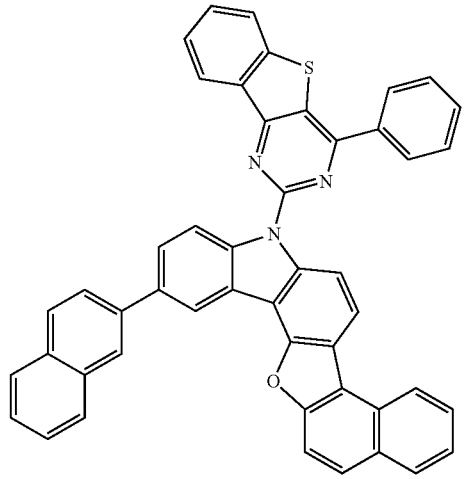
a-149
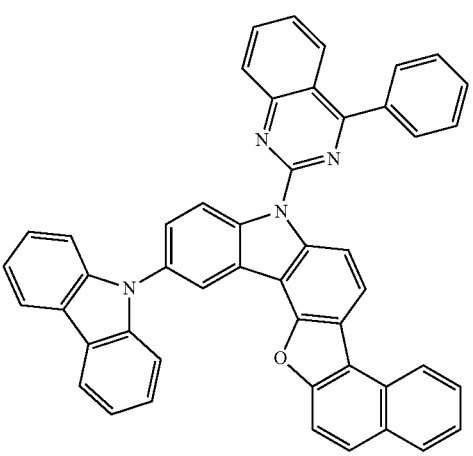
a-150
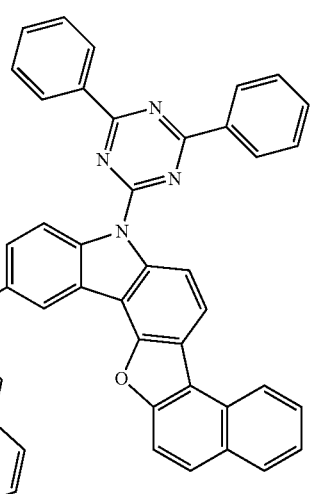

a-151
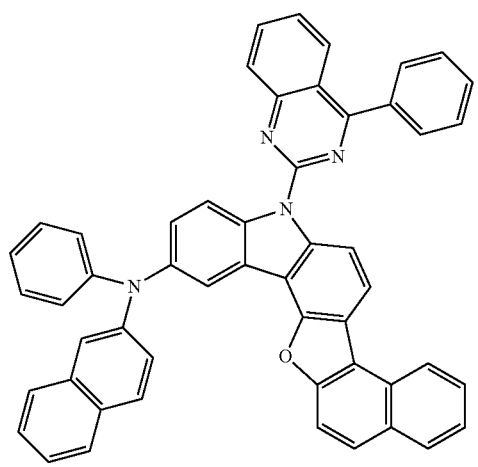
a-153
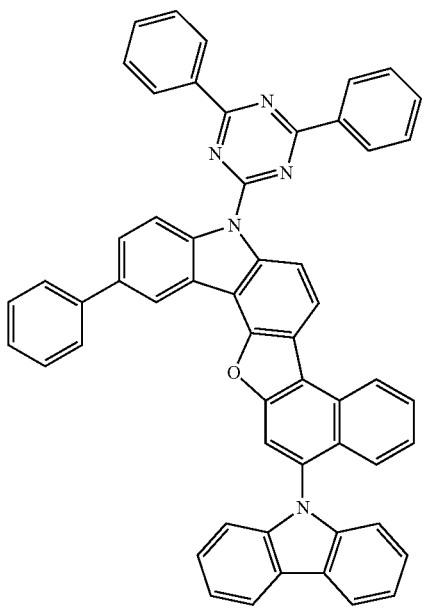
a-152
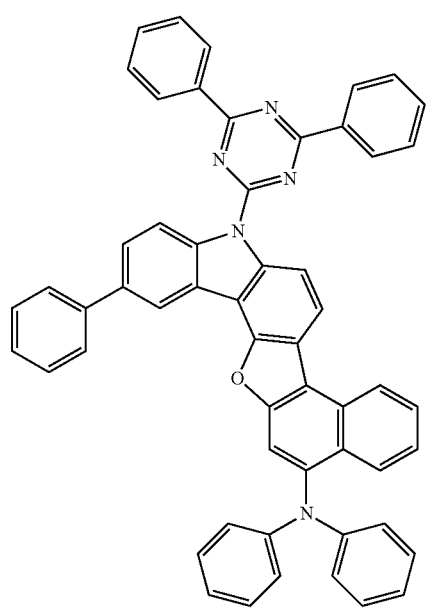
a-154
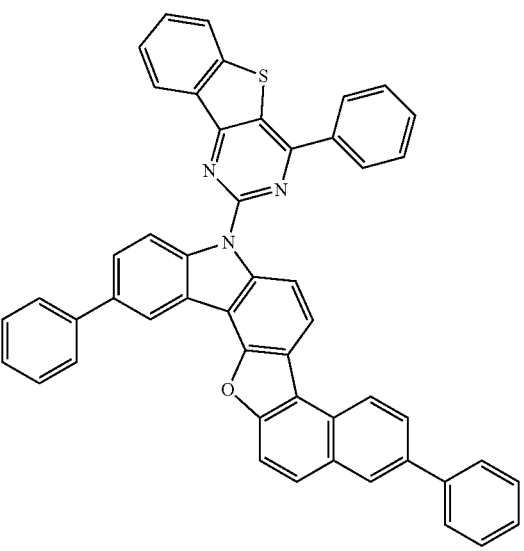

a-155
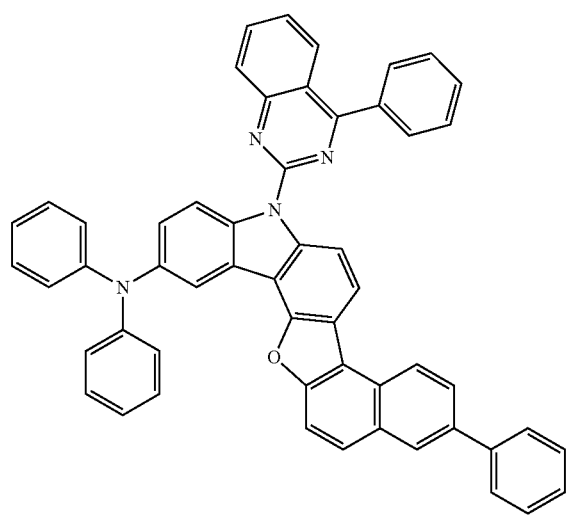
a-158
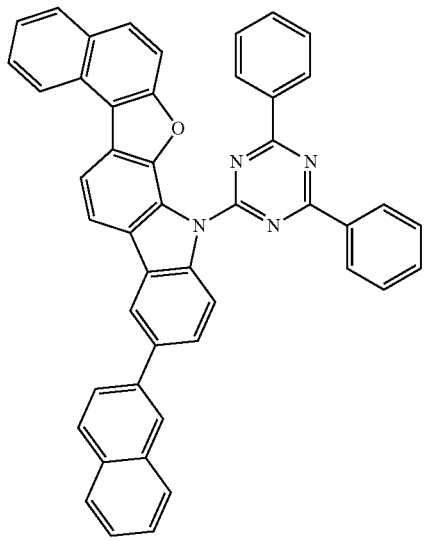
a-156
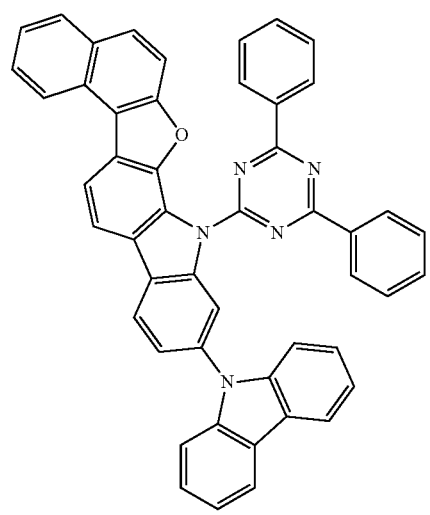
a-159
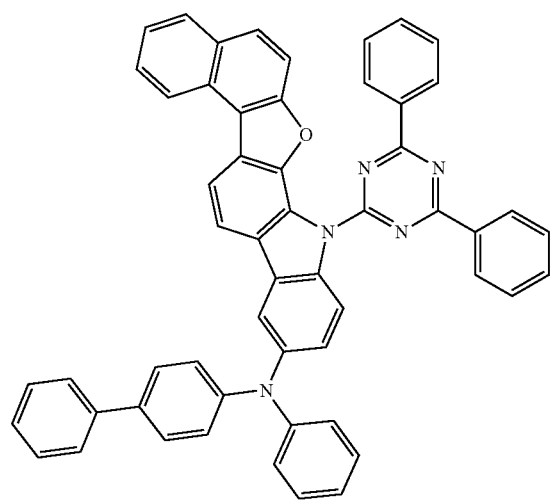
a-157
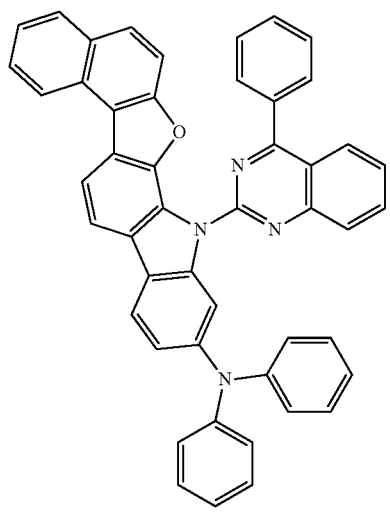
a-160
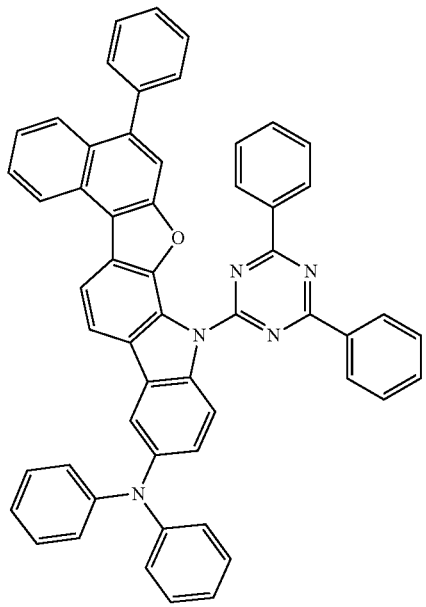

-continued
a-161
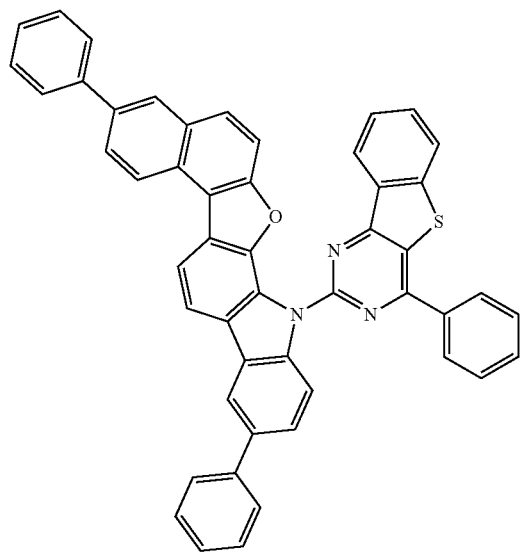
b-1
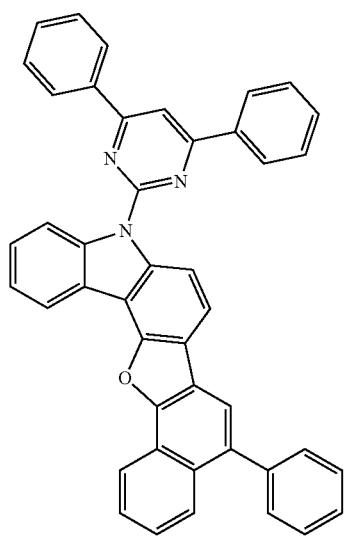
b-2
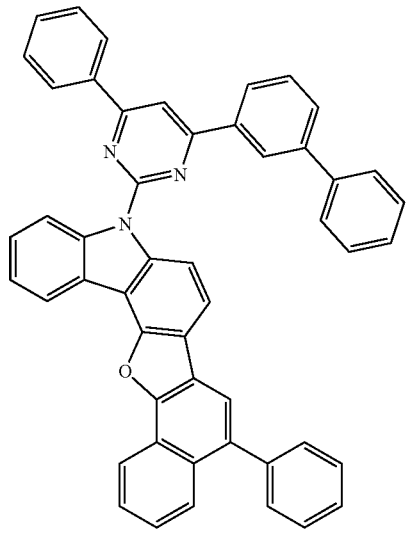
-continued
b-3
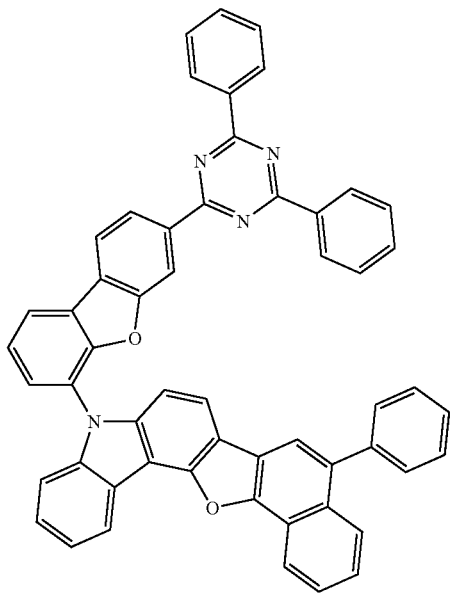
b-4
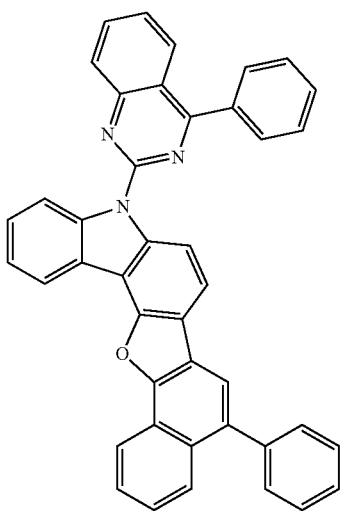
b-5
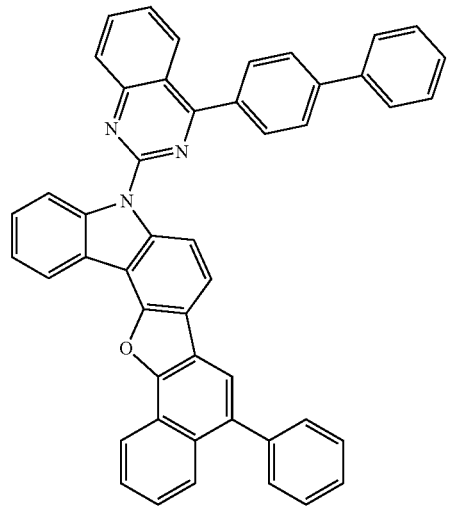

-continued
b-6
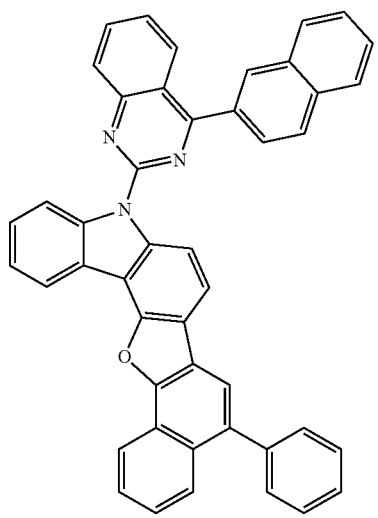
b-7
b-8
-continued
b-9
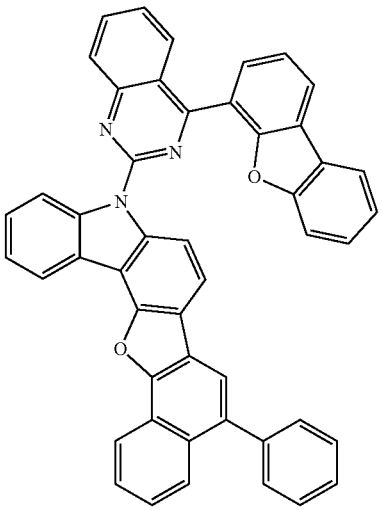
b-10
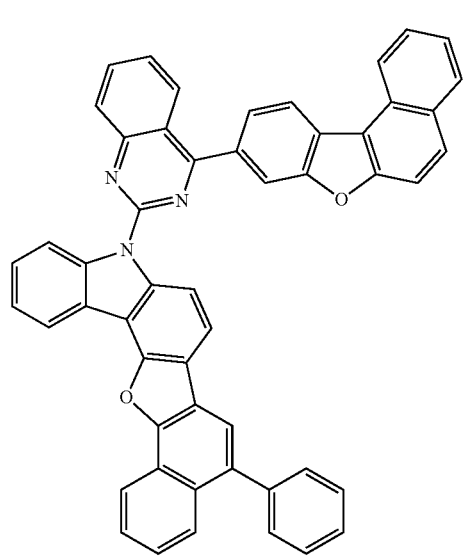
b-11
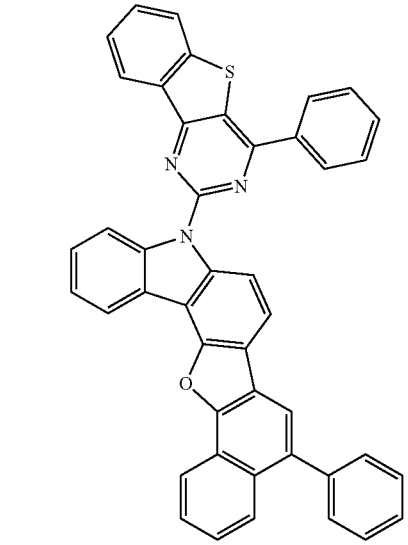

-continued
b-12
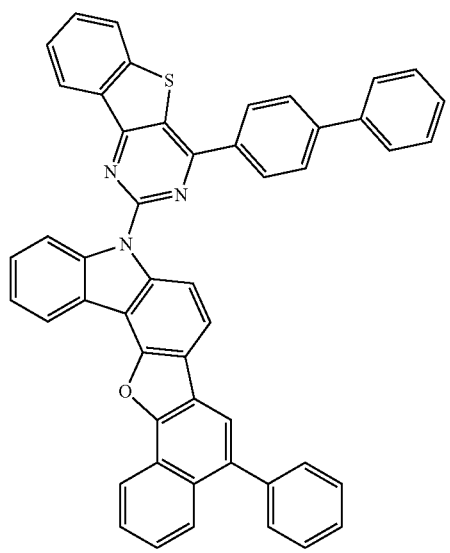
b-13
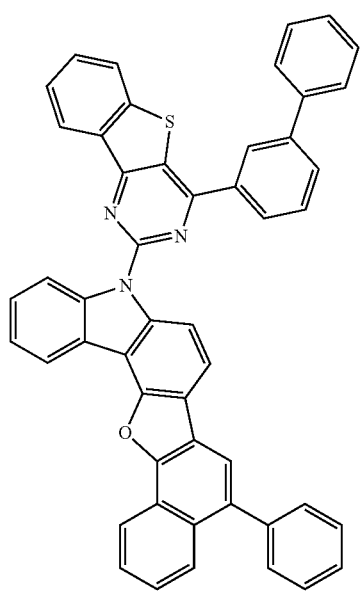
-continued
b-14
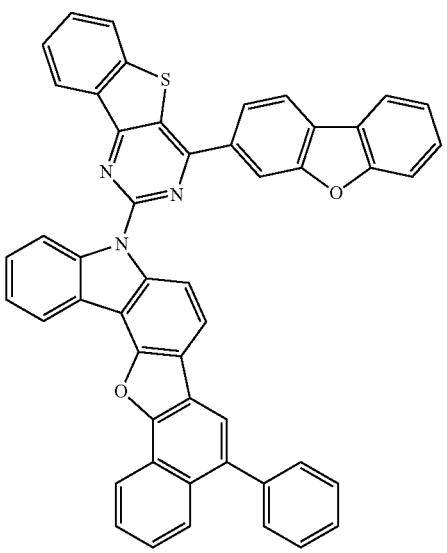
b-15
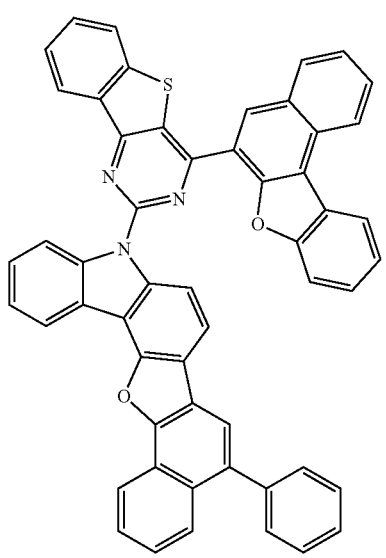
b-16

-continued
b-17
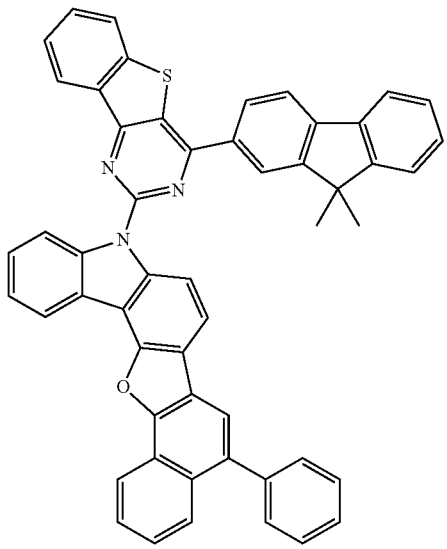
b-18
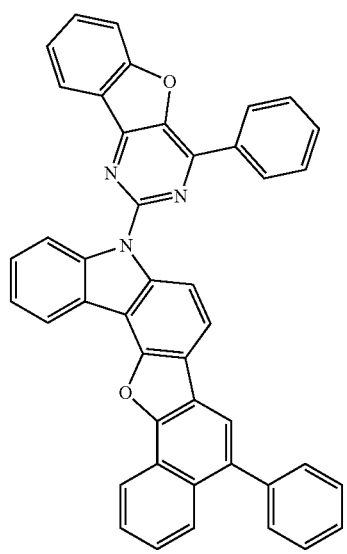
b-19
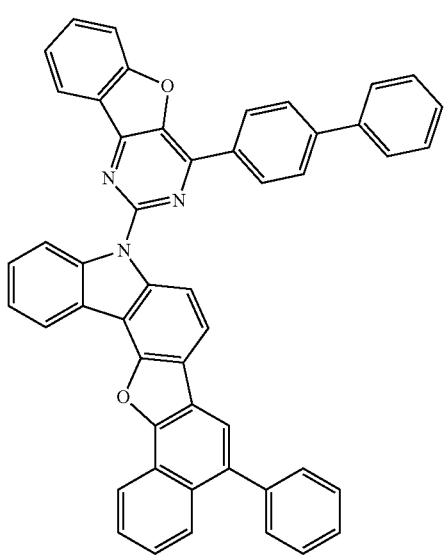
-continued
b-20
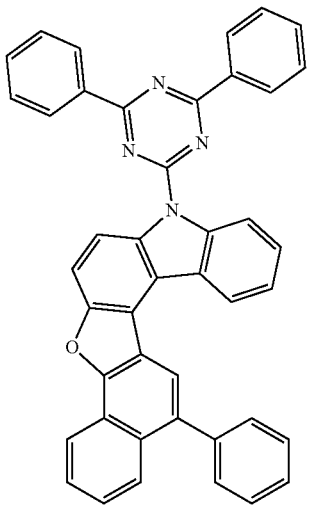
b-21
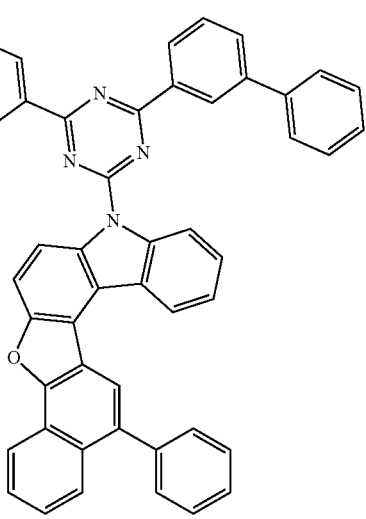
b-22
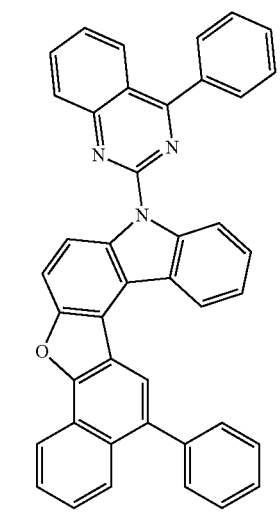

b-23
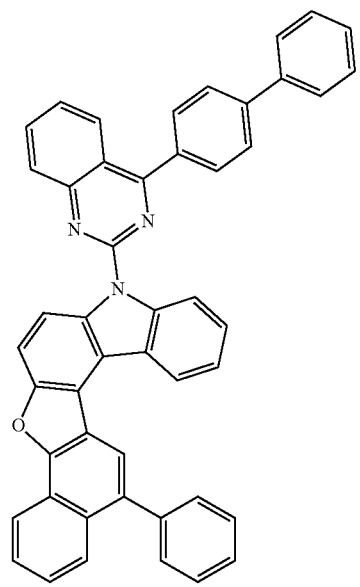
b-24
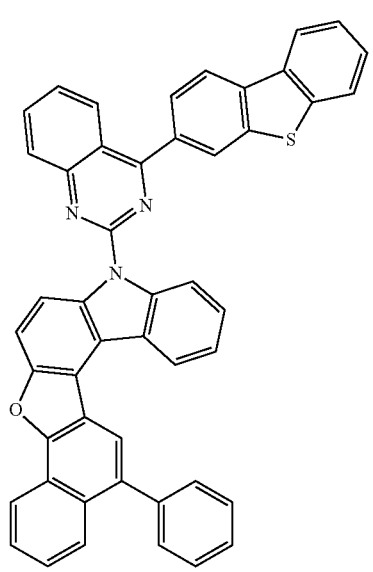
b-25
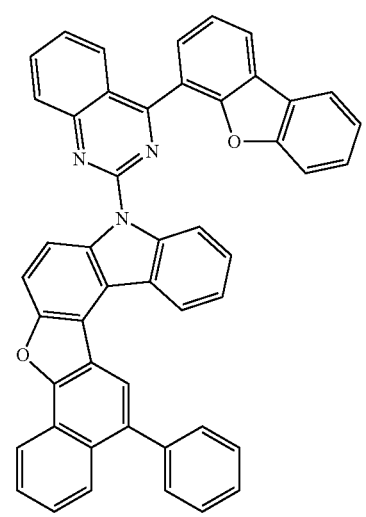
b-26
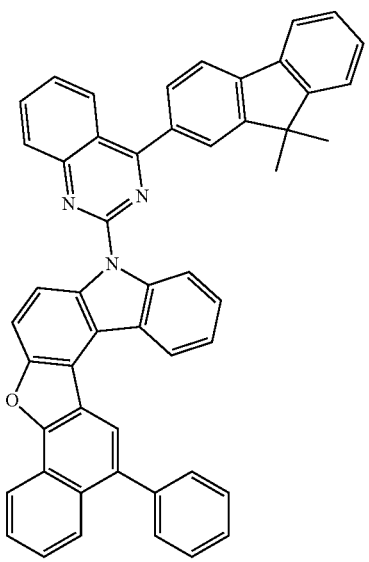
b-27
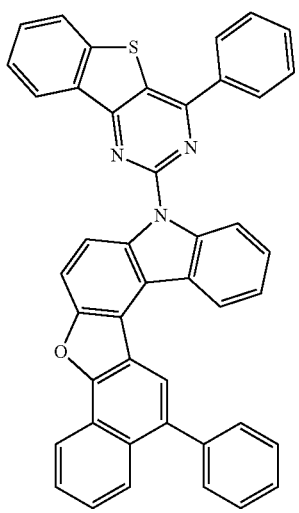
b-28
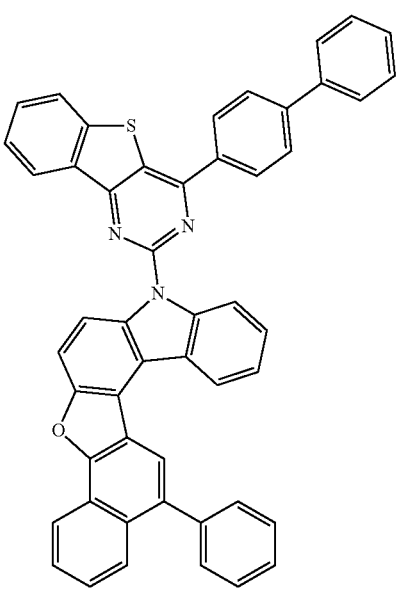

b-29
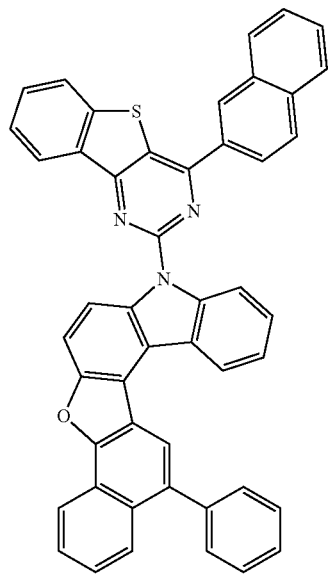
b-31
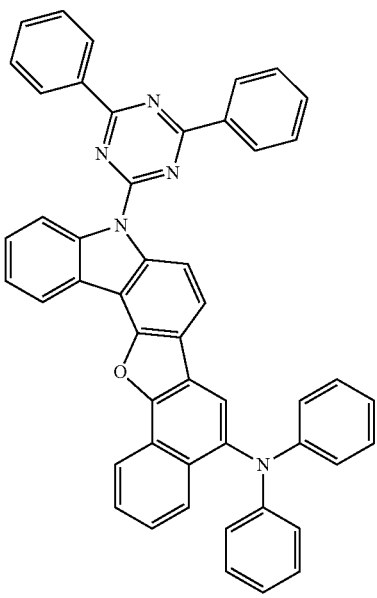
b-30
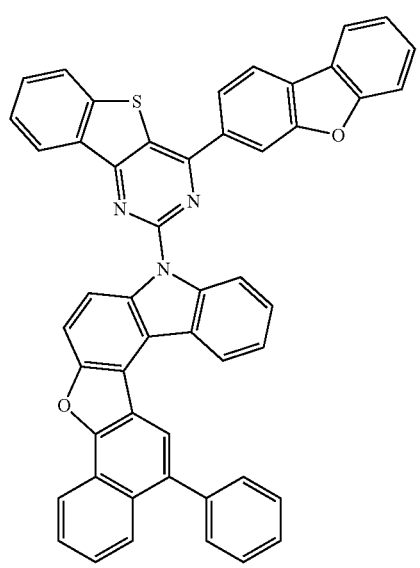
b-32
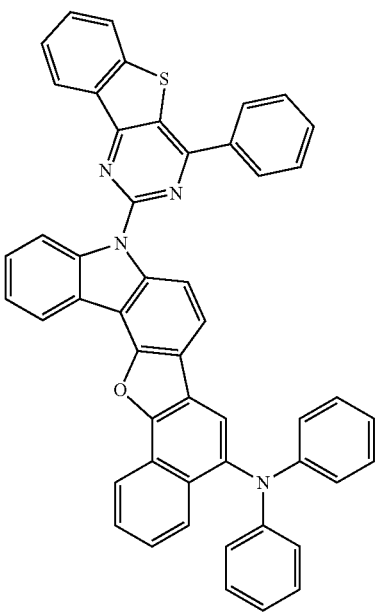

b-33
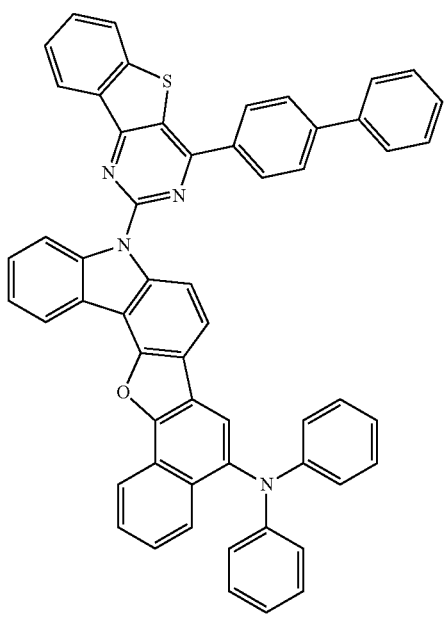
b-34
b-35
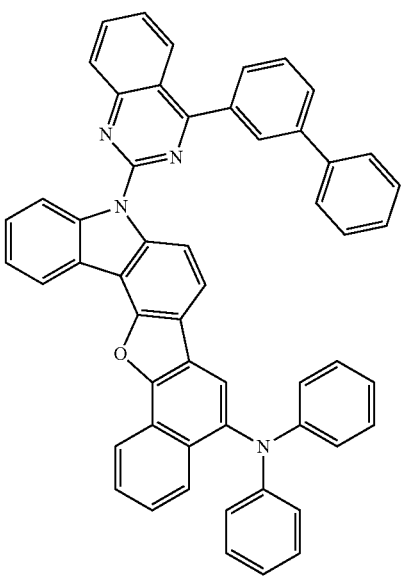
b-36 b-37
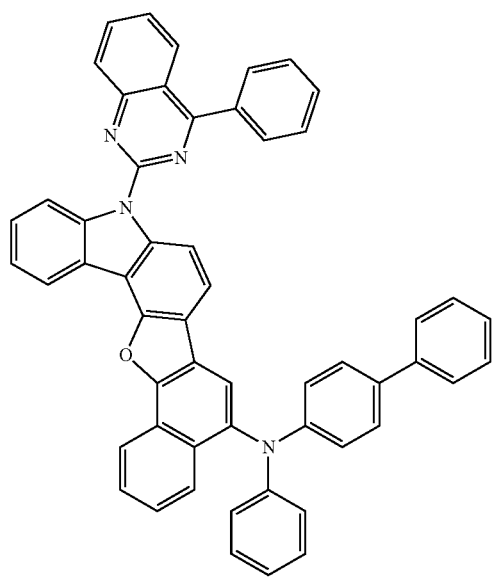
b-39
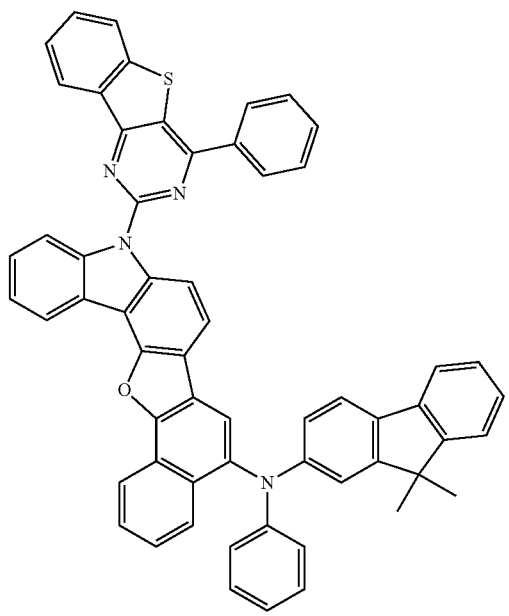
b-38
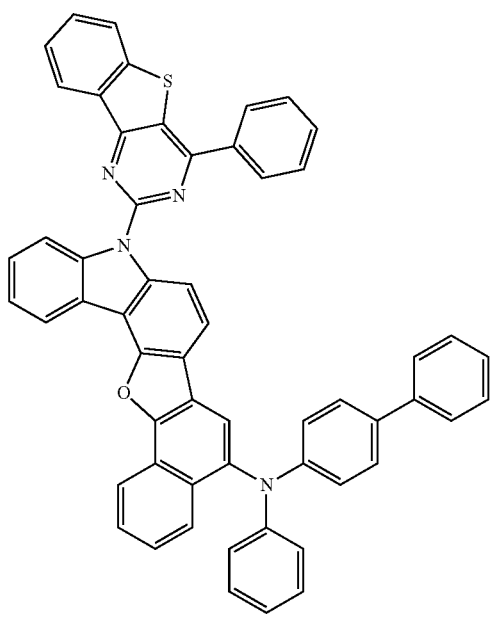
b-40
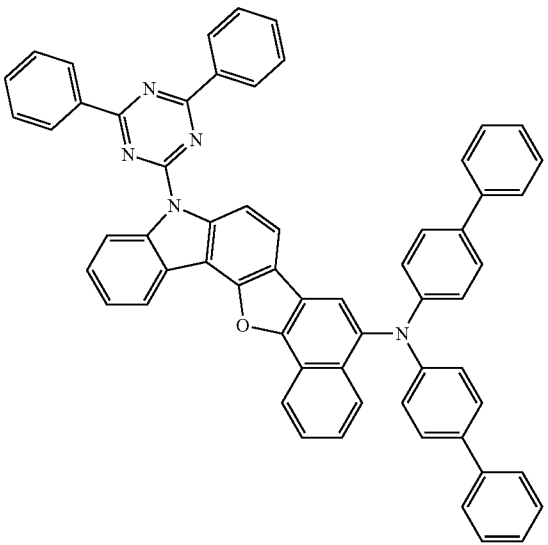

b-41
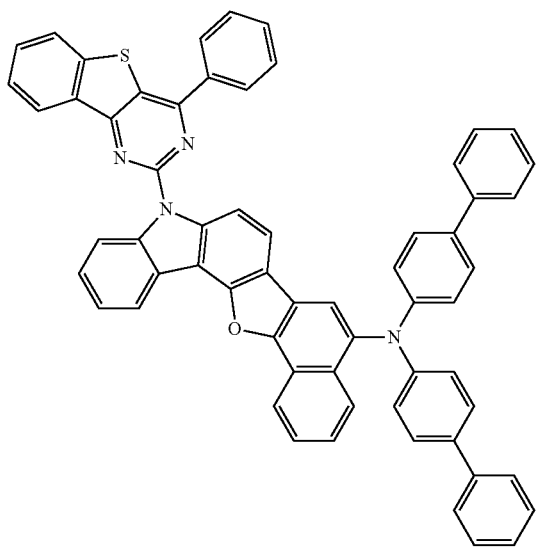
b-43
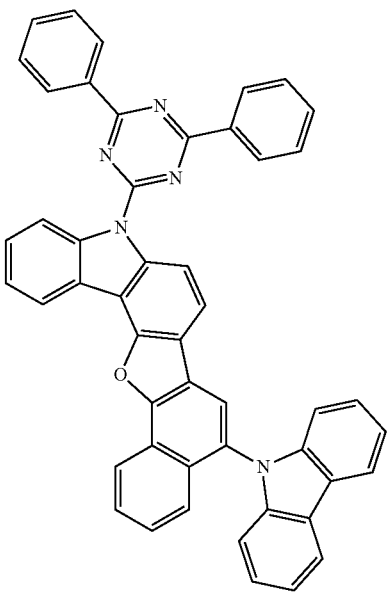
b-42
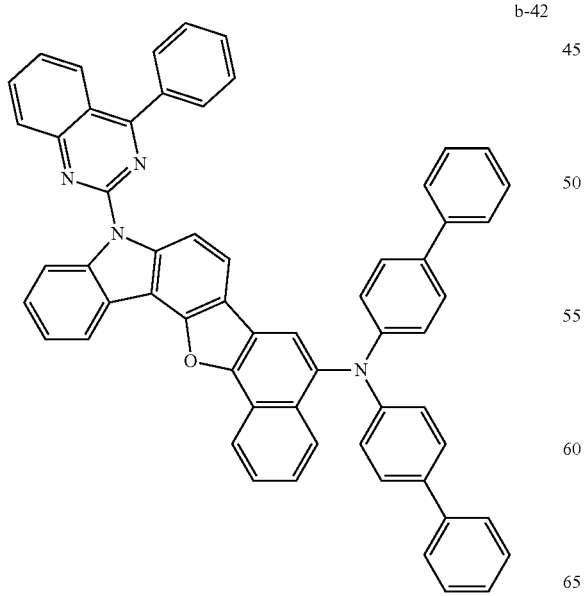
b-44
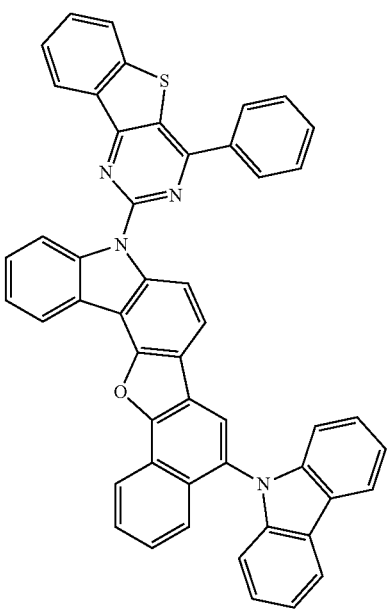

b-45
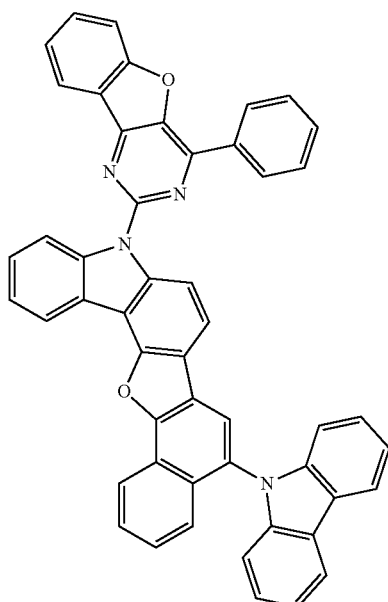
b-46
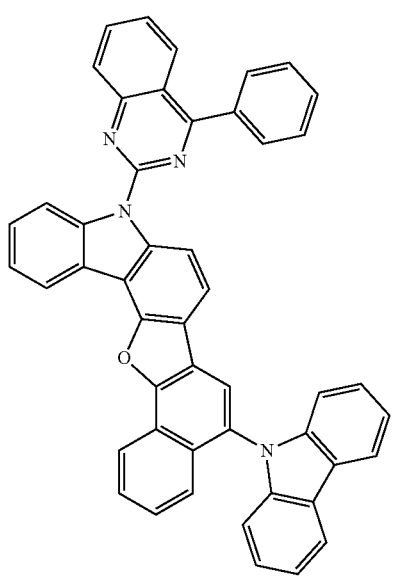
b-47
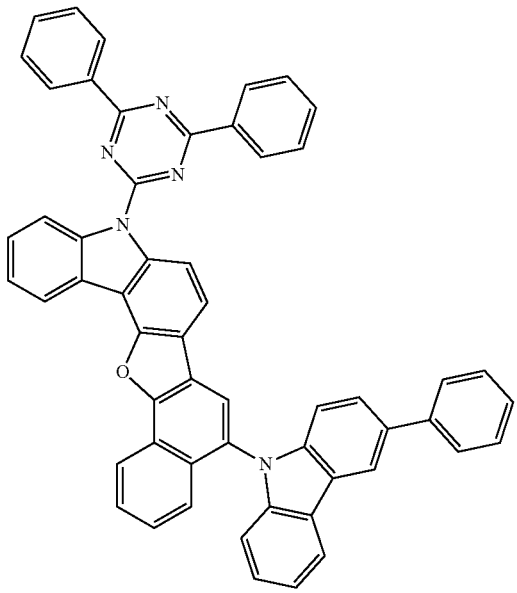
b-48
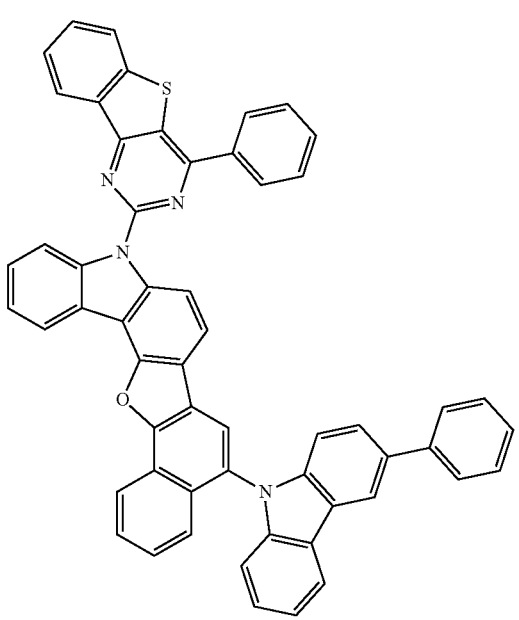

b-49
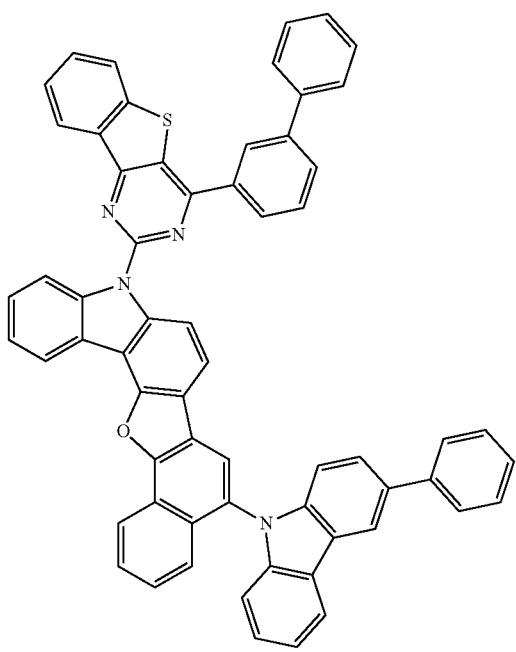
b-51
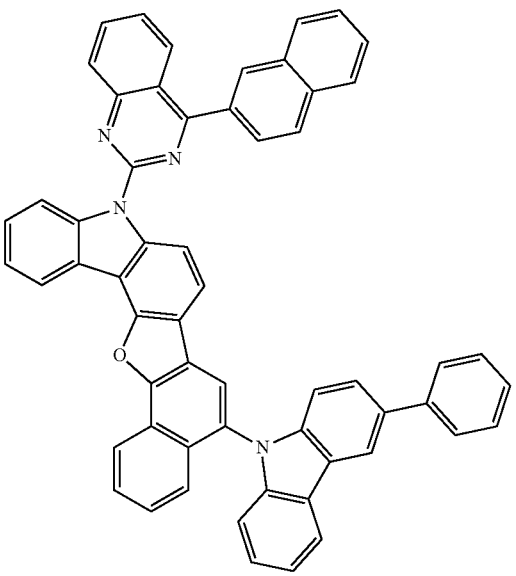
b-50
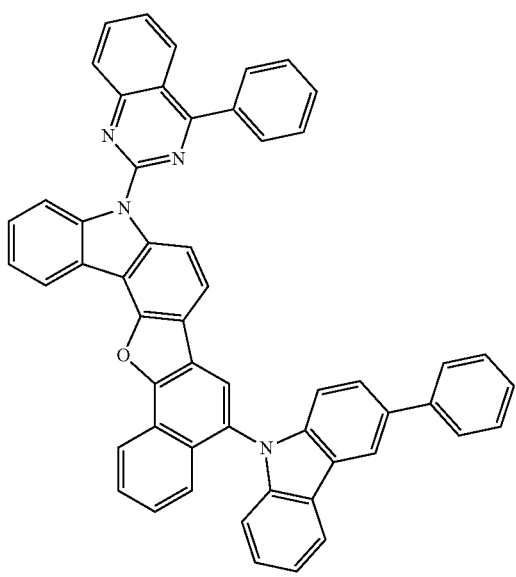
b-52
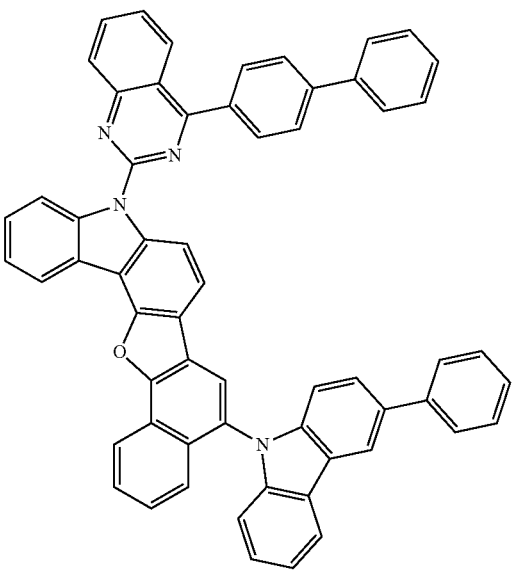

b-53
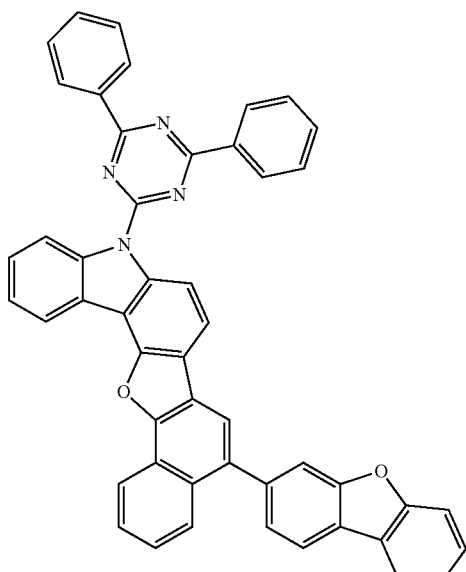
b-55
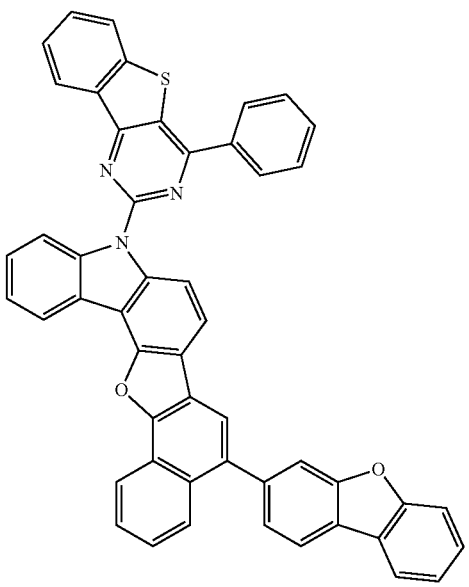
b-54
b-56
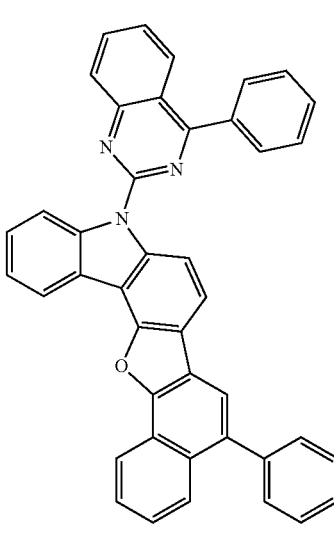

-continued
b-57
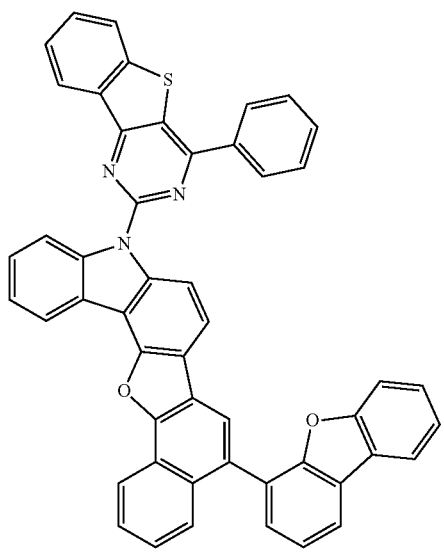
b-58
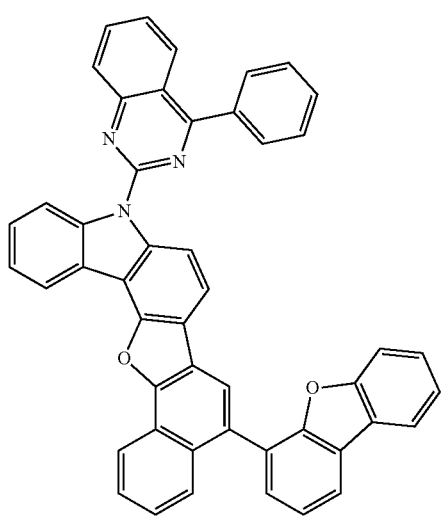
b-59
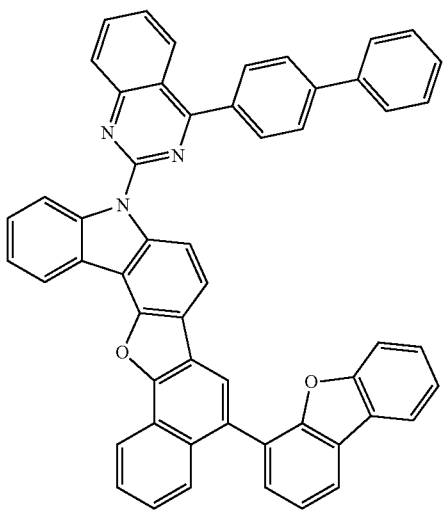
-continued
b-60
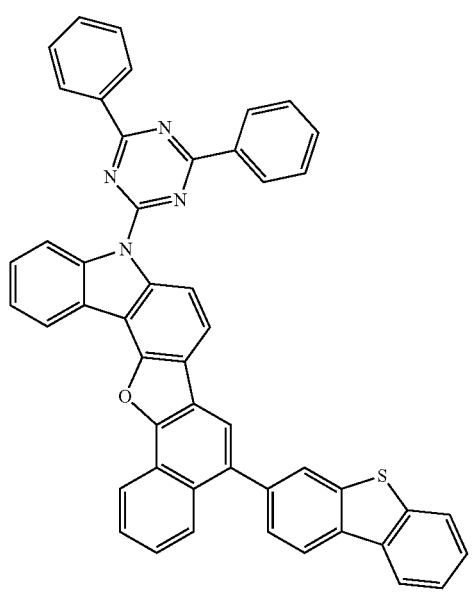
b-61
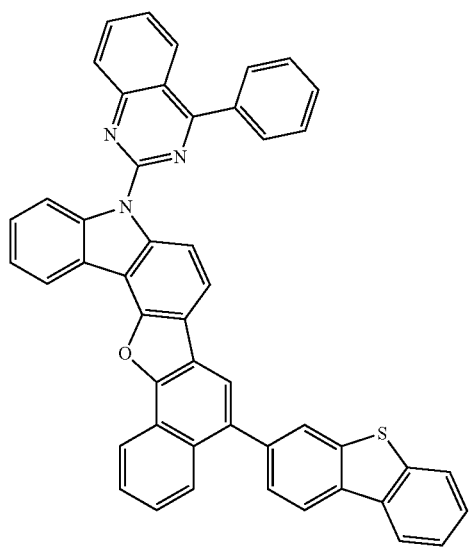

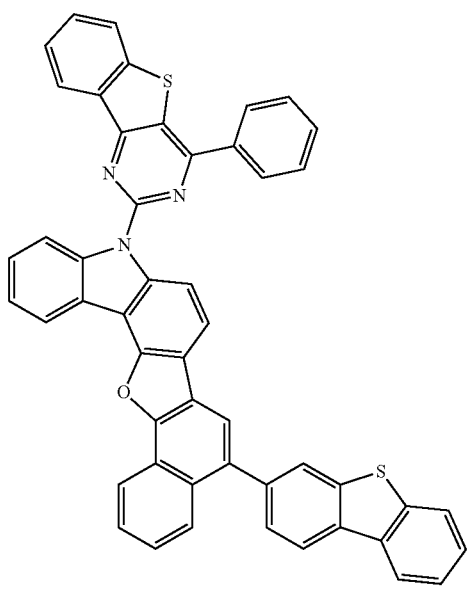
b-62
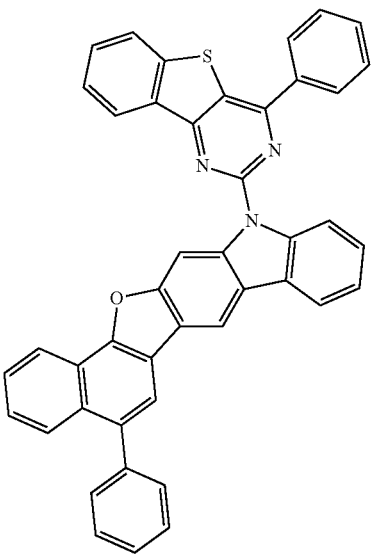
b-64
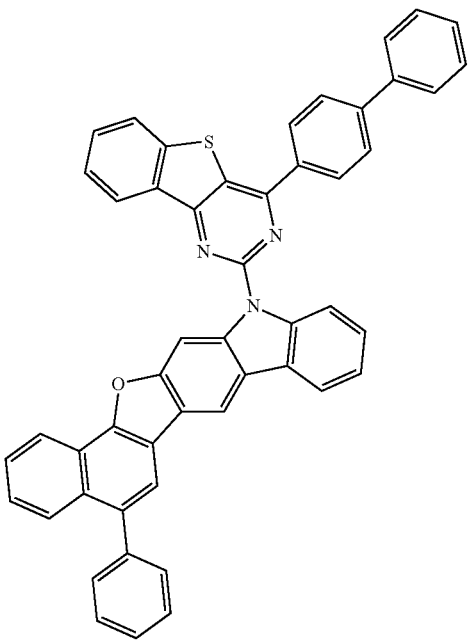
b-65
b-63 b-66
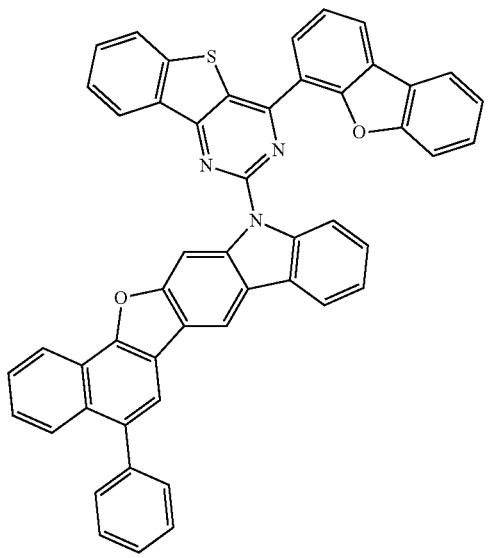
b-68
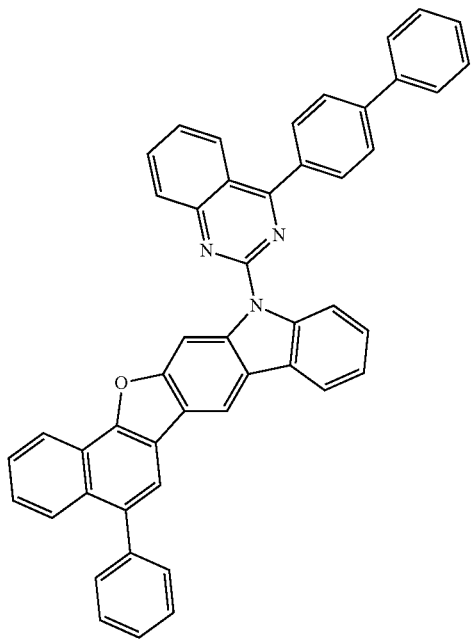
b-67
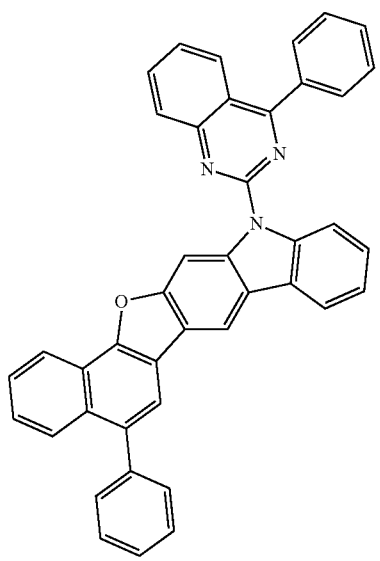
b-69
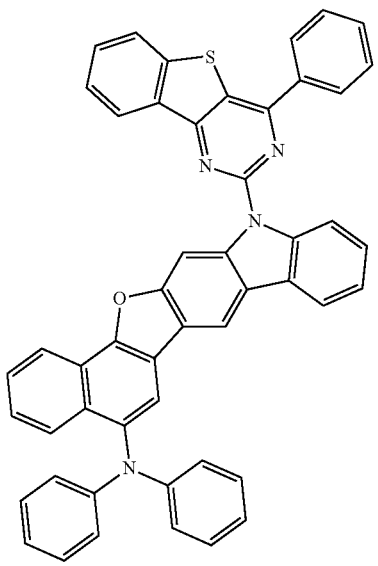

b-70
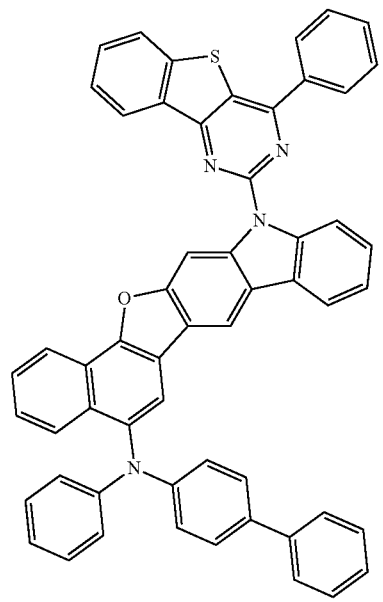
b-71
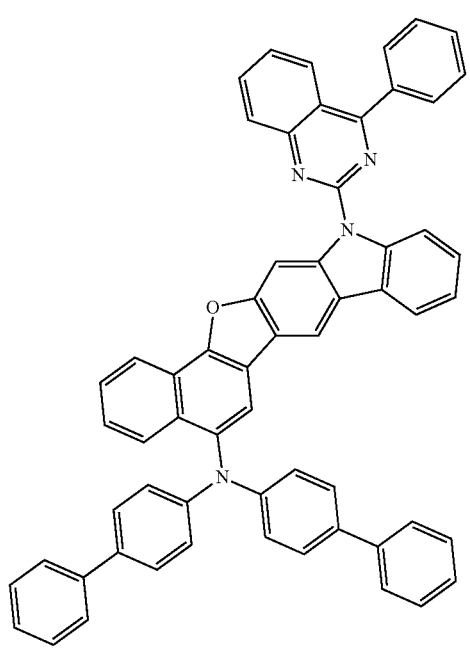
b-72
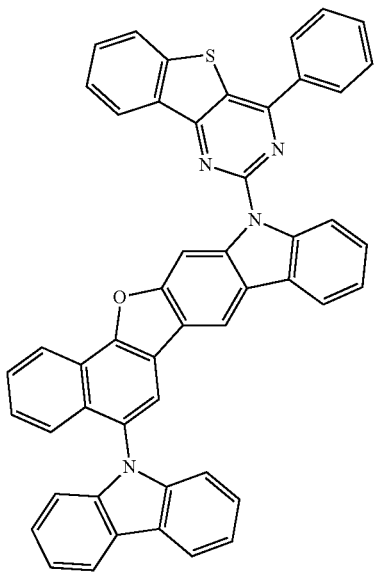
b-73
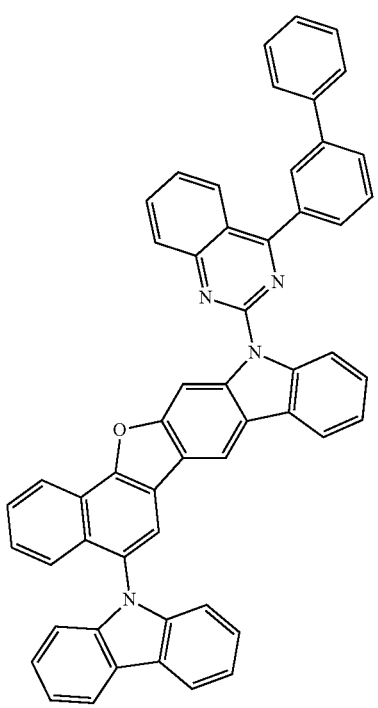

b-74
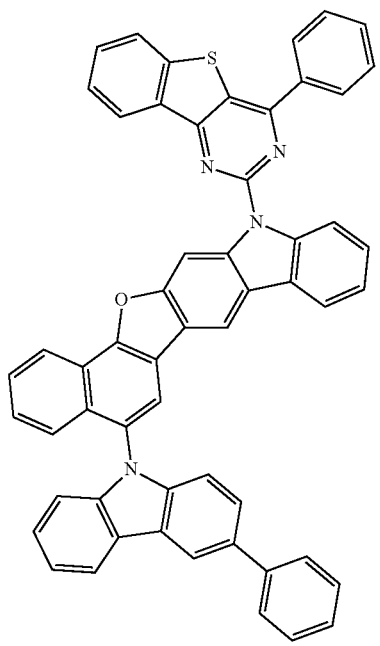
b-75
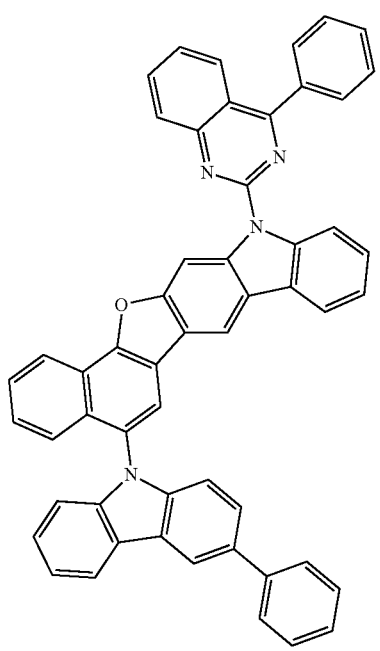
b-76
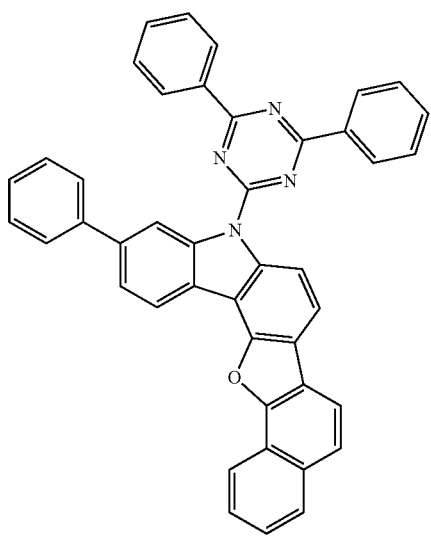
b-77
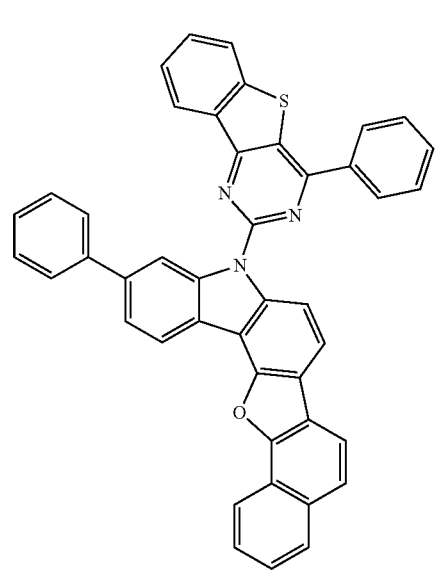
b-78
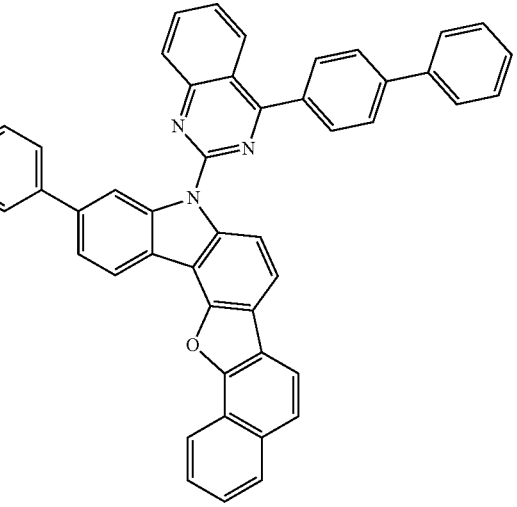

-continued
b-79
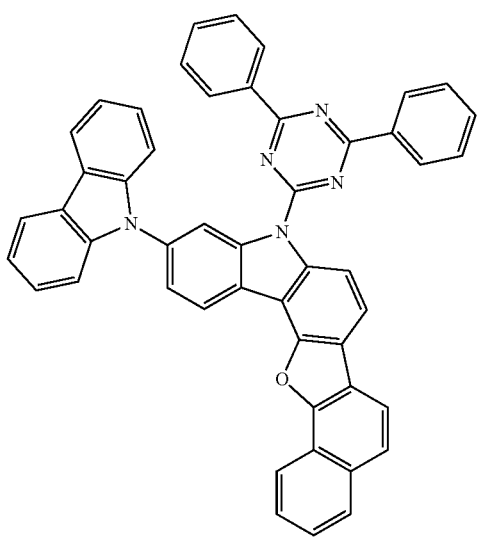
b-80
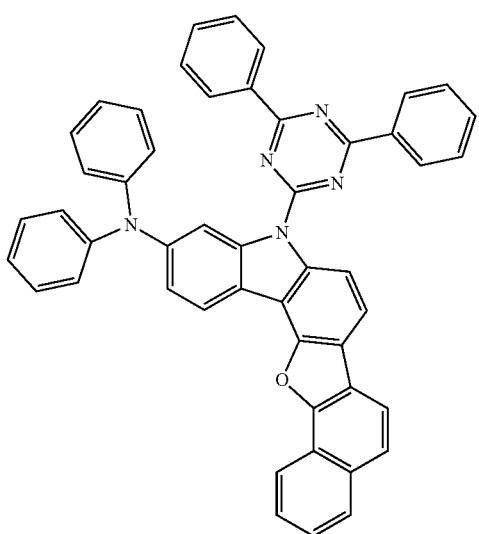
b-81
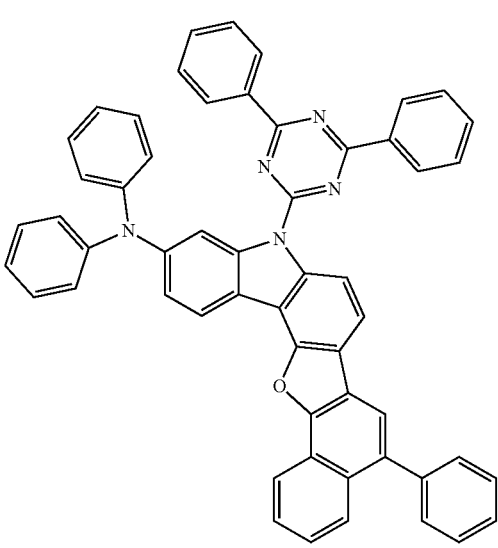
-continued
b-82
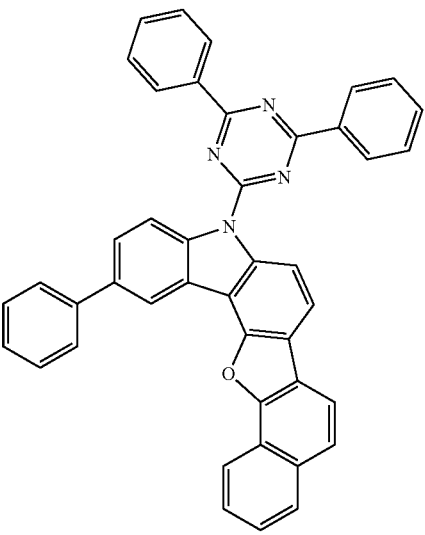
b-83
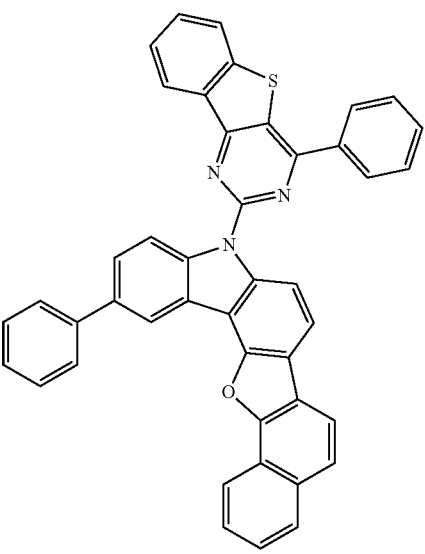
b-84
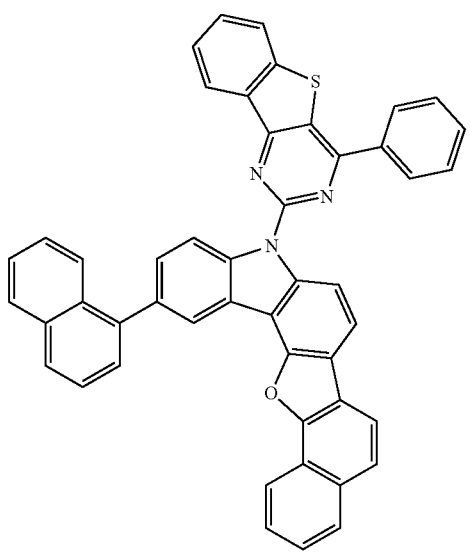

b-85
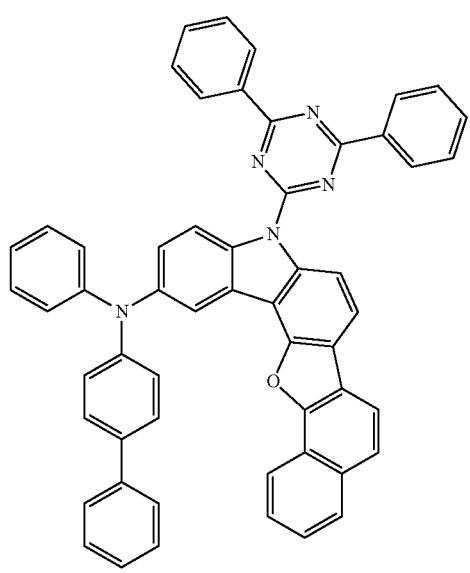
b-86
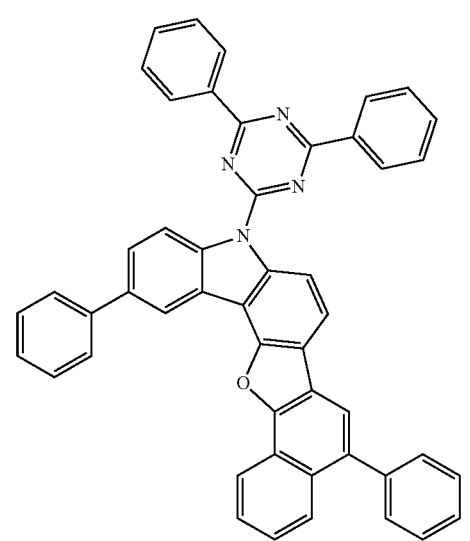
b-87
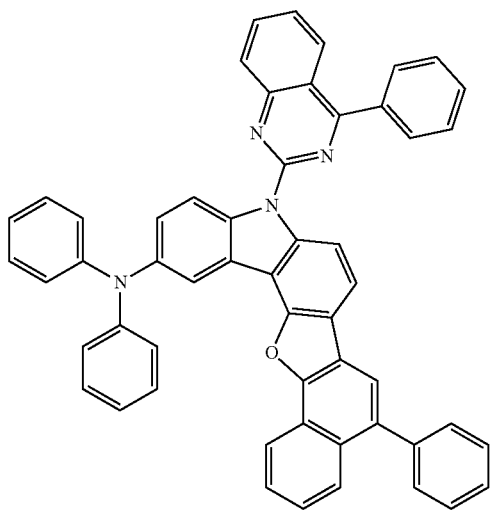
b-88
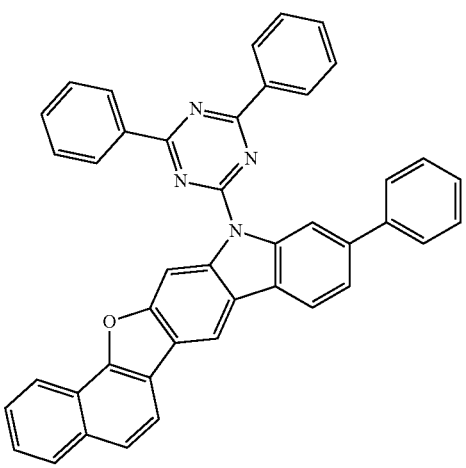
b-89
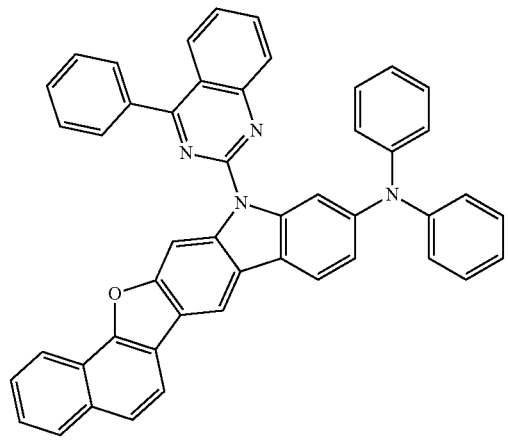
b-90
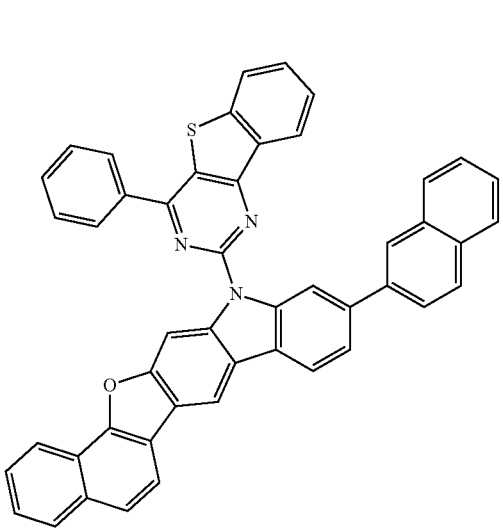

b-91
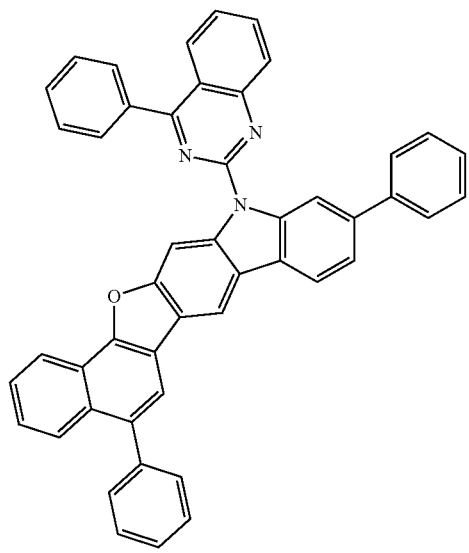
b-92
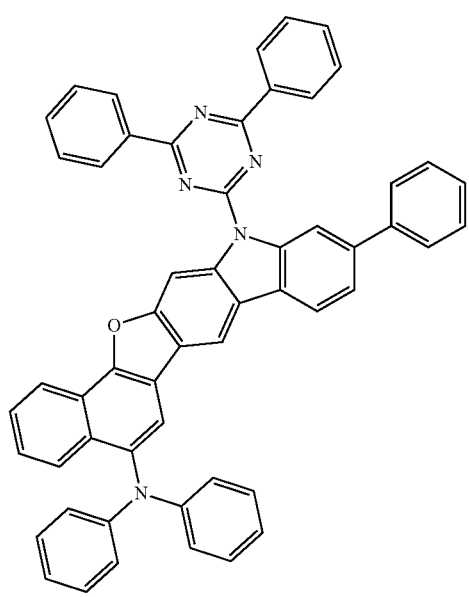
b-93
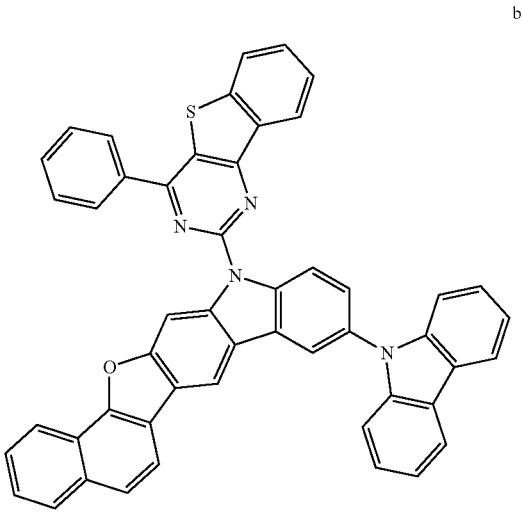
b-94
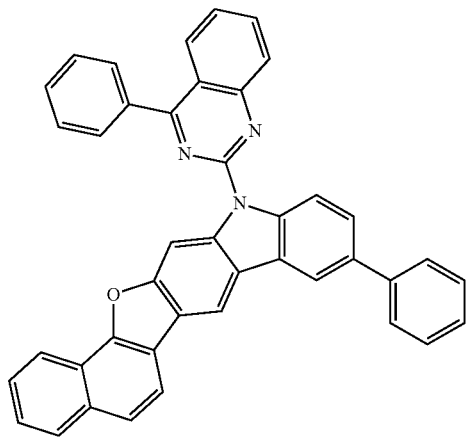
b-95
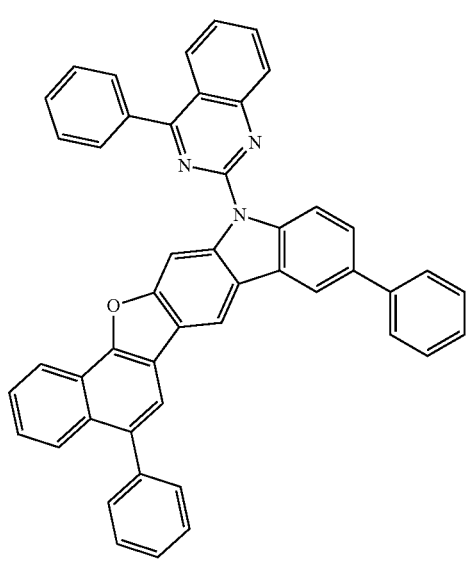
c-1
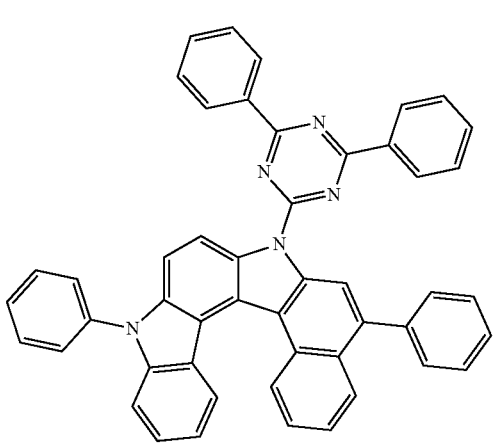

-continued
c-2
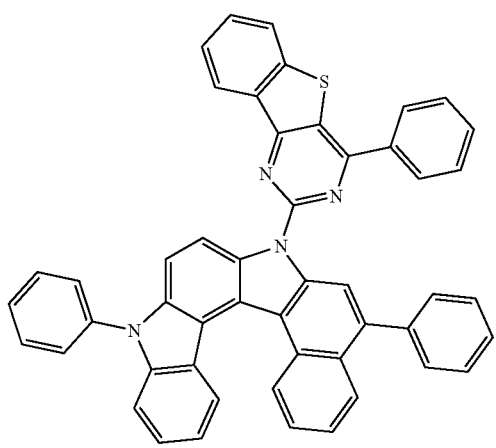
c-3
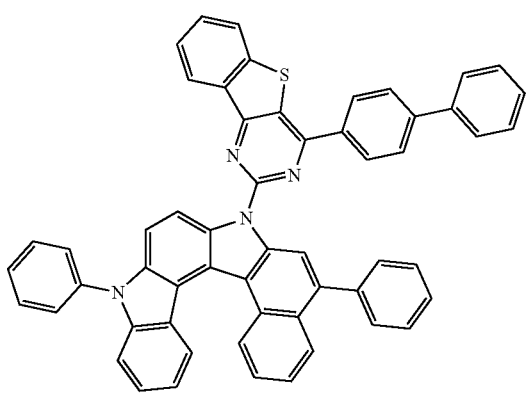
c-4
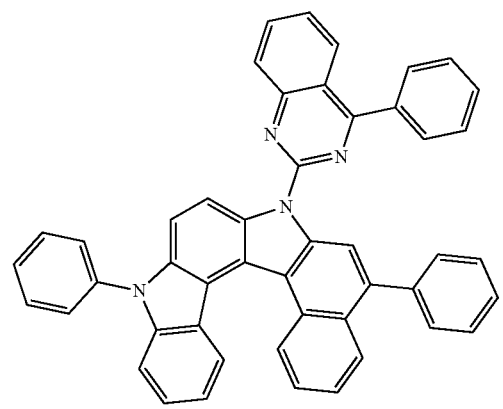
c-5
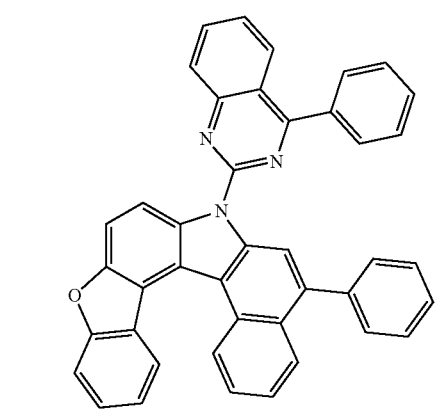
-continued
c-6
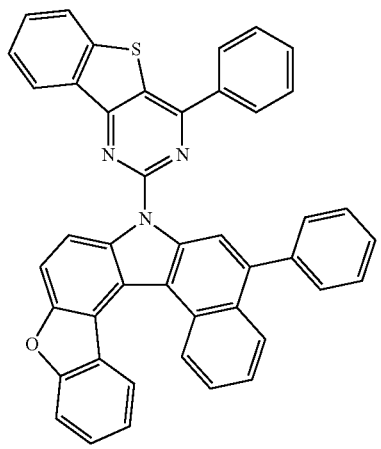
c-7
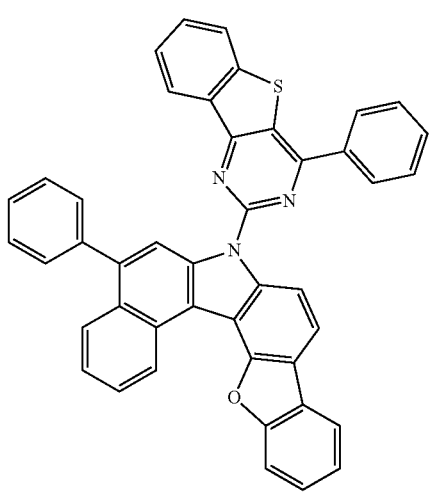
c-8
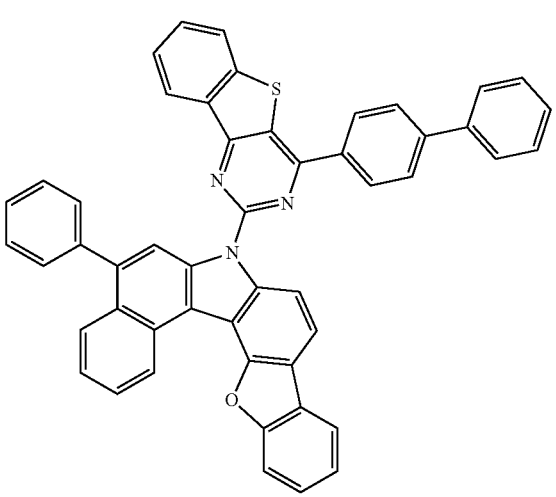

c-9
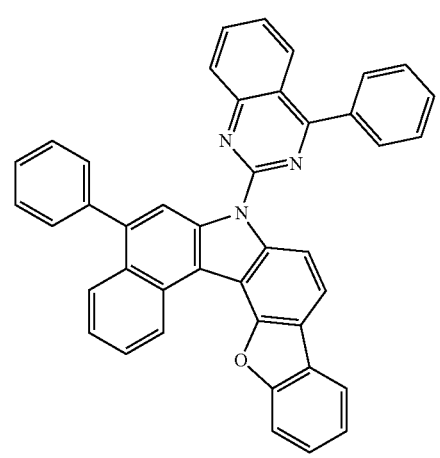
c-10
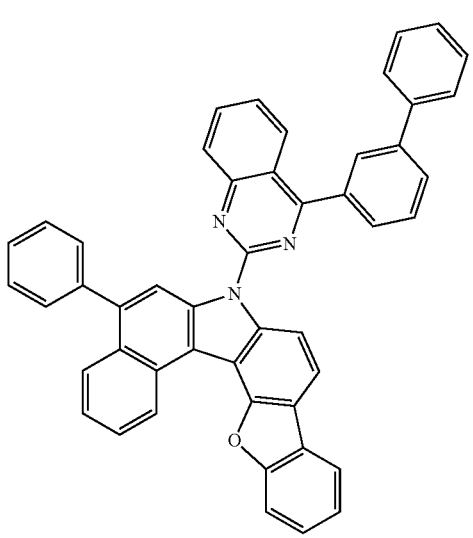
c-11
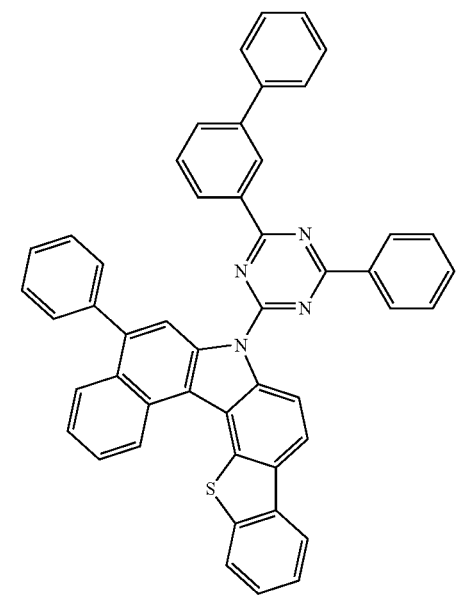
c-12
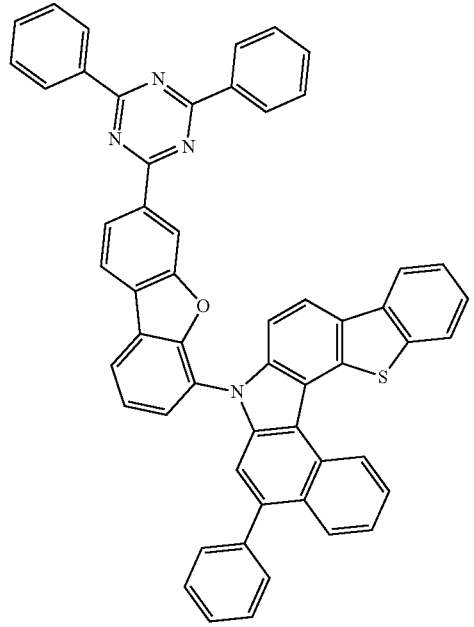
c-13
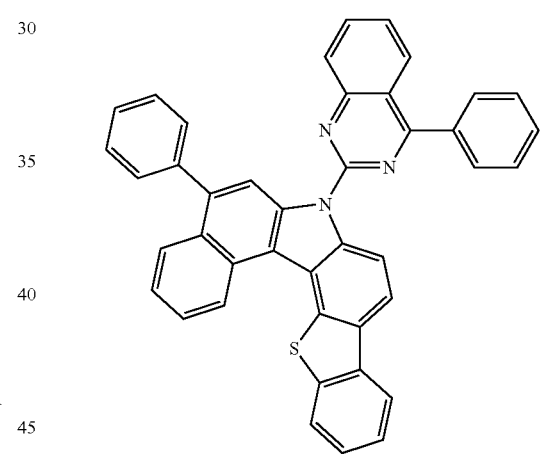
c-14
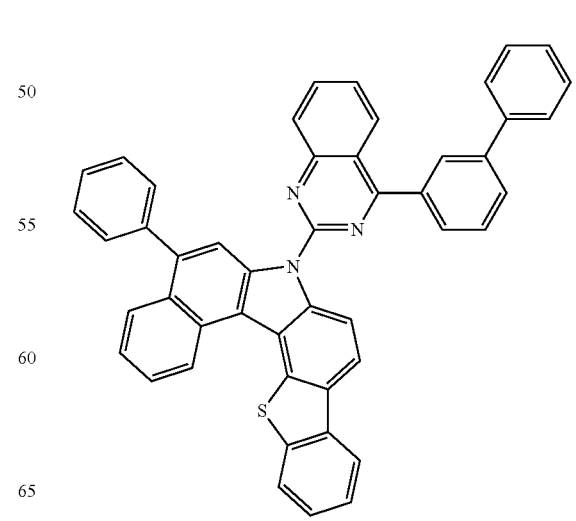

-continued
c-15
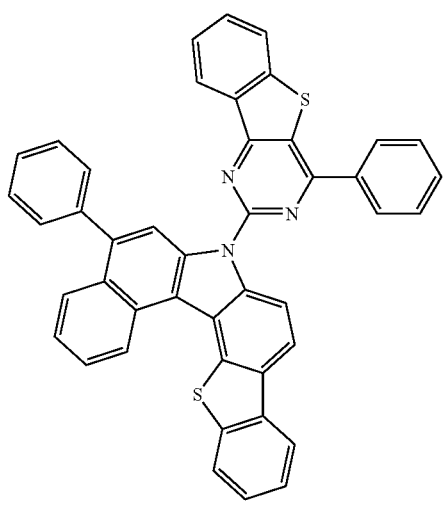
c-16
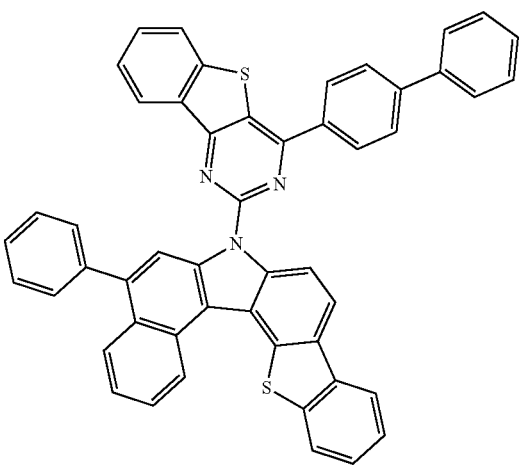
c-17
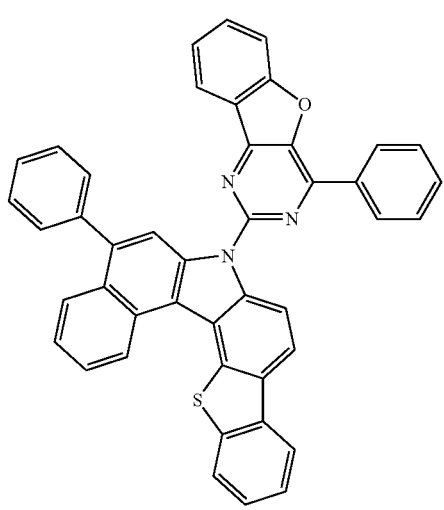
-continued
c-18
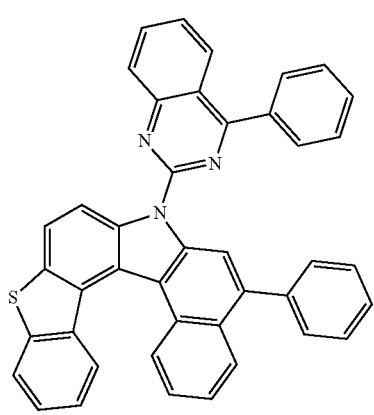
c-19
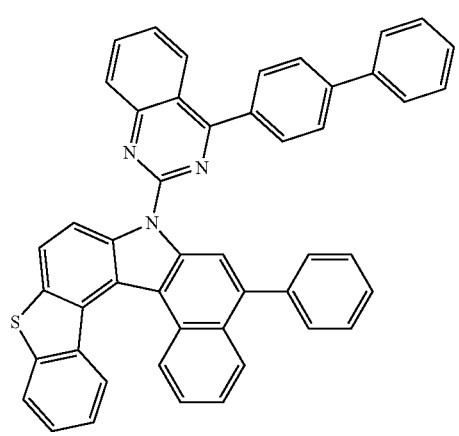
c-20
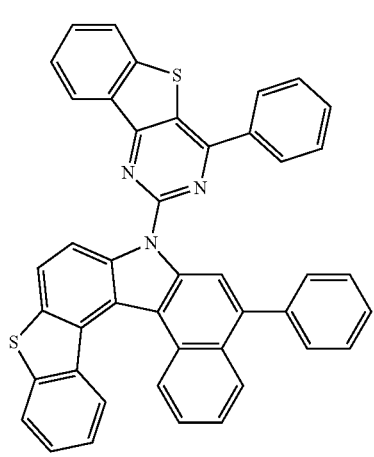

c-21
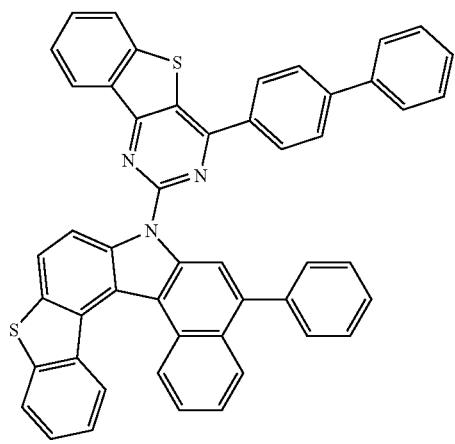
c-22
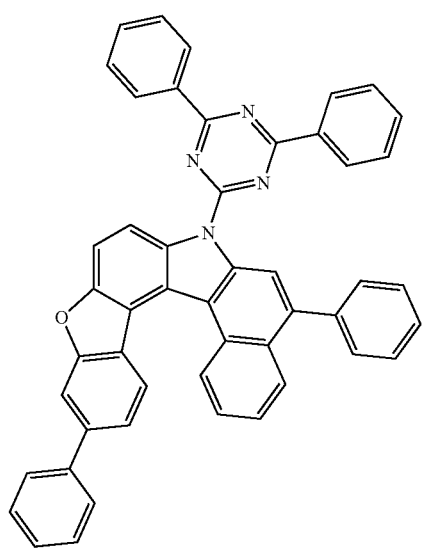
c-23
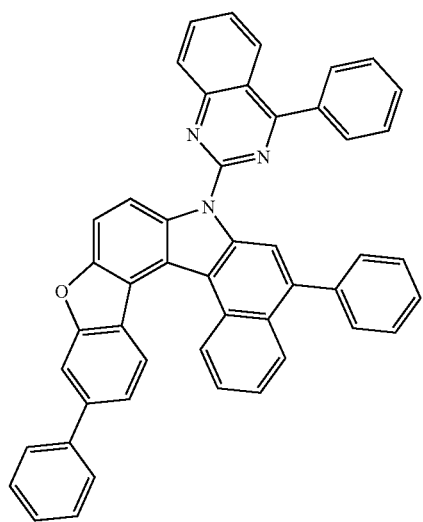
c-24
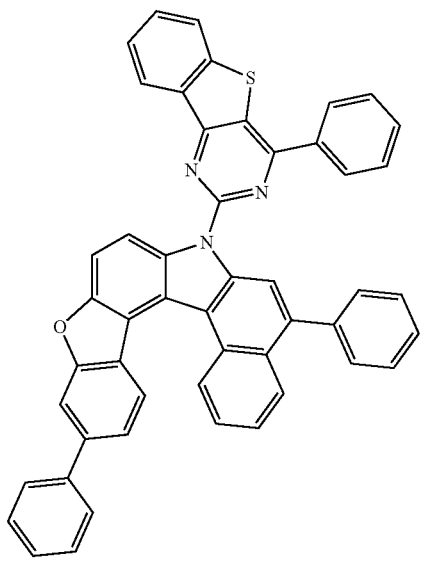
c-25
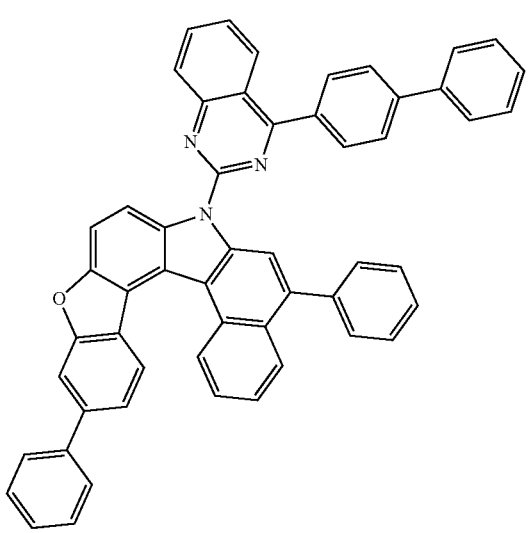
c-26
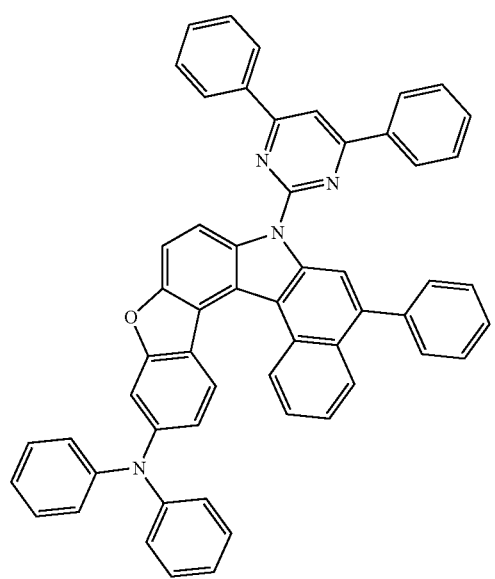

c-27
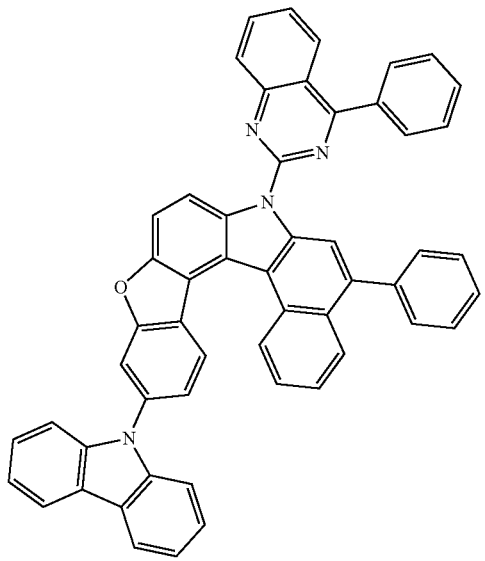
c-28
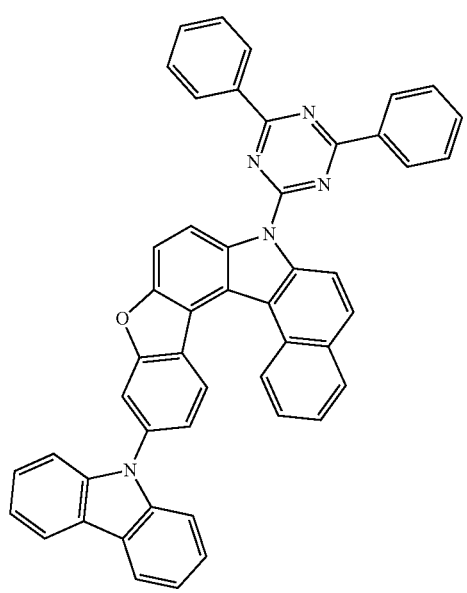
c-29
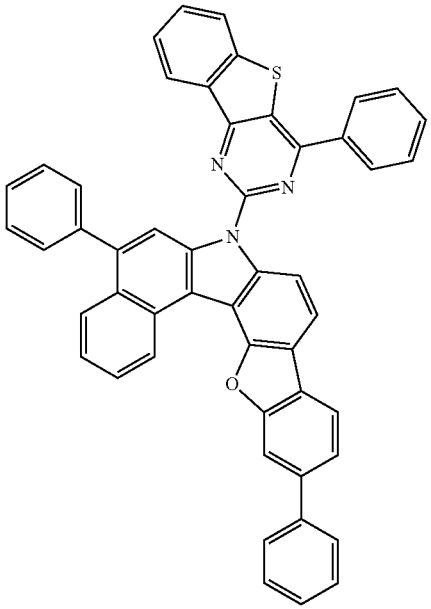
c-30
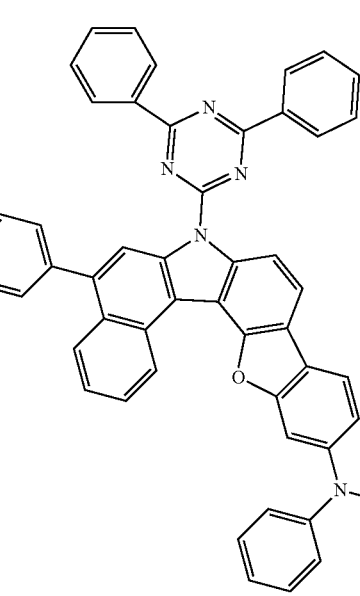

c-31
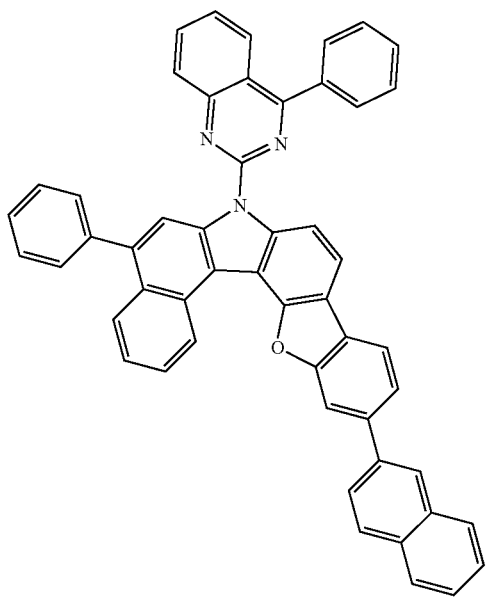
c-32
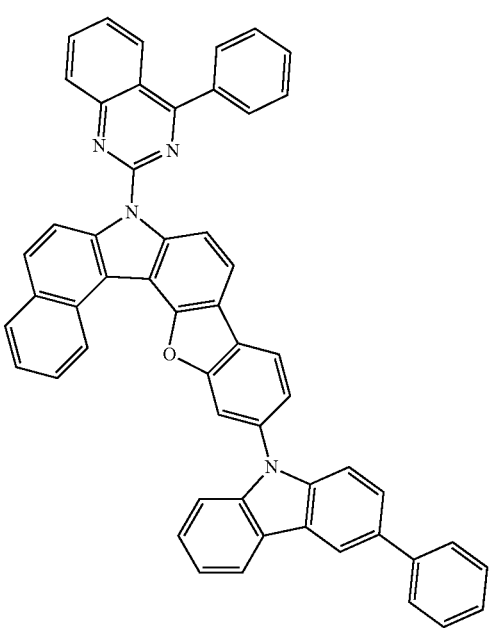
c-33
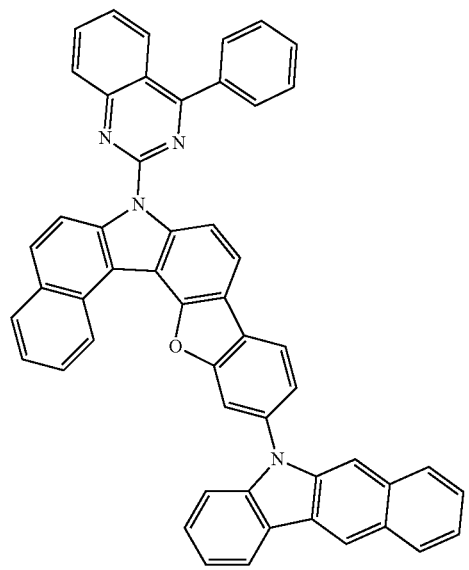
c-34
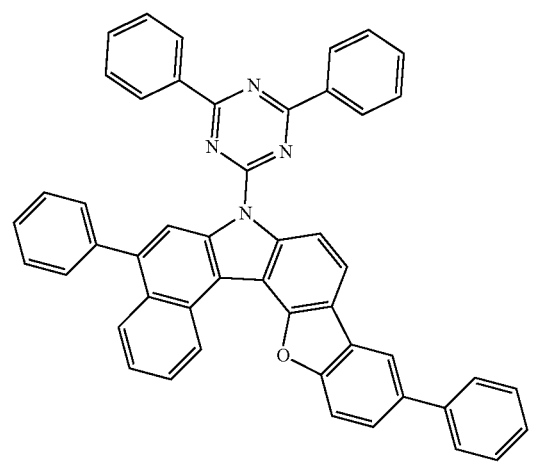
c-35
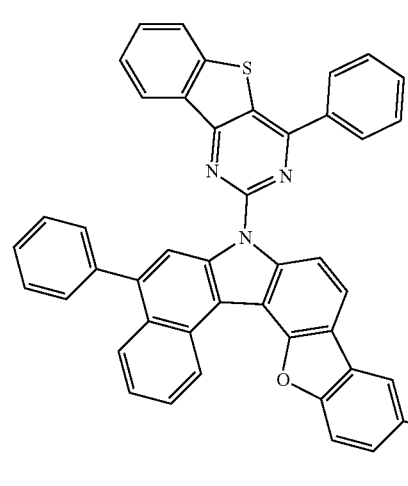

c-36
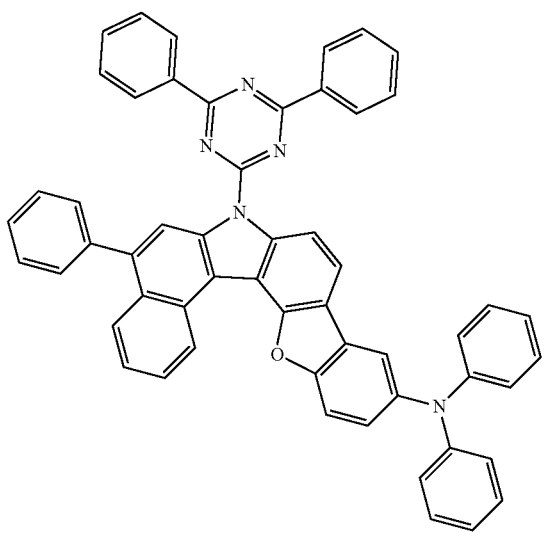
c-37
c-38
c-39
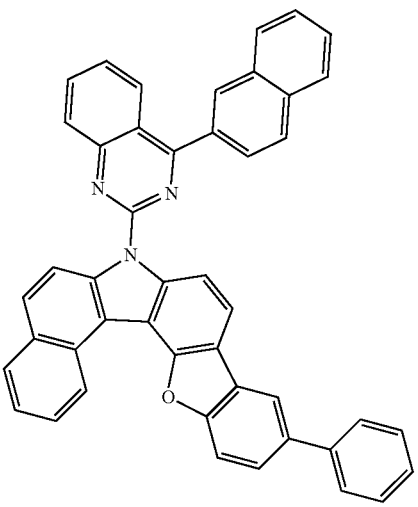
c-40
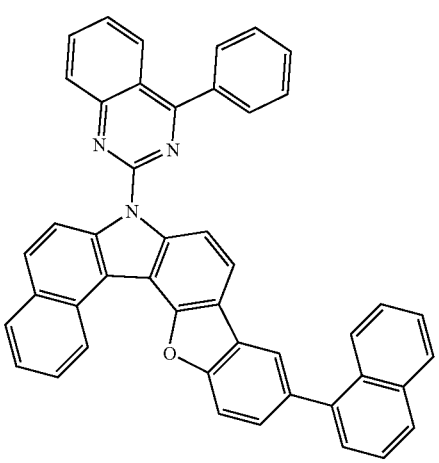
c-41
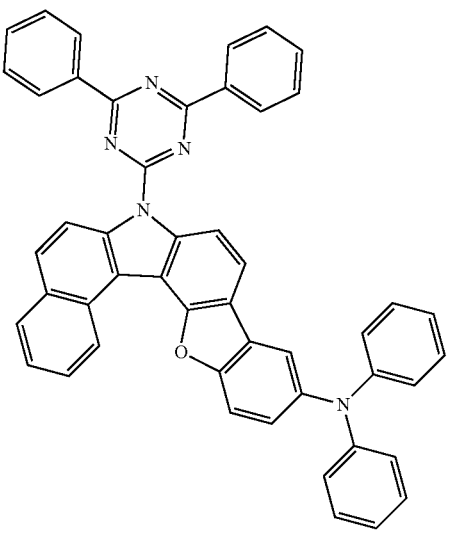

c-42
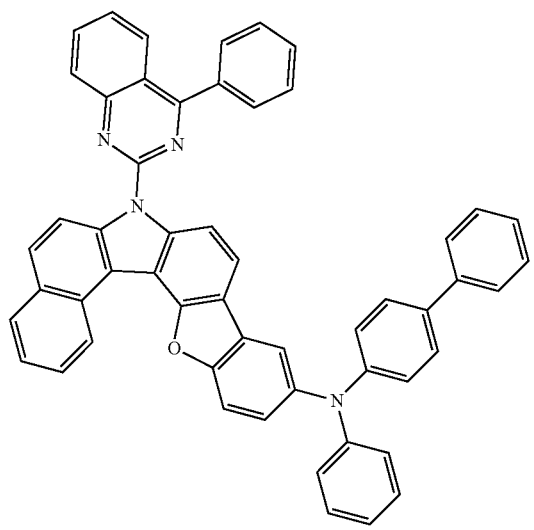
c-45
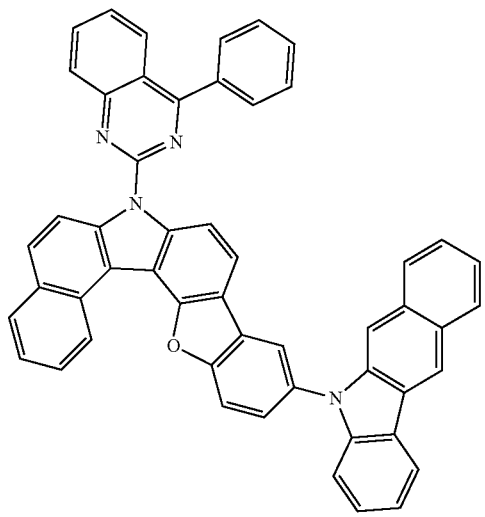
c-43
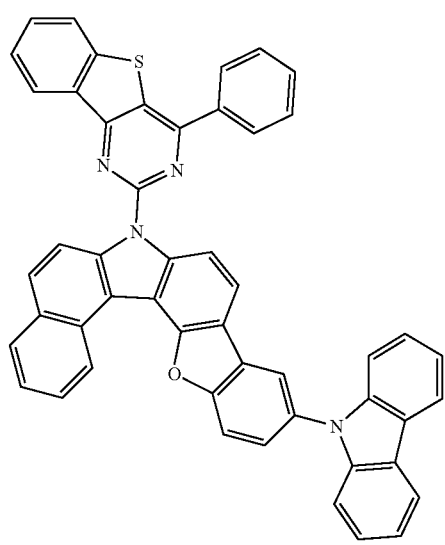
d-1
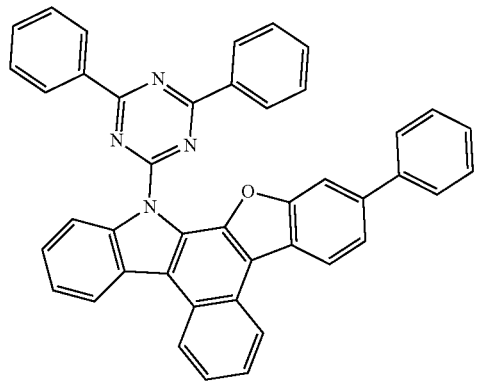
c-44
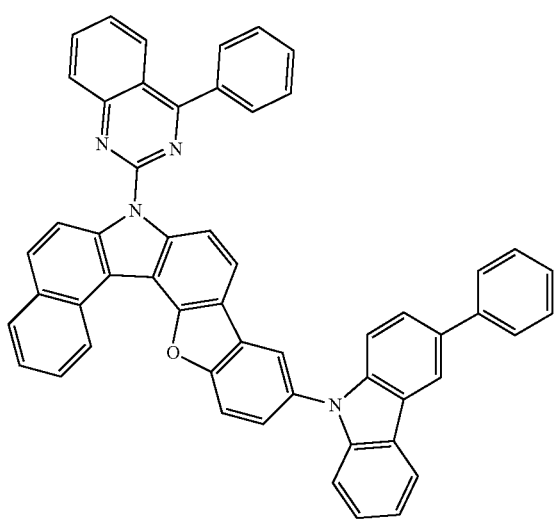
d-2
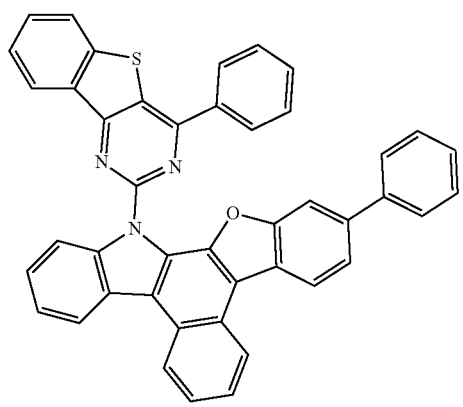

-continued
d-3
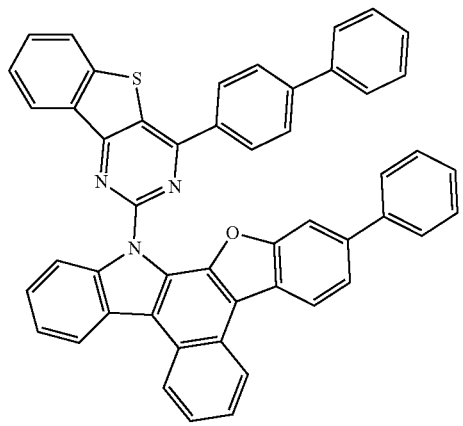
d-4
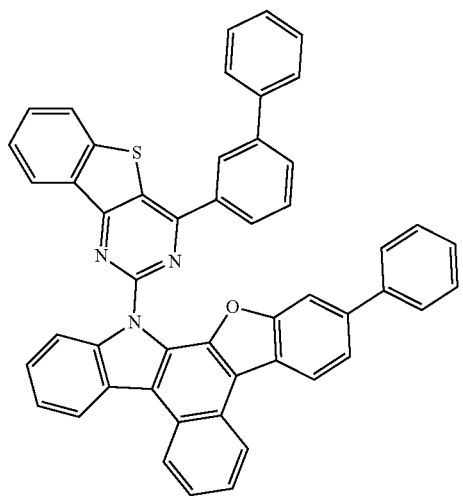
d-5
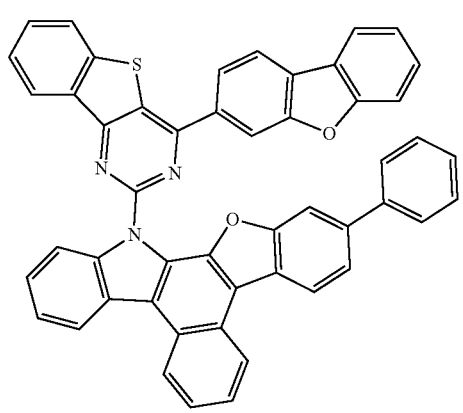
-continued
d-6
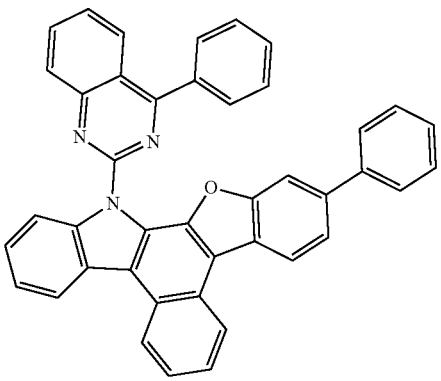
d-7
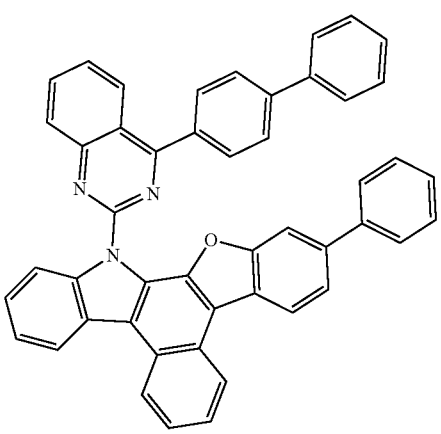
d-8
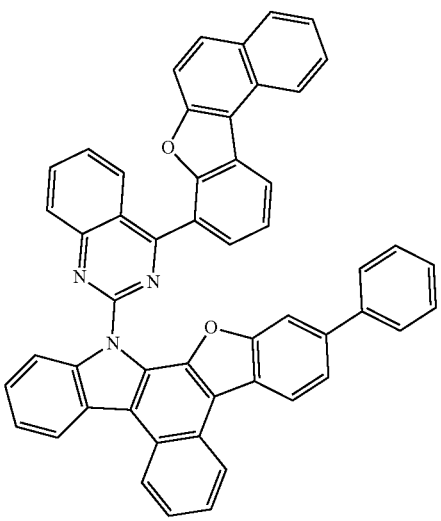

d-9
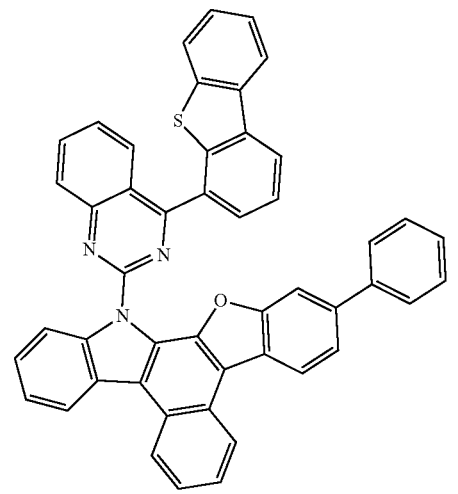
d-10
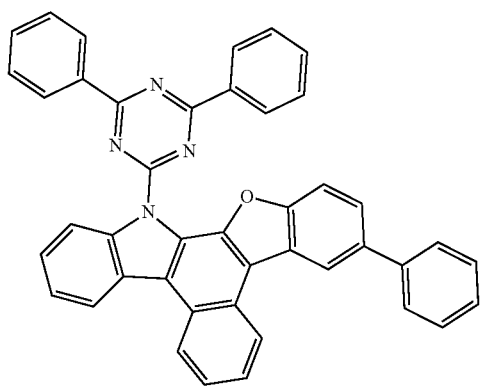
d-11
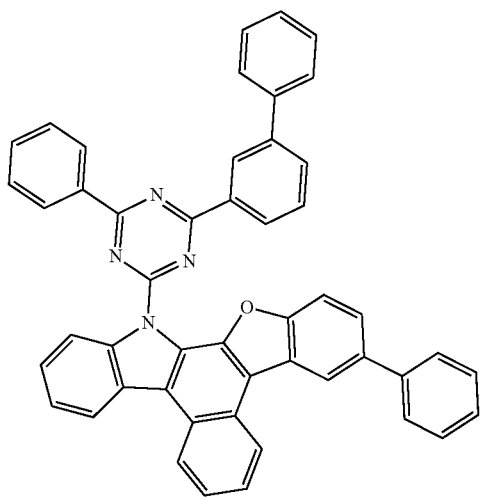
d-12
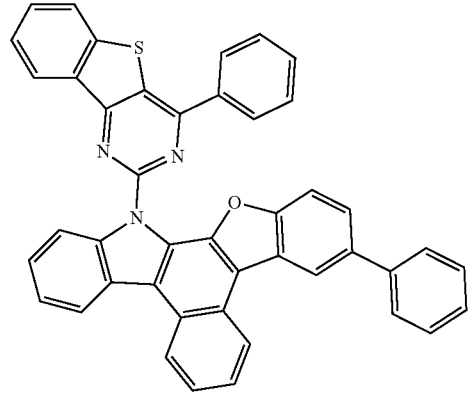
d-13
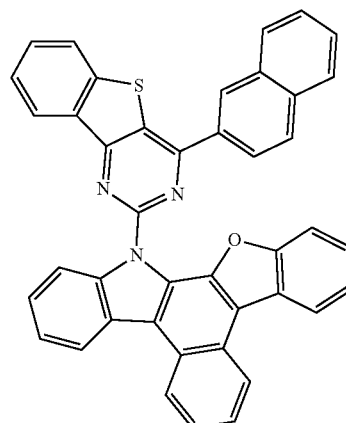
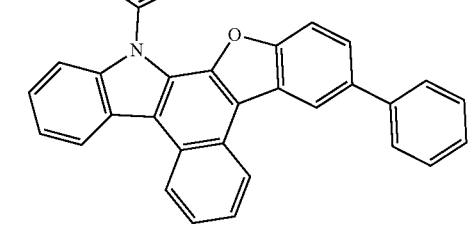
d-14
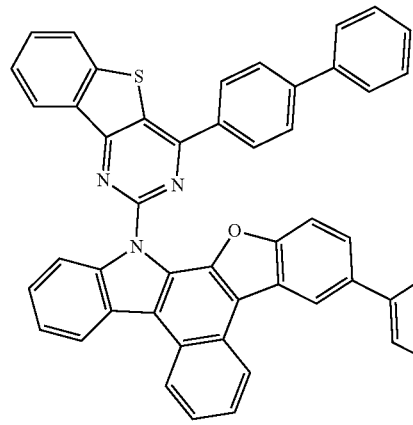
d-15
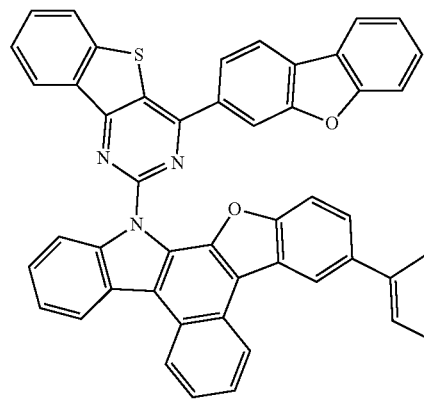

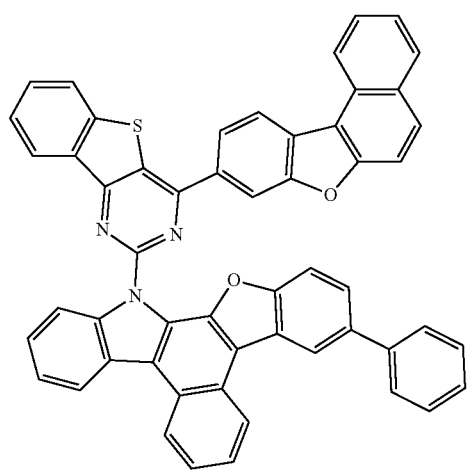
d-16
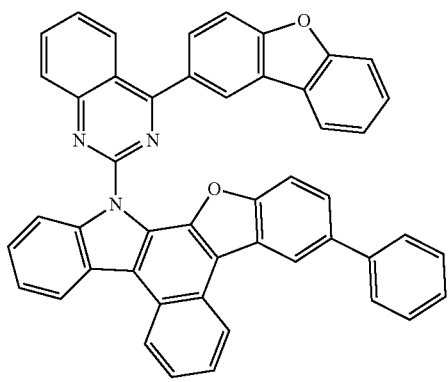
d-19
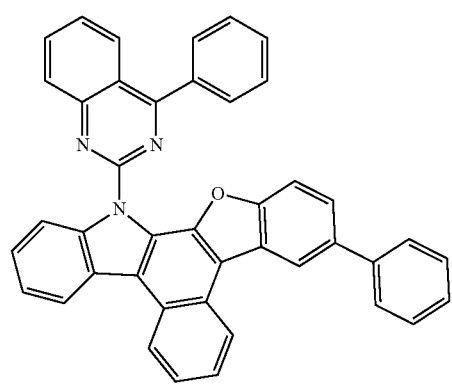
d-17
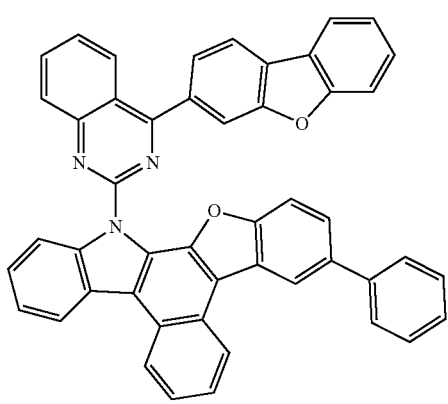
d-20
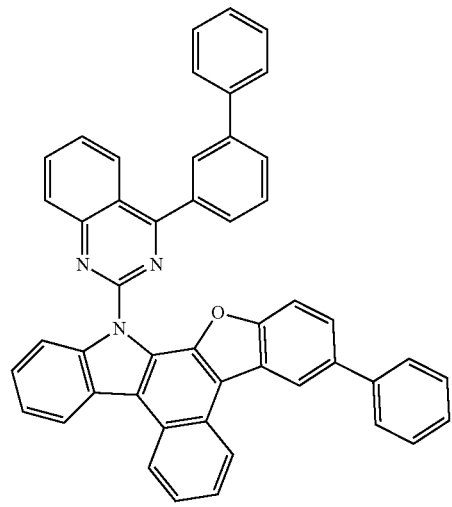
d-18
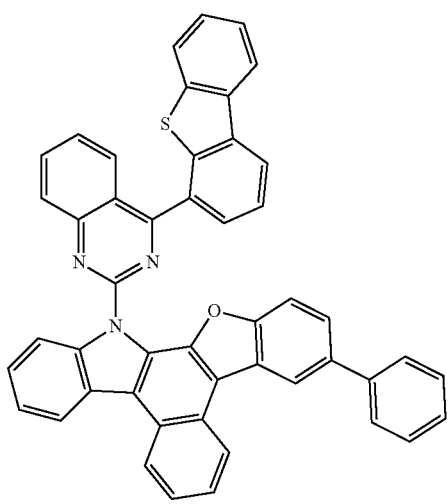
d-21

-continued
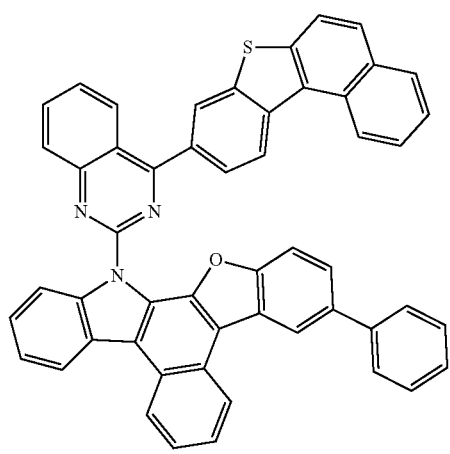
d-22
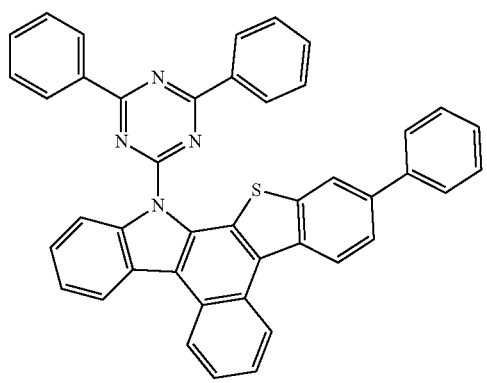
d-23
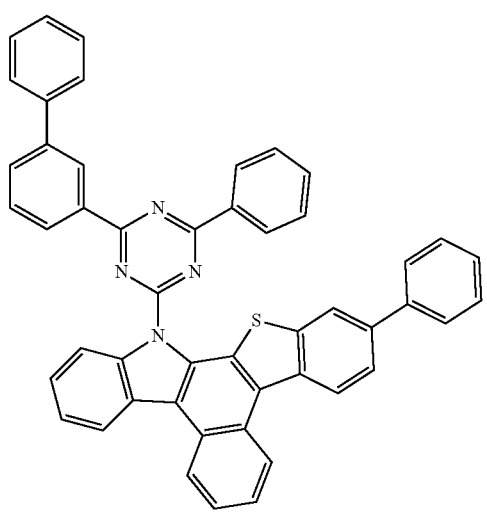
d-24
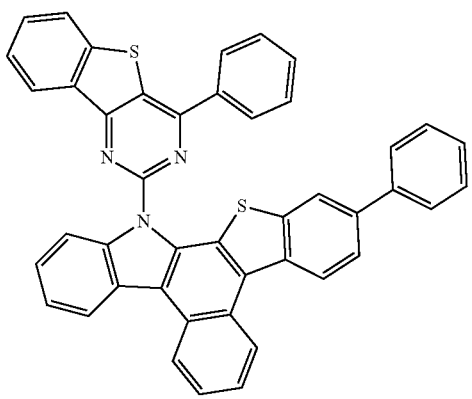
d-26
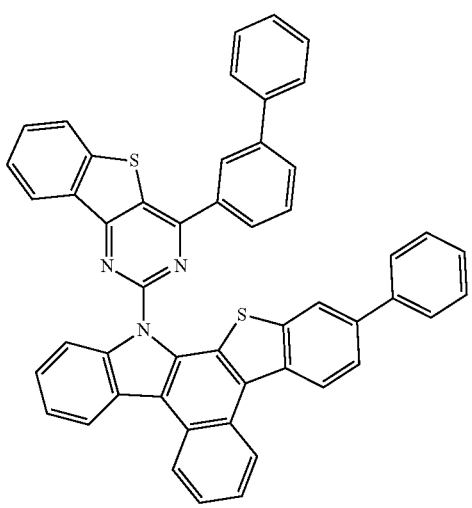
d-27
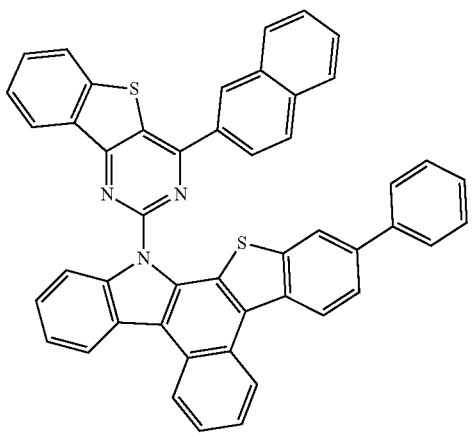
d-28

-continued
d-29
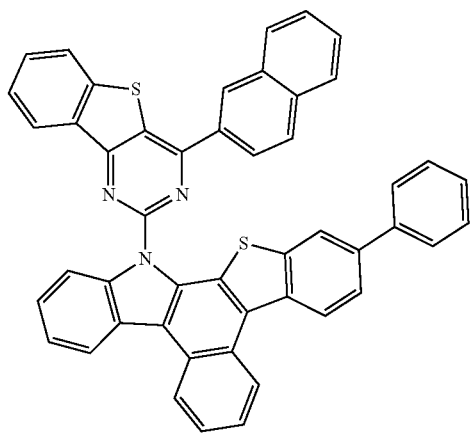
d-30
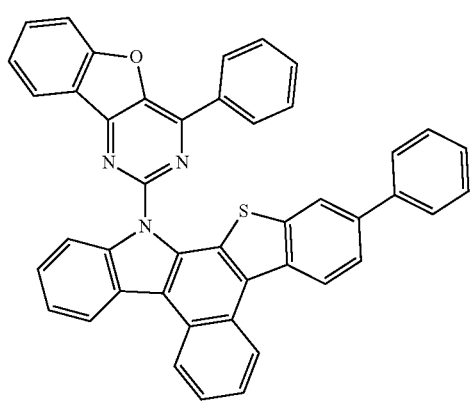
d-31
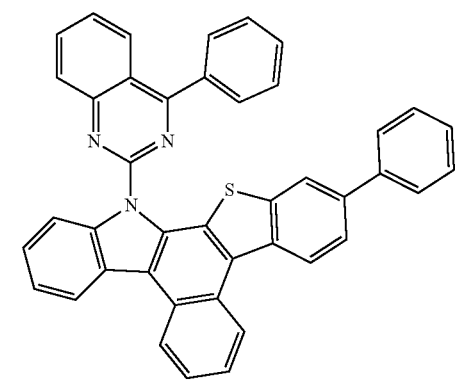
d-32
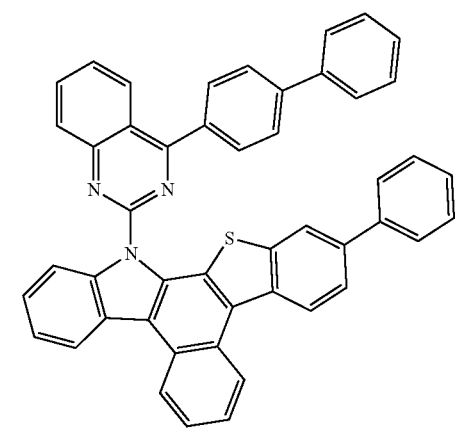
-continued
d-33
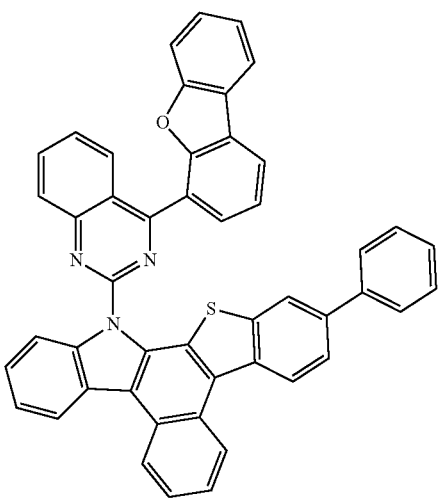
d-34
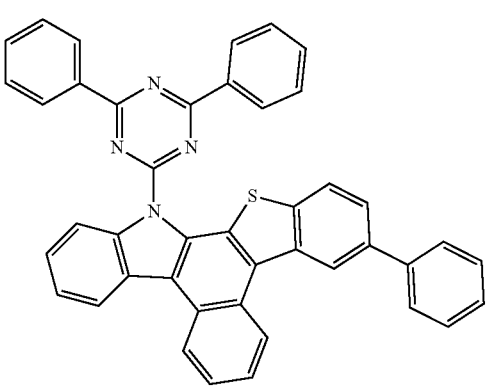
d-35
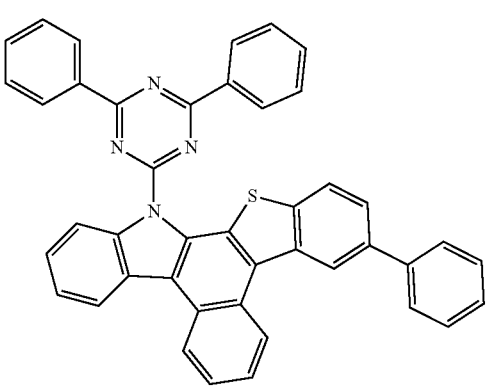

-continued
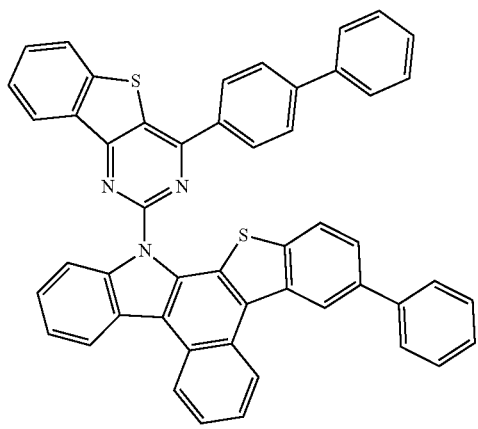
d-36
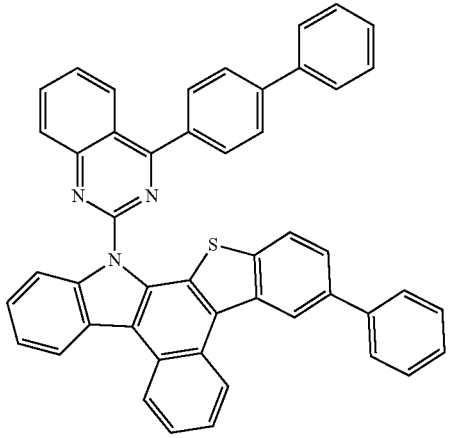
d-39
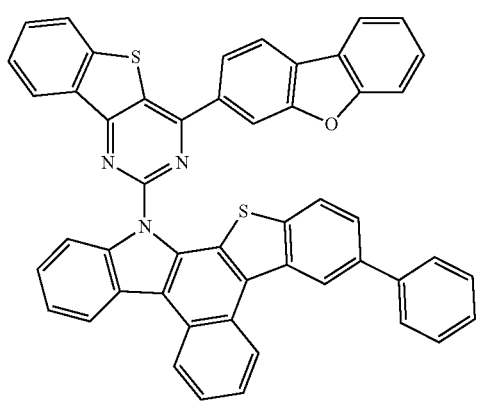
d-37
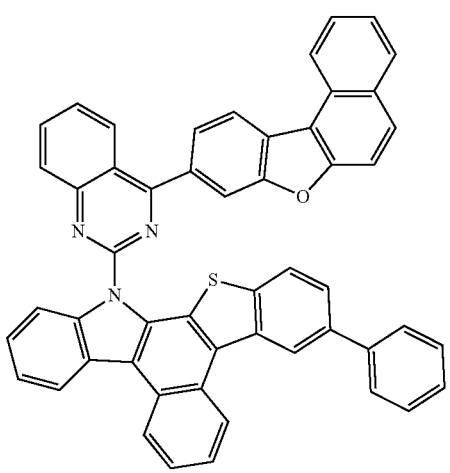
d-40
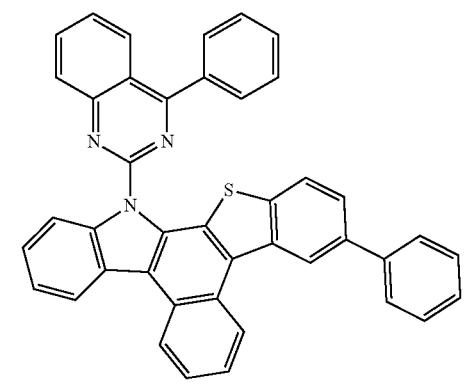
d-38
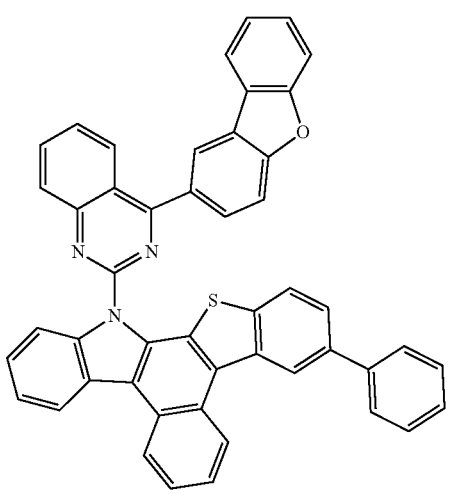
d-41 d-42
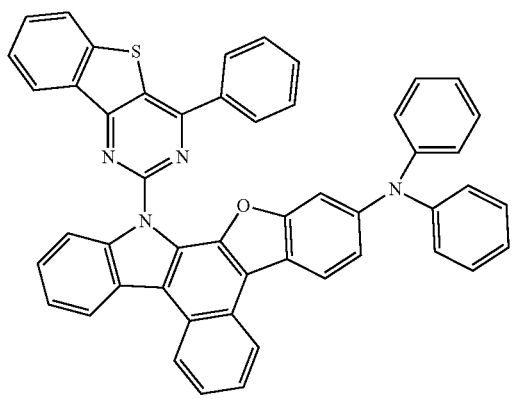
d-43
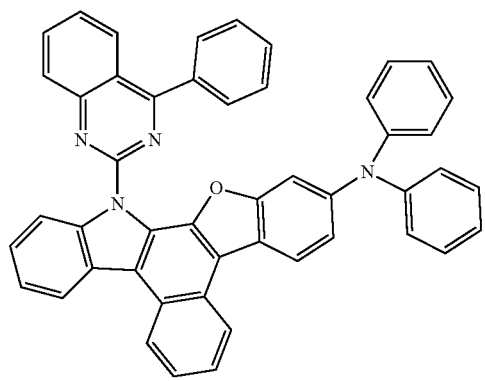
d-44
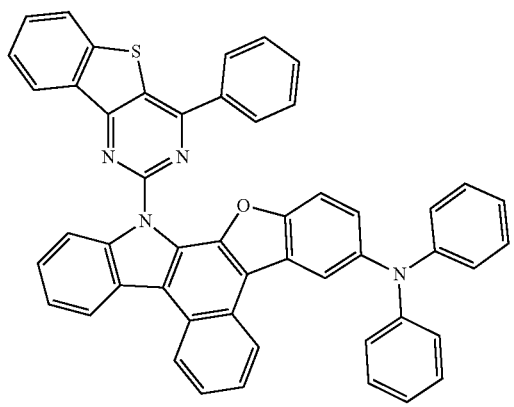
d-45
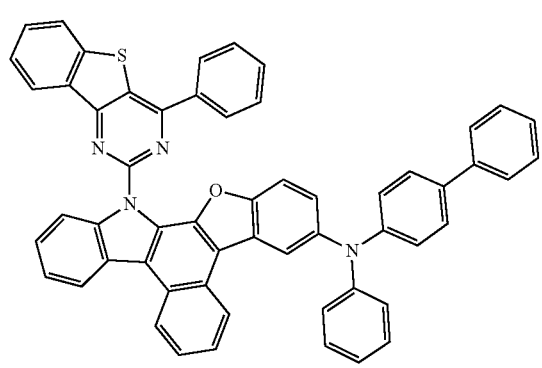
d-46
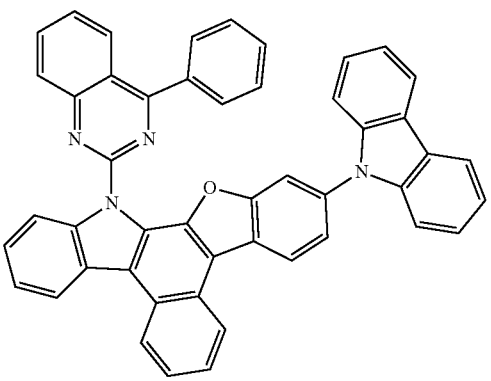
d-47
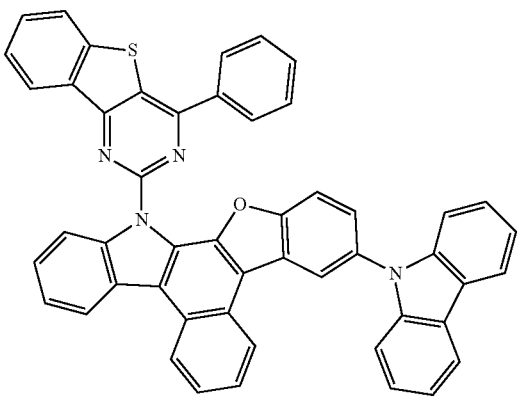
d-48
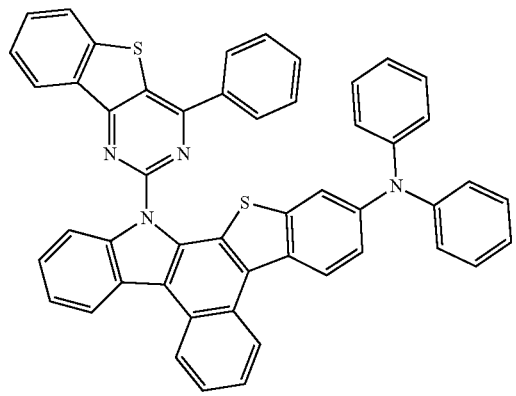
d-49
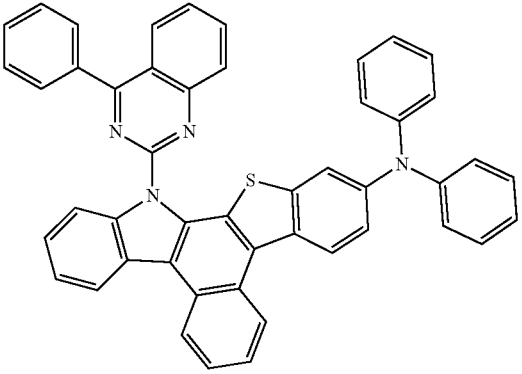

-continued
d-50
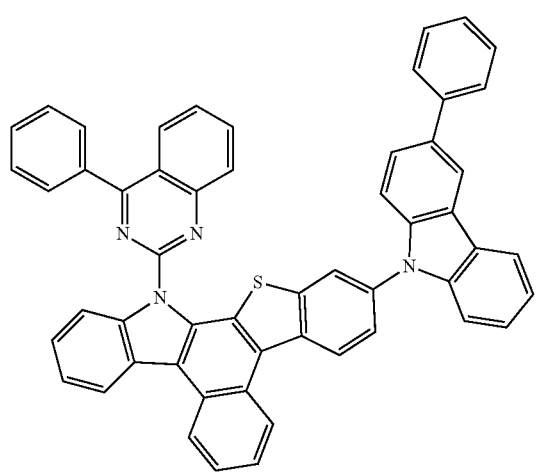
d-51
d-52
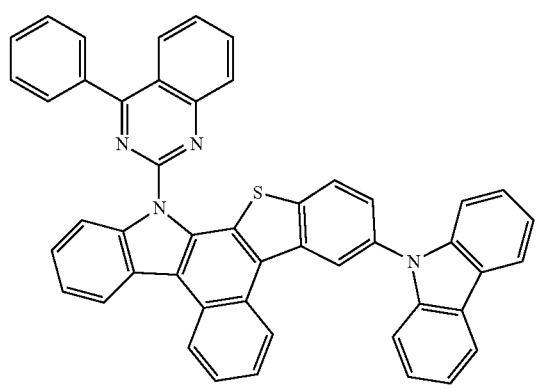
-continued
d-53
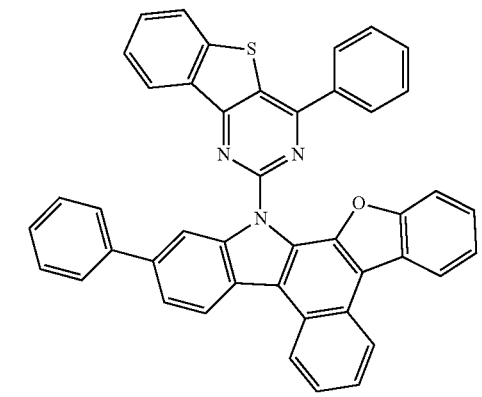
d-54
d-55
d-56
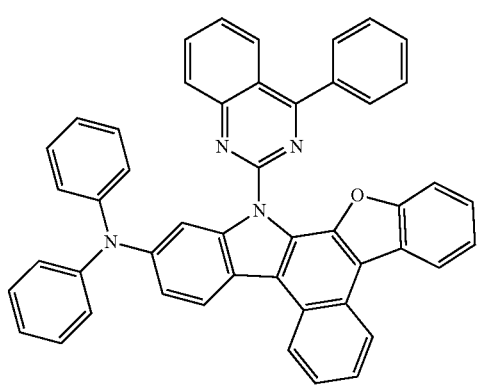

-continued
d-57
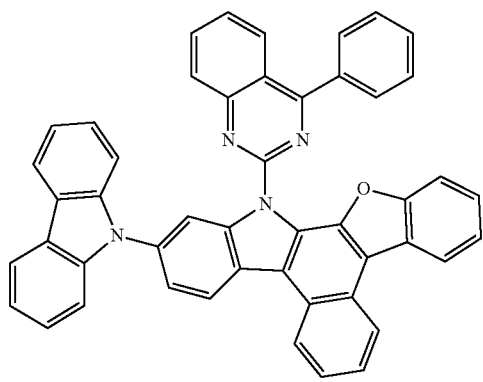
d-58
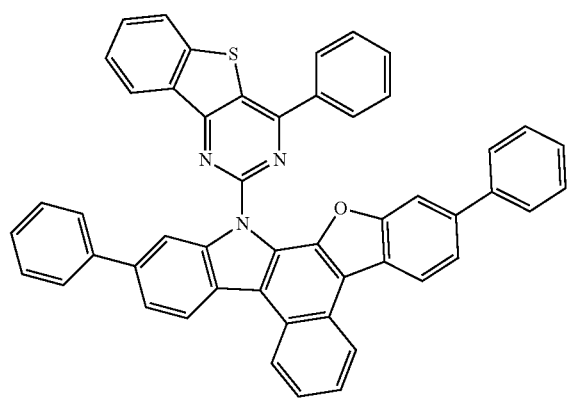
d-61
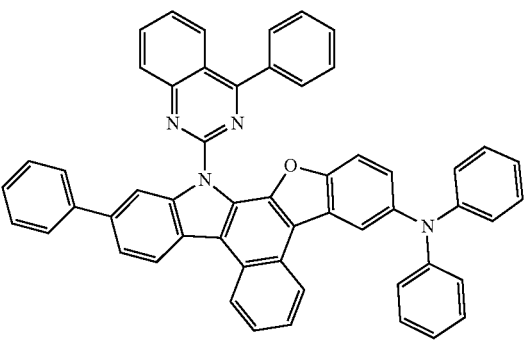
d-62
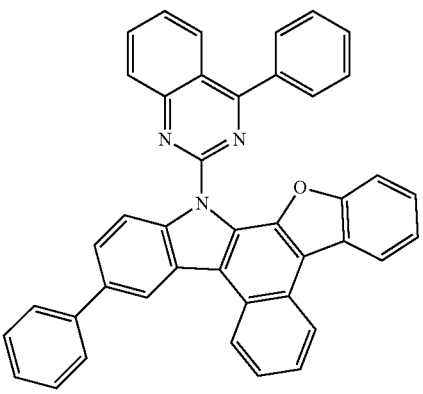
d-59
d-60
d-63
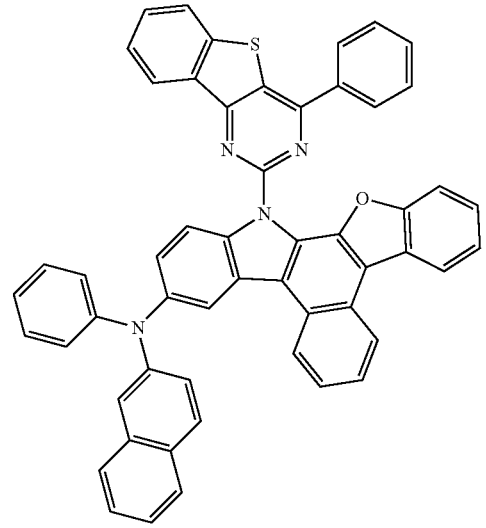

-continued
d-64
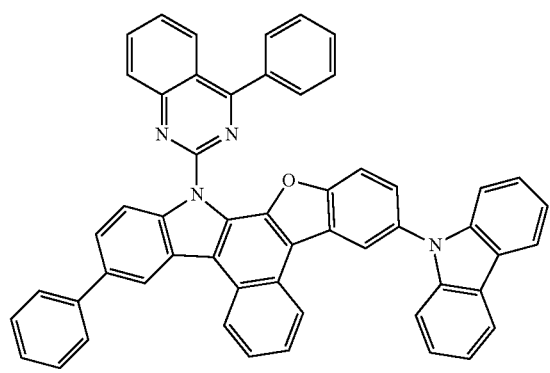
d-65
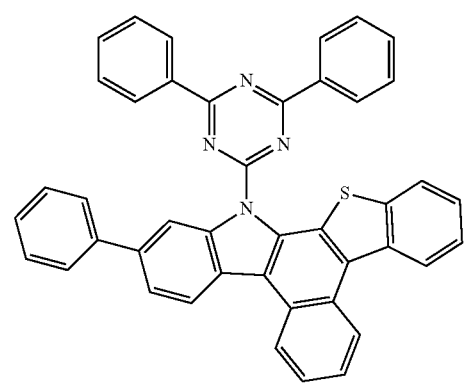
d-68
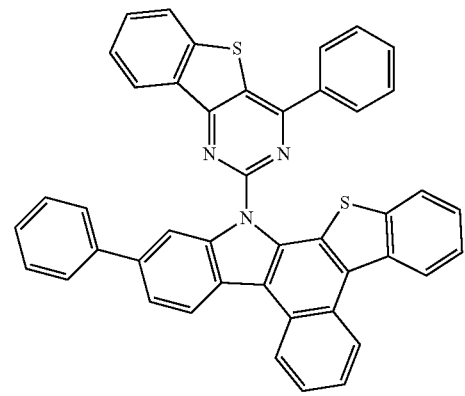
d-67
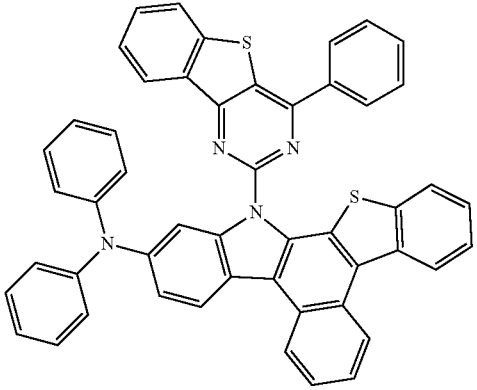
-continued
d-68
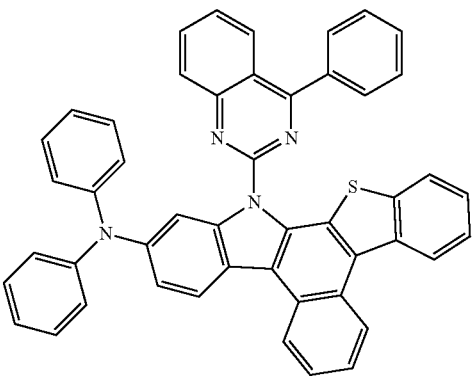
d-69
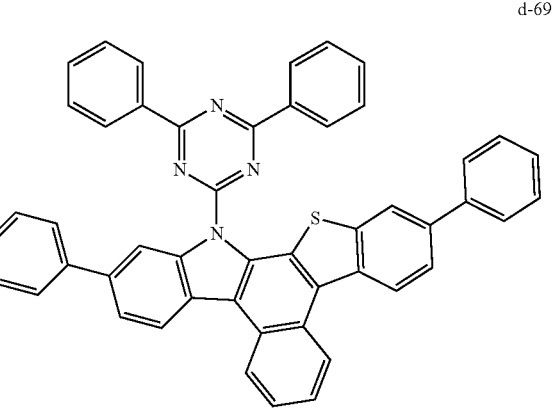
d-70
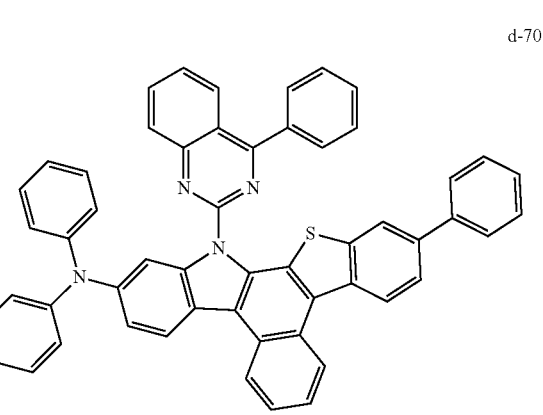
d-71
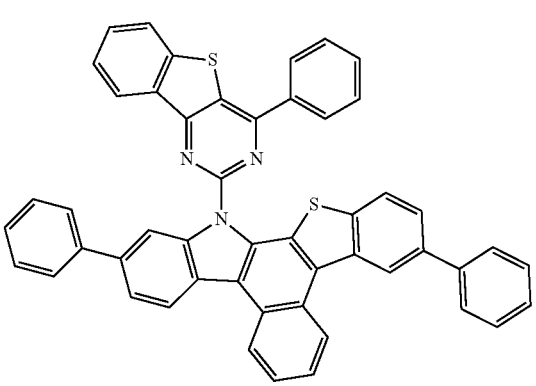

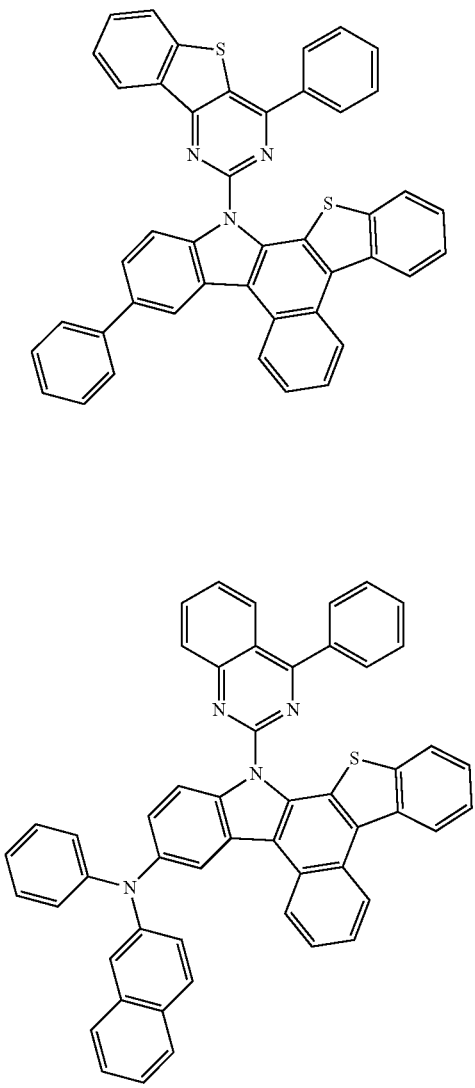

d-72 d-73 d-74

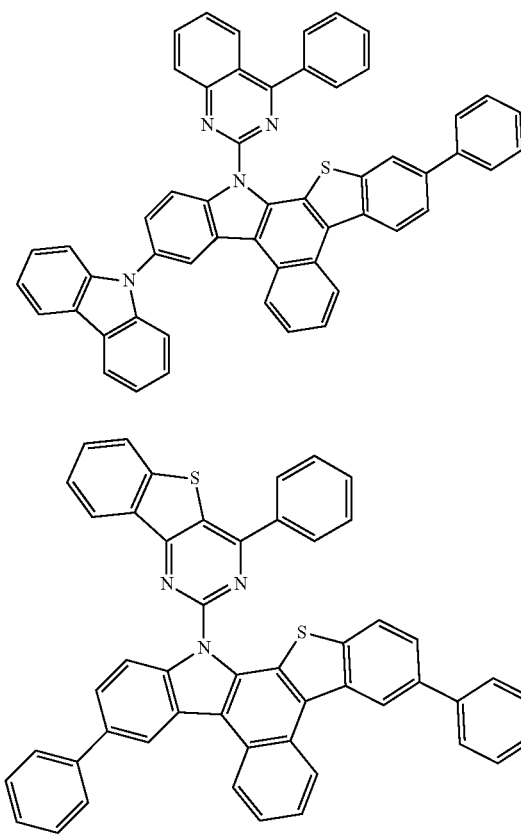

d-75 d-76

In addition, by introducing various substituents to the structure of Chemical Formula 1, compounds having unique properties of the introduced substituents can be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer can be synthesized.

In addition, by introducing various substituents to the structure of Chemical Formula 1, the energy band gap can be finely controlled, and meanwhile, properties at interfaces between organic materials are enhanced, and material applications can become diverse.

One embodiment of the present specification provides an organic light emitting device including a first electrode; a second electrode; and an organic material layer provided between the first electrode and the second electrode, wherein the organic material layer includes one or more types of the heterocyclic compound represented by Chemical Formula 1.

In one embodiment of the present specification, the organic material layer can include the heterocyclic compound represented by Chemical Formula 1 in greater than or equal to one type and less than or equal to three types.

In one embodiment of the present specification, the organic material layer can include the heterocyclic compound represented by Chemical Formula 1 in greater than or equal to one type and less than or equal to two types.

In one embodiment of the present specification, the organic material layer can include one type of the heterocyclic compound represented by Chemical Formula 1.

In one embodiment of the present specification, the organic material layer can include two types of the heterocyclic compound represented by Chemical Formula 1.

In one embodiment of the present specification, the organic material layer can further include a compound of the following Chemical Formula 11.

[Chemical Formula 11]

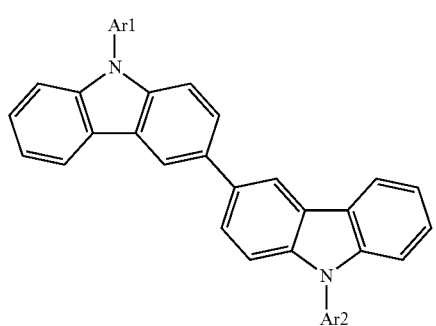

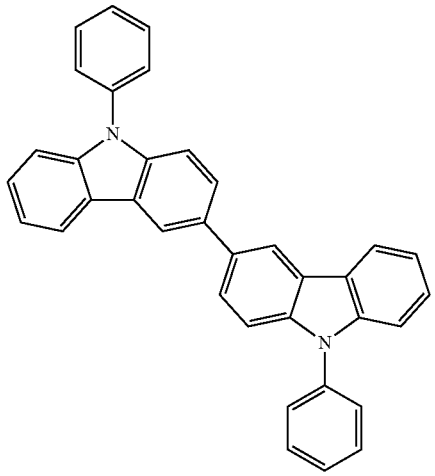

In Chemical Formula 11,

Ar1 and Ar2 are each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group.

In one embodiment of the present specification, Ar1 and Ar2 are each independently a substituted or unsubstituted aryl group; or a substituted or unsubstituted heteroaryl group.

In one embodiment of the present specification, Ar1 and Ar2 are each independently a substituted or unsubstituted C6 to C60 aryl group; or a substituted or unsubstituted C2 to C60 heteroaryl group.

In one embodiment of the present specification, Ar1 and Ar2 are each independently a substituted or unsubstituted C6 to C30 aryl group; or a substituted or unsubstituted C2 to C30 heteroaryl group.

In one embodiment of the present specification, Ar1 and Ar2 are each independently a substituted or unsubstituted phenyl group; a substituted or unsubstituted biphenyl group; a substituted or unsubstituted naphthyl group; a substituted or unsubstituted dibenzothiophene group; or a substituted or unsubstituted dibenzofuran group.

In one embodiment of the present specification, Ar1 and Ar2 are each independently a phenyl group unsubstituted or substituted with a phenyl group; a biphenyl group; a naphthyl group; a dibenzothiophene group unsubstituted or substituted with a phenyl group; or a dibenzofuran group.

In one embodiment of the present specification, Chemical Formula 11 can be represented by any one of the following compounds.

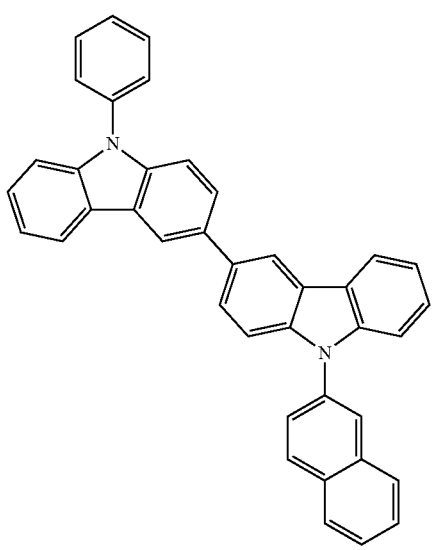

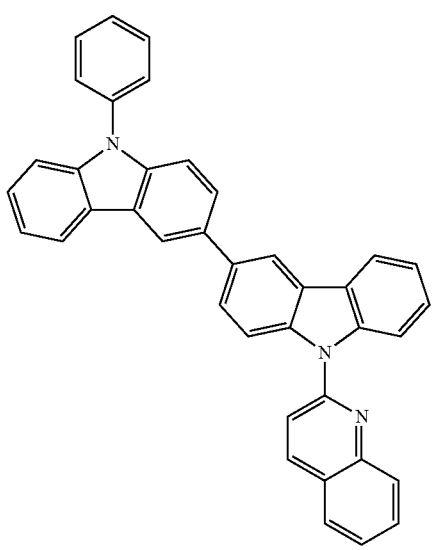

167
-continued
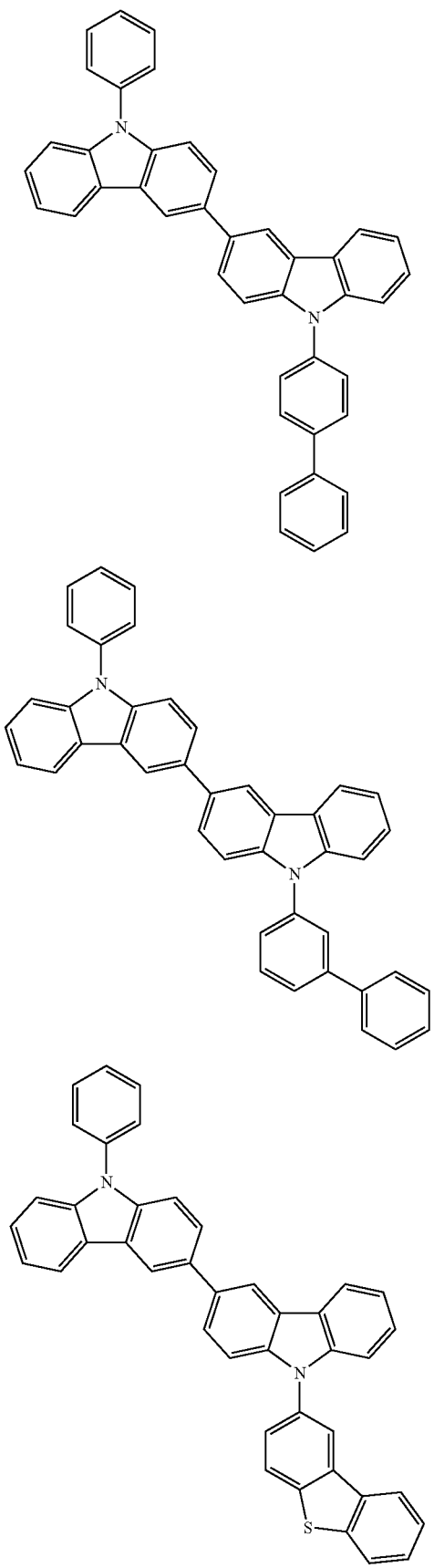
168
-continued
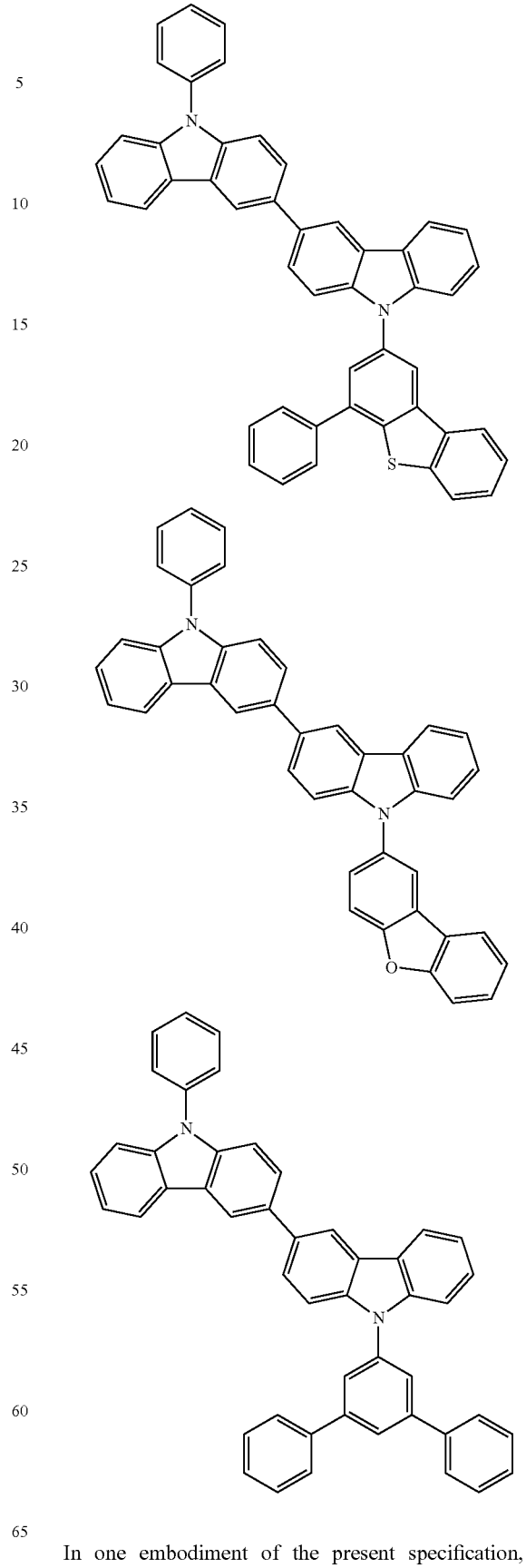
In one embodiment of the present specification, the organic material layer can include the compound represented by Chemical Formula 1 and the compound represented by Chemical Formula 11.

In one embodiment of the present specification, the first electrode can be an anode, and the second electrode can be a cathode.

In another embodiment of the present specification, the first electrode can be a cathode, and the second electrode can be an anode.

In one embodiment of the present specification, the organic light emitting device can be a blue organic light emitting device, and the heterocyclic compound according to Chemical Formula 1 can be used as a material of the blue organic light emitting device. For example, the heterocyclic compound according to Chemical Formula 1 can be included in a host material of a light emitting layer of the blue organic light emitting device.

In another embodiment of the present specification, the organic light emitting device can be a green organic light emitting device, and the heterocyclic compound according to Chemical Formula 1 can be used as a material of the green organic light emitting device. For example, the heterocyclic compound according to Chemical Formula 1 can be included in a host material of a light emitting layer of the green organic light emitting device.

In another embodiment of the present specification, the organic light emitting device can be a red organic light emitting device, and the heterocyclic compound according to Chemical Formula 1 can be used as a material of the red organic light emitting device. For example, the heterocyclic compound according to Chemical Formula 1 can be included in a host material of a light emitting layer of the red organic light emitting device.

Specific details on the heterocyclic compound represented by Chemical Formula 1 are the same as the descriptions provided above.

The organic light emitting device of the present specification can be manufactured using common organic light emitting device manufacturing methods and materials except that one or more organic material layers are formed using the heterocyclic compound described above.

The heterocyclic compound can be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification can be formed in a single layer structure, or can also be formed in a multilayer structure in which two or more organic material layers are laminated. For example, the organic light emitting device according to one embodiment of the present disclosure can have a structure including a hole injection layer, a hole transfer layer, a light emitting layer, an electron transfer layer, an electron injection layer and the like as the organic material layer. However, the structure of the organic light emitting device is not limited thereto, and can include a smaller number of organic material layers.

In the organic light emitting device of the present specification, the organic material layer includes a light emitting layer, and the light emitting layer can include the heterocyclic compound of Chemical Formula 1.

In another organic light emitting device, the organic material layer includes a light emitting layer, the light emitting layer includes a host, and the host can include one or more types of the heterocyclic compound of Chemical Formula 1. For example, the host can include two types of the heterocyclic compound of Chemical Formula 1. When forming a host by combining two types of the heterocyclic compound, a wide band gap is formed increasing an exciton-formed light emitting region in the host, and as a result, efficiency can increase.

In another organic light emitting device, the organic material layer includes a light emitting layer, and the light emitting layer includes the heterocyclic compound of Chemical Formula 1 as a host and can further include the compound of Chemical Formula 11. When including both the heterocyclic compound of Chemical Formula 1 and the compound of Chemical Formula 11, an exciplex phenomenon of emitting energy having a HOMO level size of a P-type host (donor) and a LUMO level size of an N-type host (acceptor) occurs due to an electron exchange between the two molecules. The P-type host is, for example, the compound represented by Chemical Formula 11, and the N-type host is, for example, the heterocyclic compound of Chemical Formula 1. When using a P-type host (donor) having a favorable hole transfer ability and an N-type host (acceptor) having a favorable electron transfer ability as a host of a light emitting layer, holes are injected to the P-type host and electrons are injected to the N-type host, and therefore, a driving voltage can be lowered, which helps with enhancement in the lifetime of an organic light emitting device.

In another organic light emitting device, the host can be a red host.

The organic light emitting device of the present disclosure can further include one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present specification.

However, the scope of the present application is not limited to these diagrams, and structures of organic light emitting devices known in the art can also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate can also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer cannot be included, and other necessary functional layers can be further included.

The organic material layer including the heterocyclic compound represented by Chemical Formula 1 can further include other materials as necessary.

In the organic light emitting device according to one embodiment of the present specification, materials other than the heterocyclic compound represented by Chemical Formula 1 are illustrated below, however, these are for illustrative purposes only and not for limiting the scope of the present application, and can be replaced by materials known in the art.

As the anode material, materials having relatively large work function can be used, and transparent conductive oxides, metals, conductive polymers or the like can be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly [3,4-(ethylene-1,2-dioxy)thiophene] (PEDOT), polypyrrole and polyaniline, and the like, but are not limited thereto.

As the cathode material, materials having relatively small work function can be used, and metals, metal oxides, conductive polymers or the like can be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials can be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri [phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, can be used.

As the hole transfer material, pyrazoline derivatives, arylamine-based derivatives, stilbene derivatives, triphenyl-diamine derivatives and the like can be used, and low molecular or high molecular materials can also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, can be used, and high molecular materials can also be used as well as low molecular materials.

As examples of the electron injection material, LiF is typically used in the art, however, the present application is not limited thereto.

As the light emitting material, red, green or blue light emitting materials can be used, and as necessary, two or more light emitting materials can be mixed and used. Herein, two or more light emitting materials can be used by being deposited as individual sources of supply or by being premixed and deposited as one source of supply. In addition, fluorescent materials can also be used as the light emitting material, however, phosphorescent materials can also be used. As the light emitting material, materials emitting light by bonding electrons and holes injected from an anode and a cathode, respectively, can be used alone, however, materials having a host material and a dopant material involving in light emission together can also be used.

When mixing light emitting material hosts, same series hosts can be mixed, or different series hosts can be mixed.

For example, any two or more types of materials among n-type host materials or p-type host materials can be selected, and used as a host material of a light emitting layer.

The organic light emitting device according to one embodiment of the present specification can be a top-emission type, a bottom-emission type or a dual-emission type depending on the materials used.

The heterocyclic compound according to one embodiment of the present specification can also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Intermediate E

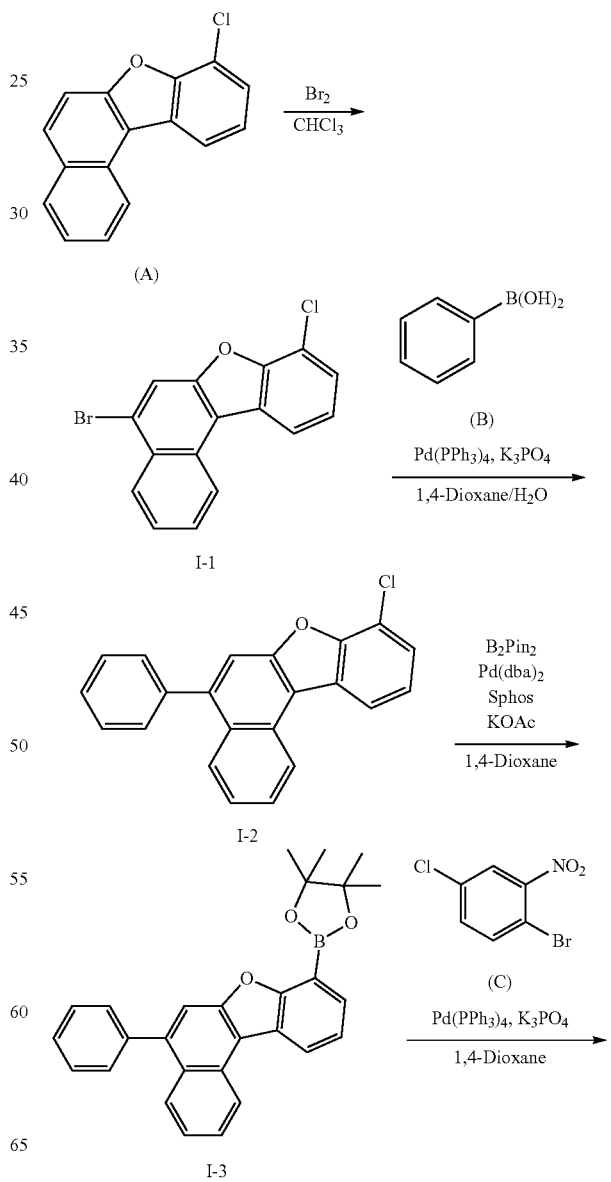

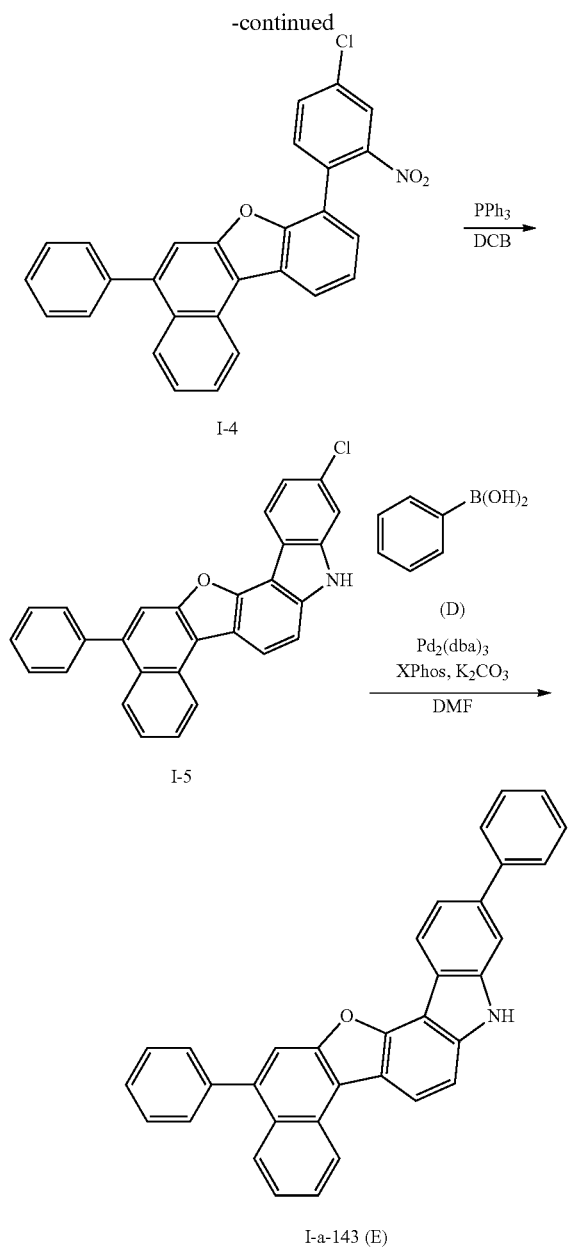

1) Preparation of Compound I-1

After dissolving 8-chloronaphtho[2,1-b]benzofuran (20 g, 79.14 mmol) in CHCl$_3$ (200 mL), bromine (4 mL, 79.14 mmol) was slowly added dropwise thereto at 0° C. After approximately 10 minutes, the temperature was raised to room temperature, and the mixture was stirred for 4 hours. The mixture solution completed with the reaction was dissolved in methylene chloride (MC) and extracted with a Na$_2$S$_2$O$_3$ 1 M solution, and the organic layer was dried with anhydrous MgSO$_4$ and then silica gel filtered. The solvent of the filtered filtrate was removed using a rotary evaporator to obtain white solid Compound I-1 (25 g) in a 96% yield.

2) Preparation of Compound I-2

After dissolving Compound I-1 (25 g, 75.39 mmol), phenylboronic acid (9.2 g, 75.39 mmol), Pd(PPh$_3$)$_4$ (tetrakis(triphenylphosphine)palladium(0)) (4.3 g, 3.77 mmol) and K$_3$PO$_4$ (32 g, 150.78 mmol) in 1,4-dioxane/H$_2$O (200 mL/50 mL), the result was stirred for 4 hours at 100° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator to obtain yellow oil Compound I-2 (23 g) in a 93% yield.

When the functional group of Intermediate B is an amine group, the compound was prepared using the following preparation method 2-1.

2-1) After dissolving Compound I-1 (10 g, 30.15 mmol), diphenylamine (5.1 g, 30.15 mmol), Pd$_2$(dba)$_3$ (tris(dibenzylideneacetone)dipalladium(0)) (2.7 g, 3.01 mmol), XPhos (2-dicyclohexylphosphino-2',4',6'-triisopropylbiphenyl) (2.8 g, 6.03 mmol) and NaOtBu (5.8 g, 60.31 mmol) in xylene (150 mL), the result was stirred for 17 hours at 100° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator, and the result was passed through column chromatography <MC/Hex (hexane)=1/1> to obtain ivory solid (6.6 g) in a 53% yield.

3) Preparation of Compound I-3

After dissolving Compound I-2 (23 g, 69.95 mmol), bis(pinacolato)diboron (36 g, 139.91 mmol), Pd(dba)$_2$ (bis(dibenzylideneacetone)palladium(0)) (4 g, 6.99 mmol), SPhos (2-dicyclohexylphosphino-2',6'-dimethoxybiphenyl) (5.7 g, 13.99 mmol) and KOAc (potassium acetate) (205 g, 209.85 mmol) in 1,4-dioxane (0.4 L), the result was stirred for 15 hours at 100° C. The mixture solution completed with the reaction was concentrated, then dissolved in methylene chloride (MC) and extracted with water, and the organic layer was dried with anhydrous MgSO$_4$ and then silica gel filtered. The solvent of the filtered filtrate was removed using a rotary evaporator, and brown solid Compound I-3 was obtained in a crude state without a separate purification process.

4) Preparation of Compound I-4

After dissolving Compound I-3 (crude, 69.95 mmol), 2-bromonitrobenzene (14 g, 69.95 mmol), Pd(PPh$_3$)$_4$ (4 g, 3.49 mmol) and K$_3$PO$_4$ (29 g, 139.9 mmol) in 1,4-dioxane/H$_2$O (600 mL/120 mL), the result was stirred for 16 hours at 100° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator, and the result was passed through column chromatography <MC/Hex=½> to obtain yellow solid Compound I-4 (15 g) in a 52% yield.

5) Preparation of Compound I-5

After dissolving Compound I-4 (15 g, 36.11 mmol) in dichlorobenzene (DCB), PPh$_3$ (19 g, 72.21 mmol) was introduced thereto, and the result was stirred for 20 hours at 180° C. The mixture solution completed with the reaction was dissolved in methylene chloride (MC) and extracted with water, and the organic layer was dried with anhydrous MgSO$_4$ and silica gel filtered. The solvent of the filtered filtrate was removed using a high-pressure rotary evaporator, and the result was passed through column chromatography <MC/Hex=1/1> to obtain white solid Compound I-5 (10.6 g) in a 77% yield.

6) Preparation of Compound I-a-143

After dissolving Compound I-5 (10 g, 75.39 mmol), phenylboronic acid (9.2 g, 75.39 mmol), Pd$_2$(dba)$_3$ (6.8 g, 7.54 mmol), XPhos (7.2 g, 15.08 mmol) and K$_2$CO$_3$ (21 g, 150.78 mmol) in DMF (150 mL), the result was stirred for 15 hours at 100° C. After the reaction was completed, precipitated solids were filtered, and washed with H₂O and methanol. The filtered solids were dried, dissolved in an excess amount of hot chloroform solvent, and silica gel filtered. The solvent of the filtered filtrate was removed using a rotary evaporator, the result was precipitated using acetone, and the precipitates were filtered to obtain ivory solid Compound I-a-143 (5.7 g) in a 62% yield.

When the functional group of Intermediate D is an amine group, the compound was prepared using the following preparation method 6-1.

6-1) Preparation of Compound I-a-142

After dissolving Compound I-5 (7 g, 16.75 mmol), diphenylamine (5.6 g, 33.51 mmol), Pd₂(dba)₃ (1.5 g, 1.67 mmol), XPhos (1.6 g, 3.35 mmol) and NaOH (1.3 g, 33.51 mmol) in xylene (100 mL), the result was stirred for 16 hours at 100° C. After the reaction was completed, precipitated solids were filtered, and washed with H₂O and methanol. The filtered solids were dried, dissolved in an excess amount of hot chloroform solvent, and silica gel filtered. The solvent of the filtered filtrate was removed using a rotary evaporator, the result was precipitated using acetone, and the precipitates were filtered to obtain yellow solid Compound I-a-142 (5.7 g) in a 62% yield.

The following Compound E was synthesized in the same manner as in Preparation Example 1 except that A, B, C and D of the following Table 1 were used as intermediates.

TABLE 1

| Compound | Intermediate A | Intermediate B | Intermediate C | Intermediate D | Compound E |
|---|---|---|---|---|---|
| I-a-1 | 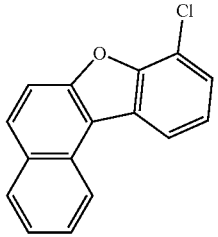 [SMILES: Clc1cccc2c1oc1ccc3ccccc3c12] | 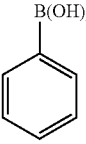 | 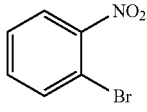 | — | 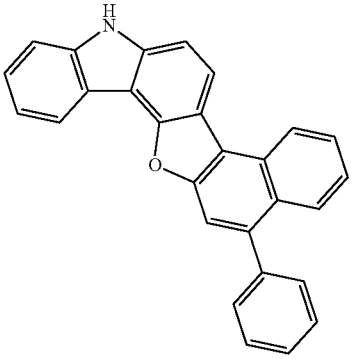 [SMILES: c1ccc(-c2cc3oc4c(ccc5[nH]c6ccccc6c54)c3c3ccccc23)cc1] |
| I-a-6 | 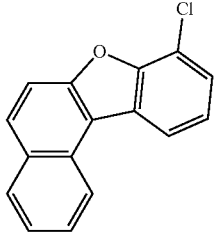 [SMILES: Clc1cccc2c1oc1ccc3ccccc3c12] | 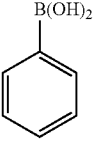 | 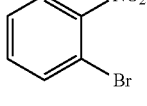 | — | 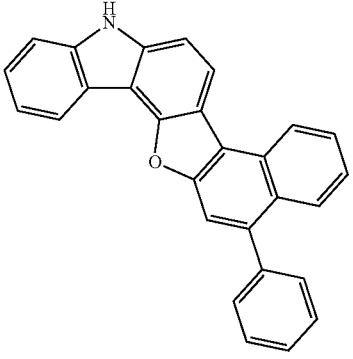 [SMILES: c1ccc(-c2cc3oc4c(ccc5[nH]c6ccccc6c54)c3c3ccccc23)cc1] |
| I-a-8 | 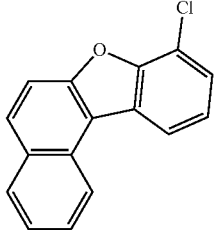 [SMILES: Clc1cccc2c1oc1ccc3ccccc3c12] | 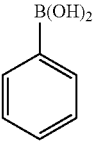 | 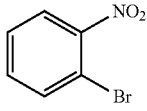 | — | 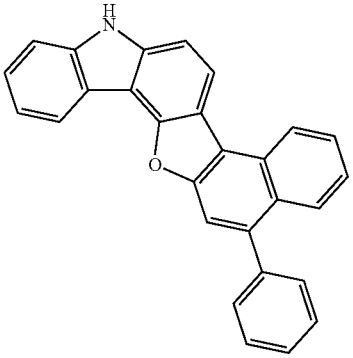 [SMILES: c1ccc(-c2cc3oc4c(ccc5[nH]c6ccccc6c54)c3c3ccccc23)cc1] |

TABLE 1-continued
| Compound | Intermediate A | Intermediate B | Intermediate C | Intermediate D | Compound E |
|---|---|---|---|---|---|
| I-a-16 | 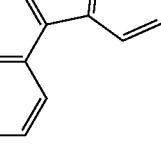 | 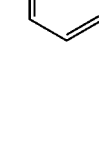 |  | — | 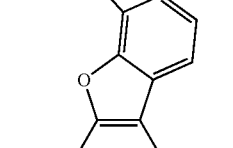 |
| I-a-26 | 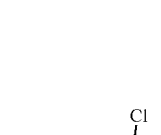 | 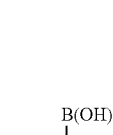 | 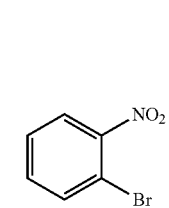 | — | 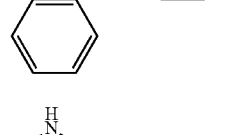 |
| I-a-30 | 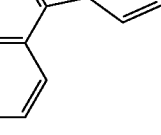 |  |  | — | 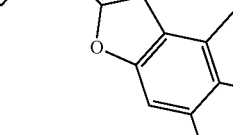 |
| I-a-33 | 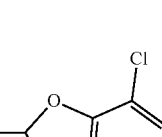 | 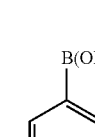 | 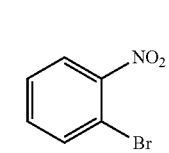 | — | 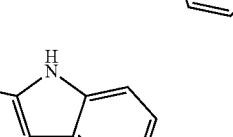 |

TABLE 1-continued
| Compound | Intermediate A | Intermediate B | Intermediate C | Intermediate D | Compound E |
|---|---|---|---|---|---|
| I-a-42 | 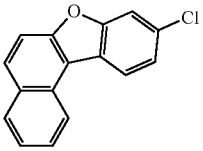 [SMILES: Clc1ccc2c(c1)oc1ccc3ccccc3c12] | 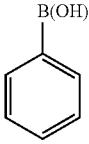 | 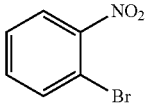 | — | 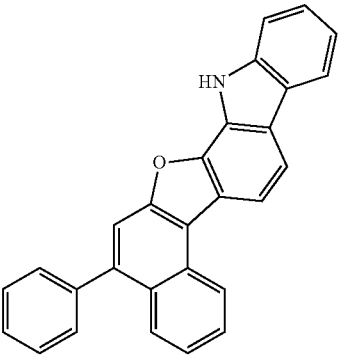 [SMILES: c1ccc(-c2cc3oc4c(ccc5c6ccccc6[nH]c54)c3c3ccccc23)cc1] |
| I-a-46 | 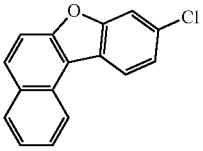 [SMILES: Clc1ccc2c(c1)oc1ccc3ccccc3c12] | 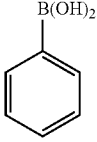 | 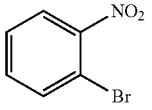 | — | 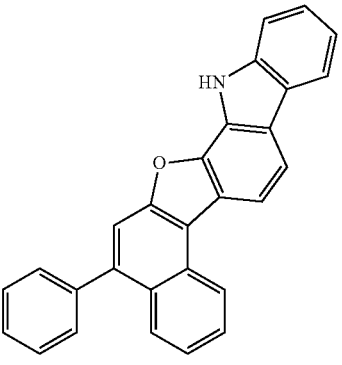 [SMILES: c1ccc(-c2cc3oc4c(ccc5c6ccccc6[nH]c54)c3c3ccccc23)cc1] |
| I-a-49 | 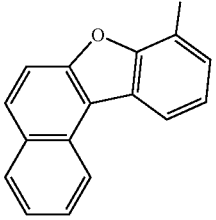 | 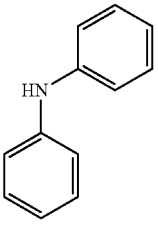 [SMILES: c1ccc(Nc2ccccc2)cc1] | 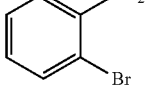 | — | 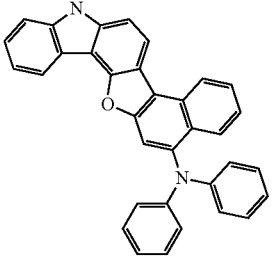 |
| I-a-55 | 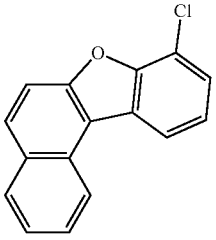 [SMILES: Clc1cccc2c1oc1ccc3ccccc3c12] | 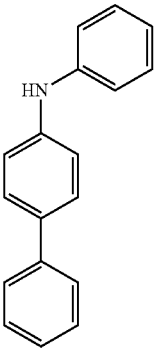 [SMILES: c1ccc(Nc2ccc(-c3ccccc3)cc2)cc1] | 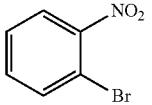 | — | 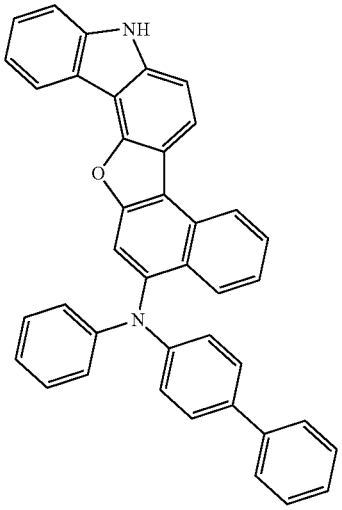 [SMILES: c1ccc(-c2ccc(N(c3ccccc3)c3cc4oc5c(ccc6[nH]c7ccccc7c65)c4c4ccccc34)cc2)cc1] |

TABLE 1-continued

| Compound | Intermediate A | Intermediate B | Intermediate C | Intermediate D | Compound E |
|---|---|---|---|---|---|
| I-a-71 | | | | — | |
| I-a-90 | | | | — | |
| I-a-104 | | | | — | |
| I-a-109 | | — | | — | |
| I-a-112 | | | | — | |

TABLE 1-continued

| Compound | Intermediate A | Intermediate B | Intermediate C | Intermediate D | Compound E |
|---|---|---|---|---|---|
| I-a-115 | | — | | — | |
| I-a-119 | | | | — | |
| I-a-131 | | | | — | |
| I-a-134 | | — | | — | |
| I-a-136 | | — | | — | |

TABLE 1-continued

| Compound | Intermediate A | Intermediate B | Intermediate C | Intermediate D | Compound E |
|---|---|---|---|---|---|
| I-a-142 | | — | | | |
| I-a-143 | | | | | |
| I-a-144 | | | | | |
| I-a-149 | | — | | | |
| I-a-152 | | | | | |

TABLE 1-continued
| Compound | Intermediate A | Intermediate B | Intermediate C | Intermediate D | Compound E |
|---|---|---|---|---|---|
| I-a-157 | 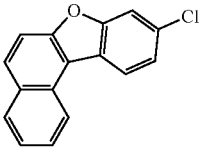 [SMILES: Clc1ccc2c(c1)oc1ccc3ccccc3c12] | — | 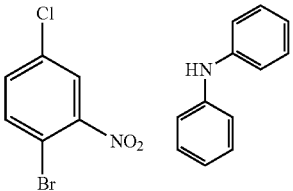 | 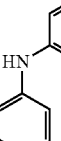 | 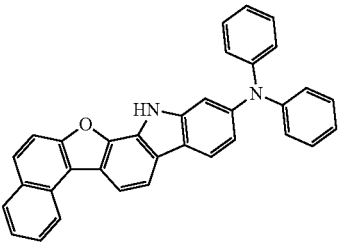 [SMILES: c1ccc(N(c2ccccc2)c2ccc3c(c2)[nH]c2c3ccc3c2oc2ccc4ccccc4c23)cc1] |
| I-b-4 | 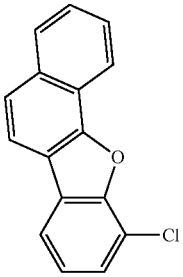 [SMILES: Clc1cccc2c1oc1c3ccccc3ccc21] | 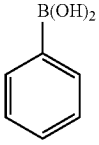 | 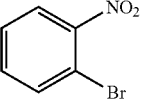 | — | 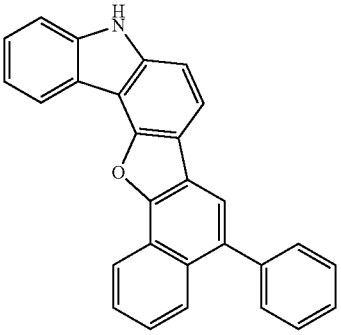 [SMILES: c1ccc(-c2cc3c4ccc5[nH]c6ccccc6c5c4oc3c3ccccc23)cc1] |
| I-b-7 | 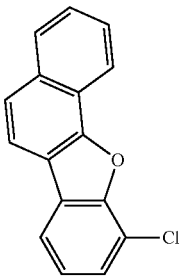 [SMILES: Clc1cccc2c1oc1c3ccccc3ccc21] | 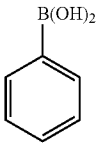 | 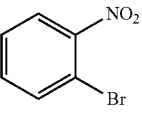 | — | 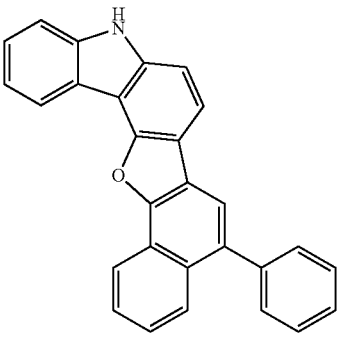 [SMILES: c1ccc(-c2cc3c4ccc5[nH]c6ccccc6c5c4oc3c3ccccc23)cc1] |
| I-b-10 | 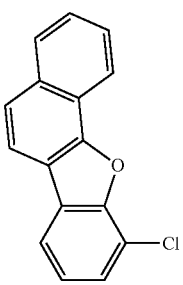 [SMILES: Clc1cccc2c1oc1c3ccccc3ccc21] | 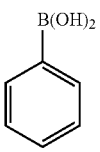 | 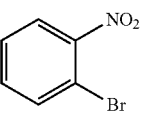 | — | 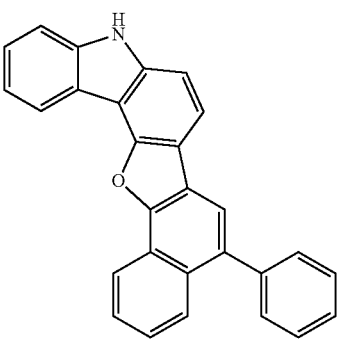 [SMILES: c1ccc(-c2cc3c4ccc5[nH]c6ccccc6c5c4oc3c3ccccc23)cc1] |

TABLE 1-continued

| Compound | Intermediate A | Intermediate B | Intermediate C | Intermediate D | Compound E |
|---|---|---|---|---|---|
| I-b-15 | | B(OH)₂ | NO₂, Br | — | |
| I-b-23 | | B(OH)₂ | NO₂, Br | — | |
| I-b-32 | | HN(Ph)₂ | NO₂, Br | — | |
| I-b-35 | | HN(Ph)₂ | NO₂, Br | — | |

TABLE 1-continued
| Compound | Intermediate A | Intermediate B | Intermediate C | Intermediate D | Compound E |
|---|---|---|---|---|---|
| I-b-44 |  |  |  | — |  |
| I-b-50 |  | 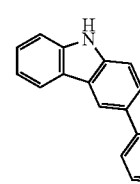 | 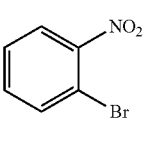 | — | 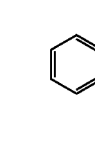 |
| I-b-57 | 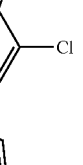 |  |  | — |  |
| I-b-65 |  | 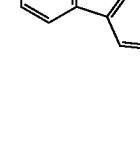 |  | — |  |
| I-b-69 |  | 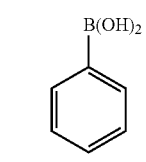 | 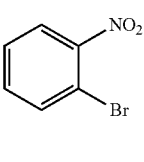 | — |  |

TABLE 1-continued
| Compound | Intermediate A | Intermediate B | Intermediate C | Intermediate D | Compound E |
|---|---|---|---|---|---|
| I-b-75 | 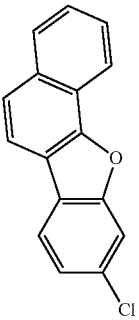 [SMILES: Clc1ccc2c(c1)oc1c3ccccc3ccc21] | 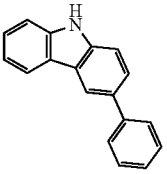 [SMILES: c1ccc(-c2ccc3[nH]c4ccccc4c3c2)cc1] | 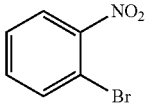 | — | 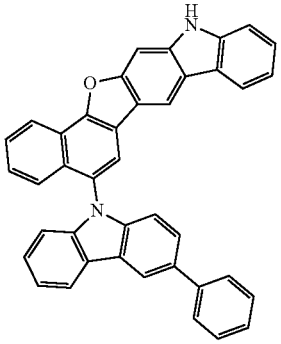 [SMILES: c1ccc(-c2ccc3c(c2)c2ccccc2n3-c2cc3c4cc5c(cc4oc3c3ccccc23)[nH]c2ccccc25)cc1] |
| I-b-77 | 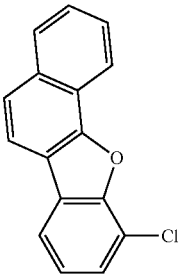 | — | 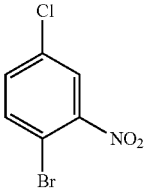 | 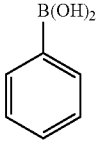 | 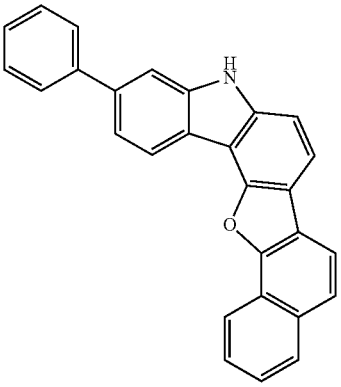 [SMILES: c1ccc(-c2ccc3c(c2)[nH]c2ccc4c5ccc6ccccc6c5oc4c23)cc1] |
| I-b-81 | 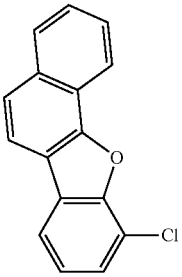 | 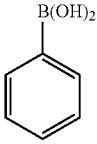 | 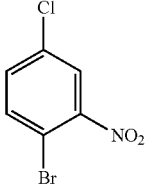 | 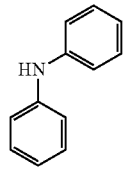 | 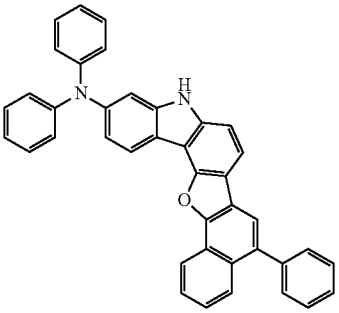 [SMILES: c1ccc(-c2cc3c4ccc5[nH]c6cc(N(c7ccccc7)c7ccccc7)ccc6c5c4oc3c3ccccc23)cc1] |

TABLE 1-continued
| Compound | Intermediate A | Intermediate B | Intermediate C | Intermediate D | Compound E |
|---|---|---|---|---|---|
| I-b-84 | | — | | | |
| I-b-91 | | | | | |
[Preparation Example 2] Preparation of Target Compound
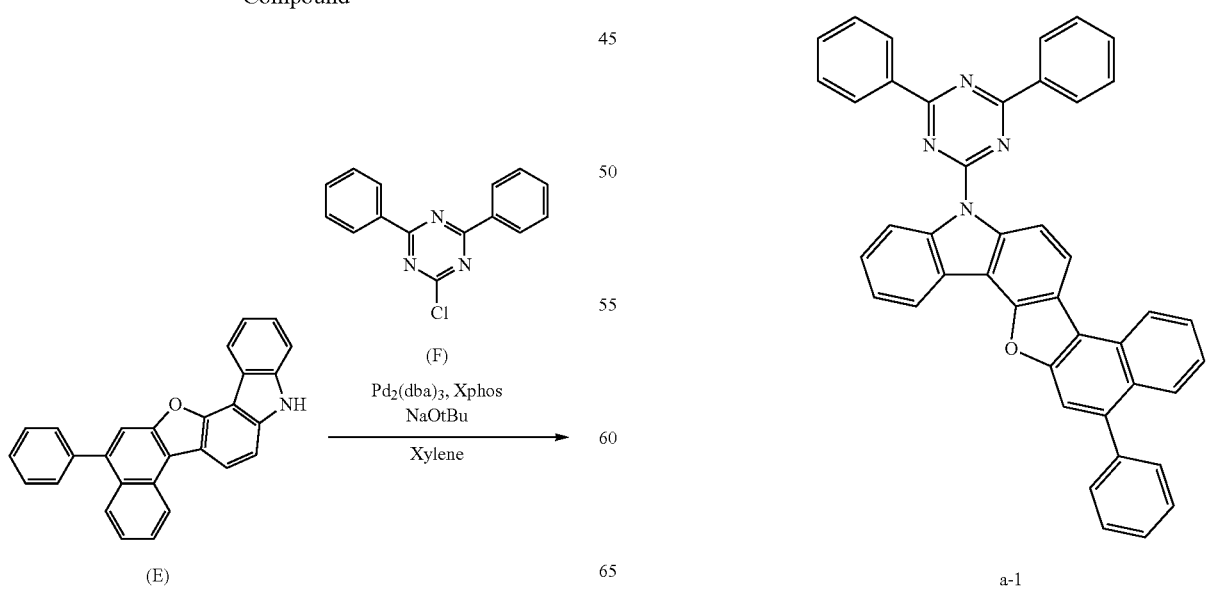

1) Preparation of Compound a-1

After dissolving Compound I-a-1 (4 g, 10.43 mmol), 2-chloro-4,6-diphenyl-1,3,5-triazine (2.8 g, 10.43 mmol), Pd$_2$(dba)$_3$ (955 mg, 1.04 mmol), XPhos (994 mg, 2.09 mmol) and NaOtBu (2 g, 20.86 mmol) in xylene (50 mL), the result was stirred for 15 hours at 100° C. After the reaction was completed, precipitated solids were filtered, and washed with H$_2$O and methanol. The filtered solids were dried, dissolved in an excess amount of hot 1,2-dichlorobenzene solvent, and silica gel filtered. The solvent of the filtered filtrate was removed using a rotary evaporator, the result was precipitated using acetone, and the precipitates were filtered to obtain yellow solid Compound a-1 (3.5 g) in a 54% yield.

The following target compounds were synthesized in the same manner as in the preparation of a-1 in Preparation Example 2 except that E and F of the following Table 2 were used as intermediates.

TABLE 2

| Compound | Intermediate F | Intermediate E | Target Compound | Yield |
|---|---|---|---|---|
| a-1 | 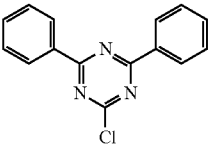 [SMILES: Clc1nc(-c2ccccc2)nc(-c2ccccc2)n1] | 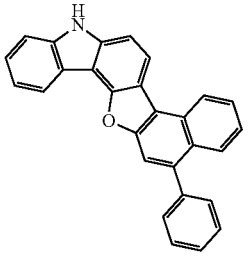 [SMILES: c1ccc(-c2cc3oc4c(ccc5[nH]c6ccccc6c54)c3c3ccccc23)cc1] | 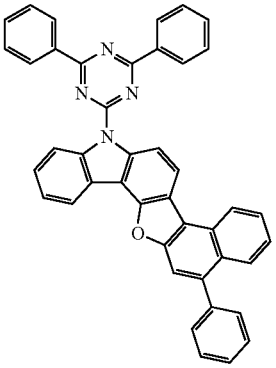 [SMILES: c1ccc(-c2nc(-c3ccccc3)nc(-n3c4ccccc4c4c5oc6cc(-c7ccccc7)c7ccccc7c6c5ccc43)n2)cc1] | 54% |
| a-6 | 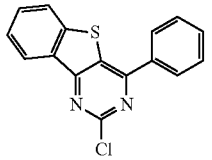 [SMILES: Clc1nc(-c2ccccc2)c2sc3ccccc3c2n1] | 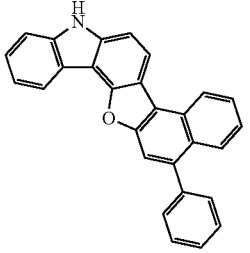 [SMILES: c1ccc(-c2cc3oc4c(ccc5[nH]c6ccccc6c54)c3c3ccccc23)cc1] | 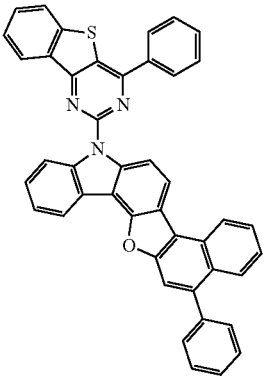 [SMILES: c1ccc(-c2cc3oc4c(ccc5c4c4ccccc4n5-c4nc(-c5ccccc5)c5sc6ccccc6c5n4)c3c3ccccc23)cc1] | 46% |
| a-8 | 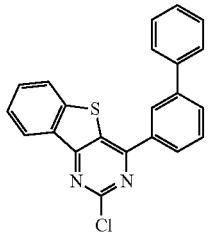 [SMILES: Clc1nc(-c2cccc(-c3ccccc3)c2)c2sc3ccccc3c2n1] | 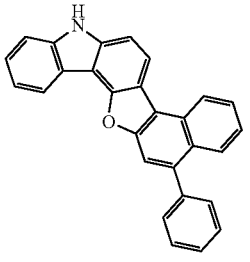 [SMILES: c1ccc(-c2cc3oc4c(ccc5[nH]c6ccccc6c54)c3c3ccccc23)cc1] | 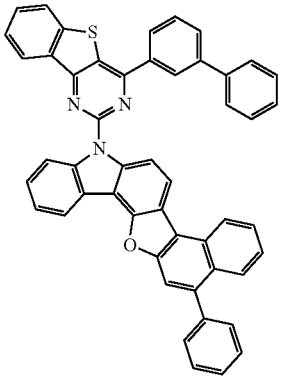 [SMILES: c1ccc(-c2cccc(-c3nc(-n4c5ccccc5c5c6oc7cc(-c8ccccc8)c8ccccc8c7c6ccc54)nc4c3sc3ccccc34)c2)cc1] | 39% |

TABLE 2-continued
| Compound | Intermediate F | Intermediate E | Target Compound | Yield |
|---|---|---|---|---|
| a-16 | 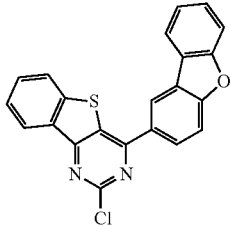 [SMILES: Clc1nc(-c2ccc3oc4ccccc4c3c2)c2sc3ccccc3c2n1] | 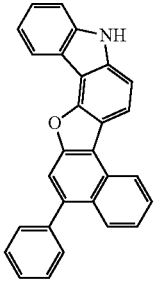 [SMILES: c1ccc(-c2cc3oc4c(ccc5[nH]c6ccccc6c54)c3c3ccccc23)cc1] | 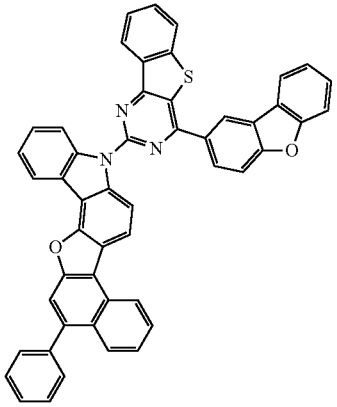 [SMILES: c1ccc(-c2cc3oc4c(ccc5c4c4ccccc4n5-c4nc(-c5ccc6oc7ccccc7c6c5)c5sc6ccccc6c5n4)c3c3ccccc23)cc1] | 51% |
| a-26 | 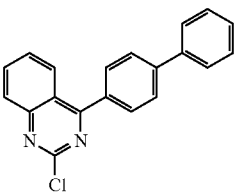 [SMILES: Clc1nc(-c2ccc(-c3ccccc3)cc2)c2ccccc2n1] | 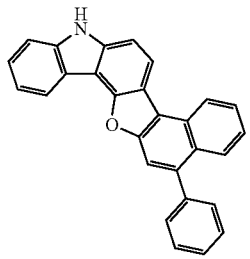 [SMILES: c1ccc(-c2cc3oc4c(ccc5[nH]c6ccccc6c54)c3c3ccccc23)cc1] | 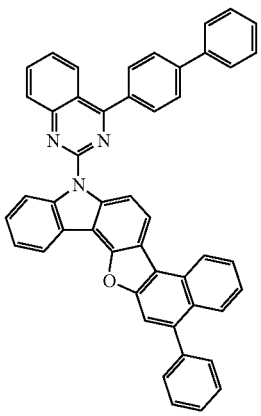 [SMILES: c1ccc(-c2ccc(-c3nc(-n4c5ccccc5c5c6oc7cc(-c8ccccc8)c8ccccc8c7c6ccc54)nc4ccccc34)cc2)cc1] | 49% |
| a-30 |  | 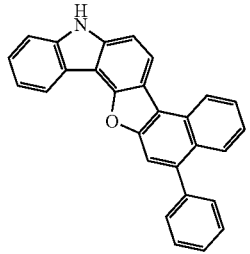 [SMILES: c1ccc(-c2cc3oc4c(ccc5[nH]c6ccccc6c54)c3c3ccccc23)cc1] | 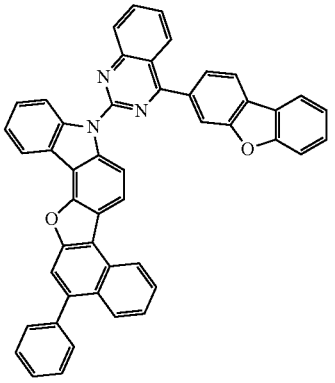 [SMILES: c1ccc(-c2cc3oc4c(ccc5c4c4ccccc4n5-c4nc(-c5ccc6c(c5)oc5ccccc56)c5ccccc5n4)c3c3ccccc23)cc1] | 50% |
| a-33 | 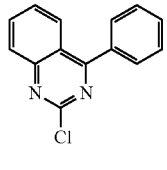 | 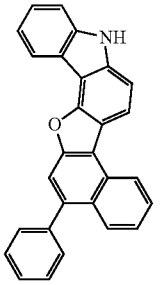 [SMILES: c1ccc(-c2cc3oc4c(ccc5[nH]c6ccccc6c54)c3c3ccccc23)cc1] | 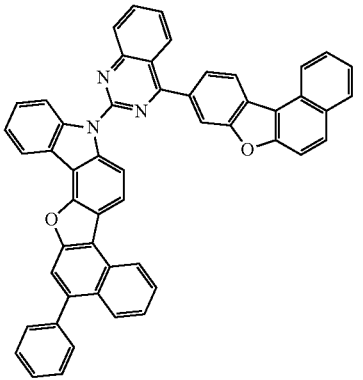 [SMILES: c1ccc(-c2cc3oc4c(ccc5c4c4ccccc4n5-c4nc(-c5ccc6c(c5)oc5ccc7ccccc7c56)c5ccccc5n4)c3c3ccccc23)cc1] | 41% |

TABLE 2-continued
| Compound | Intermediate F | Intermediate E | Target Compound | Yield |
|---|---|---|---|---|
| a-42 | 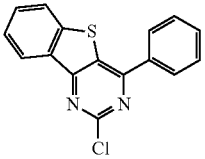 [SMILES: Clc1nc(-c2ccccc2)c2sc3ccccc3c2n1] | 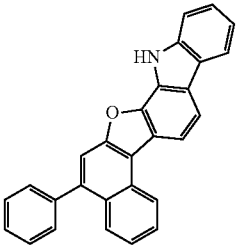 [SMILES: c1ccc(-c2cc3oc4c(ccc5c6ccccc6[nH]c54)c3c3ccccc23)cc1] | 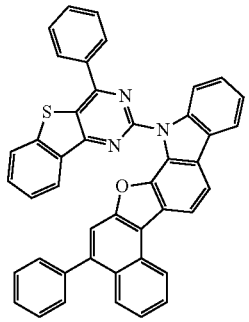 [SMILES: c1ccc(-c2cc3oc4c(ccc5c6ccccc6n(-c6nc(-c7ccccc7)c7sc8ccccc8c7n6)c54)c3c3ccccc23)cc1] | 52% |
| a-46 | 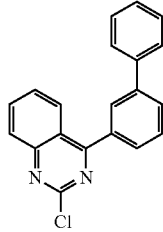 [SMILES: Clc1nc(-c2cccc(-c3ccccc3)c2)c2ccccc2n1] | 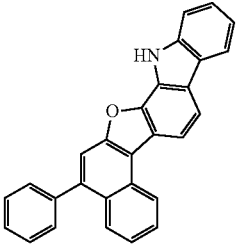 [SMILES: c1ccc(-c2cc3oc4c(ccc5c6ccccc6[nH]c54)c3c3ccccc23)cc1] | 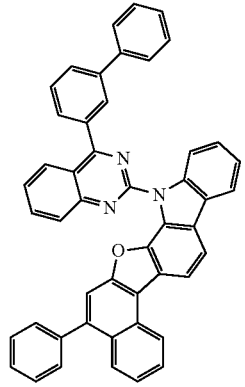 [SMILES: c1ccc(-c2cccc(-c3nc(-n4c5ccccc5c5ccc6c(oc7cc(-c8ccccc8)c8ccccc8c76)c54)nc4ccccc34)c2)cc1] | 66% |
| a-49 |  | 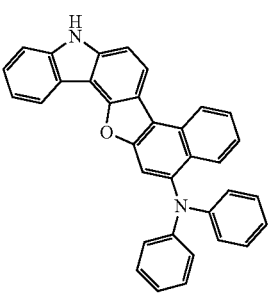 [SMILES: c1ccc(N(c2ccccc2)c2cc3oc4c(ccc5[nH]c6ccccc6c54)c3c3ccccc23)cc1] | 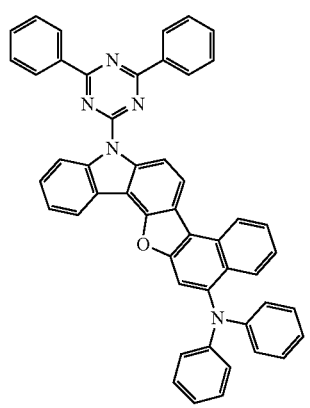 [SMILES: c1ccc(-c2nc(-c3ccccc3)nc(-n3c4ccccc4c4c5oc6cc(N(c7ccccc7)c7ccccc7)c7ccccc7c6c5ccc43)n2)cc1] | 58% |
| a-55 | 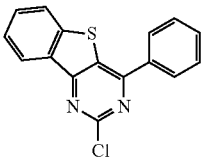 [SMILES: Clc1nc(-c2ccccc2)c2sc3ccccc3c2n1] | 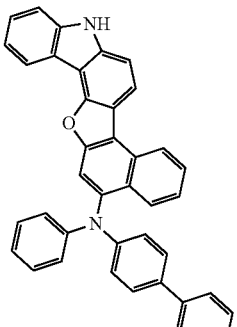 | 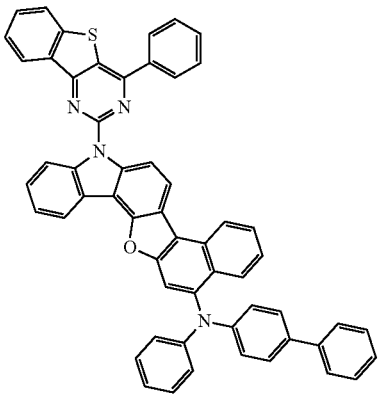 [SMILES: c1ccc(-c2ccc(N(c3ccccc3)c3cc4oc5c(ccc6c5c5ccccc5n6-c5nc(-c6ccccc6)c6sc7ccccc7c6n5)c4c4ccccc34)cc2)cc1] | 40% |

TABLE 2-continued
| Compound | Intermediate F | Intermediate E | Target Compound | Yield |
|---|---|---|---|---|
| a-71 | 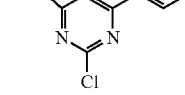 | 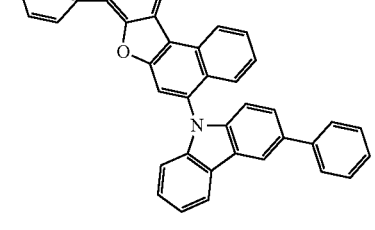 | 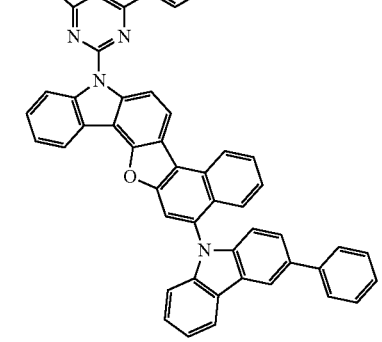 | 36% |
| a-90 | 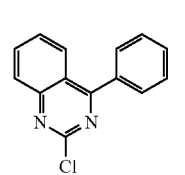 | 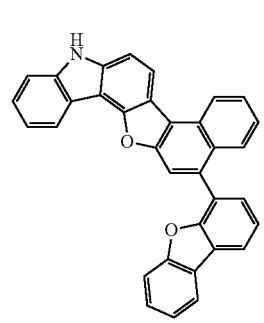 [SMILES: c1ccc2c(c1)[nH]c1ccc3c(oc4cc(-c5cccc6c5oc5ccccc56)c5ccccc5c43)c12] | 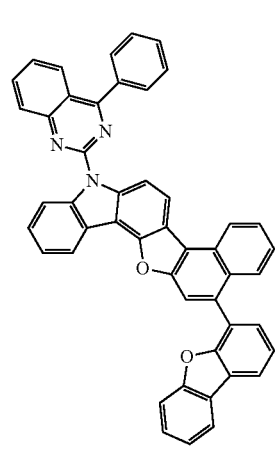 [SMILES: c1ccc(-c2nc(-n3c4ccccc4c4c5oc6cc(-c7cccc8c7oc7ccccc78)c7ccccc7c6c5ccc43)nc3ccccc23)cc1] | 42% |
| a-104 | 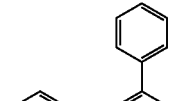 | 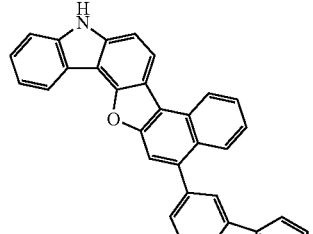 | 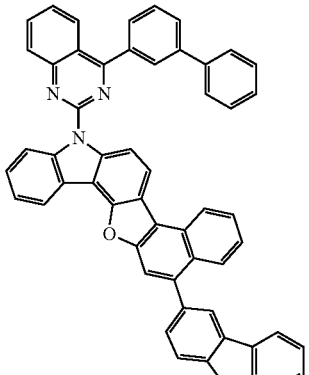 | 44% |

TABLE 2-continued
| Compound | Intermediate F | Intermediate E | Target Compound | Yield |
|---|---|---|---|---|
| a-109 | 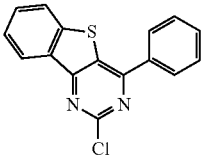 [SMILES: Clc1nc(-c2ccccc2)c2sc3ccccc3c2n1] | 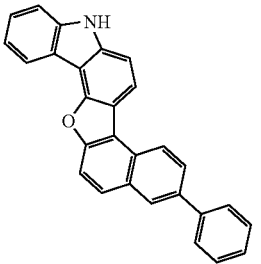 [SMILES: c1ccc(-c2ccc3c(ccc4oc5c(ccc6[nH]c7ccccc7c65)c43)c2)cc1] | 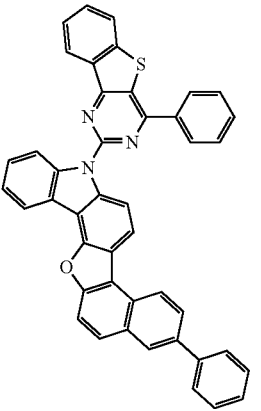 [SMILES: c1ccc(-c2ccc3c(ccc4oc5c(ccc6c5c5ccccc5n6-c5nc(-c6ccccc6)c6sc7ccccc7c6n5)c43)c2)cc1] | 42% |
| a-112 | 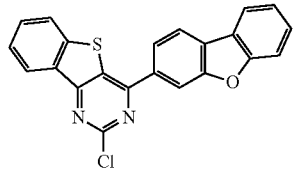 [SMILES: Clc1nc(-c2ccc3c(c2)oc2ccccc23)c2sc3ccccc3c2n1] | 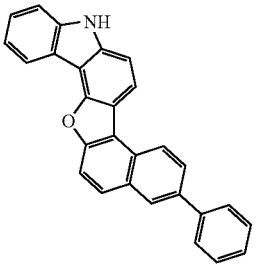 [SMILES: c1ccc(-c2ccc3c(ccc4oc5c(ccc6[nH]c7ccccc7c65)c43)c2)cc1] | 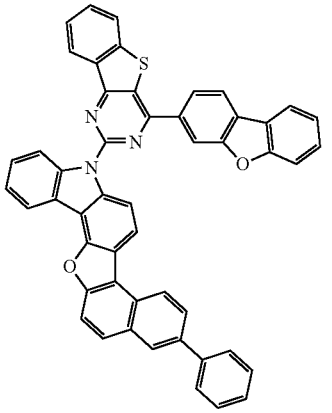 [SMILES: c1ccc(-c2ccc3c(ccc4oc5c(ccc6c5c5ccccc5n6-c5nc(-c6ccc7c(c6)oc6ccccc67)c6sc7ccccc7c6n5)c43)c2)cc1] | 55% |
| a-115 | 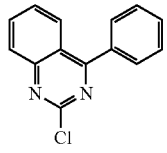 | 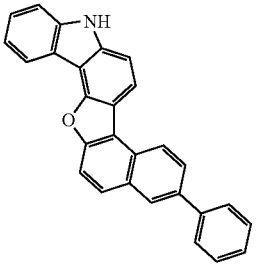 [SMILES: c1ccc(-c2ccc3c(ccc4oc5c(ccc6[nH]c7ccccc7c65)c43)c2)cc1] | 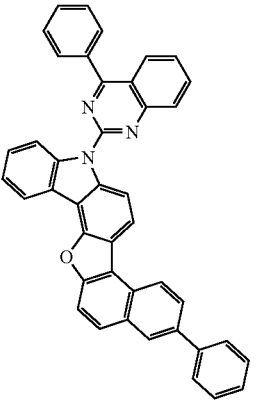 [SMILES: c1ccc(-c2ccc3c(ccc4oc5c(ccc6c5c5ccccc5n6-c5nc(-c6ccccc6)c6ccccc6n5)c43)c2)cc1] | 53% |

TABLE 2-continued

| Compound | Intermediate F | Intermediate E | Target Compound | Yield |
| --- | --- | --- | --- | --- |
| a-119 | | | | 50% |
| a-131 | | | | 45% |
| a-134 | | | | 63% |
| a-136 | | | | 66% |

TABLE 2-continued
| Compound | Intermediate F | Intermediate E | Target Compound | Yield |
|---|---|---|---|---|
| a-142 | 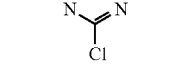 | 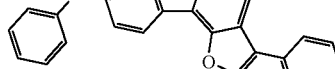 | 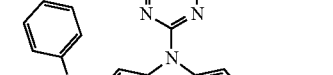 | 56% |
| a-143 | 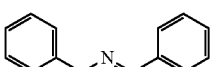 |  | 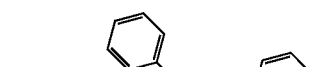 | 47% |
| a-144 | 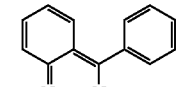 | 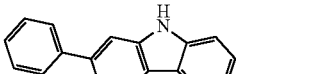 | 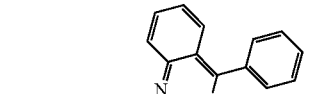 | 54% |
| a-149 | 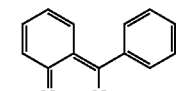 | 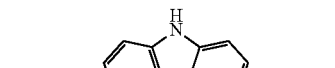 | 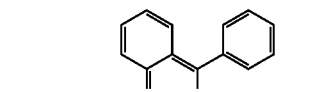 | 50% |

TABLE 2-continued

| Compound | Intermediate F | Intermediate E | Target Compound | Yield |
|---|---|---|---|---|
| a-152 | | | | 42% |
| a-157 | | | | 48% |
| b-4 | | | | 50% |
| b-7 | | | | 55% |

TABLE 2-continued

| Compound | Intermediate F | Intermediate E | Target Compound | Yield |
|---|---|---|---|---|
| b-10 | | | | 49% |
| b-15 | | | | 60% |
| b-23 | | | | 54% |

TABLE 2-continued

| Compound | Intermediate F | Intermediate E | Target Compound | Yield |
|---|---|---|---|---|
| b-32 | | | | 52% |
| b-35 | | | | 49% |
| b-44 | | | | 50% |

TABLE 2-continued
| Compound | Intermediate F | Intermediate E | Target Compound | Yield |
|---|---|---|---|---|
| b-50 | 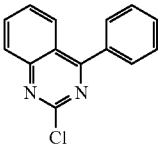 | 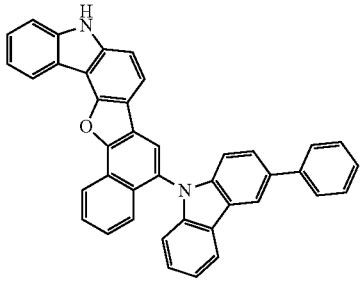 [SMILES: c1ccc(-c2ccc3c(c2)c2ccccc2n3-c2cc3c4ccc5[nH]c6ccccc6c5c4oc3c3ccccc23)cc1] | 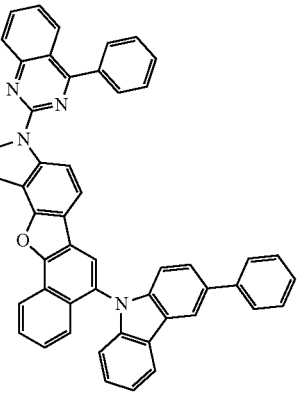 | 44% |
| b-57 | 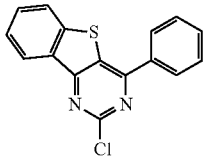 [SMILES: Clc1nc(-c2ccccc2)c2sc3ccccc3c2n1] | 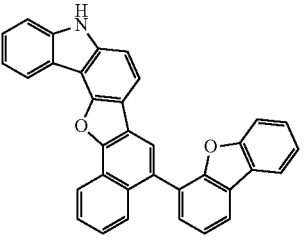 [SMILES: c1ccc2c(c1)[nH]c1ccc3c4cc(-c5cccc6c5oc5ccccc56)c5ccccc5c4oc3c12] | 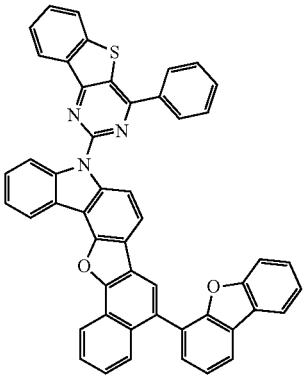 [SMILES: c1ccc(-c2nc(-n3c4ccccc4c4c5oc6c7ccccc7c(-c7cccc8c7oc7ccccc78)cc6c5ccc43)nc3c2sc2ccccc23)cc1] | 60% |
| b-65 | 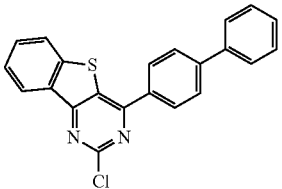 [SMILES: Clc1nc(-c2ccc(-c3ccccc3)cc2)c2sc3ccccc3c2n1] | 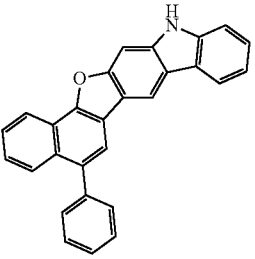 [SMILES: c1ccc(-c2cc3c4cc5c(cc4oc3c3ccccc23)[nH]c2ccccc25)cc1] | 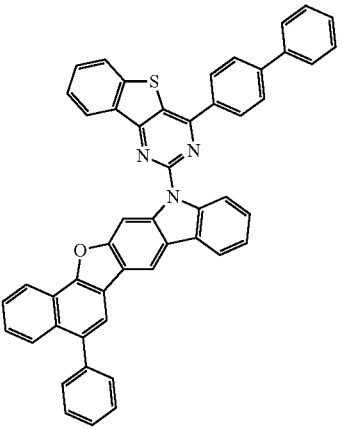 [SMILES: c1ccc(-c2ccc(-c3nc(-n4c5ccccc5c5cc6c(cc54)oc4c5ccccc5c(-c5ccccc5)cc64)nc4c3sc3ccccc34)cc2)cc1] | 57% |
| b-69 |  | 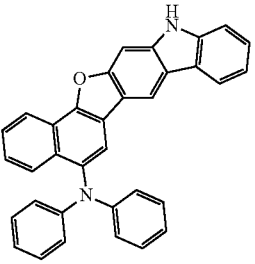 [SMILES: c1ccc(N(c2ccccc2)c2cc3c4cc5c(cc4oc3c3ccccc23)[nH]c2ccccc25)cc1] | 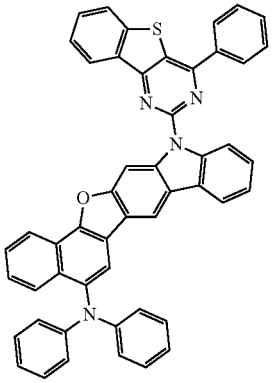 [SMILES: c1ccc(-c2nc(-n3c4ccccc4c4cc5c(cc43)oc3c4ccccc4c(N(c4ccccc4)c4ccccc4)cc53)nc3c2sc2ccccc23)cc1] | 40% |

TABLE 2-continued
| Compound | Intermediate F | Intermediate E | Target Compound | Yield |
|---|---|---|---|---|
| b-75 | 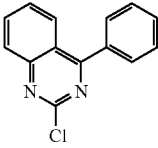 | 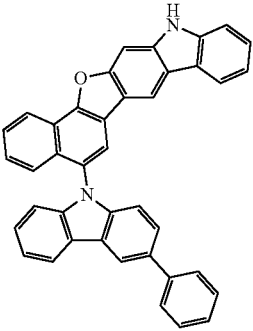 [SMILES: c1ccc(-c2ccc3c(c2)c2ccccc2n3-c2cc3c4cc5c(cc4oc3c3ccccc23)[nH]c2ccccc25)cc1] | 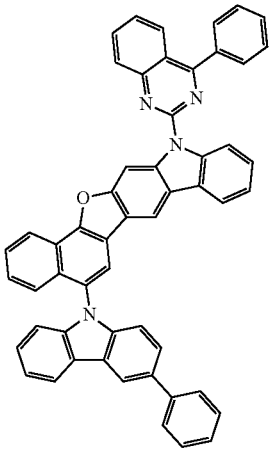 [SMILES: c1ccc(-c2ccc3c(c2)c2ccccc2n3-c2cc3c4cc5c6ccccc6n(-c6nc(-c7ccccc7)c7ccccc7n6)c5cc4oc3c3ccccc23)cc1] | 44% |
| b-77 | 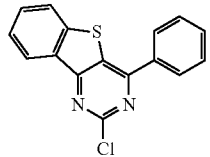 [SMILES: Clc1nc(-c2ccccc2)c2sc3ccccc3c2n1] | 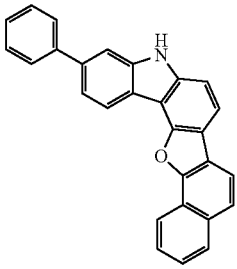 [SMILES: c1ccc(-c2ccc3c(c2)[nH]c2ccc4c5ccc6ccccc6c5oc4c23)cc1] | 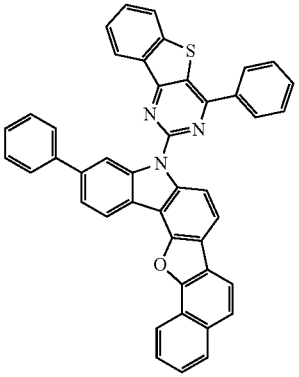 [SMILES: c1ccc(-c2ccc3c4c5oc6c7ccccc7ccc6c5ccc4n(-c4nc(-c5ccccc5)c5sc6ccccc6c5n4)c3c2)cc1] | 59% |
| b-81 | 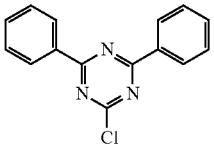 [SMILES: Clc1nc(-c2ccccc2)nc(-c2ccccc2)n1] | 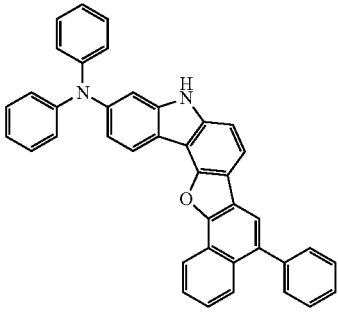 [SMILES: c1ccc(-c2cc3c4ccc5[nH]c6cc(N(c7ccccc7)c7ccccc7)ccc6c5c4oc3c3ccccc23)cc1] | 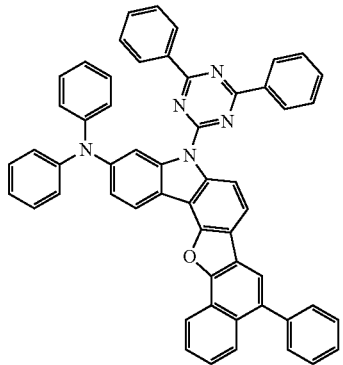 [SMILES: c1ccc(-c2nc(-c3ccccc3)nc(-n3c4cc(N(c5ccccc5)c5ccccc5)ccc4c4c5oc6c7ccccc7c(-c7ccccc7)cc6c5ccc43)n2)cc1] | 43% |

TABLE 2-continued
| Compound | Intermediate F | Intermediate E | Target Compound | Yield |
|---|---|---|---|---|
| b-84 | 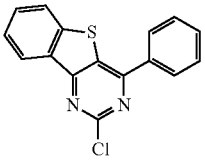 [SMILES: Clc1nc(-c2ccccc2)c2sc3ccccc3c2n1] | 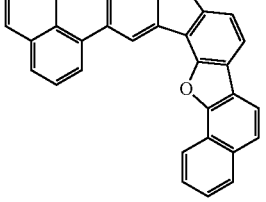 | 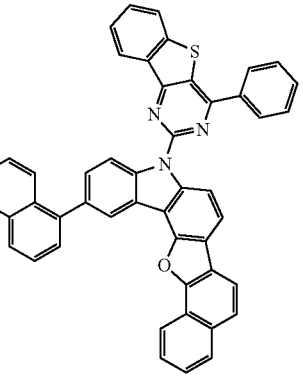 | 49% |
| b-91 | 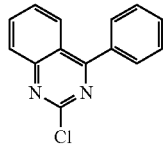 | 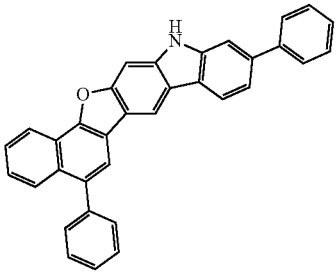 [SMILES: c1ccc(-c2ccc3c(c2)[nH]c2cc4oc5c6ccccc6c(-c6ccccc6)cc5c4cc23)cc1] | 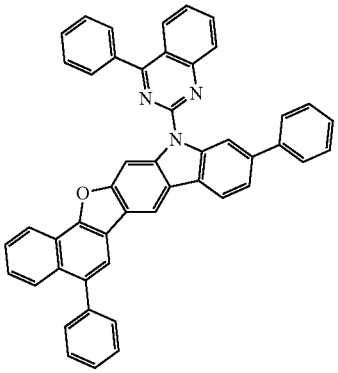 [SMILES: c1ccc(-c2ccc3c4cc5c(cc4n(-c4nc(-c6ccccc6)c6ccccc6n4)c3c2)oc2c3ccccc3c(-c3ccccc3)cc52)cc1] | 56% |
[Preparation Example 3] Preparation of Target Compound
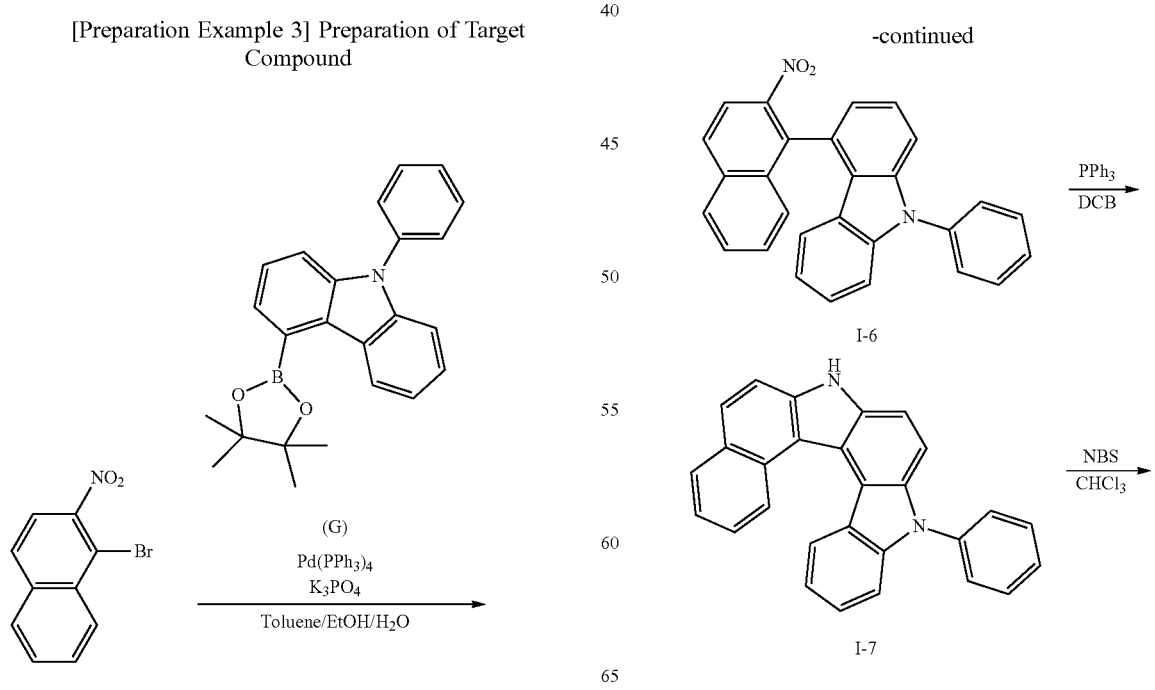

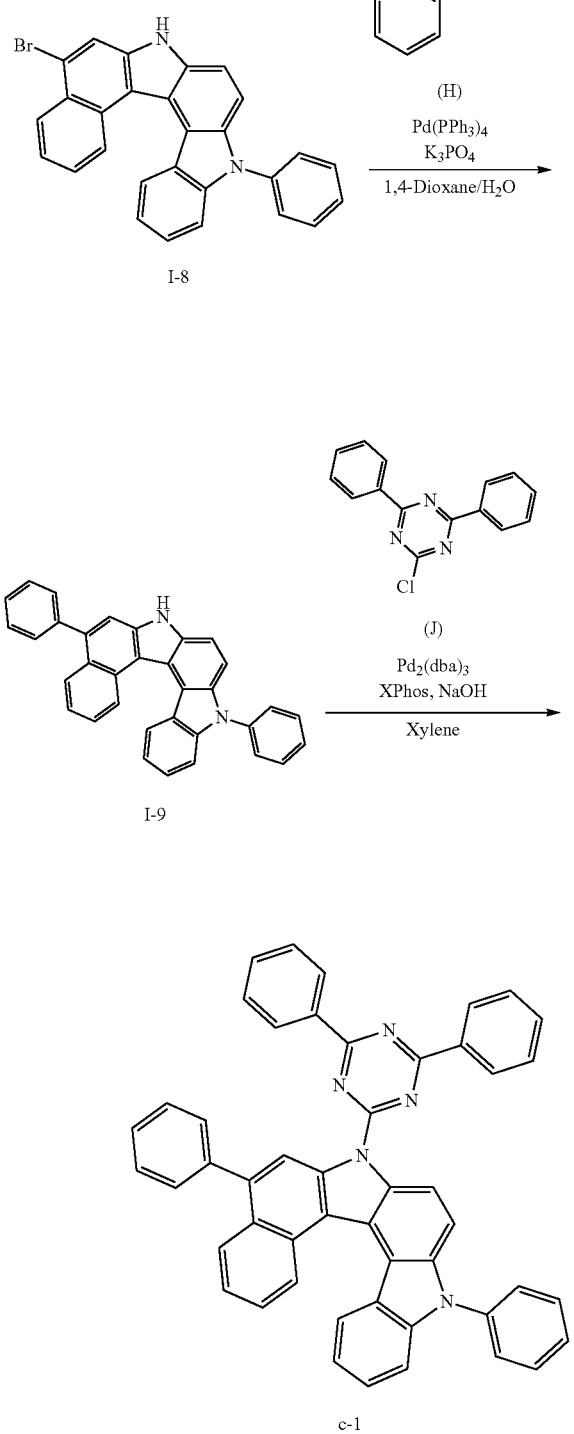

g, 152.36 mmol) in toluene/ethanol/H$_2$O (300 mL/60 mL/60 mL), the result was stirred for 6 hours at 100° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator, and the result was passed through column chromatography <MC/Hex=⅓> to obtain yellow solid Compound I-6 (13 g) in a 36% yield.

2) Preparation of Compound I-7

After dissolving Compound I-6 (13 g, 26.5 mmol) in dichlorobenzene (DCB) (150 mL), PPh$_3$ (14 g, 53.01 mmol) was introduced thereto, and the result was stirred for 20 hours at 180° C. The mixture solution completed with the reaction was dissolved in methylene chloride (MC) and extracted with water, and the organic layer was dried with anhydrous MgSO$_4$ and silica gel filtered. The solvent of the filtered filtrate was removed using a high-pressure rotary evaporator, the result was precipitated using MC/Hex, and the precipitates were filtered to obtain ivory solid Compound I-7 (11 g) in a 91% yield.

3) Preparation of Compound I-8

After dissolving Compound I-7 (11 g, 28.76 mmol) and NBS (N-bromosuccinimide) (5.1 g, 28.76 mmol) in CHCl$_3$ (150 mL), the result was stirred for 10 hours at 50° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator, the result was precipitated using hexane, and then the precipitates were filtered to obtain ivory solid Compound I-8 (15 g) in a 88% yield.

4) Preparation of Compound I-9

After dissolving Compound I-8 (15 g, 32.51 mmol), phenylboronic acid (4 g, 32.51 mmol), Pd(PPh$_3$)$_4$ (1.8 g, 1.63 mmol) and K$_3$PO$_4$ (13.8 g, 65.02 mmol) in 1,4-dioxane/H$_2$O (300 mL/60 mL), the result was stirred for 15 hours at 100° C. After the reaction was completed, precipitated solids were filtered, and washed with H$_2$O and methanol. The filtered solids were dried, dissolved in an excess amount of hot CHCl$_3$ solvent, and silica gel filtered. The solvent of the filtered filtrate was removed using a rotary evaporator, the result was precipitated using hexane/ethyl acetate (EA), and then the precipitates were filtered to obtain light yellow solid Compound I-9 (11 g) in a 76% yield.

5) Preparation of Compound c-1

After dissolving Compound I-9 (4 g, 8.72 mmol), 2-chloro-4,6-diphenyl-1,3,5-triazine (2.3 g, 8.72 mmol), Pd$_2$(dba)$_3$ (796 mg, 0.87 mmol), XPhos (830 mg, 1.74 mmol) and NaOtBu (1.6 g, 17.44 mmol) in xylene (50 mL), the result was stirred for 14 hours at 100° C. After the reaction was completed, precipitated solids were filtered, and washed with H$_2$O and methanol. The filtered solids were dried, dissolved in an excess amount of hot 1,2-dichlorobenzene solvent, and silica gel filtered. The solvent of the filtered filtrate was removed using a rotary evaporator, the result was precipitated using acetone, and the precipitates were filtered to obtain yellow solid Compound c-1 (2.7 g) in a 46% yield.

The following target compounds were synthesized in the same manner in the preparation of c-1 in Preparation Example 3 except that G, H and J of the following Table 3 were used as intermediates.

1) Preparation of Compound I-6

After dissolving 1-bromo-2-nitronaphthalene (25 g, 76.18 mmol), (9-phenyl-9H-carbazol-4-yl)boronic acid (21.9 g, 76.18 mmol), Pd(PPh$_3$)$_4$ (4.4 g, 3.81 mmol) and K$_3$PO$_4$ (32

TABLE 3
| Compound | Intermediate G | Intermediate H | Intermediate J | Target Compound | Yield |
|---|---|---|---|---|---|
| c-1 | 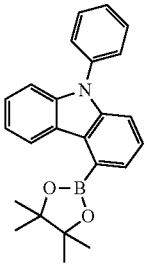 [SMILES: CC1(C)OB(c2cccc3c2c2ccccc2n3-c2ccccc2)OC1(C)C] |  | 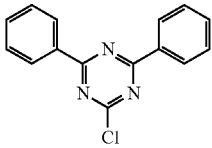 [SMILES: Clc1nc(-c2ccccc2)nc(-c2ccccc2)n1] | 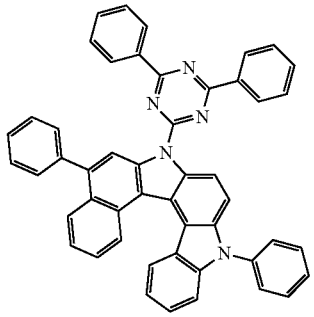 [SMILES: c1ccc(-c2nc(-c3ccccc3)nc(-n3c4cc(-c5ccccc5)c5ccccc5c4c4c5c6ccccc6n(-c6ccccc6)c5ccc43)n2)cc1] | 46% |
| c-3 | 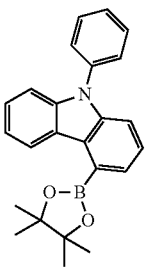 [SMILES: CC1(C)OB(c2cccc3c2c2ccccc2n3-c2ccccc2)OC1(C)C] |  | 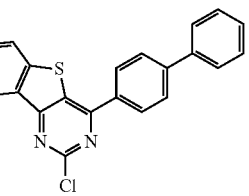 | 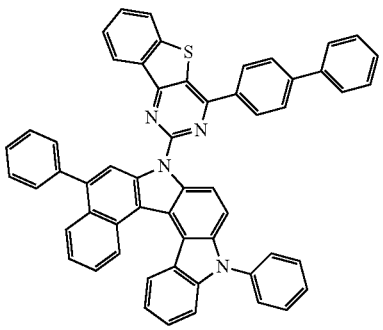 [SMILES: c1ccc(-c2ccc(-c3nc(-n4c5cc(-c6ccccc6)c6ccccc6c5c5c6c7ccccc7n(-c7ccccc7)c6ccc54)nc4c3sc3ccccc34)cc2)cc1] | 50% |
| c-7 | 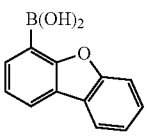 |  | 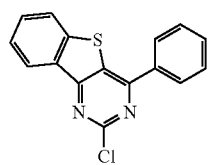 [SMILES: Clc1nc(-c2ccccc2)c2sc3ccccc3c2n1] | 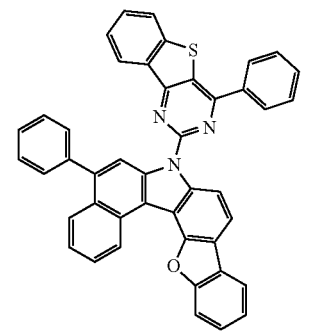 [SMILES: c1ccc(-c2cc3c(c4ccccc24)c2c4oc5ccccc5c4ccc2n3-c2nc(-c3ccccc3)c3sc4ccccc4c3n2)cc1] | 57% |
| c-8 | 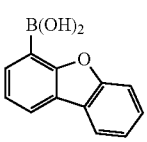 |  | 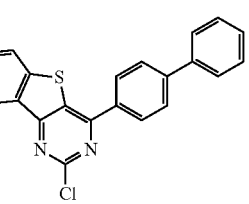 | 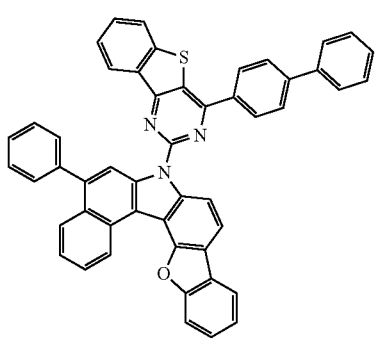 [SMILES: c1ccc(-c2ccc(-c3nc(-n4c5cc(-c6ccccc6)c6ccccc6c5c5c6oc7ccccc7c6ccc54)nc4c3sc3ccccc34)cc2)cc1] | 63% |

TABLE 3-continued
| Compound | Intermediate G | Intermediate H | Intermediate J | Target Compound | Yield |
|---|---|---|---|---|---|
| c-14 | 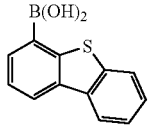 |  | 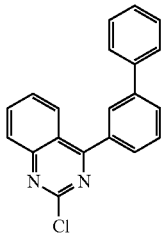 [SMILES: Clc1nc(-c2cccc(-c3ccccc3)c2)c2ccccc2n1] | 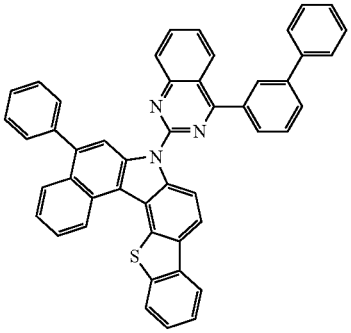 [SMILES: c1ccc(-c2cccc(-c3nc(-n4c5cc(-c6ccccc6)c6ccccc6c5c5c6sc7ccccc7c6ccc54)nc4ccccc34)c2)cc1] | 55% |
| c-16 | 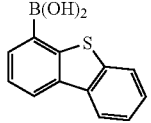 |  |  | 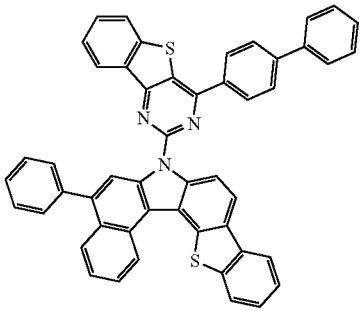 [SMILES: c1ccc(-c2ccc(-c3nc(-n4c5cc(-c6ccccc6)c6ccccc6c5c5c6sc7ccccc7c6ccc54)nc4c3sc3ccccc34)cc2)cc1] | 47% |
| c-23 | 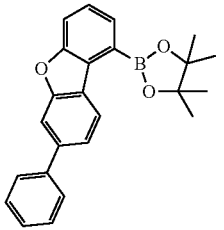 [SMILES: CC1(C)OB(c2cccc3oc4cc(-c5ccccc5)ccc4c23)OC1(C)C] |  | 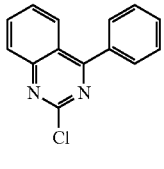 | 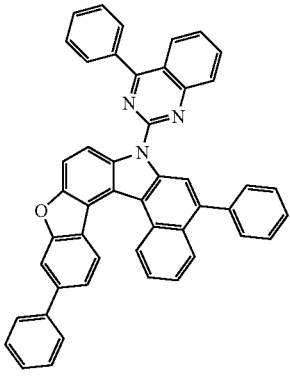 [SMILES: c1ccc(-c2ccc3c(c2)oc2ccc4c(c23)c2c3ccccc3c(-c3ccccc3)cc2n4-c2nc(-c3ccccc3)c3ccccc3n2)cc1] | 66% |
| c-29 | 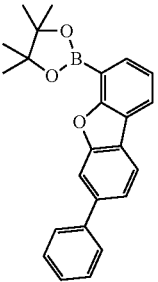 [SMILES: CC1(C)OB(c2cccc3c2oc2cc(-c4ccccc4)ccc23)OC1(C)C] |  | 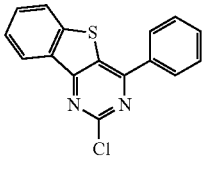 [SMILES: Clc1nc(-c2ccccc2)c2sc3ccccc3c2n1] | 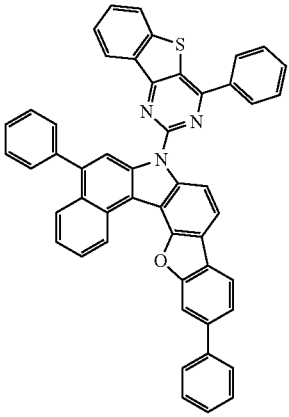 [SMILES: c1ccc(-c2ccc3c(c2)oc2c3ccc3c2c2c4ccccc4c(-c4ccccc4)cc2n3-c2nc(-c3ccccc3)c3sc4ccccc4c3n2)cc1] | 57% |

TABLE 3-continued
| Compound | Intermediate G | Intermediate H | Intermediate J | Target Compound | Yield |
|---|---|---|---|---|---|
| c-32 | 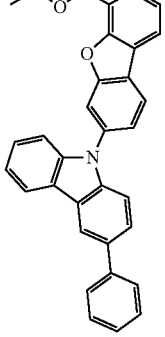 | — | 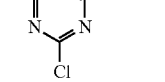 | 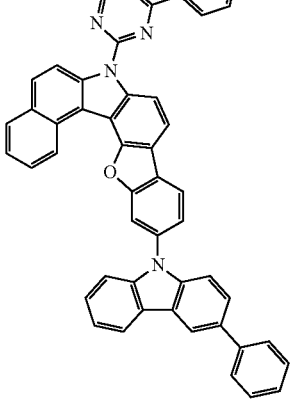 | 45% |
| c-39 | 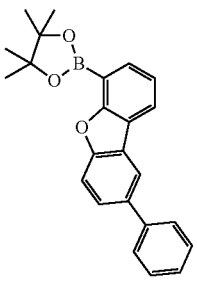 [SMILES: CC1(C)OB(c2cccc3c2oc2ccc(-c4ccccc4)cc23)OC1(C)C] | — |  | 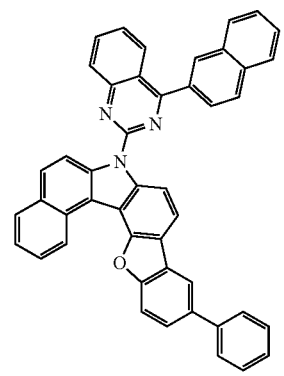 [SMILES: c1ccc(-c2ccc3oc4c(ccc5c4c4c6ccccc6ccc4n5-c4nc(-c5ccc6ccccc6c5)c5ccccc5n4)c3c2)cc1] | 61% |
| c-43 | 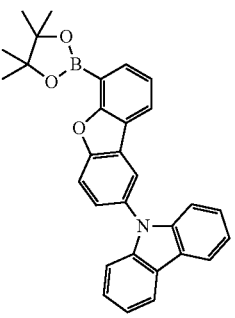 [SMILES: CC1(C)OB(c2cccc3c2oc2ccc(-n4c5ccccc5c5ccccc54)cc23)OC1(C)C] | — |  | 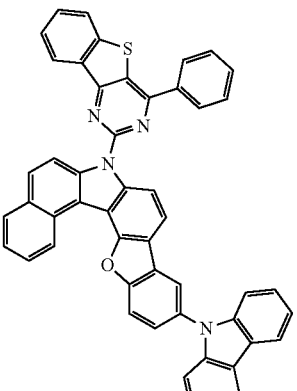 | 55% |

[Preparation Example 4] Preparation of Intermediate N

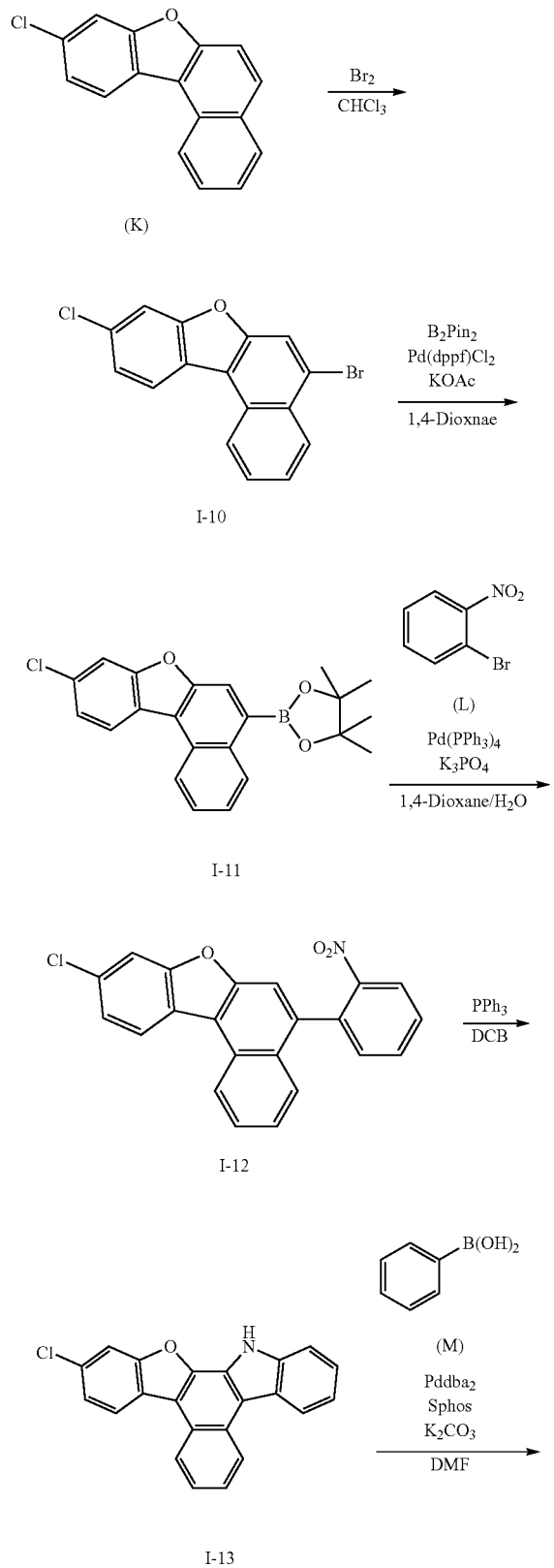

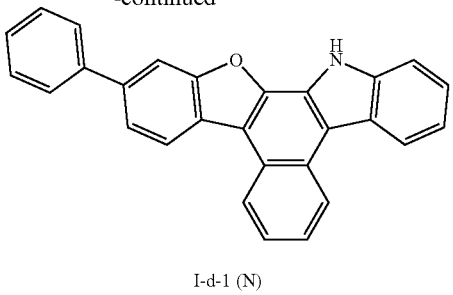

I-d-1 (N)

1) Preparation of Compound I-10

After dissolving 9-chloronaphtho[2,1-b]benzofuran (30 g, 118.72 mmol) in CHCl$_3$ (400 mL), bromine (6.3 mL, 118.72 mmol) was slowly added dropwise thereto at 0° C. After approximately 10 minutes, the temperature was raised to room temperature, and the mixture was stirred for 4 hours. The mixture solution completed with the reaction was dissolved in methylene chloride (MC) and extracted with a Na$_2$S$_2$O$_3$ 1 M solution, and the organic layer was dried with anhydrous MgSO$_4$ and then silica gel filtered. The solvent of the filtered filtrate was removed using a rotary evaporator to obtain ivory solid Compound I-10 (34 g) in a 87% yield.

2) Preparation of Compound I-11

After dissolving Compound I-10 (34 g, 102.41 mmol), bis(pinacolato)diboron (52 g, 204.82 mmol), Pd(dppf)Cl$_2$ (5.9 g, 10.24 mmol) and KOAc (30 g, 307.23 mmol) in 1,4-dioxane (500 mL), the result was stirred for 16 hours at 100° C. The mixture solution completed with the reaction was filtered to remove an inorganic salt, and the filtrate was concentrated and then silica gel filtered. The solvent of the filtered filtrate was removed using a rotary evaporator, the result was precipitated using MC/Hex, and then the precipitates were filtered to obtain brown solid Compound I-11 (27 g) in a 69% yield.

3) Preparation of Compound I-12

After dissolving Compound I-11 (27 g, 71.31 mmol), 2-bromonitrobenzene (14 g, 71.31 mmol), Pd(PPh$_3$)$_4$ (4.1 g, 3.56 mmol) and K$_3$PO$_4$ (30 g, 142.62 mmol) in 1,4-dioxane/H$_2$O (300 mL/60 mL), the result was stirred for 5 hours at 100° C. The mixture solution completed with the reaction was dissolved in MC and extracted with water, and the organic layer was dried with anhydrous MgSO$_4$ and then silica gel filtered. The solvent of the filtered filtrate was removed using a rotary evaporator, and the result was passed through column chromatography <MC/Hex=1/3> to obtain yellow solid Compound I-12 (15.8 g) in a 59% yield.

4) Preparation of Compound I-13

After dissolving Compound I-12 (15.8 g, 42.27 mmol) in dichlorobenzene (DCB) (200 mL), PPh$_3$ (22 g, 84.54 mmol) was introduced thereto, and the result was stirred for 20 hours at 180° C. The mixture solution completed with the reaction was dissolved in methylene chloride (MC) and extracted with water, and the organic layer was dried with anhydrous MgSO$_4$ and silica gel filtered. The solvent of the filtered filtrate was removed using a high-pressure rotary evaporator, the result was precipitated using MC/Hex, and then the precipitates were filtered to obtain ivory solid Compound I-13 (13 g) in a 90% yield.

5) Preparation of Compound I-d-1

After dissolving Compound I-13 (13 g, 38.01 mmol), phenylboronic acid (4.6 g, 38.01 mmol), Pd(dba)$_2$ (1.1 g, 1.91 mmol) and K$_2$CO$_3$ (10 g, 76.02 mmol) in DMF (dimethylformamide) (150 mL), the result was stirred for 13 hours at 100° C. The mixture solution completed with the reaction was dissolved in methylene chloride (MC) and extracted with water, and the organic layer was dried with anhydrous MgSO$_4$ and then silica gel filtered. The solvent of the filtered filtrate was removed using a rotary evaporator, the result was precipitated using MC/Hex, and then the precipitates were filtered to obtain white solid Compound I-d-1 (11 g) in a 75% yield.

When the functional group of Intermediate M is an amine group, the compound was prepared using the following preparation method 5-1.

5-1) Preparation of Compound I-d-44

After dissolving Compound I-13 (7 g, 20.48 mmol), diphenylamine (5 g, 40.96 mmol), Pd$_2$(dba)$_3$ (1.9 g, 2.05 mmol), XPhos (1.9 g, 4.09 mmol) and NaOH (1.6 g, 40.96 mmol) in xylene (100 mL), the result was stirred for 16 hours at 100° C. After the reaction was completed, precipitated solids were filtered, and washed with H$_2$O and methanol. The filtered solids were dried, dissolved in an excess amount of hot chloroform solvent, and silica gel filtered. The solvent of the filtered filtrate was removed using a rotary evaporator, the result was precipitated using acetone, and then the precipitates were filtered to obtain yellow solid Compound 1-d-44 (5.8 g) in a 60% yield.

The following Compound N was synthesized in the same manner as in Preparation Example 3 except that K, L and M of the following Table 4 were used as intermediates

TABLE 4

| Compound | Intermediate K | Intermediate L | Intermediate M | Intermediate N |
|---|---|---|---|---|
| I-d-1 | | | | |
| I-d-7 | | | | |
| I-d-9 | | | | |
| I-d-12 | | | | |

TABLE 4-continued
| Compound | Intermediate K | Intermediate L | Intermediate M | Intermediate N |
|---|---|---|---|---|
| I-d-26 | 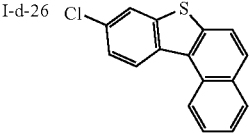 | 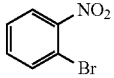 |  | 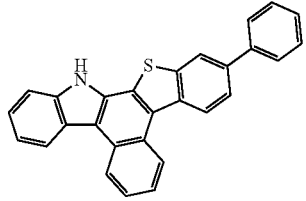 |
| I-d-30 | 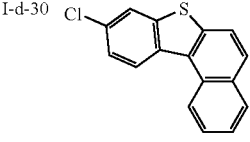 | 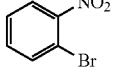 |  | 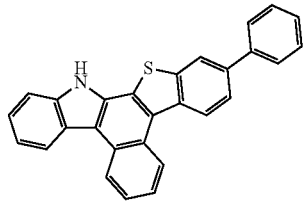 |
| I-d-39 | 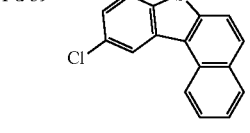 | 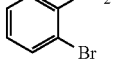 |  | 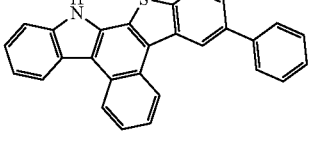 |
| I-d-41 | 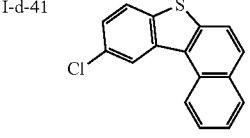 | 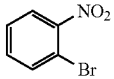 |  | 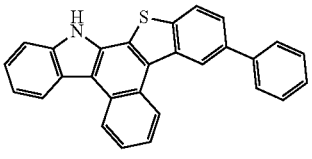 [SMILES: c1ccc(-c2ccc3sc4c5[nH]c6ccccc6c5c5ccccc5c4c3c2)cc1] |
| I-d-44 | 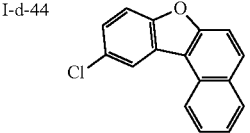 | 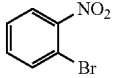 | 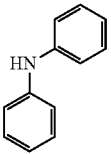 | 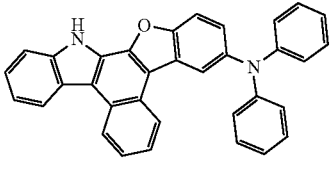 [SMILES: c1ccc(N(c2ccccc2)c2ccc3oc4c5[nH]c6ccccc6c5c5ccccc5c4c3c2)cc1] |
| I-d-52 | 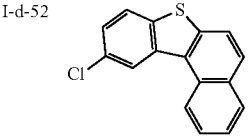 | 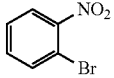 | 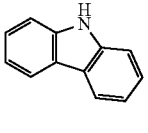 [SMILES: c1ccc2c(c1)[nH]c1ccccc12] | 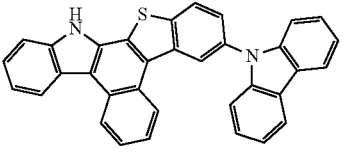 [SMILES: c1ccc2c(c1)[nH]c1c3sc4ccc(-n5c6ccccc6c6ccccc65)cc4c3c3ccccc3c21] |

TABLE 4-continued
| Compound | Intermediate K | Intermediate L | Intermediate M | Intermediate N |
|---|---|---|---|---|
| I-d-53 | | | — | |
| I-d-59 | | | | |
| I-d-64 | | | | |
| I-d-72 | | | — | |
[Preparation Example 5] Preparation of Target Compound
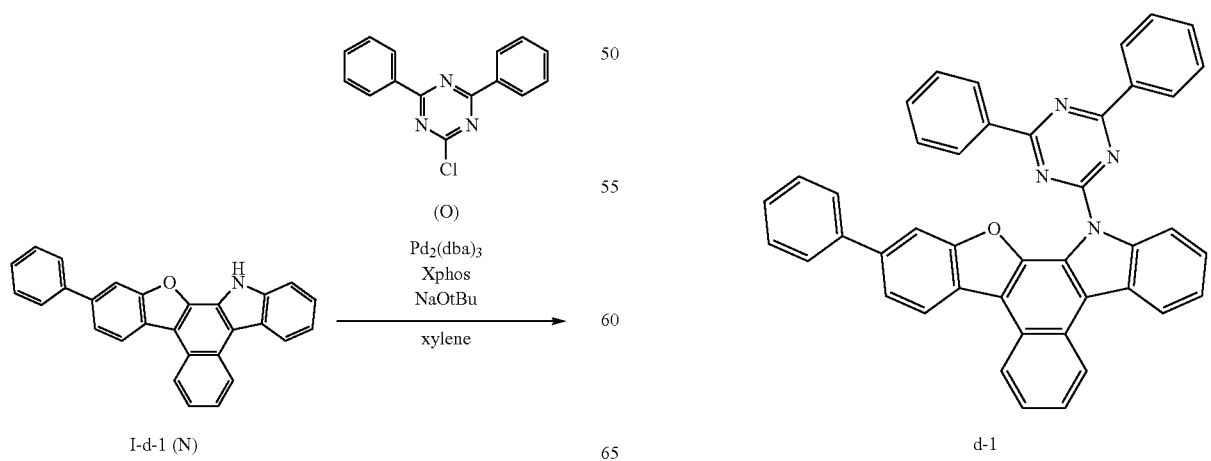

1) Preparation of Compound d-1

After dissolving Compound I-d-1 (4 g, 10.43 mmol), 2-chloro-4,6-diphenyl-1,3,5-triazine (2.8 g, 10.43 mmol), Pd$_2$(dba)$_3$ (955 mg, 1.04 mmol), XPhos (990 mg, 2.08 mmol) and NaOtBu (2 g, 20.86 mmol) in xylene (60 mL), the result was stirred for 18 hours at 100° C. After the reaction was completed, precipitated solids were filtered, and washed with H$_2$O and methanol. The filtered solids were dried, dissolved in an excess amount of hot 1,2-dichlorobenzene solvent, and silica gel filtered. The solvent of the filtered filtrate was removed using a rotary evaporator, the result was precipitated using acetone, and the precipitates were filtered to obtain yellow solid Compound d-1 (4.2 g) in a 66% yield.

The following target compounds were synthesized in the same manner as in the preparation of d-1 in Preparation Example 5 except that N and O of the following Table 5 were used as intermediates.

TABLE 5

| Compound | Intermediate O | Intermediate N | Target Compound | Yield |
|---|---|---|---|---|
| d-1 | 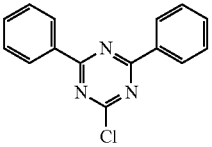 [SMILES: Clc1nc(-c2ccccc2)nc(-c2ccccc2)n1] | 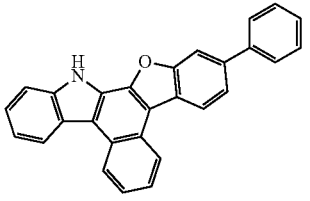 | 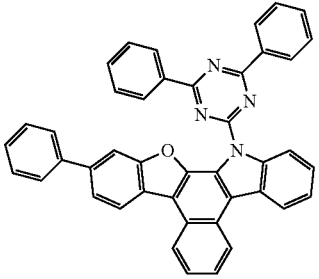 [SMILES: c1ccc(-c2ccc3c(c2)oc2c3c3ccccc3c3c4ccccc4n(-c4nc(-c5ccccc5)nc(-c5ccccc5)n4)c23)cc1] | 66% |
| d-7 | 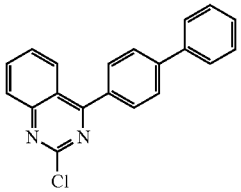 [SMILES: Clc1nc(-c2ccc(-c3ccccc3)cc2)c2ccccc2n1] | 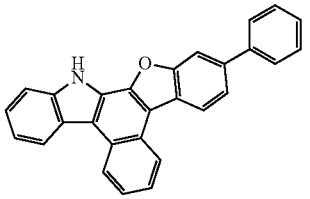 | 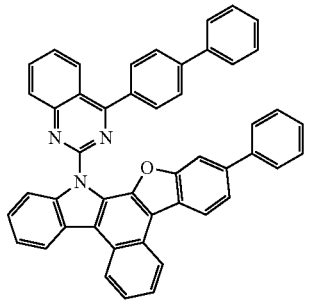 [SMILES: c1ccc(-c2ccc(-c3nc(-n4c5ccccc5c5c6ccccc6c6c7ccc(-c8ccccc8)cc7oc6c54)nc4ccccc34)cc2)cc1] | 48% |
| d-9 | 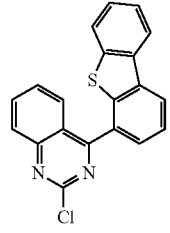 [SMILES: Clc1nc(-c2cccc3c2sc2ccccc23)c2ccccc2n1] | 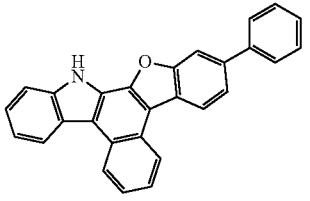 [SMILES: c1ccc(-c2ccc3c(c2)oc2c4[nH]c5ccccc5c4c4ccccc4c32)cc1] | 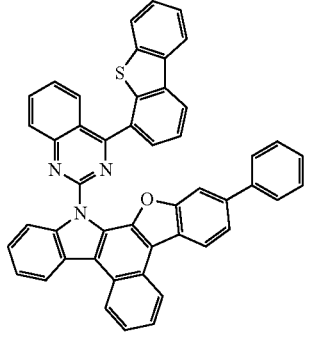 [SMILES: c1ccc(-c2ccc3c(c2)oc2c3c3ccccc3c3c4ccccc4n(-c4nc(-c5cccc6c5sc5ccccc56)c5ccccc5n4)c23)cc1] | 42% |
| d-12 | 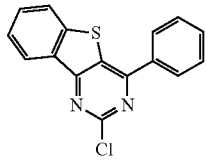 [SMILES: Clc1nc(-c2ccccc2)c2sc3ccccc3c2n1] | 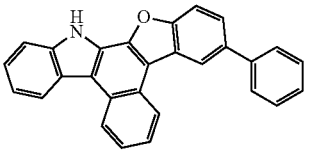 | 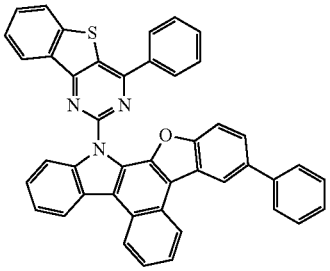 [SMILES: c1ccc(-c2ccc3oc4c(c3c2)c2ccccc2c2c3ccccc3n(-c3nc(-c5ccccc5)c5sc6ccccc6c5n3)c42)cc1] | 59% |

TABLE 5-continued

| Compound | Intermediate O | Intermediate N | Target Compound | Yield |
|---|---|---|---|---|
| d-26 | | | | 55% |
| d-30 | | | | 40% |
| d-39 | | | | 62% |
| d-41 | | | | 52% |
| d-44 | | | | 43% |

TABLE 5-continued

| Compound | Intermediate O | Intermediate N | Target Compound | Yield |
| --- | --- | --- | --- | --- |
| d-52 | | | | 46% |
| d-53 | | | | 51% |
| d-59 | | | | 47% |
| d-64 | | | | 43% |
| d-72 | | | | 57% |

The compounds were prepared in the same manner as in the preparation examples, and the synthesis identification results are shown in the following Tables 6 and 7.

TABLE 6

| NO | $^1$H NMR (CDCl$_3$, 300 Mz) |
|---|---|
| a-1 | 7.12 (d, 1H), 7.28-7.39 (m, 5H), 7.44-7.56 (m, 6H), 7.70-7.75 (m, 4H), 7.80-7.82 (d, 2H), 7.98-8.12 (m, 2H), 8.28 (m, 4H), 8.55 (dd, 2H) |
| a-6 | 7.13 (d, 1H), 7.29 (m, 1H), 7.41-7.55 (m, 13H), 7.79-7.80 (m, 4H), 7.89 (d, 1H), 7.98-8.12 (m, 3H), 8.55 (m, 2H) |
| a-8 | 7.13 (d, 1H), 7.29 (m, 1H), 7.41-7.64 (m, 17H), 7.75-7.79 (m, 4H), 7.89 (d, 1H), 7.98-8.12 (m, 3H), 8.56 (m, 2H) |
| a-16 | 7.13 (d, 1H), 7.30 (m, 1H), 7.41-7.63 (m, 13H), 7.80-7.89 (m, 6H), 8.05-8.12 (4H), 8.30 (d, 2H), 8.55 (m, 2H) |
| a-26 | 7.25-7.33 (m, 2H), 7.41-7.47 (m, 4H), 7.50-7.58 (m, 12H), 7.79 (m, 4H), 7.85 (m 2H), 7.92-7.94 (m, 2H), 8.02 (d, 1H), 8.21-8.23 (m 2H), 8.30 (m, 2H), 8.55 (d, 1H) |
| a-33 | 7.13 (d, 1H), 7.30 (m, 1H), 7.45-7.67 (m, 12H), 7.79-7.96 (m, 7H), 8.06-8.13 (4H), 8.32 (d, 2H), 8.49 (m, 2H) |
| a-30 | 7.13 (d, 1H), 7.39-7.60 (m, 15H), 7.71-7.90 (m, 5H), 8.10-8.22 (3H), 8.35 (d, 1H), 8.49 (m, 2H) |
| a-42 | 7.25-7.41 (m, 4H), 7.50-7.55 (m, 10H), 7.79-7.80 (m, 5H), 7.89-7.98 (m, 4H), 8.55 (m, 2H) |
| a-46 | 7.23-7.42 (m, 6H), 7.48-7.53 (m, 11H), 7.80-7.85 (m, 5H), 7.89-7.94 (m, 2H), 8.05-8.06 (m, 2H), 8.16 (d, 1H), 8.55 (m, 2H) |
| a-49 | 6.63 (m, 4H), 6.81 (t, 2H), 7.13-7.29 (m, 6H), 7.41-7.62 (m, 11H), 7.89 (d, 1H), 8.12 (m, 2H), 8.28 (m, 4H), 8.55 (d, 1H) |
| a-55 | 6.63-6.69 (m, 4H), 6.81 (m, 1H), 7.20-7.29 (m, 4H), 7.42-7.60 (m, 17H), 7.79 (d, 2H), 7.89 (d, 1H), 7.79-8.11 (m, 4H), 8.55 (d, 1H) |
| a-71 | 7.13 (d, 1H), 7.25-7.41 (m, 10H), 7.52-7.77 (m, 12H), 7.89-8.11 (m, 7H), 8.56 (dd, 2H) |
| a-90 | 7.13 (d, 1H), 7.24-7.38 (m, 6H), 7.52-7.70 (m, 9H), 7.79-7.80 (m, 5H), 7.89-8.10 (m, 4H), 8.56 (d, 2H) |
| a-104 | 7.14 (d, 1H), 7.29 (m, 1H), 7.41-7.60 (m, 13H), 7.70-7.85 (m, 5H), 8.00-8.15 (m, 8H), 8.45 (m, 1H), 8.56 (d, 2H) |
| a-109 | 7.13 (d, 1H), 7.30 (t, 1H), 7.40-7.77 (m, 18H), 7.89 (d, 1H), 8.00-8.13 (m, 4H) |
| a-112 | 7.12 (d, 1H), 7.30 = 7.66 (m, 19H), 7.95-7.98 (m, 3H), 8.05-8.13 (m, 3H) |
| a-115 | 7.14 (d, 1H), 7.30 (t, 1H), 7.41-7.66 (m, 11H), 7.73-7.80 (m, 6H), 7.90 (d, 1H), 8.05-8.16 (m, 5H) |
| a-119 | 6.60-6.63 (m, 4H), 6.80-6.82 (m, 2H), 7.20-7.51 (m, 15H), 7.79-7.80 (m, 2H), 7.94-7.98 (m, 5H), 8.55 (m, 2H) |
| a-131 | 7.25-7.50 (m, 15H), 7.77-87.93 (m, 10H), 8.05-8.16 (m, 5H), 8.55 (m, 2H) |
| a-134 | 7.25-7.50 (m, 15H), 7.66-7.78 (m, 4H), 7.98-8.06 (m, 5H), 8.55 (d, 1H) |
| a-136 | 7.26-7.41 (m, 8H), 7.52-7.80 (m, 10H), 7.89-7.94 (m, 2H), 8.05-8.06 (m, 3H), 8.16 (d, 1H), 8.55 (d, 1H) |
| a-142 | 5.85 (d, 1H), 6.60-6.63 (m, 5H), 6.81 (m, 2H), 7.13-7.20 (m, 6H), 7.41-7.55 (m, 11H), 7.79-7.80 (m, 4H), 7.98-8.05 (m, 2H), 8.18 (d, 1H), 8.55 (m, 2H) |
| a-143 | 7.13 (d, 1H), 7.30-7.44 (m, 6H), 7.51-7.70 (m, 7H), 7.72-7.75 (m, 4H), 7.80-7.82 (d, 2H), 7.89 (d, 1H), 7.98-8.12 (m, 2H), 8.18 (d, 1H), 8.28 (m, 4H), 8.55 (dd, 2H) |
| a-144 | 7.13 (d, 1H), 7.25-7.55 (m, 15H), 7.79-7.80 (m, 4H), 7.89-7.94 (m, 2H), 8.05-8.16 (m, 7H), 8.49-8.55 (m, 3H) |
| a-149 | 7.10 (d, 1H), 7.20-7.56 (m, 17H), 7.79-7.99 (m, 6H), 8.04-8.18 (m, 2H), 8.49-8.55 (m, 2H) |
| a-152 | 6.63 (d, 4H), 6.81 (m, 2H), 7.13-7.20 (m, 5H), 7.41-7.55 (m, 14H), 7.77 (s, 1H), 7.89-8.00 (m, 2H), 8.08-8.16 (m, 2H), 8.28 (m, 4H), 8.55 (m, 1H) |
| a-157 | 7.40-7.55 (m, 6H), 7.59-7.77 (m, 10H), 7.88-8.01 (m, 5H), 8.16-8.18 (m, 2H), 8.27-8.28 (m, 4H), 8.54 (m, 1H) |
| b-4 | 7.12 (d, 1H), 7.35-7.50 (m, 10H), 7.71 (s, 1H), 7.79-7.80 (m, 5H), 7.89-7.94 (m, 2H), 8.05-8.06 (m, 2H), 8.16-8.18 (m, 2H), 8.55-8.57 (m, 2H) |
| b-7 | 7.13 (d, 1H), 7.30-7.51 (m, 10H), 7.71 (s, 1H), 7.80-8.16 (m, 13H), 8.45 (d, 1H), 8.55 (m, 1H) |
| b-10 | 7.13 (d, 1H), 7.30-7.41 (m, 7H), 7.55-7.76 (m, 11H), 7.80-7.81 (m, 3H), 7.90-8.04 (m, 4H), 8.54-8.56 (m, 3H) |
| b-15 | 7.13 (d, 1H), 7.23-7.40 (m, 8H), 7.51-7.74 (m, 10H), 7.89-8.05 (m, 5H), 8.16-8.18 (m, 2H), 8.54-8.55 (m, 3H) |
| b-23 | 7.19-7.33 (m, 3H), 7.41-7.55 (m, 10H), 7.66-7.71 (m, 2H), 7.79-7.85 (m, 5H), 7.95 (d, 1H), 8.05-8.06 (m, 2H), 8.16-8.18 (m, 2H), 8.30 (d, 2H), 8.54-8.55 (m, 2H) |
| b-32 | 6.62-6.63 (m, 4H), 6.81 (m, 2H), 7.13-7.30 (m, 5H), 7.41-7.55 (m, 9H), 7.63 (s, 1H), 7.79 (m, 2H), 7.89-8.05 (m, 5H), 8.18 (d, 1H), 8.55 (d, 1H) |
| b-35 | 6.63-6.64 (m, 4H), 6.81 (m, 1H), 7.14-7.33 (m, 7H), 7.42-7.55 (m, 10H), 7.70-7.79 (m, 4H), 7.89-7.94 (m, 2H), 8.06-8.18 (m, 5H), 8.55 (d, 1H) |
| b-44 | 7.13 (d, 1H), 7.26-7.42 (m, 8H), 7.51-7.63 (m, 6H), 7.79-7.80 (m, 3H), 7.94-8.18 (m, 8H), 8.55 (m, 2H) |
| b-50 | 7.14 (d, 1H), 7.26-7.51 (m, 14H), 7.69 (d, 1H), 7.80-7.94 (m, 9H), 8.05-8.08 (m, 3H), 8.16-8.18 (m, 2H), 8.55 (m, 2H) |
| b-57 | 7.13 (d, 1H), 7.26-7.50 (m, 12H), 7.66-7.70 (m, 2H), 7.80-8.05 (m, 9H), 8.18 (m, 1H), 8.55-8.56 (m, 2H) |
| b-65 | 7.29 (t, 1H), 7.41-7.63 (m, 16H), 7.71 (s, 1H), 7.79-7.85 (m, 4H), 7.98-8.12 (m, 4H), 8.30 (m, 2H), 8.55 (m, 1H) |
| b-69 | 6.65 (m, 4H), 6.81 (m, 2H), 7.20-7.29 (m, 5H), 7.41-7.66 (m, 12H), 7.79 (d, 2H), 7.99-8.13 (m, 5H) |
| b-75 | 7.29-7.50 (m, 10H), 7.55-7.69 (m, 8H), 7.77-7.94 (m, 7H), 8.08-8.16 (m, 6H), 8.55 (d, 1H) |
| b-77 | 7.13 (d, 1H), 7.40-7.52 (m, 11H), 7.62-7.65 (m, 3H), 7.79-7.80 (m, 2H), 7.89 (d, 2H), 7.98-8.15 (m, 5H), 8.49 (d, 1H) |
| b-81 | 5.88 (d, 1H), 6.60-6.63 (m, 6H), 6.81 (m, 2H), 7.11-7.20 (m, 5H), 7.41-7.55 (m, 11H), 7.71 (s, 1H), 7.79-7.89 (m, 2H), 8.18-8.27 (m, 6H), 8.56 (m, 1H) |
| b-84 | 7.12 (d, 1H), 7.42-7.60 (m, 11H), 7.77-7.79 (m, 3H), 7.89 (d, 2H), 7.98-8.05 (m 8H), 8.42 (d, 1H), 8.58 (m, 1H) |
| b-91 | 7.41-7.49 (m, 7H), 7.55-7.60 (m, 10H), 7.71 (s, 1H), 7.79-7.80 (m, 5H), 8.05-8.06 (m, 2H), 8.16-8.18 (m, 2H), 8.55 (m, 1H) |
| c-1 | 7.12 (d, 1H), 7.32-7.50 (m, 10H), 7.55-7.66 (m, 7H), 7.79 (m, 2H), 7.89-7.90 (m, 3H), 7.94 (d, 1H), 8.12 (d, 1H), 8.28-8.29 (m, 4H), 8.55 (m, 2H) |
| c-3 | 7.12 (d, 1H), 7.32-7.51 (m, 10H), 7.55-7.66 (m, 8H), 7.75-7.79 (m, 3H), 7.89-7.90 (m, 4H), 8.28-8.29 (m, 4H), 8.55-8.56 (m, 2H) |
| c-10 | 7.13 (d, 1H), 7.32-7.44 (m, 8H), 7.51-7.62 (m, 6H), 7.79-7.81 (m, 4H), 7.89 (d, 2H), 7.98-8.05 (m, 2H), 8.55 (m, 2H) |
| c-11 | 7.12 (d, 1H), 7.35-7.41 (m, 9H), 7.52-7.63 (m, 7H), 7.78-7.9 (m, 4H), 7.88 (d, 2H), 7.98-8.03 (m, 2H), 8.30 (d, 2H), 8.55 (m, 2H) |
| c-17 | 7.33-7.51 (m, 16H), 7.75-80 (m, 5H), 7.90-8.05 (m, 4H), 8.16 (d, 1H), 8.45 (d, 1H), 8.55 (m, 2H) |
| c-19 | 7.33 (d, 1H), 7.42-7.55 (m, 15H), 7.79-7.85 (m, 4H), 7.99-8.03 (m, 4H), 8.30 (d, 2H), 8.45 (m, 1H), 8.55 (m, 2H) |
| c-23 | 7.19 (d, 1H), 7.41-7.52 (m, 15H), 7.75-7.79 (m, 4H), 7.95 (m, 1H), 8.06-8.16 (m, 6H), 8.55 (m, 2H) |
| c-29 | 7.14 (d, 1H), 7.42-7.52 (m, 15H), 7.62-7.64 (m, 2H), 7.75-7.79 (m, 5H), 7.95-7.98 (m, 4H), 8.55 (m, 2H) |
| c-32 | 7.13 (d, 1H), 7.25-7.52 (m, 12H), 7.69-7.96 (m, 13H), 8.05-8.06 (m, 2H), 8.16-8.17 (m, 2H), 8.54-8.55 (m, 2H) |
| c-39 | 7.12 (m, 1H), 7.40-7.59 (10H), 7.67-7.99 (m, 12H), 8.16-8.17 (m, 2H), 8.34 (s, 1H), 8.54 (m, 1H) |
| c-43 | 7.12 (d, 1H), 7.33-7.40 (m, 4H), 7.50-7.53 (m, 6H), 7.66-7.67 (m, 4H), 7.79-7.80 (m, 3H), 7.89-8.15 (m, 8H), 8.45-8.55 (m, 2H) |
| d-1 | 7.26-7.39 (m, 6H), 7.51-7.52 (m, 5H), 7.64-7.67 (m, 3H), 7.75-7.85 (m, 4H), 7.94-7.95 (m, 2H), 8.28 (m, 4H), 8.55 (dd, 2H) |
| d-7 | 7.26-7.41 (m, 8H), 7.51-7.52 (m, 5H), 7.64-7.67 (m, 3H), 7.75-7.85 (m, 4H), 7.94-7.95 (m, 2H), 8.05-8.06 (m, 2H), 8.16 (m, 1H), 8.30 (m, 2H), 8.55 (m, 2H) |
| d-9 | 7.26-7.40 (m, 8H), 7.51-7.67 (m, 8H), 7.95-8.05 (m, 5H), 8.16 (m, 1H), 8.41-8.45 (m, 2H), 8.54-8.55 (m, 3H) |
| d-12 | 7.30-7.52 (m, 12H), 7.67-7.79 (m, 7H), 7.94-8.05 (m, 3H), 8.55 (m, 3H) |
| d-26 | 7.31-7.41 (m, 5H), 7.51-7.52 (m, 7H), 7.67 (m, 2H), 7.79 (m, 2H), 8.05-8.11 (m, 6H), 8.54-8.55 (m, 3H) |
| d-30 | 7.33-7.42 (m, 5H), 7.50-7.52 (m, 7H), 7.67-7.70 (m, 4H), 7.79 (m, 2H), 8.00-8.11 (m, 4H), 8.54-8.55 (m, 3H) |
| d-39 | 7.33-7.41 (m, 4H), 7.50-7.53 (m, 8H), 7.67 (m, 4H), 7.85-7.88 (m, 4H), 7.94-8.07 (m, 5H), 8.16 (m, 1H), 8.30 (m, 2H), 8.54-8.55 (m, 3H) |
| d-41 | 7.31-7.42 (m, 6H), 7.51-7.53 (m, 7H), 7.66-7.70 (m, 4H), 7.79-7.80 (m, 2H), 8.00-8.10 (m, 4H), 8.54-8.55 (m, 3H) |
| d-44 | 6.63 (d, 1H), 6.63 (m, 4H), 6.81 (m, 2H), 7.20-7.33 (m, 6H), 7.41-7.50 (m, 6H), 7.65-7.67 (m, 3H), 7.79 (m, 2H), 7.98-8.05 (m, 3H), 8.54-8.55 (m, 3H) |
| d-52 | 7.29-7.51 (m, 10H), 7.63-7.66 (m, 3H), 7.79-7.80 (m, 3H), 7.94-8.12 (m, 8H), 8.54-8.55 (m, 4H) |
| d-53 | 7.32-7.38 (m, 3H), 7.41-7.52 (m 10H), 7.66-7.67 (m, 3H), 7.79 (m, 2H), 7.89-8.05 (m, 4H), 8.49-8.55 (m, 3H) |

TABLE 6-continued

| NO | $^1$H NMR (CDCl$_3$, 300 Mz) |
|---|---|
| d-59 | 5.86 (d, 1H), 6.60-6.63 (m, 5H), 6.81 (m, 2H), 7.20-7.21 (m, 4H), 7.41-7.51 (m, 8H), 7.64-7.75 (m, 7H), 7.95 (d, 1H), 8.05-8.16 (m, 4H), 8.54 (m, 2H) |
| d-64 | 7.25-7.33 (m, 3H), 7.41-7.52 (m, 10H), 7.63-7.67 (m, 4H), 7.77-7.80 (m, 4H), 8.05-8.12 (m, 8H), 8.54-8.55 (m, 3H) |
| d-72 | 7.44-7.52 (m, 12H), 7.67-7.68 (m, 2H), 7.77-7.79 (m, 3H), 7.98-8.05 (m, 4H), 8.18 (d, 1H), 8.45-8.54 (m, 3H) |

TABLE 7

| Compound | FD-MS | Compound | FD-MS |
|---|---|---|---|
| a-1 | m/z = 614.21 (C$_{43}$H$_{26}$N$_4$O = 614.69) | a-2 | m/z = 690.24 (C$_{49}$H$_{30}$N$_4$O = 690.79) |
| a-3 | m/z = 780.25 (C$_{55}$H$_{32}$N$_4$O$_2$ = 780.87) | a-4 | m/z = 780.25 (C$_{55}$H$_{32}$N$_4$O$_2$ = 780.87) |
| a-5 | m/z = 704.22 (C$_{49}$H$_{28}$N$_4$O$_2$ = 704.77) | a-6 | m/z = 643.17 (C$_{44}$H$_{25}$N$_3$OS = 643.75) |
| a-7 | m/z = 719.20 (C$_{50}$H$_{29}$N$_3$OS = 719.85) | a-8 | m/z = 719.20 (C$_{50}$H$_{29}$N$_3$OS = 719.85) |
| a-9 | m/z = 759.23 (C$_{53}$H$_{33}$N3OS = 759.91) | a-10 | m/z = 693.19 (C$_{48}$H$_{27}$N$_3$OS = 693.81) |
| a-11 | m/z = 808.23 (C$_{56}$H$_{32}$N$_4$OS = 808.94) | a-12 | m/z = 749.16 (C$_{50}$H$_{27}$N$_3$OS$_2$ = 749.90) |
| a-13 | m/z = 749.16 (C$_{50}$H$_{27}$N$_3$OS$_2$ = 749.90) | a-14 | m/z = 799.18 (C$_{54}$H$_{29}$N$_3$OS$_2$ = 799.96) |
| a-15 | m/z = 799.18 (C$_{54}$H$_{29}$N$_3$OS$_2$ = 799.96) | a-16 | m/z = 733.18 (C$_{50}$H$_{27}$N$_3$O$_2$S = 733.83) |
| a-17 | m/z = 733.18. (C$_{50}$H$_{27}$N$_3$O$_2$S = 733.83) | a-18 | m/z = 783.20 (C$_{54}$H$_{29}$N$_3$O$_2$S = 783.89) |
| a-19 | m/z = 783.20 (C$_{54}$H$_{29}$N$_3$O$_2$S = 783.89) | a-20 | m/z = 783.20 (C$_{54}$H$_{29}$N$_3$O$_2$S = 783.89) |
| a-21 | m/z = 627.19 (C$_{44}$H$_{25}$N$_3$O$_2$ = 627.69) | a-22 | m/z = 703.23 (C$_{50}$H$_{29}$N$_3$O$_2$ = 703.78) |
| a-23 | m/z = 677.21 (C$_{48}$H$_{27}$N$_3$O$_2$ = 677.75) | a-24 | m/z = 733.18 (C$_{50}$H$_{27}$N$_3$O$_2$S = 733.83) |
| a-25 | m/z = 587.20 (C$_{42}$H$_{25}$N$_3$O = 587.67) | a-26 | m/z = 663.23 (C$_{48}$H$_{29}$N$_3$O = 663.75) |
| a-27 | m/z = 663.23 (C$_{48}$H$_{29}$N$_3$O = 663.75) | a-28 | m/z = 637.22 (C$_{46}$H$_{27}$N$_3$O = 637.73) |
| a-29 | m/z = 703.23 (C$_{50}$H$_{29}$N$_3$O$_2$ = 703.78) | a-30 | m/z = 677.21 (C$_{48}$H$_{27}$N$_3$O$_2$ = 677.75) |
| a-31 | m/z = 677.21 (C$_{48}$H$_{27}$N$_3$O$_2$ = 677.75) | a-32 | m/z = 677.21 (C$_{48}$H$_{27}$N$_3$O$_2$ = 677.75) |
| a-33 | m/z = 727.23 (C$_{52}$H$_{29}$N$_3$O$_2$ = 727.81) | a-34 | m/z = 727.23 (C$_{52}$H$_{29}$N$_3$O$_2$ = 727.81) |
| a-35 | m/z = 727.23 (C$_{52}$H$_{29}$N$_3$O$_2$ = 727.81) | a-36 | m/z = 693.19 (C$_{48}$H$_{27}$N$_3$OS = 693.81) |
| a-37 | m/z = 693.19 (C$_{48}$H$_{27}$N$_3$OS = 693.81) | a-38 | m/z = 743.20 (C$_{52}$H$_{29}$N$_3$OS = 743.87) |
| a-39 | m/z = 743.20 (C$_{52}$H$_{29}$N$_3$OS = 743.87) | a-40 | m/z = 743.20 (C$_{52}$H$_{29}$N$_3$OS = 743.87) |
| a-41 | m/z = 752.26 (C$_{54}$H$_{32}$N$_4$O = 752.86) | a-42 | m/z = 643.17 (C$_{44}$H$_{25}$N$_3$OS = 643.75) |
| a-43 | m/z = 719.20 (C$_{50}$H$_{29}$N$_3$OS = 719.85) | a-44 | m/z = 693.19 (C$_{48}$H$_{27}$N$_3$OS = 693.81) |
| a-45 | m/z = 587.20 (C$_{42}$H$_{25}$N$_3$O = 587.67) | a-46 | m/z = 663.76 (C$_{48}$H$_{29}$N$_3$O = 663.76) |
| a-47 | m/z = 693.19 (C$_{48}$H$_{27}$N$_3$OS = 693.81) | a-48 | m/z = 677.21 (C$_{48}$H$_{27}$N$_3$O$_2$ = 677.75) |
| a-49 | m/z = 705.25 (C$_{49}$H$_{31}$N$_5$O = 705.80) | a-50 | m/z = 734.21 (C$_{50}$H$_{30}$N$_4$O$_S$ = 734.86) |
| a-51 | m/z = 810.25 (C$_{56}$H$_{34}$N$_4$OS = 810.96) | a-52 | m/z = 678.24 (C$_{48}$H$_{30}$N$_4$O = 678.78) |
| a-53 | m/z = 754.27 (C$_{54}$H$_{34}$N$_4$O = 754.87) | a-54 | m/z = 754.27 (C$_{54}$H$_{34}$N$_4$O = 754.87) |
| a-55 | m/z = 810.25 (C$_{56}$H$_{3}$4N$_4$OS = 810.95) | a-56 | m/z = 830.30 (C$_{60}$H$_{38}$N$_4$O = 830.97) |
| a-57 | m/z = 886.28 (C$_{62}$H$_{38}$N$_4$OS = 887.06) | a-58 | m/z = 728.26 (C$_{52}$H$_{32}$N$_4$O = 728.84) |
| a-59 | m/z = 784.23 (C$_{54}$H$_{32}$N$_4$O = 784.92) | a-60 | m/z = 794.30 (C$_{57}$H$_{38}$N$_4$O = 794.94) |
| a-61 | m/z = 834.30 (C$_{59}$H$_{38}$N$_4$O2 = 834.96) | a-62 | m/z = 703.23 (C$_{50}$H$_{29}$N$_3$O$_2$ = 703.78) |
| a-63 | m/z = 779.27 (C$_{55}$H$_{33}$N$_5$O = 779.88) | a-64 | m/z = 676.23 (C$_{48}$H$_{28}$N$_4$O = 676.76) |
| a-65 | m/z = 752.26 (C$_{54}$H$_{32}$N$_4$O = 752.86) | a-66 | m/z = 752.26 (C$_{54}$H$_{32}$N$_4$O = 752.86) |
| a-67 | m/z = 732.20 (C$_{50}$H$_{28}$N$_4$OS = 732.85) | a-68 | m/z = 808.23 (C$_{56}$H$_{32}$N$_4$OS = 808.94) |
| a-69 | m/z = 808.23 (C$_{56}$H$_{32}$N$_4$OS = 808.94) | a-70 | m/z = 716.22 (C$_{50}$H$_{28}$N$_4$O$_2$ = 716.78) |
| a-71 | m/z = 808.23 (C$_{56}$H$_{32}$N$_4$OS = 808.94) | a-72 | m/z = 752.26 (C$_{54}$H$_{32}$N$_4$O = 752.86) |
| a-73 | m/z = 704.22 (C$_{49}$H$_{28}$N$_4$O$_2$ = 704.77) | a-74 | m/z = 780.25 (C$_{55}$H$_{32}$N$_4$O$_2$ = 780.87) |
| a-75 | m/z = 733.18 (C$_{50}$H$_{27}$N$_3$O$_2$S = 733.83) | a-76 | m/z = 809.21 (C$_{56}$H$_{31}$N$_3$O$_2$S = 809.93) |
| a-77 | m/z = 809.21 (C$_{56}$H$_{31}$N$_3$O$_2$S = 809.93) | a-78 | m/z = 783.20 (C$_{54}$H$_{29}$N$_3$O$_2$S = 783.89) |
| a-79 | m/z = 677.21 (C$_{48}$H$_{27}$N$_3$O$_2$ = 677.75) | a-80 | m/z = 753.24 (C$_{54}$H$_{31}$N$_3$O$_2$ = 753.84) |
| a-81 | m/z = 717.21 (C$_{50}$H$_{27}$N$_3$O$_3$ = 717.77) | a-82 | m/z = 704.22 (C$_{49}$H$_{28}$N$_4$O$_2$ = 704.77) |
| a-83 | m/z = 780.25 (C$_{55}$H$_{32}$N$_4$O$_2$ = 780.87) | a-84 | m/z = 780.25 (C$_{55}$H$_{32}$N$_4$O$_2$ = 780.87) |
| a-85 | m/z = 754.27 (C$_{54}$H$_{34}$N$_4$O = 754.87) | a-86 | m/z = 733.18 (C$_{50}$H$_{27}$N$_3$O$_2$S = 733.83) |
| a-87 | m/z = 809.21 (C$_{56}$H$_{31}$N$_3$O$_2$S = 809.93) | a-88 | m/z = 809.21 (C$_{56}$H$_{31}$N$_3$O$_2$S = 809.93) |
| a-89 | m/z = 849.24 (C$_{59}$H$_{35}$N$_3$O$_2$S = 849.99) | a-90 | m/z = 677.21 (C$_{48}$H$_{27}$N$_3$O$_2$ = 677.75) |
| a-91 | m/z = 753.24 (C$_{54}$H$_{31}$N$_3$O$_2$ = 753.84) | a-92 | m/z = 753.24 (C$_{54}$H$_{31}$N$_3$O$_2$ = 753.84) |
| a-93 | m/z = 727.23 (C$_{52}$H$_{29}$N$_3$O$_2$ = 727.81) | a-94 | m/z = 793.27 (C$_{57}$H$_{35}$N$_3$O$_2$ = 793.91) |
| a-95 | m/z = 717.21 (C$_{50}$H$_{27}$N$_3$O$_3$ = 717.77) | a-96 | m/z = 793.27 (C$_{57}$H$_{35}$N$_3$O$_2$ = 793.91) |
| a-97 | m/z = 720.20 (C$_{49}$H$_{28}$N$_4$OS = 720.84) | a-98 | m/z = 796.23 (C$_{55}$H$_{32}$N$_4$OS = 796.93) |
| a-99 | m/z = 749.16 (C$_{50}$H$_{27}$N$_3$OS$_2$ = 749.9) | a-100 | m/z = 825.19 (C$_{56}$H$_{31}$N$_3$OS$_2$ = 825.99) |
| a-101 | m/z = 825.19 (C$_{56}$H$_{31}$N$_3$OS$_2$ = 825.99) | a-102 | m/z = 799.18 (C$_{54}$H$_{29}$N$_3$OS$_2$ = 799.96) |
| a-103 | m/z = 693.19 (C$_{48}$H$_{27}$N$_3$OS = 693.81) | a-104 | m/z = 769.22 (C$_{54}$H$_{29}$N$_3$OS$_2$ = 769.91) |
| a-105 | m/z = 769.22 (C$_{54}$H$_{29}$N$_3$OS$_2$ = 769.91) | a-106 | m/z = 743.20 (C$_{52}$H$_{29}$N$_3$OS = 743.87) |
| a-107 | m/z = 614.21 (C$_{43}$H$_{26}$N$_4$O = 614.69) | a-108 | m/z = 780.25 (C$_{55}$H$_{32}$N$_4$O$_2$ = 780.87) |
| a-109 | m/z = 643.17 (C$_{44}$H$_{25}$N$_3$OS = 643.75) | a-110 | m/z = 719.20 (C$_{50}$H$_{29}$N$_3$OS = 719.85) |
| a-111 | m/z = 719.20 (C$_{50}$H$_{29}$N$_3$OS = 719.85) | a-112 | m/z = 733.18 (C$_{50}$H$_{27}$N$_3$O$_2$S = 733.83) |
| a-113 | m/z = 733.18 (C$_{50}$H$_{27}$N$_3$O$_2$S = 733.83) | a-114 | m/z = 796.23 (C$_{55}$H$_{32}$N$_4$OS = 796.93) |
| a-115 | m/z = 587.20 (C$_{42}$H$_{25}$N$_3$O = 587.67) | a-116 | m/z = 663.23 (C$_{48}$H$_{29}$N$_3$O = 663.76) |
| a-117 | m/z = 637.22 (C$_{46}$H$_{27}$N$_3$O = 637.73) | a-118 | m/z = 693.19 (C$_{48}$H$_{27}$N$_3$OS = 693.81) |
| a-119 | m/z = 734.21 (C$_{50}$H$_{30}$N$_4$O = 734.86) | a-120 | m/z = 678.24 (C$_{48}$H$_{30}$N$_4$O = 678.78) |
| a-121 | m/z = 734.21 (C$_{50}$H$_{30}$N$_4$O = 734.86) | a-122 | m/z = 810.25 (C$_{56}$H$_{34}$N$_4$OS = 810.96) |
| a-123 | m/z = 678.24 (C$_{48}$H$_{30}$N$_4$O = 678.78) | a-124 | m/z = 810.25 (C$_{56}$H$_{34}$N$_4$OS = 810.96) |
| a-125 | m/z = 754.27 (C$_{54}$H$_{34}$N$_4$O = 754.87) | a-126 | m/z = 830.30 (C$_{60}$H$_{38}$N$_4$O = 830.97) |
| a-127 | m/z = 732.20 (C$_{50}$H$_{28}$N$_3$OS = 732.85) | a-128 | m/z = 676.23 (C$_{48}$H$_{28}$N$_4$O = 676.76) |
| a-129 | m/z = 752.26 (C$_{54}$H$_{32}$N$_4$O = 752.86) | a-130 | m/z = 808.23 (C$_{56}$H$_{32}$N$_4$OS = 808.94) |
| a-131 | m/z = 752.26 (C$_{54}$H$_{32}$N$_4$O = 752.86) | a-132 | m/z = 704.22 (C$_{49}$H$_{28}$N$_4$O$_2$ = 704.77) |
| a-133 | m/z = 733.18 (C$_{50}$H$_{27}$N$_3$O$_2$S = 733.83) | a-134 | m/z = 643.17 (C$_{44}$H$_{25}$N$_3$OS = 643.75) |

TABLE 7-continued

| Compound | FD-MS | Compound | FD-MS |
|---|---|---|---|
| a-135 | m/z = 719.20 (C$_{50}$H$_{29}$N$_3$OS = 719.85) | a-136 | m/z = 587.20 (C$_{42}$H$_{25}$N$_3$O = 587.67) |
| a-137 | m/z = 743.20 (C$_{52}$H$_{29}$N$_3$OS = 743.87) | a-138 | m/z = 614.21 (C$_{43}$H$_{26}$N$_4$O = 614.69) |
| a-139 | m/z = 643.17 (C$_{44}$H$_{25}$N$_3$OS = 643.75) | a-140 | m/z = 693.19 (C$_{48}$H$_{27}$N$_3$OS = 693.81) |
| a-141 | m/z = 587.20 (C$_{42}$H$_{25}$N$_3$O = 587.67) | a-142 | m/z = 810.25 (C$_{56}$H$_{34}$N$_4$OS = 810.96) |
| a-143 | m/z = 690.24 (C$_{49}$H$_{30}$N$_4$O = 690.79) | a-144 | m/z = 752.26 (C$_{54}$H$_{32}$N$_4$O = 752.86) |
| a-145 | m/z = 719.20 (C$_{50}$H$_{29}$N$_3$OS = 719.85) | a-146 | m/z = 754.27 (C$_{54}$H$_{34}$N$_4$O = 754.87) |
| a-147 | m/z = 614.21 (C$_{43}$H$_{26}$N$_4$O = 614.69) | a-148 | m/z = 693.19 (C$_{48}$H$_{27}$N$_3$OS = 693.81) |
| a-149 | m/z = 676.23 (C$_{48}$H$_{28}$N$_4$O = 676.76) | a-150 | m/z = 753.24 (C$_{54}$H$_{31}$N$_3$O$_2$ = 753.84) |
| a-151 | m/z = 728.26 (C$_{52}$H$_{32}$N$_4$O = 728.84) | a-152 | m/z = 781.28 (C$_{55}$H$_{35}$N$_5$O = 781.90) |
| a-153 | m/z = 779.27 (C$_{55}$H$_{33}$N$_5$O = 779.88) | a-154 | m/z = 719.20 (C$_{50}$H$_{29}$N$_3$OS = 719.85) |
| a-155 | m/z = 754.27 (C$_{54}$H$_{34}$N$_4$O = 754.87) | a-156 | m/z = 703.23 (C$_{50}$H$_{29}$N$_3$O$_2$ = 703.78) |
| a-157 | m/z = 678.24 (C$_{48}$H$_{30}$N$_4$O = 678.78) | a-158 | m/z = 664.23 (C$_{47}$H$_{28}$N$_4$O = 664.75) |
| a-159 | m/z = 781.28 (C$_{55}$H$_{35}$N$_5$O = 781.90) | a-160 | m/z = 781.28 (C$_{55}$H$_{35}$N$_5$O = 781.90) |
| a-161 | m/z = 719.20 (C$_{50}$H$_{29}$N$_3$OS = 719.85) | b-1 | m/z = 614.21 (C$_{43}$H$_{26}$N$_4$O = 614.69) |
| b-2 | m/z = 690.24 (C$_{49}$H$_{30}$N$_4$O = 690.79) | b-3 | m/z = 780.25 (C$_{55}$H$_{32}$N$_4$O = 780.87) |
| b-4 | m/z = 587.20 (C$_{42}$H$_{25}$N$_3$O = 587.67) | b-5 | m/z = 663.23 (C$_{48}$H$_{29}$N$_3$O = 663.76) |
| b-6 | m/z = 637.22 (C$_{46}$H$_{27}$N$_3$O = 637.73) | b-7 | m/z = 693.19 (C$_{48}$H$_{27}$N$_3$OS = 693.81) |
| b-8 | m/z = 693.19 (C$_{48}$H$_{27}$N$_3$OS = 693.81) | b-9 | m/z = 677.21 (C$_{48}$H$_{27}$N$_3$O$_2$ = 677.75) |
| b-10 | m/z = 727.23 (C$_{52}$H$_{29}$N$_3$O$_2$ = 727.81) | b-11 | m/z = 643.17 (C$_{44}$H$_{25}$N$_3$OS = 643.75) |
| b-12 | m/z = 719.20 (C$_{50}$H$_{29}$N$_3$OS = 719.85) | b-13 | m/z = 719.20 (C$_{50}$H$_{29}$N$_3$OS = 719.85) |
| b-14 | m/z = 733.18 (C$_{50}$H$_{27}$N$_3$O$_2$S = 733.83) | b-15 | m/z = 783.20 (C$_{54}$H$_{29}$N$_3$O$_2$S = 783.89) |
| b-16 | m/z = 809.21 (C$_{56}$H$_{31}$N$_3$O$_2$S = 809.93) | b-17 | m/z = 759.23 (C$_{50}$H$_{27}$N$_3$O$_2$S = 759.91) |
| b-18 | m/z = 627.19 (C$_{44}$H$_{25}$N$_3$O$_2$ = 627.69) | b-19 | m/z = 809.21 (C$_{53}$H$_{33}$N$_3$OS = 809.93) |
| b-20 | m/z = 614.21 (C$_{43}$H$_{26}$N$_4$O = 614.69) | b-21 | m/z = 690.24 (C$_{49}$H$_{30}$N$_4$O = 690.79) |
| b-22 | m/z = 587.20 (C$_{42}$H$_{25}$N$_3$O = 587.67) | b-23 | m/z = 663.76 (C$_{48}$H$_{29}$N$_3$O = 663.76) |
| b-24 | m/z = 693.19 (C$_{48}$H$_{27}$N$_3$OS = 693.81) | b-25 | m/z = 677.21 (C$_{48}$H$_{27}$N$_3$O$_2$ = 677.75) |
| b-26 | m/z = 703.23 (C$_{50}$H$_{29}$N$_3$O$_2$ = 703.78) | b-27 | m/z = 643.17 (C$_{44}$H$_{25}$N$_3$OS = 643.75) |
| b-28 | m/z = 719.20 (C$_{50}$H$_{29}$N$_3$OS = 719.85) | b-29 | m/z = 693.19 (C$_{48}$H$_{27}$N$_3$OS = 693.81) |
| b-30 | m/z = 733.18 (C$_{50}$H$_{27}$N$_3$O$_2$S = 733.83) | b-31 | m/z = 705.25 (C$_{49}$H$_{31}$N$_5$O = 705.80) |
| b-32 | m/z = 734.21 (C$_{50}$H$_{30}$N$_4$OS = 734.86) | b-33 | m/z = 810.25 (C$_{56}$H$_{34}$N$_4$OS = 810.96) |
| b-34 | m/z = 678.24 (C$_{48}$H$_{30}$N$_4$O = 678.78) | b-35 | m/z = 754.27 (C$_{54}$H$_{34}$N$_4$O = 754.87) |
| b-36 | m/z = 754.27 (C$_{54}$H$_{34}$N$_4$O = 754.87) | b-37 | m/z = 754.27 (C$_{54}$H$_{34}$N$_4$O = 754.87) |
| b-38 | m/z = 810.25 (C$_{56}$H$_{34}$N$_4$OS = 810.96) | b-39 | m/z = 850.28 (C$_{59}$H$_{38}$N$_4$OS = 851.02) |
| b-40 | m/z = 857.32 (C$_{61}$H$_{39}$N$_5$O = 858.00) | b-41 | m/z = 886.28 (C$_{62}$H$_{38}$N$_4$OS = 887.06) |
| b-42 | m/z = 830.30 (C$_{60}$H$_{38}$N$_4$O = 830.97) | b-43 | m/z = 703.23 (C$_{50}$H$_{29}$N$_3$O$_2$ = 703.78) |
| b-44 | m/z = 732.20 (C$_{50}$H$_{28}$N$_3$OS = 732.85) | b-45 | m/z = 716.22 (C$_{50}$H$_{28}$N$_4$O = 716.78) |
| b-46 | m/z = 676.23 (C$_{48}$H$_{28}$N$_4$O = 676.76) | b-47 | m/z = 779.27 (C$_{55}$H$_{33}$N$_5$O = 779.88) |
| b-48 | m/z = 808.23 (C$_{56}$H$_{32}$N$_4$OS = 808.94) | b-49 | m/z = 884.26 (C$_{62}$H$_{36}$N$_4$OS = 885.04) |
| b-50 | m/z = 752.26 (C$_{54}$H$_{32}$N$_4$O = 752.86) | b-51 | m/z = 802.27 (C$_{58}$H$_{34}$N$_4$O = 802.92) |
| b-52 | m/z = 828.29 (C$_{60}$H$_{36}$N$_4$O = 828.95) | b-53 | m/z = 704.22 (C$_{49}$H$_{28}$N$_4$O$_2$ = 704.77) |
| b-54 | m/z = 704.22 (C$_{49}$H$_{28}$N$_4$O$_2$ = 704.77) | b-55 | m/z = 733.18 (C$_{50}$H$_{27}$N$_3$O$_2$S = 733.83) |
| b-56 | m/z = 677.21 (C$_{48}$H$_{27}$N$_3$O$_2$ = 677.75) | b-57 | m/z = 733.18 (C$_{50}$H$_{27}$N$_3$O$_2$S = 733.83) |
| b-58 | m/z = 677.21 (C$_{48}$H$_{27}$N$_3$O$_2$ = 677.75) | b-59 | m/z = 753.24 (C$_{54}$H$_{31}$N$_3$O$_2$ = 753.84) |
| b-60 | m/z = 720.20 (C$_{49}$H$_{28}$N$_4$OS = 720.84) | b-61 | m/z = 693.19 (C$_{48}$H$_{27}$N$_3$OS = 693.81) |
| b-62 | m/z = 749.16 (C$_{50}$H$_{27}$N$_3$OS$_2$ = 749.90) | b-63 | m/z = 733.18 (C$_{50}$H$_{27}$N$_3$O$_2$S = 733.83) |
| b-64 | m/z = 643.17 (C$_{44}$H$_{25}$N$_3$OS = 643.75) | b-65 | m/z = 719.20 (C$_{50}$H$_{29}$N$_3$OS = 719.85) |
| b-66 | m/z = 733.18. (C$_{50}$H$_{27}$N$_3$O$_2$S = 733.83) | b-67 | m/z = 587.20 (C$_{42}$H$_{25}$N$_3$O = 587.67) |
| b-68 | m/z = 663.23 (C$_{48}$H$_{29}$N$_3$O = 663.76) | b-69 | m/z = 734.21 (C$_{50}$H$_{30}$N$_4$OS = 734.86) |
| b-70 | m/z = 810.25 (C$_{56}$H$_{34}$N$_4$OS = 810.96) | b-71 | m/z = 830.30 (C$_{60}$H$_{38}$N$_4$O = 830.97) |
| b-72 | m/z = 732.20 (C$_{50}$H$_{28}$N$_3$OS = 732.85) | b-73 | m/z = 752.26 (C$_{54}$H$_{32}$N$_4$O = 752.86) |
| b-74 | m/z = 808.23 (C$_{56}$H$_{32}$N$_4$OS = 808.94) | b-75 | m/z = 752.26 (C$_{54}$H$_{32}$N$_4$O = 752.86) |
| b-76 | m/z = 614.21 (C$_{43}$H$_{26}$N$_4$O = 614.69) | b-77 | m/z = 643.17 (C$_{44}$H$_{25}$N$_3$OS = 643.75) |
| b-78 | m/z = 663.23 (C$_{48}$H$_{29}$N$_3$O = 663.76) | b-79 | m/z = 703.23 (C$_{50}$H$_{29}$N$_3$O$_2$ = 703.78) |
| b-80 | m/z = 678.24 (C$_{48}$H$_{30}$N$_4$O = 678.78) | b-81 | m/z = 781.28 (C$_{55}$H$_{35}$N$_5$O = 781.90) |
| b-82 | m/z = 614.21 (C$_{43}$H$_{26}$N$_4$O = 614.69) | b-83 | m/z = 643.17 (C$_{44}$H$_{25}$N$_3$OS = 643.75) |
| b-84 | m/z = 693.19 (C$_{48}$H$_{27}$N$_3$OS = 693.81) | b-85 | m/z = 781.28 (C$_{55}$H$_{35}$N$_5$O = 781.90) |
| b-86 | m/z = 690.24 (C$_{49}$H$_{30}$N$_4$O = 690.79) | b-87 | m/z = 754.27 (C$_{54}$H$_{34}$N$_4$O = 754.87) |
| b-88 | m/z = 614.21 (C$_{43}$H$_{26}$N$_4$O = 614.69) | b-89 | m/z = 678.24 (C$_{48}$H$_{30}$N$_4$O = 678.78) |
| b-90 | m/z = 693.19 (C$_{48}$H$_{27}$N$_3$OS = 693.81) | b-91 | m/z = 663.23 (C$_{48}$H$_{29}$N$_3$O = 663.76) |
| b-92 | m/z = 781.28 (C$_{55}$H$_{35}$N$_5$O = 781.90) | b-93 | m/z = 732.20 (C$_{50}$H$_{28}$N$_3$OS = 732.85) |
| b-94 | m/z = 587.20 (C$_{42}$H$_{25}$N$_3$O = 587.67) | b-95 | m/z = 663.23 (C$_{48}$H$_{29}$N$_3$O = 663.76)e |
| c-1 | m/z = 689.26 (C$_{49}$H$_{31}$N$_5$ = 689.80) | c-2 | m/z = 718.22 (C$_{50}$H$_{30}$N$_4$S = 718.87) |
| c-3 | m/z = 794.25 (C$_{55}$H$_{34}$N$_4$S = 794.96) | c-4 | m/z = 662.25 (C$_{48}$H$_{30}$N$_4$ = 662.78) |
| c-5 | m/z = 587.20 (C$_{42}$H$_{25}$N$_3$ = 587.67) | c-6 | m/z = 643.17 (C$_{44}$H$_{25}$N$_3$OS = 643.75) |
| c-7 | m/z = 643.17 (C$_{44}$H$_{25}$N$_3$OS = 643.75) | c-8 | m/z = 780.25 (C$_{55}$H$_{32}$N$_4$O = 780.87) |
| c-9 | m/z = 587.20 (C$_{42}$H$_{25}$N$_3$O = 587.67) | c-10 | m/z = 643.17 (C$_{44}$H$_{25}$N$_3$OS = 643.75) |
| c-11 | m/z = 719.20 (C$_{50}$H$_{29}$N$_3$OS = 719.85) | c-12 | m/z = 796.23 (C$_{55}$H$_{32}$N$_4$OS = 796.93) |
| c-13 | m/z = 603.18 (C$_{42}$H$_{25}$N$_3$S = 603.73) | c-14 | m/z = 679.21 (C$_{48}$H$_{29}$N$_3$S = 679.83) |
| c-15 | m/z = 659.15 (C$_{44}$H$_{25}$N$_3$S$_2$ = 659.82) | c-16 | m/z = 735.18 (C$_{50}$H$_{29}$N$_3$S$_2$ = 735.92) |
| c-17 | m/z = 643.17 (C$_{44}$H$_{25}$N$_3$OS = 643.75) | c-18 | m/z = 603.18 (C$_{42}$H$_{25}$N$_3$S = 603.73) |
| c-19 | m/z = 735.18 (C$_{50}$H$_{29}$N$_3$S$_2$ = 735.92) | c-20 | m/z = 659.15 (C$_{44}$H$_{25}$N$_3$S$_2$ = 659.82) |
| c-21 | m/z = 735.18 (C$_{50}$H$_{29}$N$_3$S$_2$ = 735.92) | c-22 | m/z = 690.24 (C$_{49}$H$_{30}$N$_4$O = 690.79) |
| c-23 | m/z = 663.23 (C$_{48}$H$_{29}$N$_3$O = 663.76) | c-24 | m/z = 719.20 (C$_{50}$H$_{29}$N$_3$OS = 719.85) |
| c-25 | m/z = 739.26 (C$_{54}$H$_{33}$N$_3$O = 739.86) | c-26 | m/z = 781.28 (C$_{55}$H$_{35}$N$_5$O = 781.90) |
| c-27 | m/z = 752.26 (C$_{54}$H$_{32}$N$_4$O = 752.86) | c-28 | m/z = 703.23 (C$_{50}$H$_{29}$N$_3$O$_2$ = 703.78) |
| c-29 | m/z = 719.20 (C$_{50}$H$_{29}$N$_3$OS = 719.85) | c-30 | m/z = 781.28 (C$_{55}$H$_{35}$N$_5$O = 781.90) |
| c-31 | m/z = 713.25 (C$_{52}$H$_{31}$N$_3$O = 713.82) | c-32 | m/z = 752.26 (C$_{54}$H$_{32}$N$_4$O = 752.86) |
| c-33 | m/z = 726.24 (C$_{52}$H$_{30}$N$_4$O = 726.82) | c-34 | m/z = 690.24 (C$_{49}$H$_{30}$N$_4$O = 690.79) |

TABLE 7-continued

| Compound | FD-MS | Compound | FD-MS |
|---|---|---|---|
| c-35 | m/z = 719.20 ($C_{50}H_{29}N_3OS$ = 719.85) | c-36 | m/z = 781.28 ($C_{55}H_{35}N_5O$ = 781.90) |
| c-37 | m/z = 740.26 ($C_{53}H_{32}N_4O$ = 740.85) | c-38 | m/z = 719.20 ($C_{50}H_{29}N_3OS$ = 719.85) |
| c-39 | m/z = 637.22 ($C_{46}H_{27}N_3O$ = 637.73) | c-40 | m/z = 637.22 ($C_{46}H_{27}N_3O$ = 637.73) |
| c-41 | m/z = 705.25 ($C_{49}H_{31}N_5O$ = 705.80) | c-42 | m/z = 754.27 ($C_{54}H_{34}N_4O$ = 754.87) |
| c-43 | m/z = 732.20 ($C_{50}H_{28}N_3OS$ = 732.85) | c-44 | m/z = 752.26 ($C_{54}H_{32}N_4O$ = 752.86) |
| c-45 | m/z = 726.24 ($C_{52}H_{30}N_4O$ = 726.82) | d-1 | m/z = 614.21 ($C_{43}H_{26}N_4O$ = 614.69) |
| d-2 | m/z = 643.17 ($C_{44}H_{25}N_3OS$ = 643.75) | d-3 | m/z = 719.20 ($C_{50}H_{29}N_3OS$ = 719.85) |
| d-4 | m/z = 719.20 ($C_{50}H_{29}N_3OS$ = 719.85) | d-5 | m/z = 733.18. ($C_{50}H_{27}N_3O_2S$ = 733.83) |
| d-6 | m/z = 587.20 ($C_{42}H_{25}N_3O$ = 587.67) | d-7 | m/z = 663.76 ($C_{48}H_{29}N_3O$ = 663.76) |
| d-8 | m/z = 727.23 ($C_{52}H_{29}N_3O_2$ = 727.81) | d-9 | m/z = 693.19 ($C_{48}H_{27}N_3OS$ = 693.81) |
| d-10 | m/z = 614.21 ($C_{43}H_{26}N_4O$ = 614.69) | d-11 | m/z = 690.24 ($C_{49}H_{30}N_4O$ = 690.79) |
| d-12 | m/z = 643.17 ($C_{44}H_{25}N_3OS$ = 643.75) | d-13 | m/z = 693.19 ($C_{48}H_{27}N_3OS$ = 693.81) |
| d-14 | m/z = 719.20 ($C_{50}H_{29}N_3OS$ = 719.85) | d-15 | m/z = 733.18 ($C_{50}H_{27}N_3O_2S$ = 733.83) |
| d-16 | m/z = 783.20 ($C_{54}H_{29}N_3O_2S$ = 783.89) | d-17 | m/z = 587.20 ($C_{42}H_{25}N_3O$ = 587.67) |
| d-18 | m/z = 663.23 ($C_{48}H_{29}N_3O$ = 663.76) | d-19 | m/z = 677.21 ($C_{48}H_{27}N_3O_2$ = 677.75) |
| d-20 | m/z = 677.21 ($C_{48}H_{27}N_3O_2$ = 677.75) | d-21 | m/z = 693.19 ($C_{48}H_{27}N_3OS$ = 693.81) |
| d-22 | m/z = 743.20 ($C_{52}H_{29}N_3OS$ = 743.87) | d-23 | m/z = 630.19 ($C_{43}H_{26}N_4S$ = 630.76) |
| d-24 | m/z = 706.22 ($C_{49}H_{30}N_4S$ = 706.85) | d-25 | m/z = 659.15 ($C_{44}H_{25}N_3S_2$ = 659.82) |
| d-26 | m/z = 659.15 ($C_{44}H_{25}N_3S_2$ = 659.82) | d-27 | m/z = 735.18 ($C_{50}H_{29}N_3S_2$ = 735.29) |
| d-28 | m/z = 709.16 ($C_{48}H_{27}N_3S_2$ = 709.88) | d-29 | m/z = 709.16 ($C_{48}H_{27}N_3S_2$ = 709.88) |
| d-30 | m/z = 643.17 ($C_{44}H_{25}N_3OS$ = 643.75) | d-31 | m/z = 603.18 ($C_{42}H_{25}N_3S$ = 603.73) |
| d-32 | m/z = 679.21 ($C_{48}H_{29}N_3S$ = 679.83) | d-33 | m/z = 693.19 ($C_{48}H_{27}N_3OS$ = 693.81) |
| d-34 | m/z = 630.19 ($C_{43}H_{26}N_4S$ = 630.76) | d-35 | m/z = 659.15 ($C_{44}H_{25}N_3S_2$ = 659.82) |
| d-36 | m/z = 735.18 ($C_{50}H_{29}N_3S_2$ = 735.29) | d-37 | m/z = 749.16 ($C_{50}H_{27}N_3OS_2$ = 749.90) |
| d-38 | m/z = 603.18 ($C_{42}H_{25}N_3S$ = 603.73) | d-39 | m/z = 679.21 ($C_{48}H_{29}N_3S$ = 679.83) |
| d-40 | m/z = 743.20 ($C_{52}H_{29}N_3OS$ = 743.87) | d-41 | m/z = 693.19 ($C_{48}H_{27}N_3OS$ = 693.81) |
| d-42 | m/z = 734.20 ($C_{50}H_{30}N_4OS$ = 734.86) | d-43 | m/z = 678.24 ($C_{48}H_{30}N_4O$ = 678.78) |
| d-44 | m/z = 734.21 ($C_{50}H_{30}N_4OS$ = 734.86) | d-45 | m/z = 810.25 ($C_{56}H_{34}N_4OS$ = 810.96) |
| d-46 | m/z = 676.23 ($C_{48}H_{28}N_4O$ = 676.76) | d-47 | m/z = 732.20 ($C_{50}H_{28}N_3OS$ = 732.85) |
| d-48 | m/z = 750.19 ($C_{50}H_{30}N_4S_2$ = 750.93) | d-49 | m/z = 694.22 ($C_{48}H_{30}N_4S$ = 694.84) |
| d-50 | m/z = 768.23 ($C_{54}H_{32}N_4S$ = 768.92) | d-51 | m/z = 748.18 ($C_{50}H_{28}N_4S_2$ = 748.91) |
| d-52 | m/z = 692.20 ($C_{48}H_{28}N_4S$ = 692.83) | d-53 | m/z = 643.17 ($C_{44}H_{25}N_3OS$ = 643.75) |
| d-54 | m/z = 693.19 ($C_{48}H_{27}N_3OS$ = 693.81) | d-55 | m/z = 734.21 ($C_{50}H_{30}N_4OS$ = 734.86) |
| d-56 | m/z = 678.24 ($C_{48}H_{30}N_4O$ = 678.78) | d-57 | m/z = 676.23 ($C_{48}H_{28}N_4O$ = 676.76) |
| d-58 | m/z = 719.20 ($C_{50}H_{29}N_3OS$ = 719.85) | d-59 | m/z = 754.27 ($C_{54}H_{34}N_4O$ = 754.87) |
| d-60 | m/z = 719.20 ($C_{50}H_{29}N_3OS$ = 719.85) | d-61 | m/z = 754.27 ($C_{54}H_{34}N_4O$ = 754.87) |
| d-62 | m/z = 587.20 ($C_{42}H_{25}N_3O$ = 587.67) | d-63 | m/z = 784.23 ($C_{54}H_{32}N_4OS$ = 784.92) |
| d-64 | m/z = 752.26 ($C_{54}H_{32}N_4O$ = 752.86) | d-65 | m/z = 630.19 ($C_{43}H_{26}N_4S$ = 630.76) |
| d-66 | m/z = 659.15 ($C_{44}H_{25}N_3S_2$ = 659.82) | d-67 | m/z = 750.19 ($C_{50}H_{30}N_4S_2$ = 750.93) |
| d-68 | m/z = 694.22 ($C_{48}H_{30}N_4S$ = 694.84) | d-69 | m/z = 706.22 ($C_{49}H_{30}N_4S$ = 706.85) |
| d-70 | m/z = 770.25 ($C_{54}H_{34}N_4S$ = 772.94) | d-71 | m/z = 735.18 ($C_{50}H_{29}N_3S_2$ = 735.92) |
| d-72 | m/z = 659.15 ($C_{44}H_{25}N_3S_2$ = 659.82) | d-73 | m/z = 744.23 ($C_{52}H_{32}N_4S$ = 744.90) |
| d-74 | m/z = 748.18 ($C_{50}H_{28}N_4S_2$ = 748.91) | d-75 | m/z = 768.23 ($C_{54}H_{32}N_4S$ = 768.92) |
| d-76 | m/z = 735.18 ($C_{50}H_{29}N_3S_2$ = 735.92) | — | — |

1) Manufacture of Organic Light Emitting Device

<Experimental Example 1>—Manufacture of Organic Light Emitting Device

1) Manufacture of Organic Light Emitting Device (Red Single Host)

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treated for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-Di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 500 Å using a compound described in the following Table 8 as a red host, and using $(piq)_2(Ir)$ (acac) as a red phosphorescent dopant by 3% doping the $(piq)_2(Ir)$ (acac) to the host. After that, BCP (bathocuproine, 2,9-dimethyl-4,7-diphenyl-1,10-phenanthroline) was deposited to 60 Å as a hole blocking layer, and $Alq_3$ was deposited to 200 Å thereon as an electron transfer layer. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For the organic electroluminescent device manufactured as above, electroluminescent (EL) properties were measured using M7000 manufactured by McScience Inc., and with the measurement results, $T_{90}$ was measured when standard luminance was 6,000 cd/m² using a lifetime measurement system (M6000) manufactured by McScience Inc. Properties of the organic electroluminescent device of the present disclosure are as shown in the following Table 8.

TABLE 8

| | Compound | Driving Voltage (V) | Efficiency (cd/A) | Color Coordinate (x, y) | Lifetime ($T_{90}$) |
|---|---|---|---|---|---|
| Comparative Example 1 | Comparative Compound A | 5.35 | 14.5 | 0.672, 0.328 | 60 |
| Comparative Example 2 | Comparative Compound B | 5.74 | 13.19 | 0.676, 0.324 | 45 |
| Comparative Example 3 | Comparative Compound C | 5.50 | 13.7 | 0.680, 0.320 | 57 |
| Comparative Example 4 | Comparative Compound D | 5.70 | 14.5 | 0.677, 0.322 | 55 |
| Comparative Example 5 | Comparative Compound E | 5.45 | 14.2 | 0.689, 0.311 | 65 |
| Comparative Example 6 | Comparative Compound F | 5.78 | 13.2 | 0.689, 0.311 | 70 |
| Comparative Example 7 | Comparative Compound G | 5.34 | 14.9 | 0.684, 0.316 | 73 |
| Comparative Example 8 | Comparative Compound H | 5.62 | 14.5 | 0.688, 0.312 | 62 |
| Example 1 | Compound a-6 | 3.94 | 21.2 | 0.678, 0.321 | 99 |
| Example 2 | Compound a-8 | 4.01 | 22.7 | 0.679, 0.321 | 112 |
| Example 3 | Compound a-16 | 4.27 | 21.7 | 0.691, 0.309 | 125 |
| Example 4 | Compound a-26 | 3.97 | 24.0 | 0.681, 0.319 | 103 |
| Example 5 | Compound a-30 | 4.20 | 18.5 | 0.692, 0.308 | 111 |
| Example 6 | Compound a-33 | 4.00 | 25.0 | 0.681, 0.319 | 127 |
| Example 7 | Compound a-42 | 4.25 | 17.5 | 0.678, 0.322 | 80 |
| Example 8 | Compound a-46 | 3.99 | 22.0 | 0.679, 0.321 | 88 |
| Example 9 | Compound a-49 | 4.21 | 19.2 | 0.679, 0.321 | 101 |
| Example 10 | Compound a-55 | 4.19 | 18.9 | 0.684, 0.316 | 113 |
| Example 11 | Compound a-71 | 4.00 | 22.8 | 0.689, 0.311 | 120 |
| Example 12 | Compound a-90 | 4.01 | 21.0 | 0.689, 0.310 | 89 |
| Example 13 | Compound a-104 | 4.19 | 20.0 | 0.692, 0.308 | 90 |
| Example 14 | Compound a-109 | 4.00 | 22.0 | 0.679, 0.321 | 101 |
| Example 15 | Compound a-112 | 4.16 | 19.0 | 0.685, 0.315 | 121 |
| Example 16 | Compound a-115 | 3.89 | 21.2 | 0.685, 0.314 | 96 |
| Example 17 | Compound a-119 | 4.32 | 17.0 | 0.688, 0.312 | 121 |
| Example 18 | Compound a-131 | 4.05 | 20.1 | 0.691, 0.309 | 98 |
| Example 19 | Compound a-134 | 4.10 | 21.0 | 0.684, 0.316 | 94 |
| Example 20 | Compound a-136 | 4.09 | 20.9 | 0.687, 0.313 | 89 |
| Example 21 | Compound a-142 | 4.18 | 19.8 | 0.681, 0.319 | 121 |
| Example 22 | Compound a-144 | 4.02 | 23.9 | 0.682, 0.318 | 125 |
| Example 23 | Compound a-149 | 4.09 | 20.9 | 0.687, 0.313 | 89 |
| Example 24 | Compound a-152 | 4.25 | 17.5 | 0.681, 0.319 | 89 |
| Example 25 | Compound a-157 | 4.12 | 18.7 | 0.682, 0.318 | 85 |
| Example 26 | Compound b-4 | 3.80 | 22.9 | 0.684, 0.316 | 120 |
| Example 27 | Compound b-7 | 4.02 | 19.9 | 0.682, 0.318 | 119 |
| Example 28 | Compound b-10 | 4.26 | 18.9 | 0.685, 0.315 | 125 |
| Example 29 | Compound b-15 | 4.04 | 20.7 | 0.688, 0.312 | 128 |
| Example 30 | Compound b-23 | 3.97 | 23.4 | 0.682, 0.318 | 128 |
| Example 31 | Compound b-32 | 4.21 | 17.6 | 0.676, 0.322 | 90 |
| Example 32 | Compound b-35 | 4.22 | 19.0 | 0.685, 0.315 | 110 |
| Example 33 | Compound b-44 | 4.22 | 20.9 | 0.682, 0.318 | 118 |
| Example 34 | Compound b-50 | 3.95 | 21.9 | 0.680, 0.319 | 132 |
| Example 35 | Compound b-57 | 4.11 | 19.9 | 0.685, 0.314 | 98 |
| Example 36 | Compound b-65 | 4.30 | 22.5 | 0.684, 0.315 | 98 |
| Example 37 | Compound b-69 | 4.44 | 19.5 | 0.681, 0.319 | 88 |
| Example 38 | Compound b-75 | 3.97 | 19.9 | 0.685, 0.314 | 110 |
| Example 39 | Compound b-77 | 3.95 | 21.8 | 0.682, 0.318 | 120 |
| Example 40 | Compound b-81 | 4.28 | 18.5 | 0.685, 0.314 | 112 |
| Example 41 | Compound b-84 | 4.01 | 19.8 | 0.681, 0.319 | 87 |
| Example 42 | Compound b-91 | 4.44 | 22.5 | 0.678, 0.321 | 98 |
| Example 43 | Compound c-3 | 4.47 | 21.8 | 0.672, 0.327 | 120 |
| Example 44 | Compound c-10 | 3.99 | 19.9 | 0.680, 0.319 | 98 |
| Example 45 | Compound c-11 | 4.08 | 21.9 | 0.680, 0.319 | 87 |
| Example 46 | Compound c-17 | 4.02 | 20.9 | 0.682, 0.318 | 97 |
| Example 47 | Compound c-19 | 3.93 | 21.2 | 0.684, 0.315 | 98 |
| Example 48 | Compound c-23 | 4.12 | 21.7 | 0.679, 0.321 | 100 |
| Example 49 | Compound c-29 | 4.19 | 20.6 | 0.683, 0.317 | 103 |
| Example 50 | Compound c-32 | 4.21 | 20.1 | 0.689, 0.311 | 127 |
| Example 51 | Compound c-39 | 3.99 | 22.6 | 0.679, 0.321 | 125 |
| Example 52 | Compound c-43 | 3.99 | 22.5 | 0.681, 0.319 | 112 |
| Example 53 | Compound d-7 | 3.93 | 21.2 | 0.684, 0.315 | 98 |
| Example 54 | Compound d-9 | 4.28 | 20.2 | 0.684, 0.315 | 119 |
| Example 55 | Compound d-12 | 3.90 | 23.2 | 0.685, 0.314 | 117 |
| Example 56 | Compound d-26 | 3.89 | 22.9 | 0.681, 0.319 | 120 |
| Example 57 | Compound d-30 | 4.14 | 21.3 | 0.691, 0.309 | 100 |
| Example 58 | Compound d-39 | 3.99 | 21.7 | 0.679, 0.321 | 111 |
| Example 59 | Compound d-41 | 4.21 | 18.3 | 0.685, 0.315 | 125 |
| Example 60 | Compound d-44 | 4.11 | 20.3 | 0.683, 0.317 | 113 |
| Example 61 | Compound d-52 | 4.08 | 21.2 | 0.684, 0.316 | 131 |
| Example 62 | Compound d-53 | 3.99 | 22.9 | 0.680, 0.320 | 98 |
| Example 63 | Compound d-59 | 4.28 | 19.2 | 0.687, 0.313 | 112 |
| Example 64 | Compound d-64 | 4.39 | 17.9 | 0.688, 0.312 | 128 |
| Example 65 | Compound d-72 | 3.99 | 22.7 | 0.674, 0.325 | 116 |

TABLE 8-continued
| Compound | Driving Voltage (V) | Efficiency (cd/A) | Color Coordinate (x, y) | Lifetime (T90) |
|---|---|---|---|---|
| 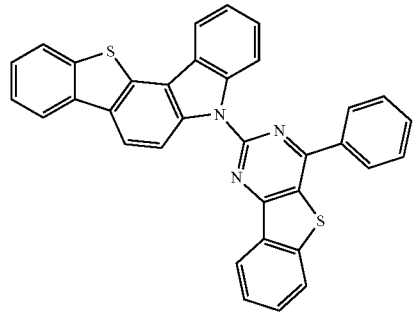 A | | | | |
| 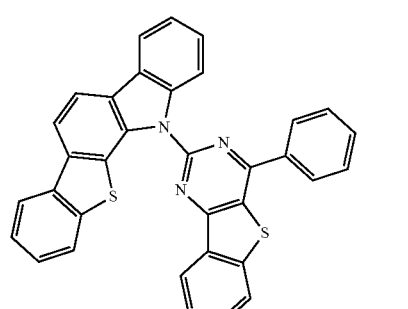 B | | | | |
| 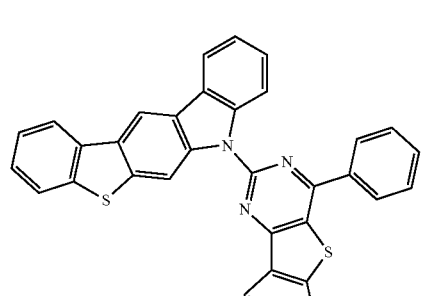 C | | | | |
| 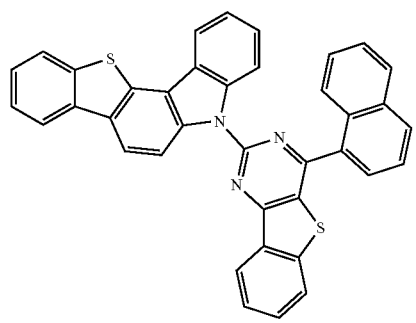 D | | | | |
| 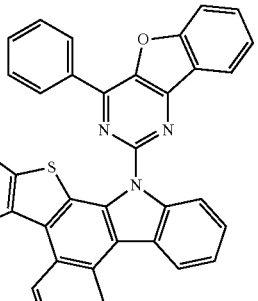 E | | | | |
| 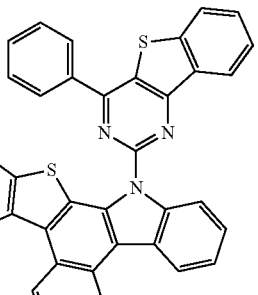 F | | | | |
| 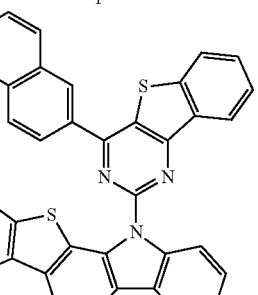 G | | | | |
| 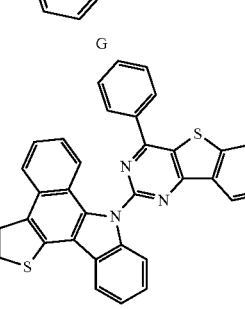 H | | | | |
<Experimental Example 2>—Manufacture of Organic Light Emitting Device (Red N+N Mixed Host)
A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-Tris[2-naphthyl(phenyl)amino]triphenylamine) and a hole transfer layer NPB (N,N'-Di(1-naphthyl)-N,N'-diphenyl-(1,1'-biphenyl)-4,4'-diamine), which are common layers, were formed.

A light emitting layer was thermal vacuum deposited thereon as follows. As the light emitting layer, two types of compounds as in the following Table 9 were pre-mixed and deposited to 400 Å in one source of supply as a red host, and $(piq)_2(Ir)$ (acac) was deposited as a red phosphorescent dopant by 3% doping. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For the organic electroluminescent device manufactured as above, electroluminescent (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

TABLE 9

| | Light Emitting Layer Compound | Ratio (N:N) | Driving Voltage (V) | Efficiency (cd/A) | Color Coordinate (x, y) | Lifetime ($T_{90}$) |
|---|---|---|---|---|---|---|
| Example 1 | Compound c-11:a-33 | 1:1 | 4.32 | 24.9 | 0.679, 0.321 | 365 |
| Example 2 | Compound d-7:a-55 | 1:1 | 4.18 | 25.5 | 0.680, 0.319 | 377 |
| Example 3 | Compound a-26:a-71 | 1:1 | 4.28 | 24.9 | 0.680, 0.319 | 369 |
| Example 4 | Compound a-90:a-142 | 1:1 | 4.26 | 24.2 | 0.681, 0.319 | 389 |
| Example 5 | Compound c-10:b-35 | 1:1 | 4.20 | 26.8 | 0.681, 0.319 | 408 |
| Example 6 | Compound b-23:b-44 | 1:1 | 4.26 | 26.2 | 0.681, 0.319 | 414 |
| Example 7 | Compound a-115:c-3 | 1:1 | 4.38 | 24.9 | 0.678, 0.321 | 369 |
| Example 8 | Compound d-39:c-43 | 1:1 | 4.18 | 24.6 | 0.691, 0.309 | 389 |
| Example 9 | Compound a-30:d-44 | 1:1 | 4.20 | 25.5 | 0.681, 0.319 | 400 |
| Example 10 | Compound b-4:d-59 | 1:1 | 4.23 | 26.2 | 0.681, 0.319 | 405 |

<Experimental Example 3>—Manufacture of Organic Light Emitting Device (Red N+P Mixed Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-Tris[2-naphthyl(phenyl)amino]triphenylamine) and a hole transfer layer NPB (N,N'-Di(1-naphthyl)-N,N'-diphenyl-(1,1'-biphenyl)-4,4'-diamine), which are common layers, were formed.

A light emitting layer was thermal vacuum deposited thereon as follows. As the light emitting layer, two types of compounds as in the following Table 10 were pre-mixed and deposited to 400 Å in one source of supply as a red host, and $(piq)_2(Ir)$ (acac) was deposited as a red phosphorescent dopant by 3% doping. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For the organic electroluminescent device manufactured as above, electroluminescent (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

TABLE 10

| | Light Emitting Layer Compound | Ratio (N:P) | Driving Voltage (V) | Efficiency (cd/A) | Color Coordinate (x, y) | Lifetime (T90) |
|---|---|---|---|---|---|---|
| Example 1 | a-6:P-Host A | 3:1 | 4.16 | 27.5 | 0.672, 0.326 | 388 |
| Example 2 | | 2:1 | 4.20 | 25.0 | 0.678, 0.322 | 376 |
| Example 3 | | 1:1 | 4.31 | 23.6 | 0.674, 0.325 | 361 |
| Example 4 | | 1:2 | 4.42 | 21.7 | 0.679, 0.321 | 355 |
| Example 5 | | 1:3 | 4.70 | 20.1 | 0.678, 0.322 | 342 |

TABLE 10-continued

| | Light Emitting Layer Compound | Ratio (N:P) | Driving Voltage (V) | Efficiency (cd/A) | Color Coordinate (x, y) | Lifetime (T90) |
|---|---|---|---|---|---|---|
| Example 6 | a-26:P-Host B | 3:1 | 4.11 | 28.4 | 0.674, 0.325 | 426 |
| Example 7 | | 2:1 | 4.18 | 28.2 | 0.687, 0.313 | 419 |
| Example 8 | | 1:1 | 4.22 | 24.2 | 0.681, 0.319 | 377 |
| Example 9 | | 1:2 | 4.44 | 22.2 | 0.680, 0.319 | 354 |
| Example 10 | | 1:3 | 4.78 | 22.2 | 0.682, 0.317 | 310 |
| Example 11 | a-33:P-Host C | 3:1 | 4.29 | 24.5 | 0.682, 0.317 | 402 |
| Example 12 | a-46:P-Host D | 3:1 | 4.23 | 27.2 | 0.682, 0.317 | 356 |
| Example 13 | a-71:P-Host E | 3:1 | 4.23 | 26.8 | 0.685, 0.315 | 395 |
| Example 14 | a-115:P-Host F | 3:1 | 4.18 | 27.4 | 0.679, 0.321 | 378 |
| Example 15 | a-144:P-Host G | 3:1 | 4.24 | 26.8 | 0.680, 0.319 | 400 |
| Example 16 | b-4:P-Host H | 3:1 | 4.10 | 28.9 | 0.680, 0.319 | 380 |
| Example 17 | b-15:P-Host A | 3:1 | 4.23 | 27.5 | 0.682, 0.318 | 377 |
| Example 18 | b-23:P-Host B | 3:1 | 4.15 | 29.9 | 0.681, 0.319 | 380 |
| Example 19 | b-50:P-Host C | 3:1 | 4.28 | 26.2 | 0.685, 0.315 | 402 |
| Example 20 | b-77:P-Host D | 3:1 | 4.11 | 27.9 | 0.679, 0.321 | 396 |
| Example 21 | c-10:P-Host E | 3:1 | 4.29 | 27.3 | 0.678, 0.322 | 366 |
| Example 22 | c-32:P-Host F | 3:1 | 4.20 | 28.8 | 0.680, 0.319 | 390 |
| Example 23 | d-12:P-Host G | 3:1 | 4.22 | 27.7 | 0.682, 0.317 | 390 |
| Example 24 | d-72:P-Host H | 3:1 | 4.10 | 27.5 | 0.679, 0.321 | 395 |

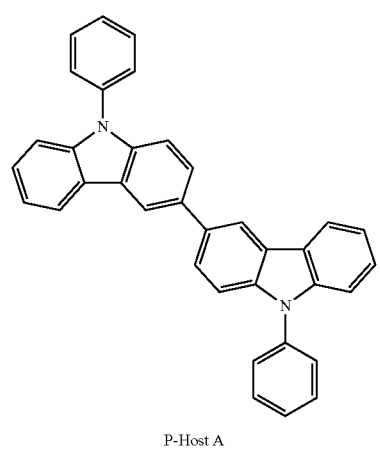 [SMILES: c1ccc(-n2c3ccccc3c3cc(-c4ccc5c(c4)c4ccccc4n5-c4ccccc4)ccc32)cc1]

P-Host A

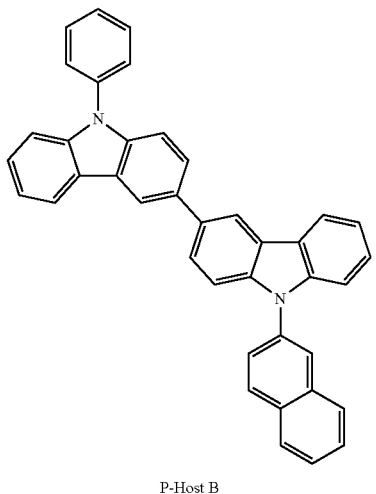 [SMILES: c1ccc(-n2c3ccccc3c3cc(-c4ccc5c(c4)c4ccccc4n5-c4ccc5ccccc5c4)ccc32)cc1]

P-Host B

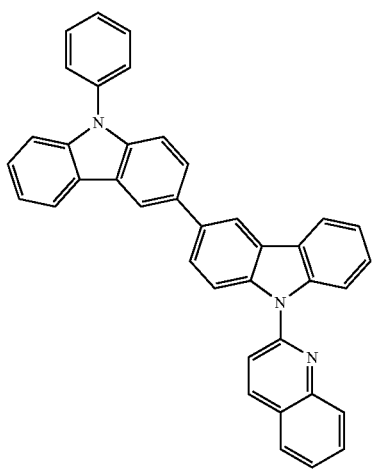

P-Host C

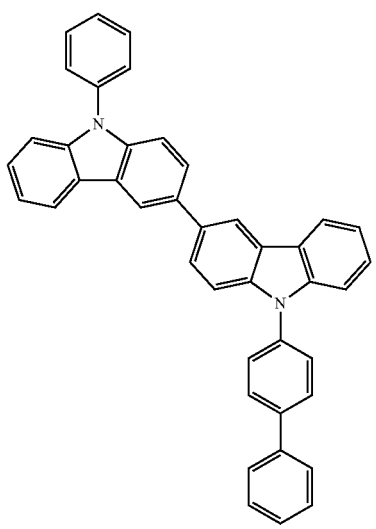

P-Host D

TABLE 10-continued

| Light Emitting Layer Compound | Ratio (N:P) | Driving Voltage (V) | Efficiency (cd/A) | Color Coordinate (x, y) | Lifetime (T90) |
|---|---|---|---|---|---|

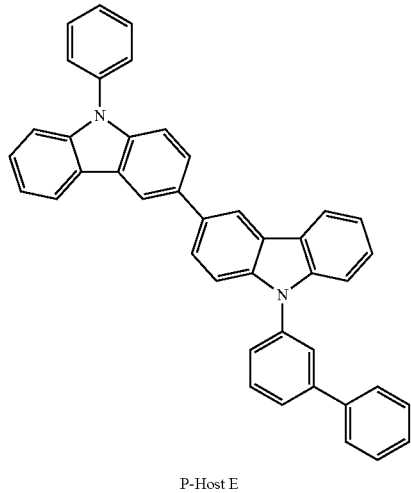 [SMILES: c1ccc(-c2cccc(-n3c4ccccc4c4cc(-c5ccc6c(c5)c5ccccc5n6-c5ccccc5)ccc43)c2)cc1]

P-Host E

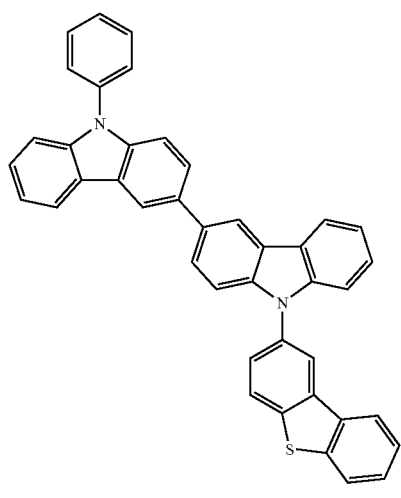

P-Host F

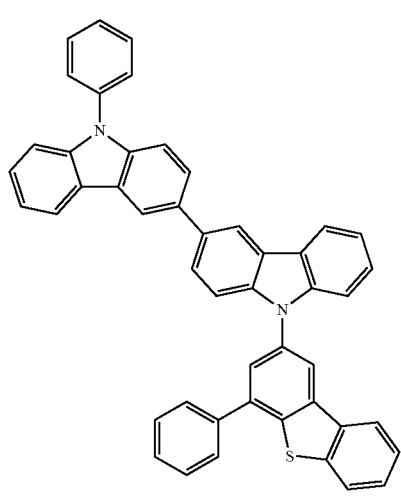

P-Host G

TABLE 10-continued

| Light Emitting Layer Compound | Ratio (N:P) | Driving Voltage (V) | Efficiency (cd/A) | Color Coordinate (x, y) | Lifetime (T90) |
|---|---|---|---|---|---|

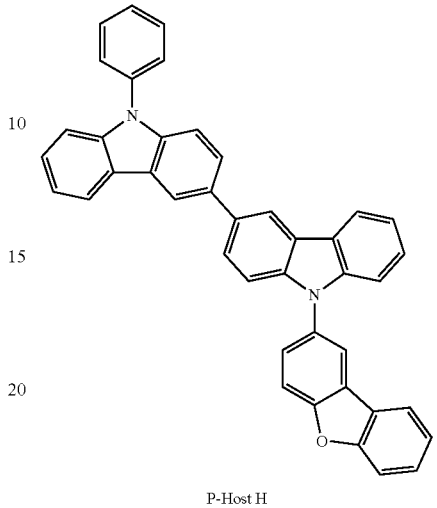

P-Host H

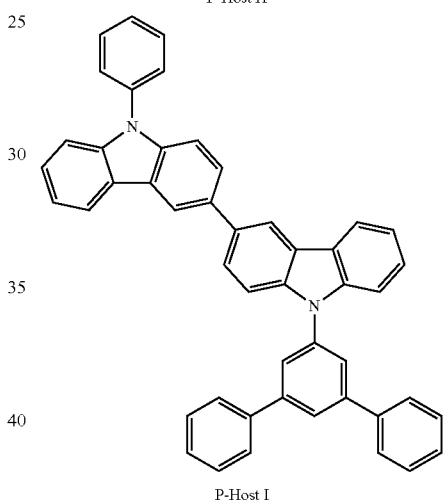

P-Host I

As shown in Table 8, it was identified that, when using the compound corresponding to Chemical Formula 1 as a light emitting layer of an organic light emitting device, superior effects were obtained in terms of properties of lifetime, efficiency and driving voltage compared to when not using the compound.

As shown in Table 9 and Table 10, when including both the N+N compound or the N+P compound in the organic material layer of the organic light emitting device, more superior efficiency and lifetime effects were obtained. This result can lead to a prediction of exciplex phenomenon occurring. Particularly, the exciplex phenomenon of the N+P compound is a phenomenon of emitting energy having a HOMO level size of a donor (p-host) and a LUMO level size of an acceptor (n-host) due to an electron exchange between the two molecules. When using a donor (p-host) having a favorable hole transfer ability and an acceptor (n-host) having a favorable electron transfer ability as a host of a light emitting layer, holes are injected to the p-host and electrons are injected to the n-host, and therefore, a driving voltage can be lowered, which helps with enhancement in the lifetime.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A heterocyclic compound represented by the following Chemical Formula 1:

[Chemical Formula 1]

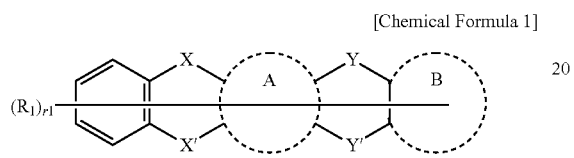

in Chemical Formula 1,
one of X and X' is O; S; or $NR_{21}$, and the other one is a direct bond;
one of Y and Y' is O; S; or $NR_{22}$, and the other one is a direct bond;
A and B are each independently a C6 to C60 aryl ring, and at least one thereof is a C10 to C60 aryl ring;
$R_1$ is selected from the group consisting of a substituted or unsubstituted phenyl group; a substituted or unsubstituted naphthyl group; a substituted or unsubstituted amine group; a substituted or unsubstituted carbazole group; a substituted or unsubstituted benzocarbazole group; a substituted or unsubstituted dibenzofuran group; and a substituted or unsubstituted dibenzothiophene group;
$R_{21}$ and $R_{22}$ are each independently a substituted or unsubstituted aryl group; or a substituted or unsubstituted heteroaryl group;
r1 is an integer of 1 to 12; and
when r1 is an integer of 2 or greater, substituents in the parentheses are the same as or different from each other.

2. The heterocyclic compound of claim 1, wherein Chemical Formula 1 is represented by the following Chemical Formula 2 or Chemical Formula 3:

[Chemical Formula 2]

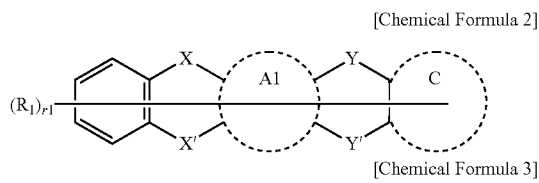

[Chemical Formula 3]

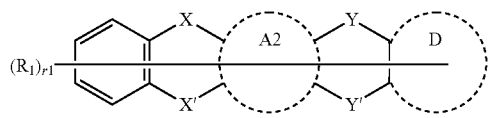

in Chemical Formulae 2 and 3,
X, X', Y, Y', $R_1$ and r1 have the same definitions as in Chemical Formula 1;
A1 is benzene;
A2 is naphthalene;
C is a C10 to C60 aryl ring; and
D is a C6 to C60 aryl ring.

3. The heterocyclic compound of claim 1, wherein Chemical Formula 1 is represented by any one of the following Chemical Formula 4 to Chemical Formula 10:

[Chemical Formula 4]

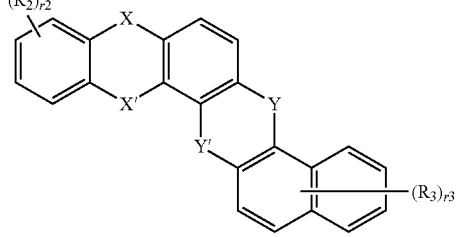

[Chemical Formula 5]

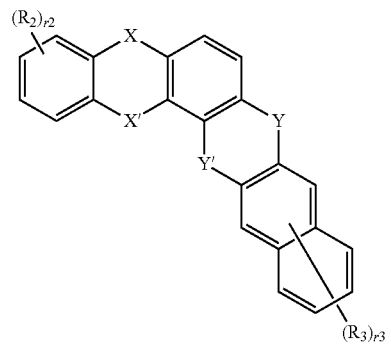

[Chemical Formula 6]

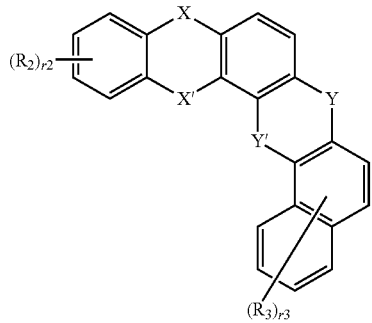

[Chemical Formula 7]

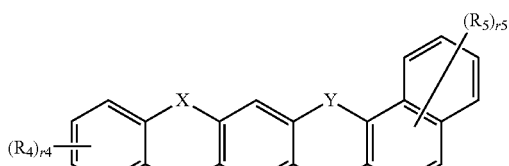

[Chemical Formula 8]

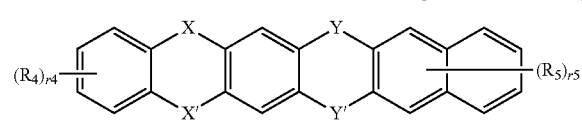

[Chemical Formula 9]

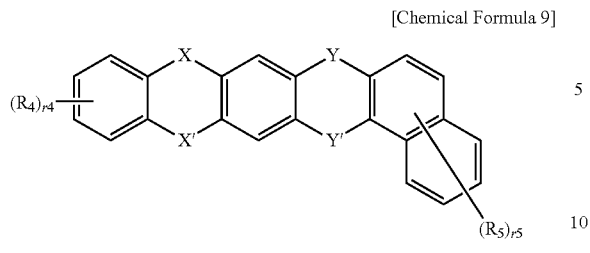

[Chemical Formula 10]

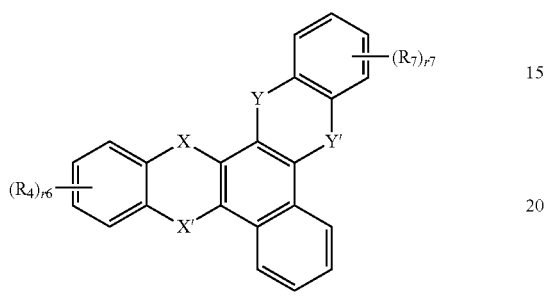

in Chemical Formulae 4 to 10,

X, X', Y and Y' have the same definitions as in Chemical Formula 1;

$R_2$ to $R_7$ are each independently selected from the group consisting of hydrogen; a substituted or unsubstituted phenyl group; a substituted or unsubstituted naphthyl group; a substituted or unsubstituted amine group; a substituted or unsubstituted carbazole group; a substituted or unsubstituted benzocarbazole group; a substituted or unsubstituted dibenzofuran group; and a substituted or unsubstituted dibenzothiophene group;

r2, r4, r6 and r7 are each an integer of 1 to 4;

r3 and r5 are each an integer of 1 to 6; and when r2 to r7 are each an integer of 2 or greater, substituents in the parentheses are the same as or different from each other.

4. The heterocyclic compound of claim 1, wherein one of A and B is benzene, and the other one is naphthalene.

5. The heterocyclic compound of claim 1, wherein $R_{21}$ and $R_{22}$ are selected from among the following structural formulae:

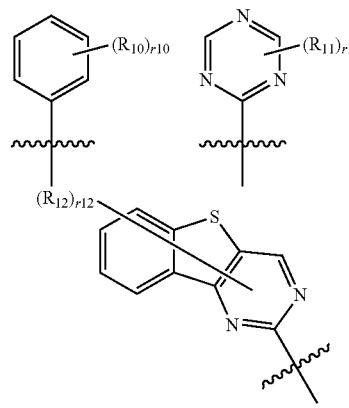

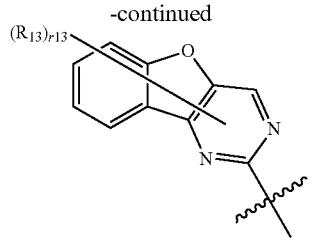

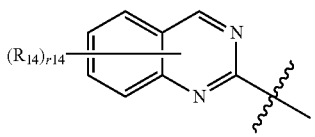

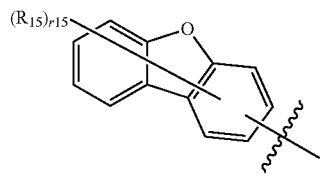

in the structural formulae, $R_{10}$ to $R_{15}$ are each independently hydrogen; a substituted or unsubstituted aryl group; or a substituted or unsubstituted heteroaryl group;

r11 is 1 or 2;

r10 and r12 to r14 are each independently an integer of 1 to 5;

r15 is an integer of 1 to 7; and when r10 to r15 are each an integer of 2 or greater, substituents in the parentheses are the same as or different from each other.

6. The heterocyclic compound claim 1, wherein Chemical Formula 1 is represented by any one of the following compounds:

a-1

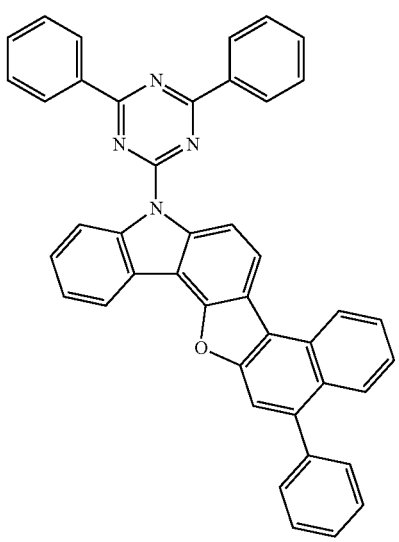

a-2
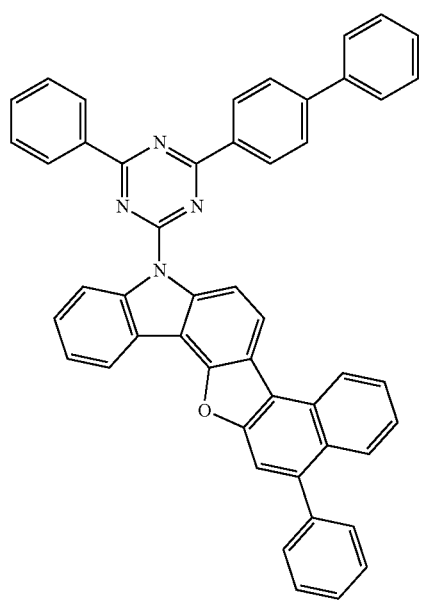
a-3
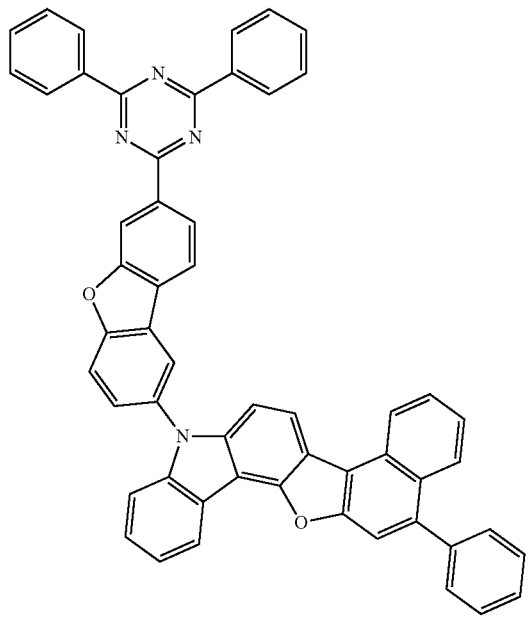
a-4
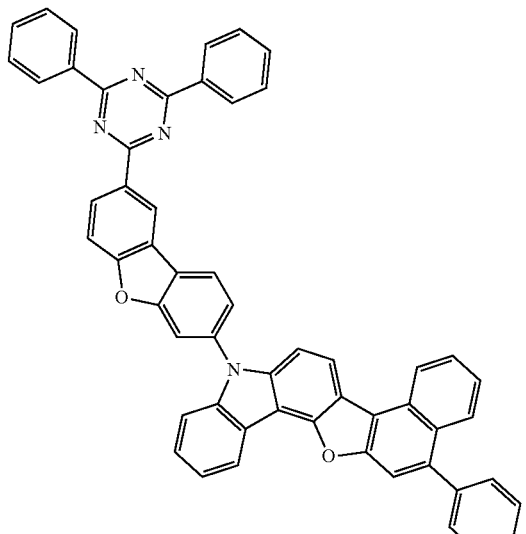
a-5
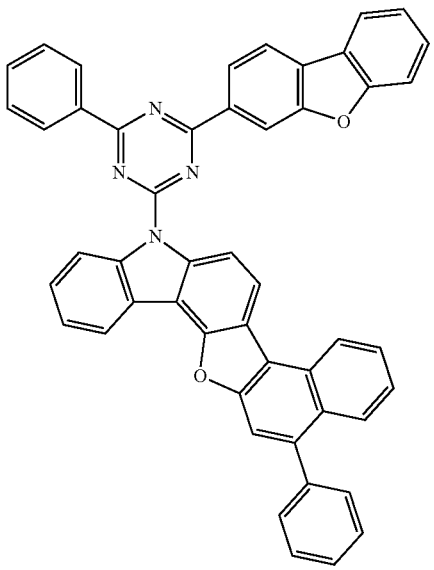

a-6
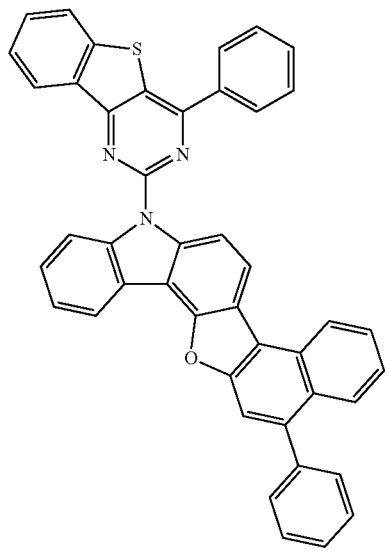
a-8
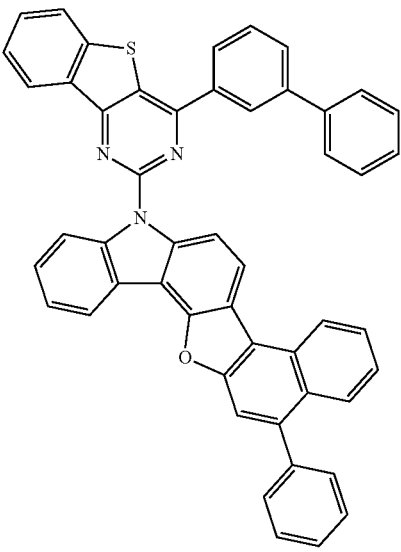
a-7
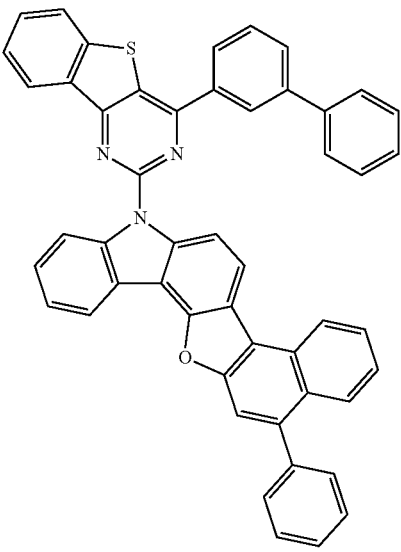
a-9
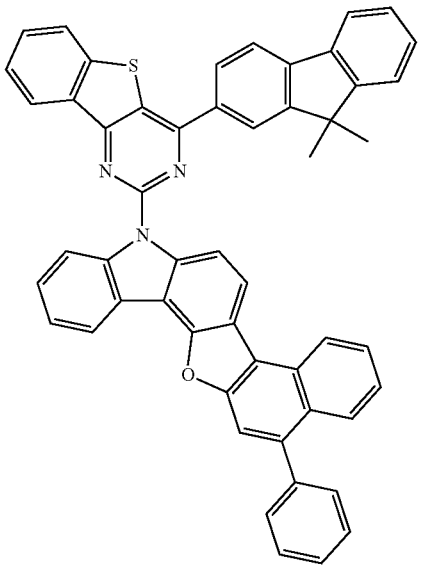

a-10
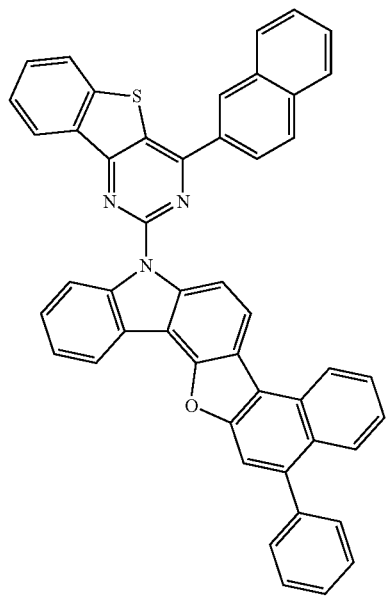
a-12
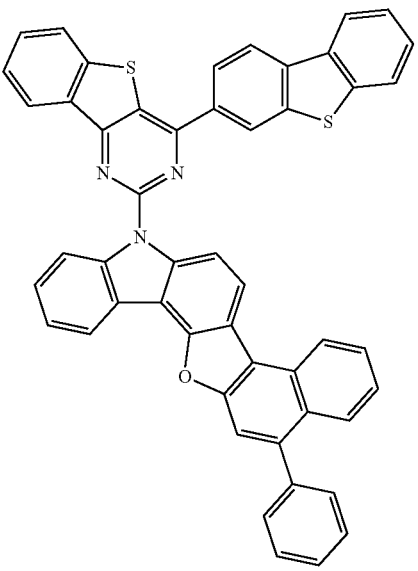
a-11
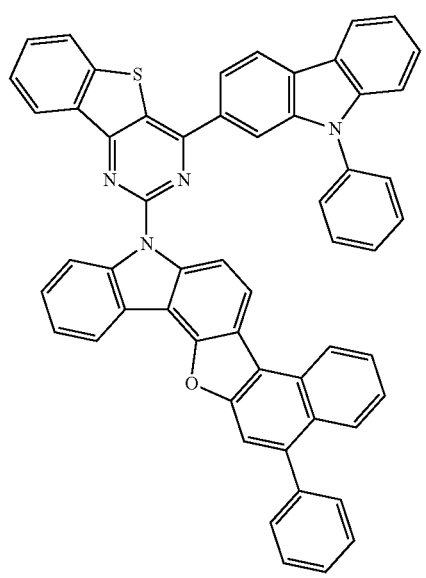
a-13
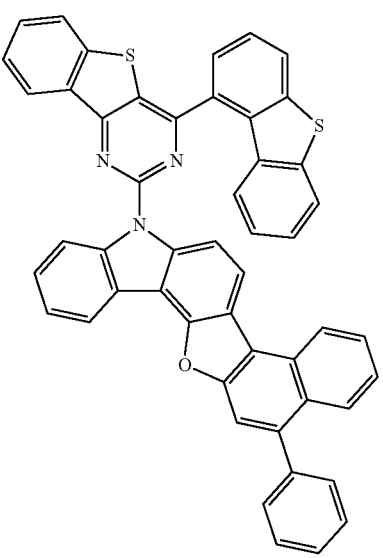

a-14
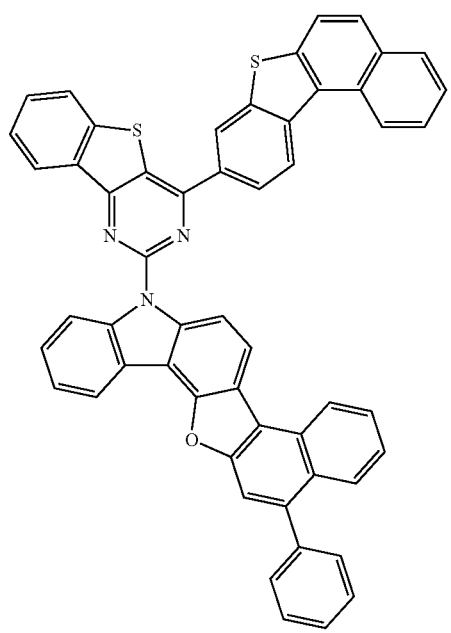
a-15
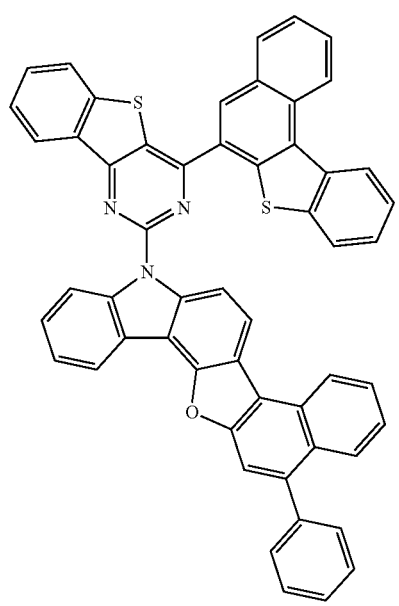
a-16
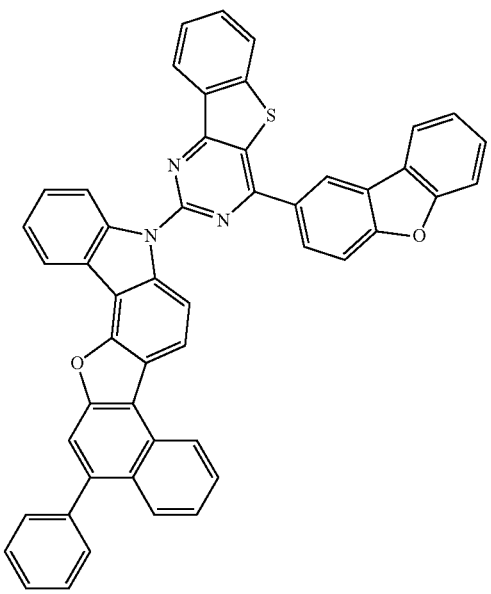
a-17
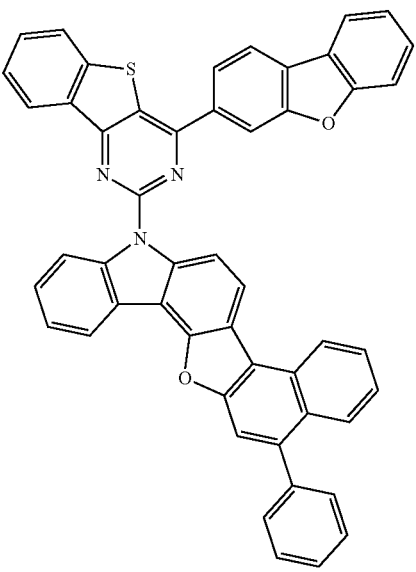

a-18
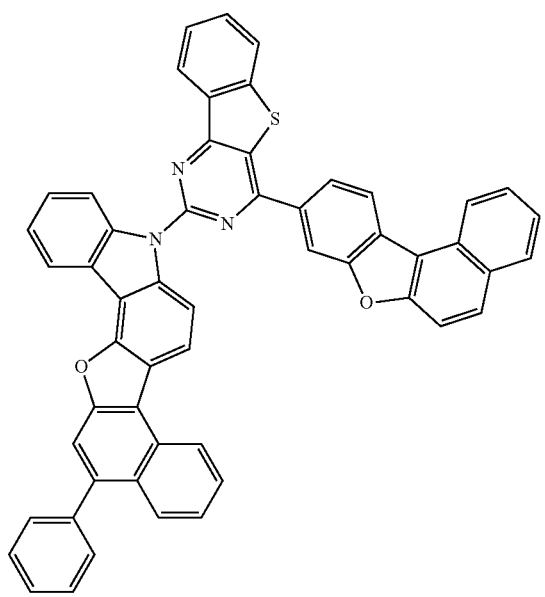
a-20
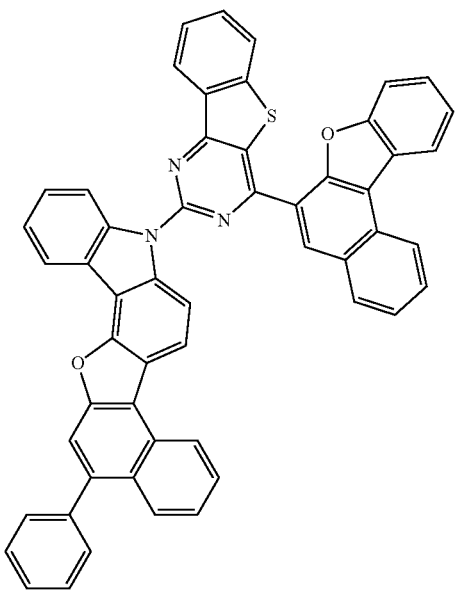
a-19
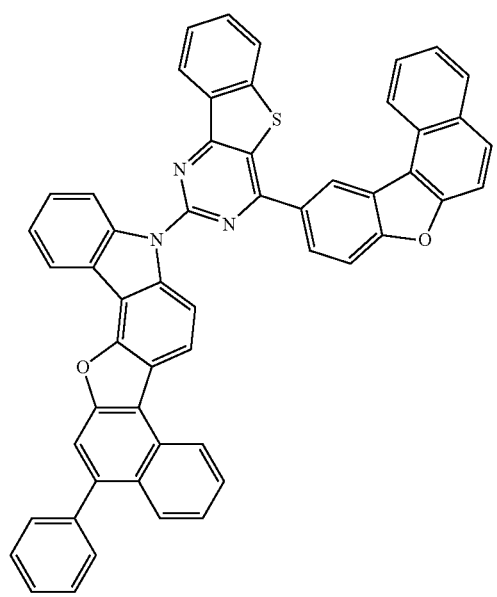
a-21
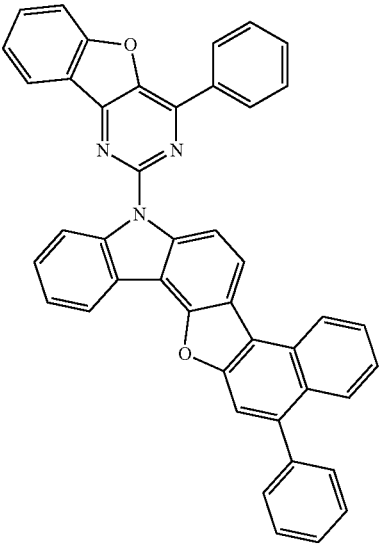

a-22
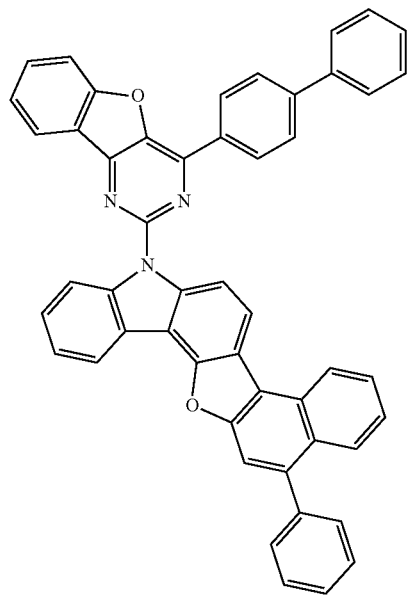
a-23
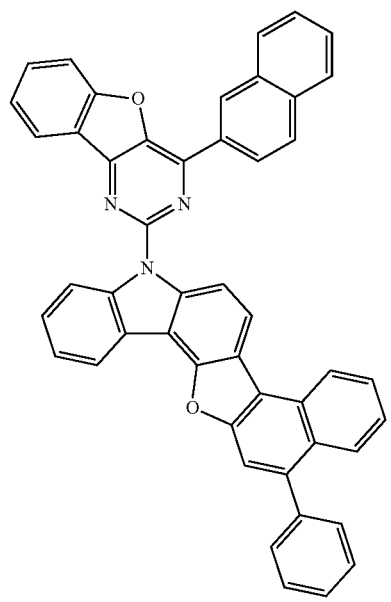
a-24
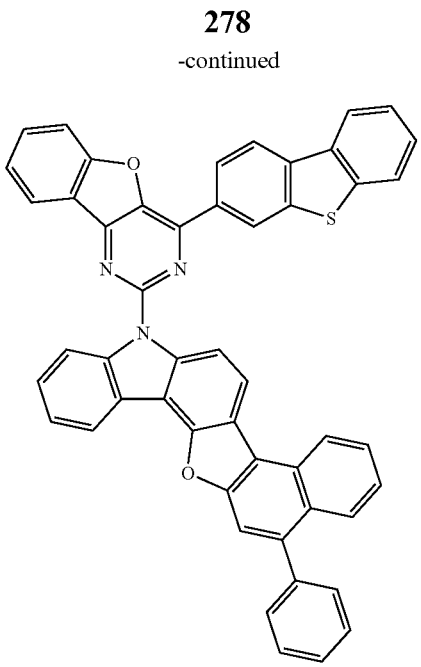
a-25
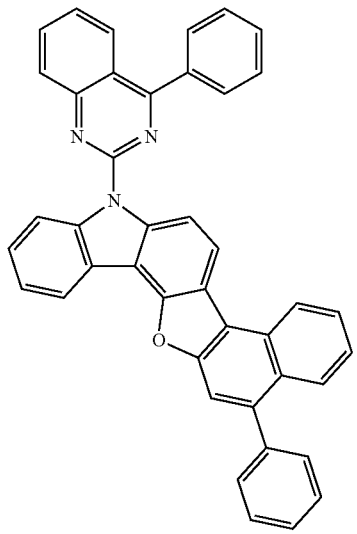

a-26
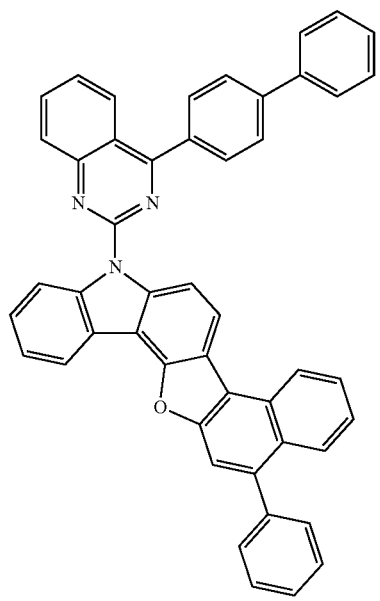
a-28
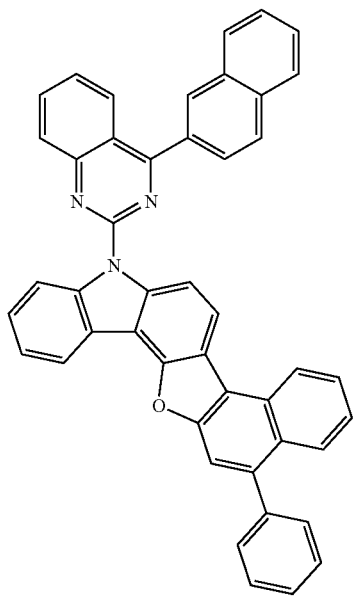
a-27
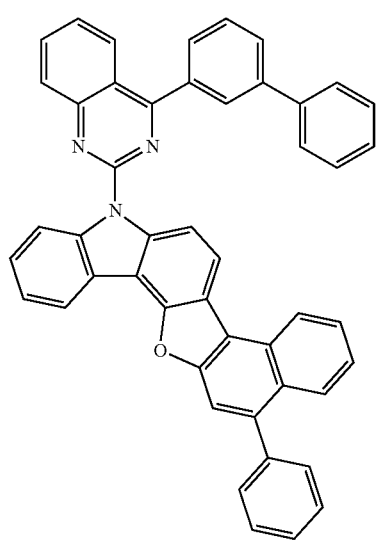
a-29
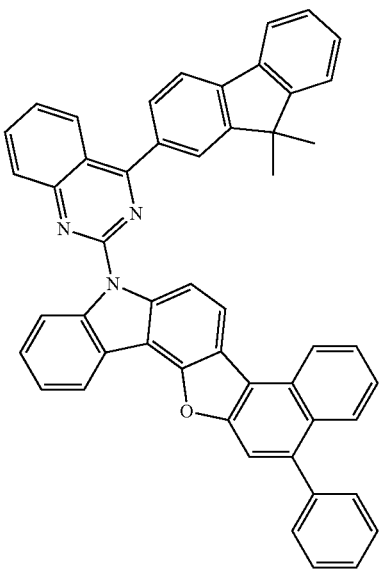

a-30
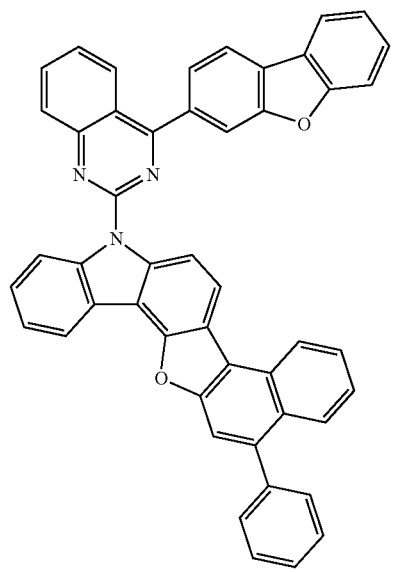
a-32
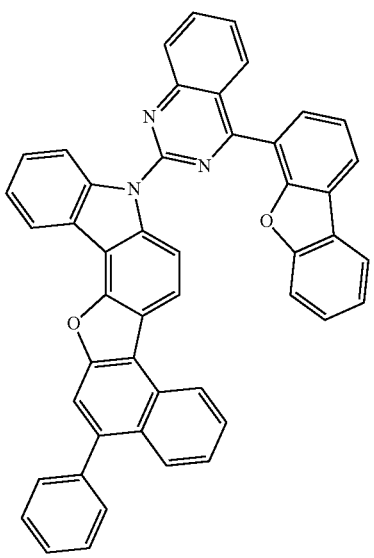
a-31
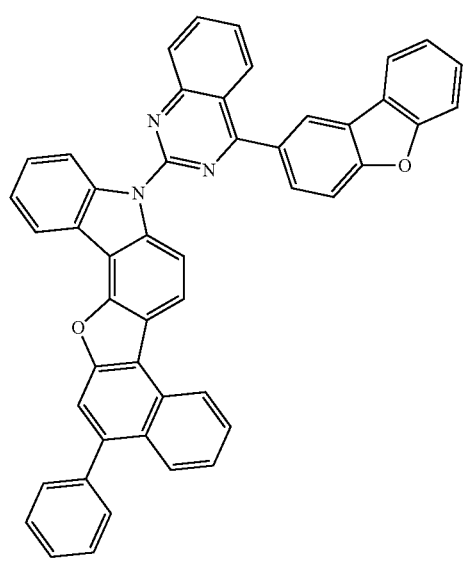
a-33
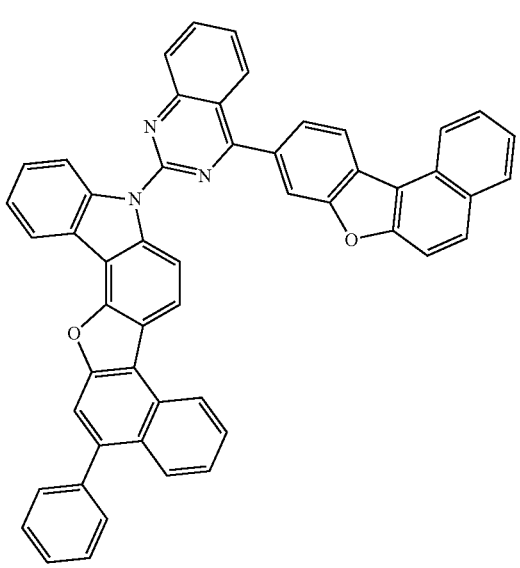

a-34
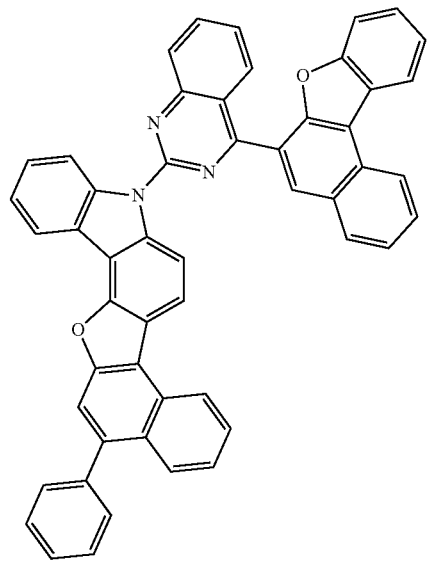
a-35
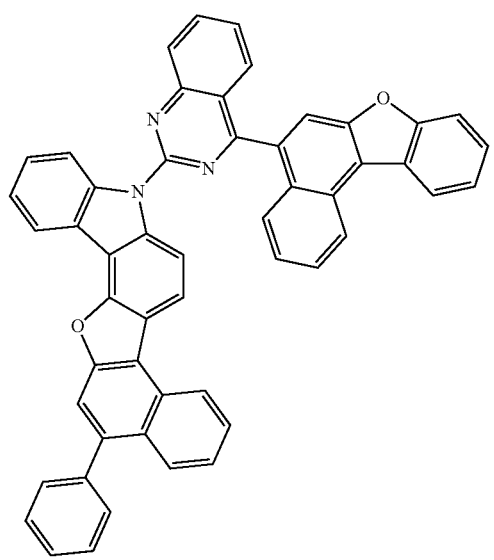
a-36
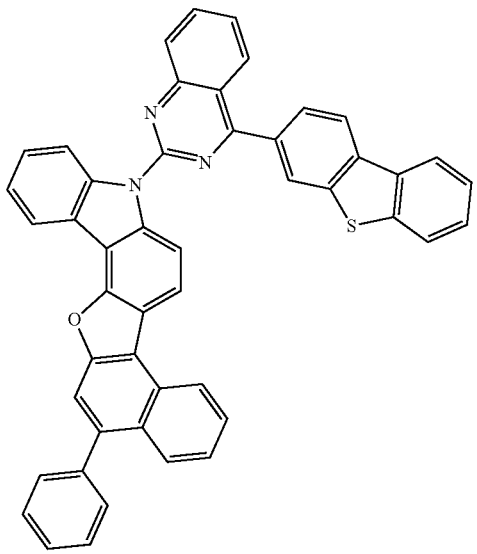
a-37
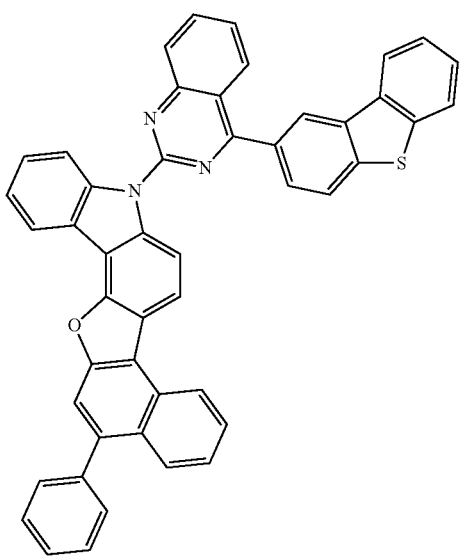

a-38
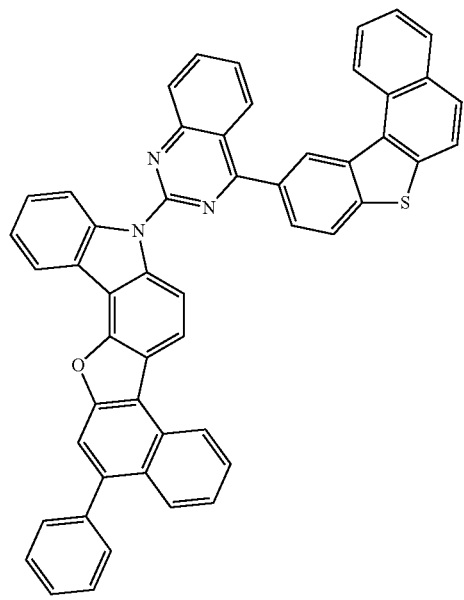
a-39
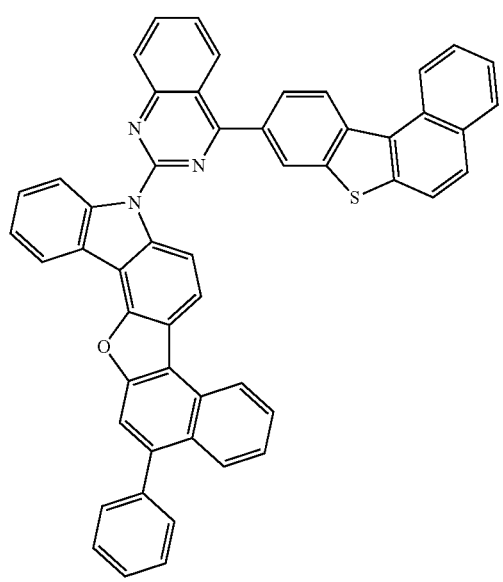
a-40
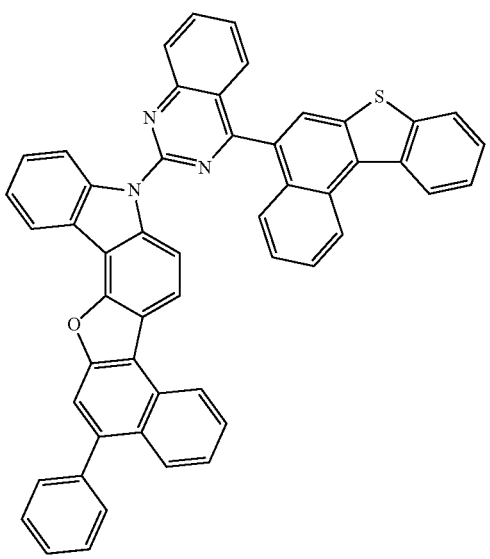
a-41
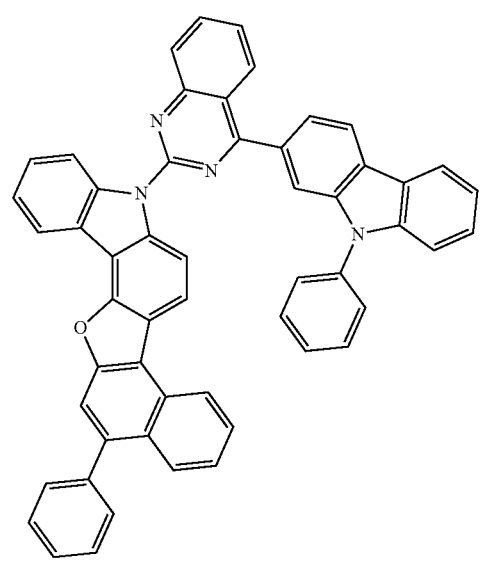
a-42
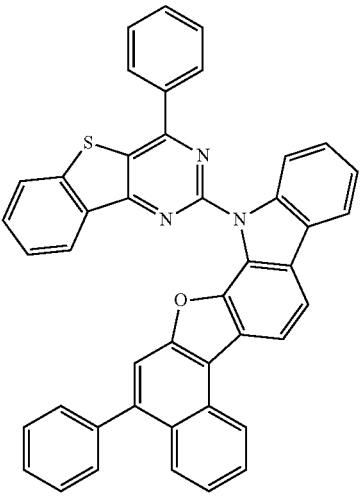

-continued
a-43
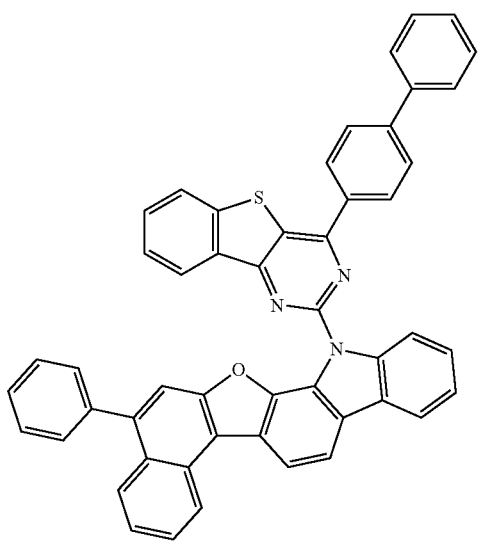
a-44
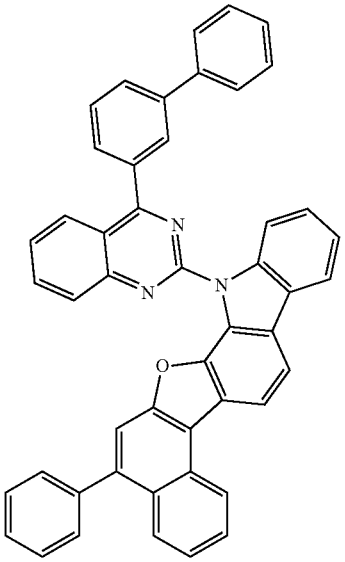
a-45
-continued
a-46
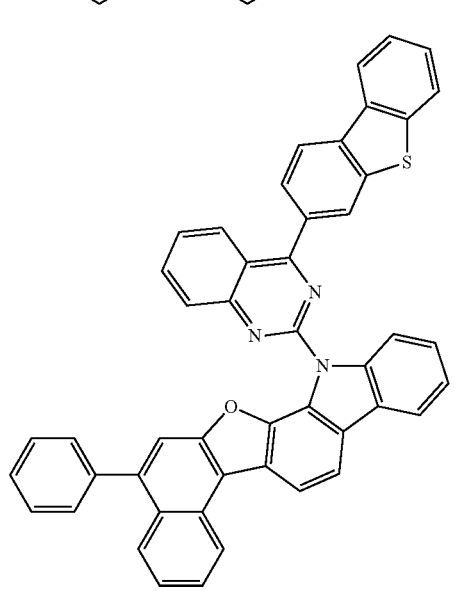
a-47
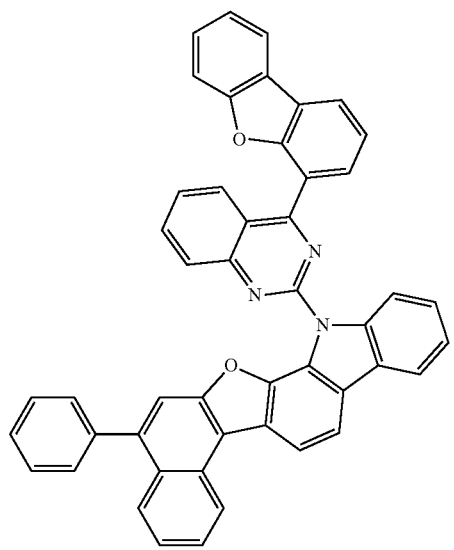
a-48 a-49
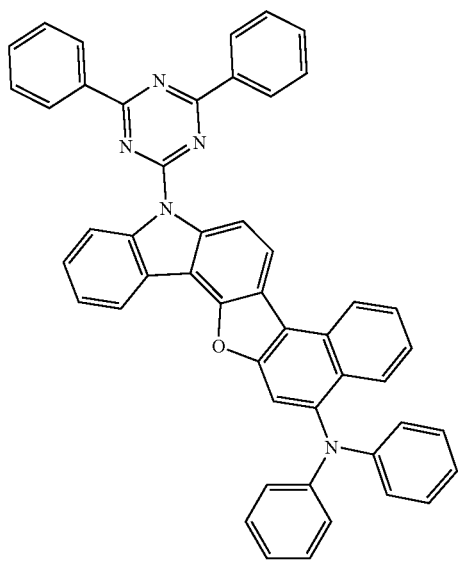
a-51
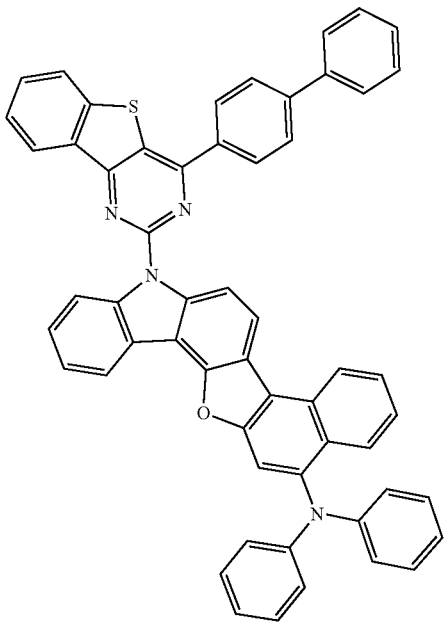
a-50
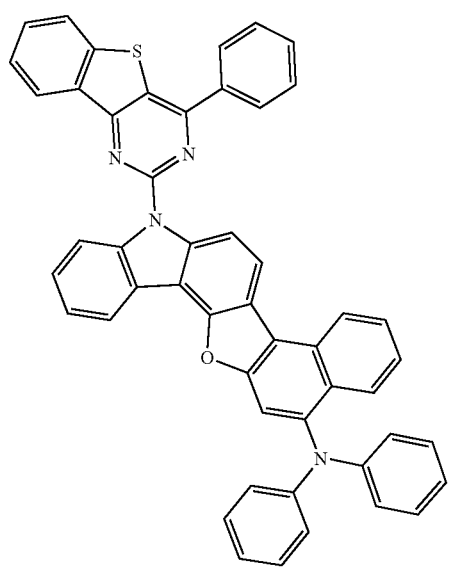
a-52
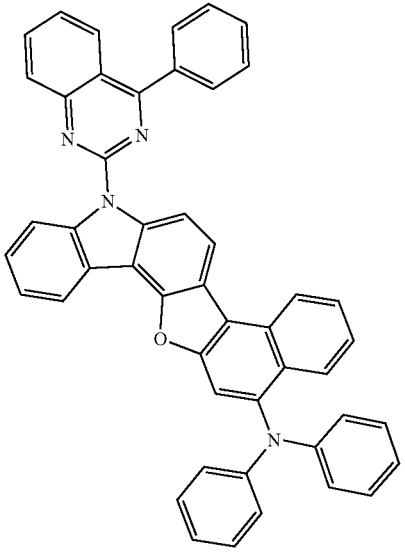

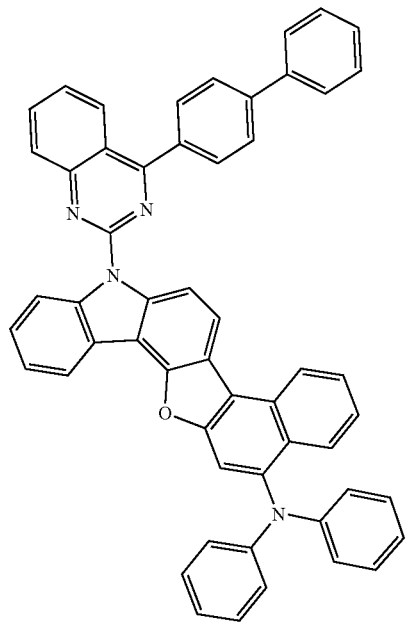
a-53
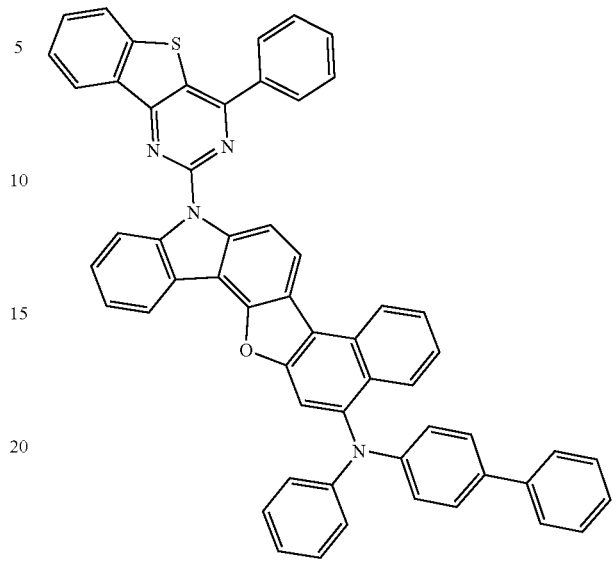
a-55
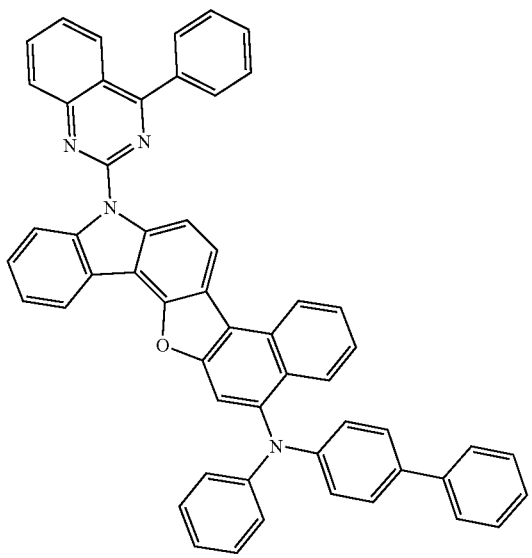
a-54
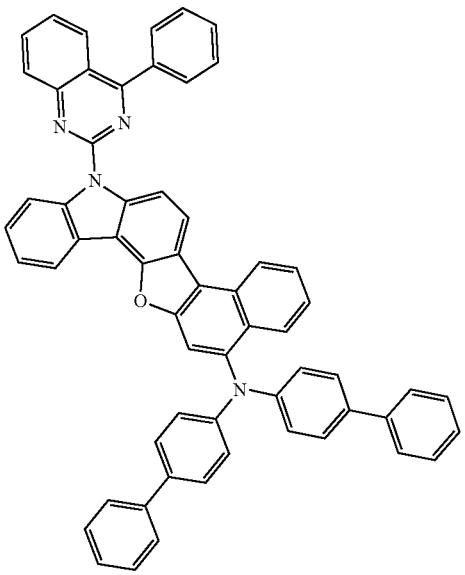
a-56 a-57
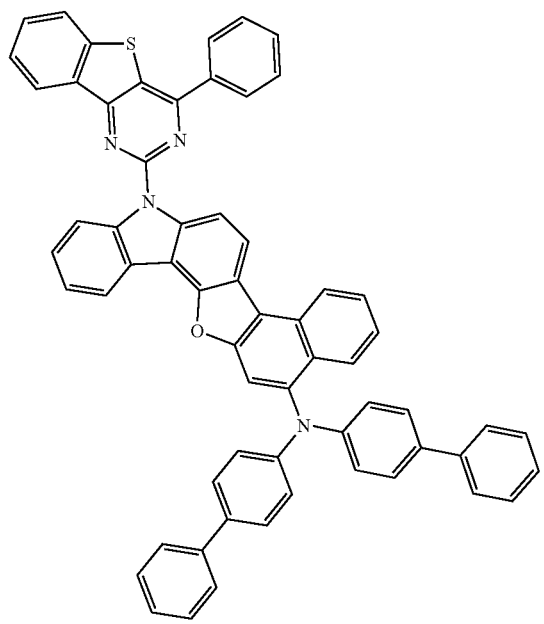
a-58
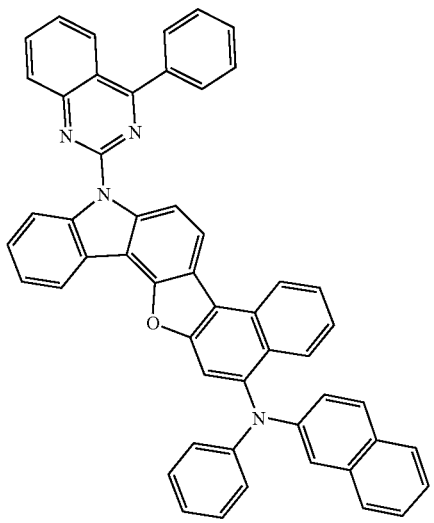
a-59
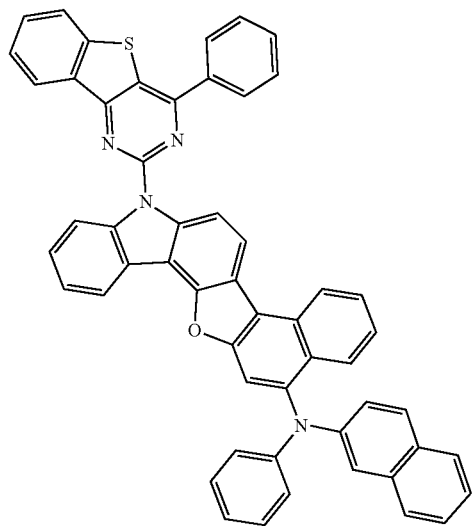
a-60
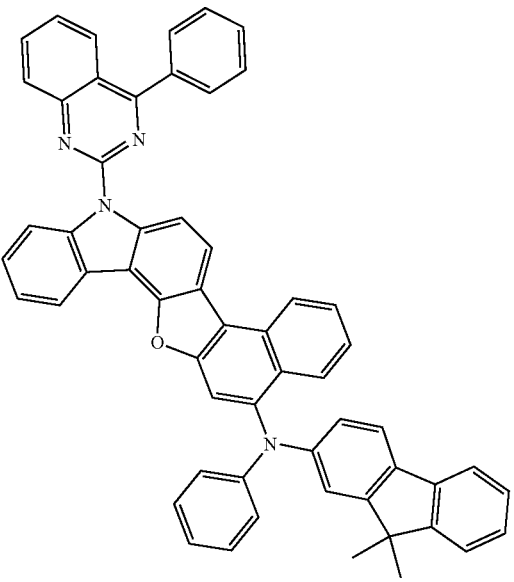

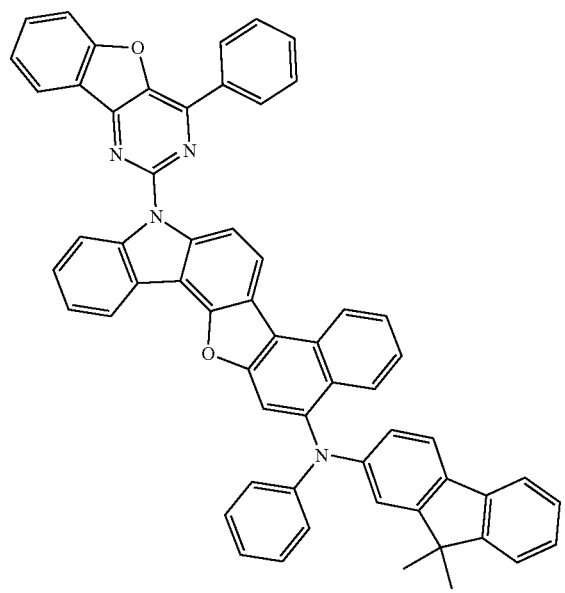
a-61
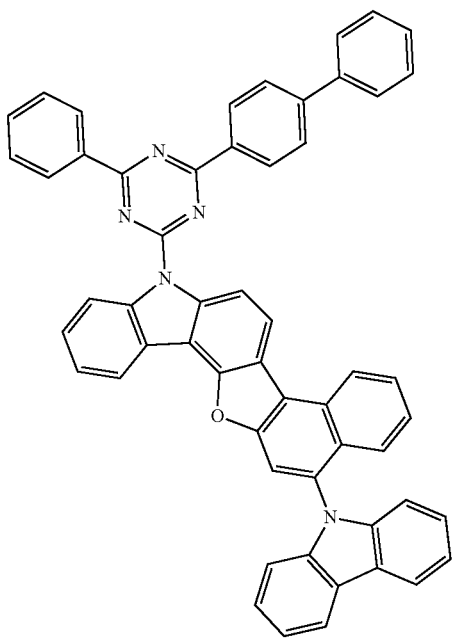
a-63
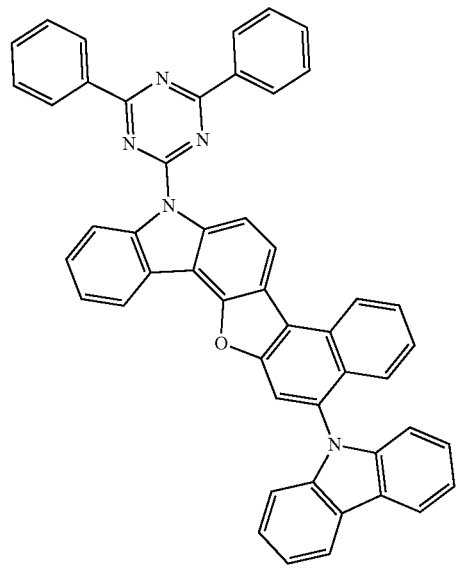
a-62
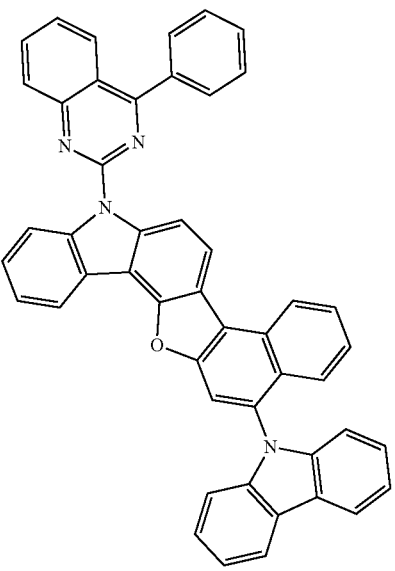
a-64

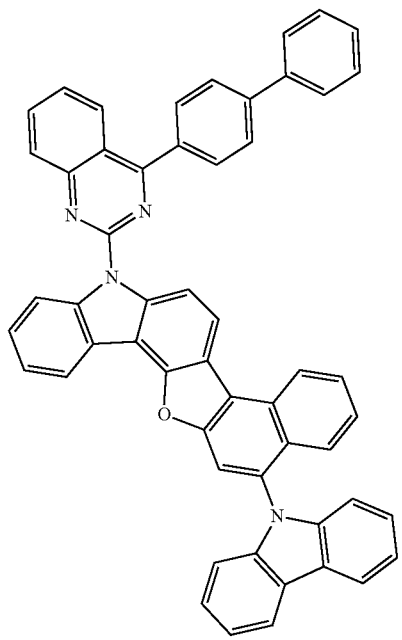
a-65
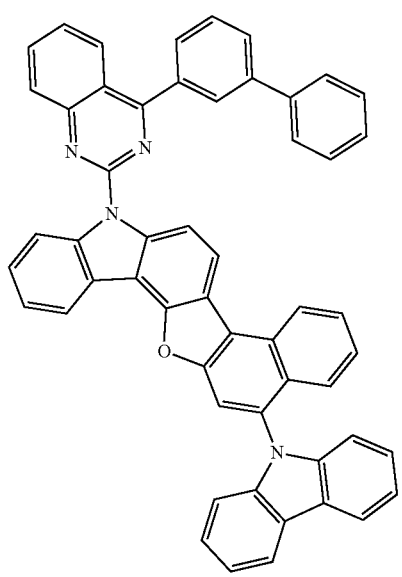
a-66
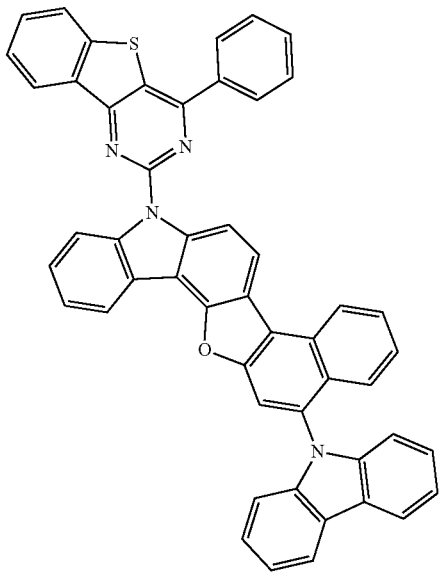
a-67
a-68 a-69
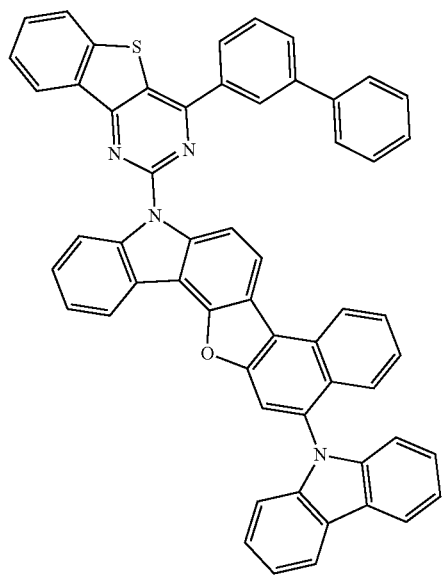
a-70
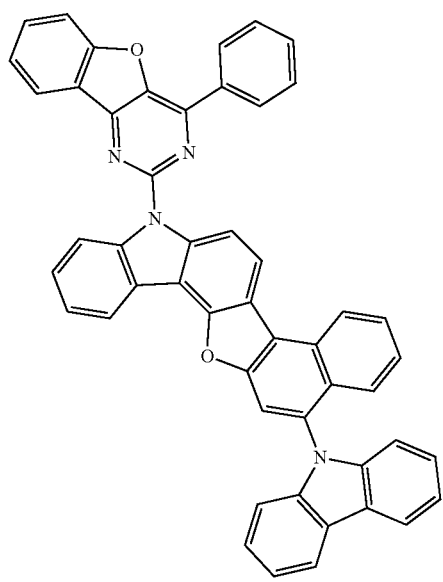
a-71
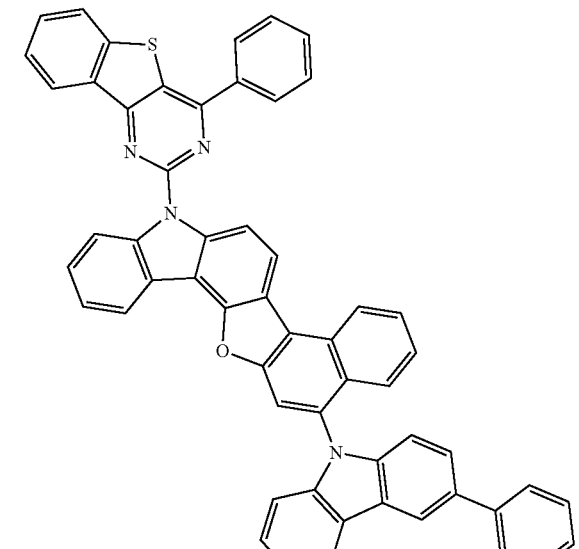
a-72
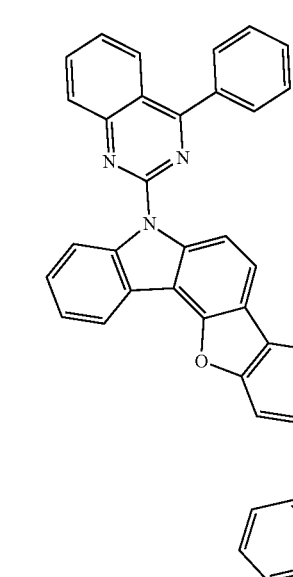

a-73
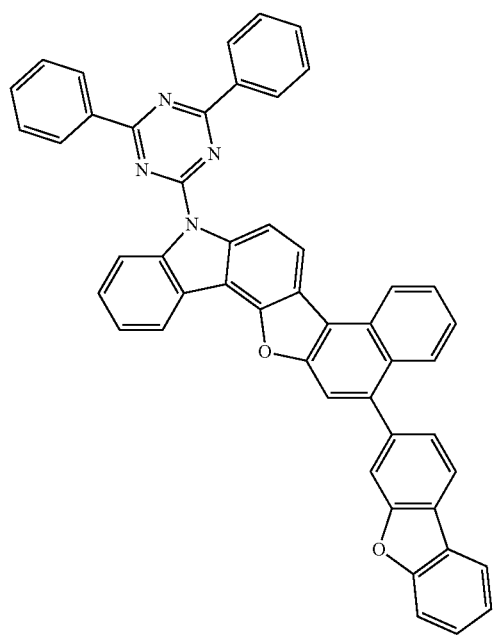
a-75
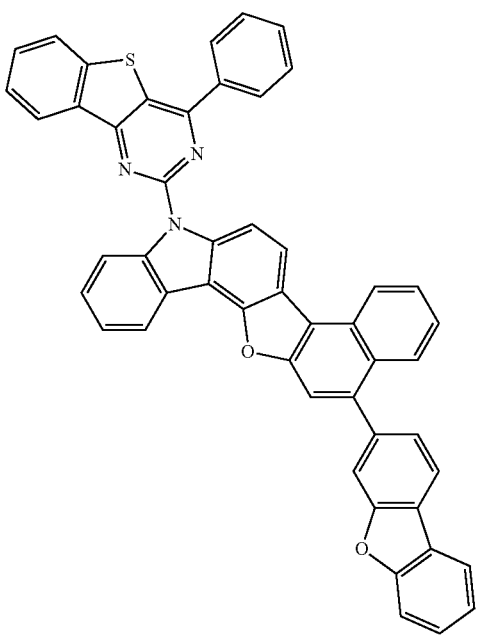
a-74
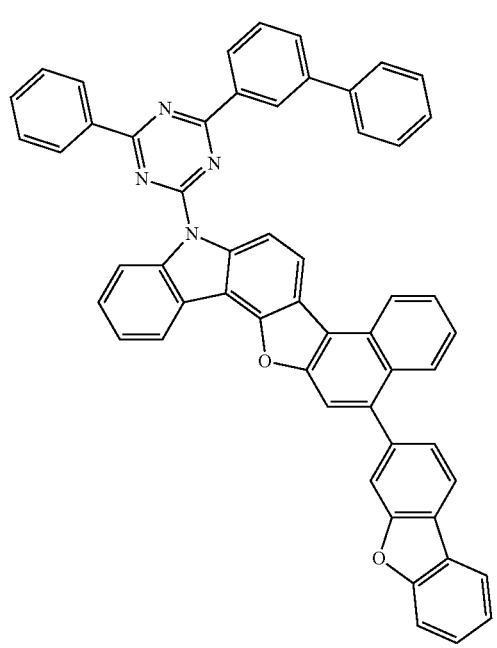
a-76 a-77
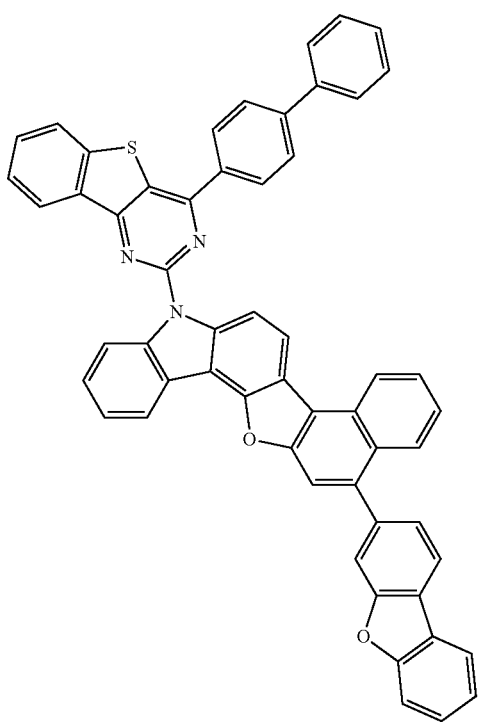
a-78
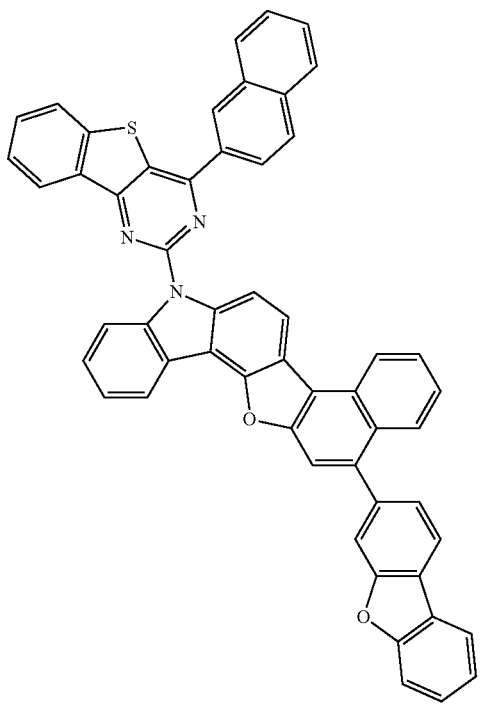
a-79
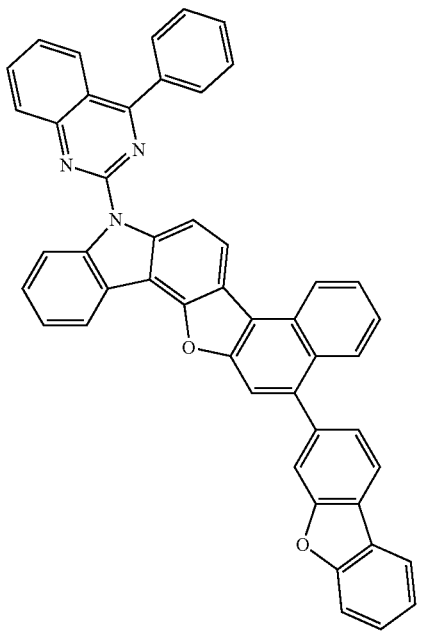
a-80
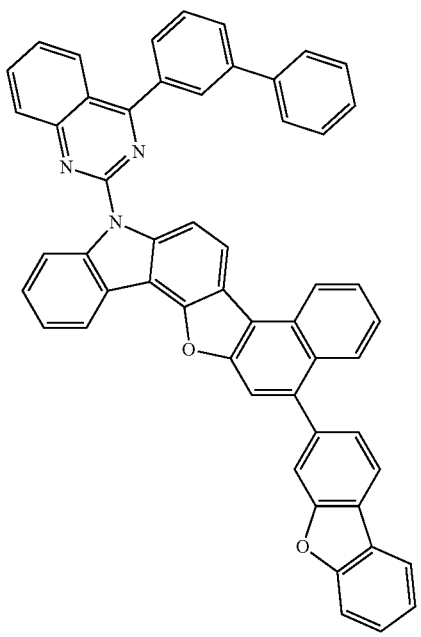

a-81
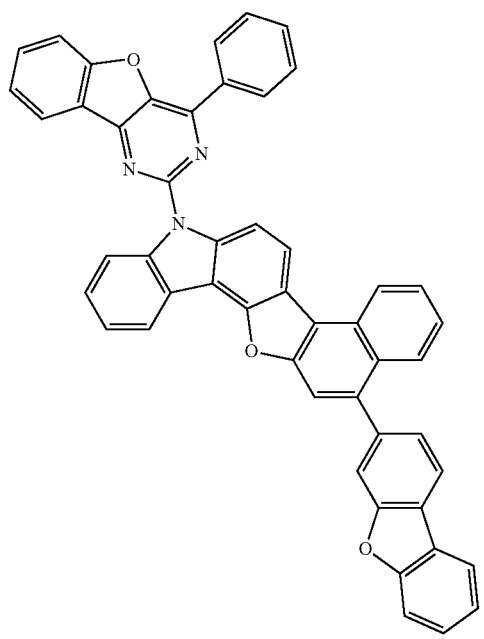
a-83
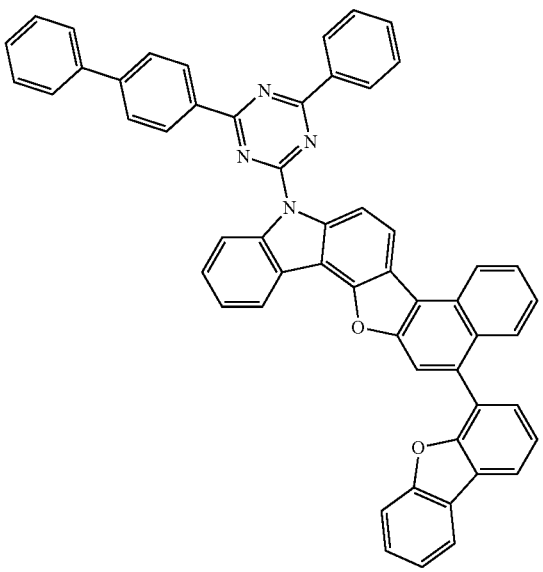
a-82
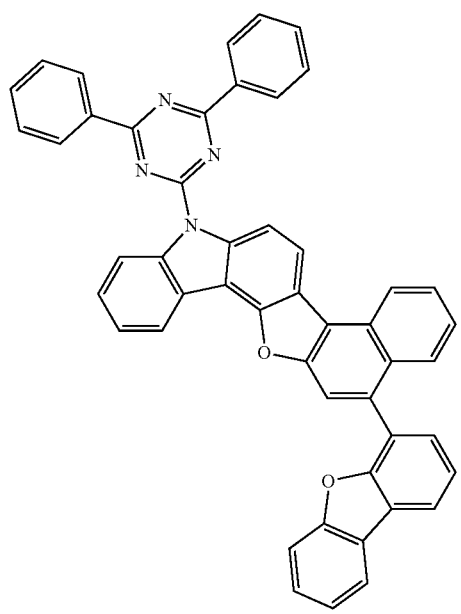
a-84
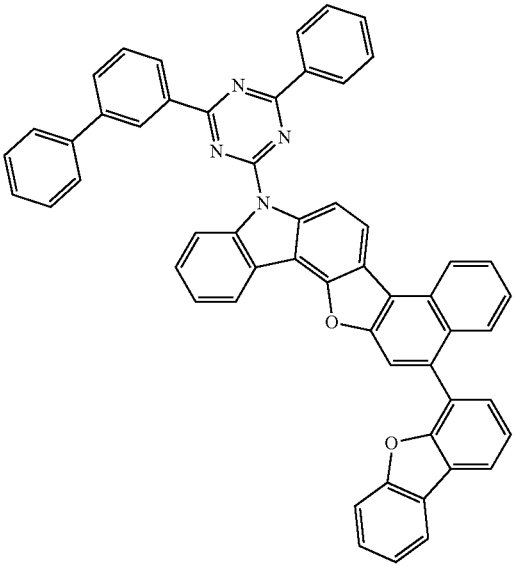

a-85
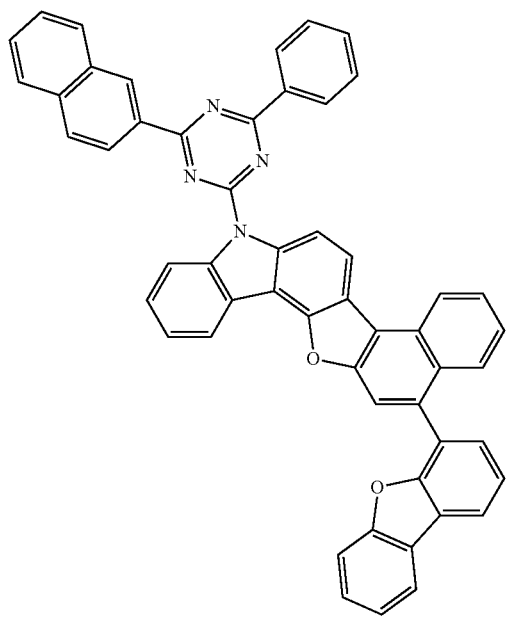
a-86
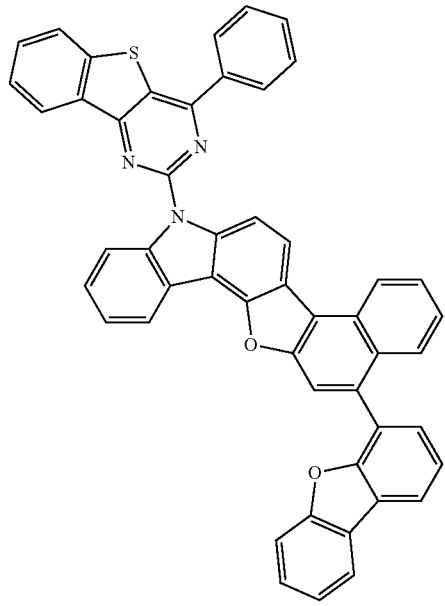
a-87
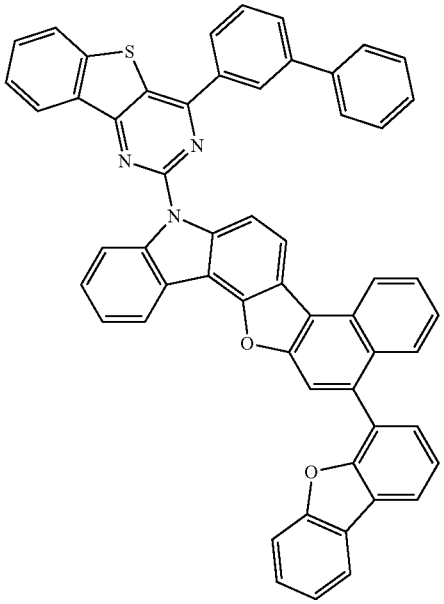
a-88
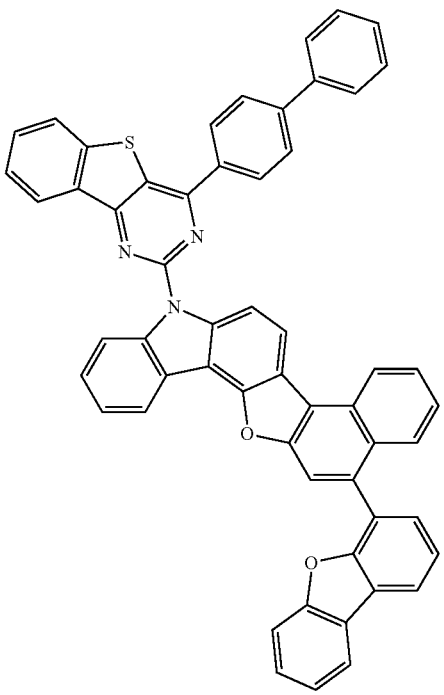

-continued
a-89
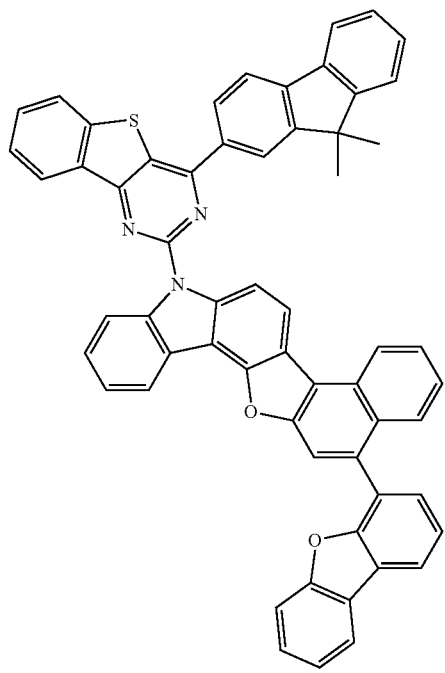
a-90
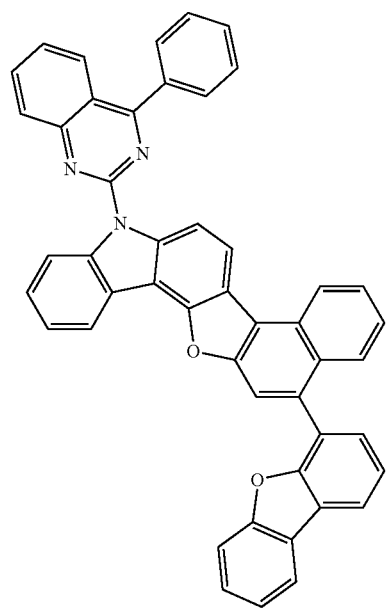
a-91
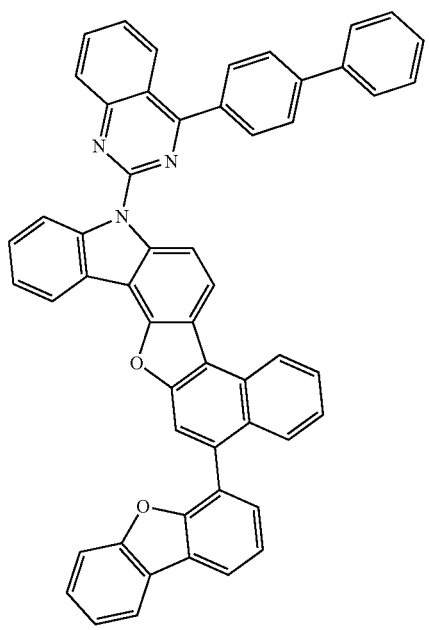
a-92
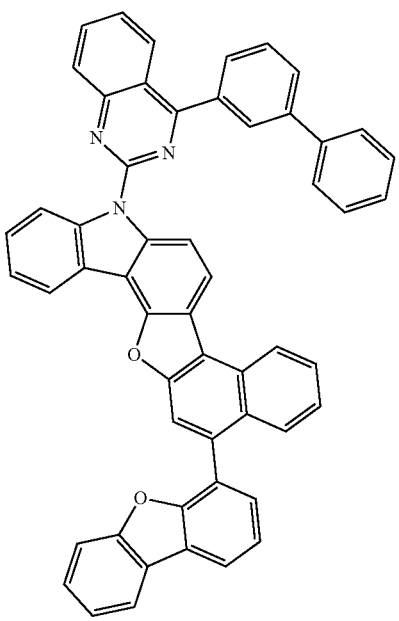

a-93
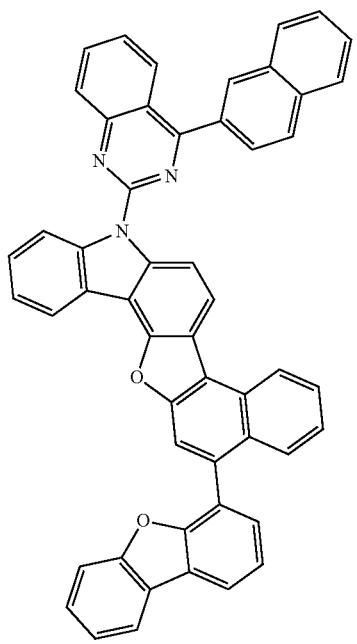
a-95
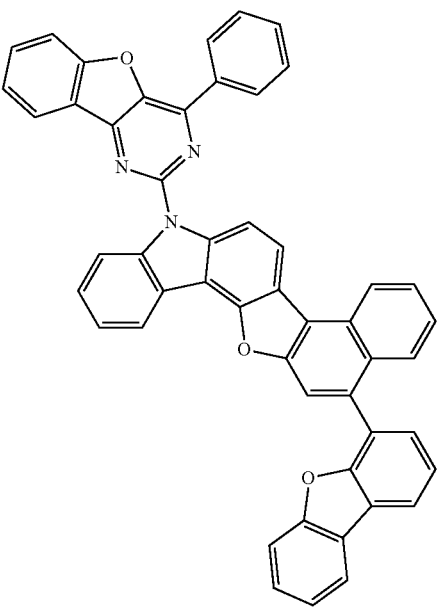
a-94
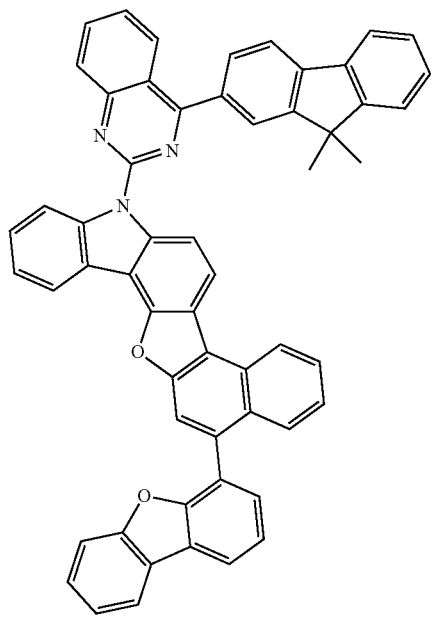
a-96
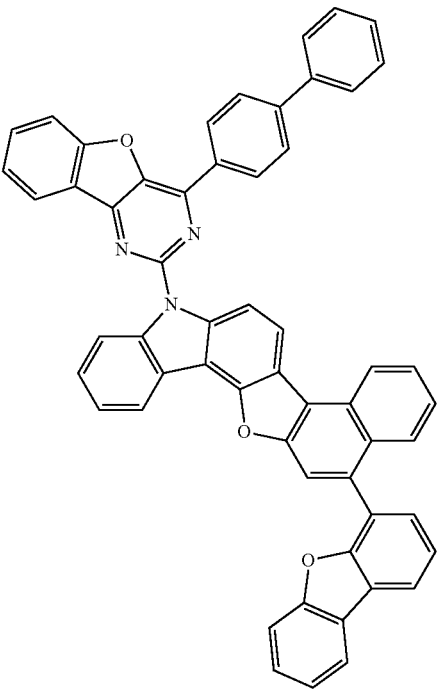

a-97
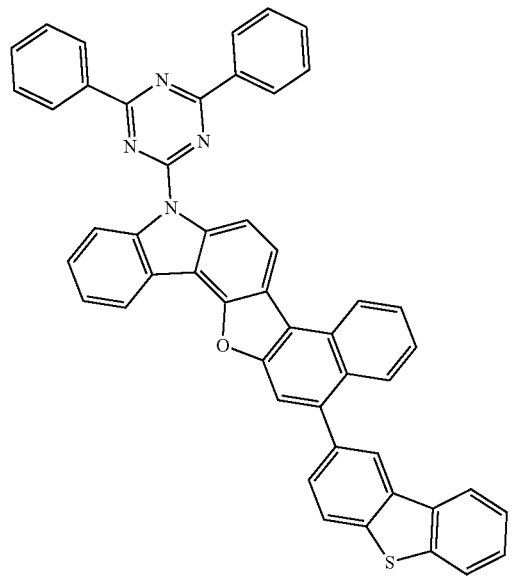
a-99
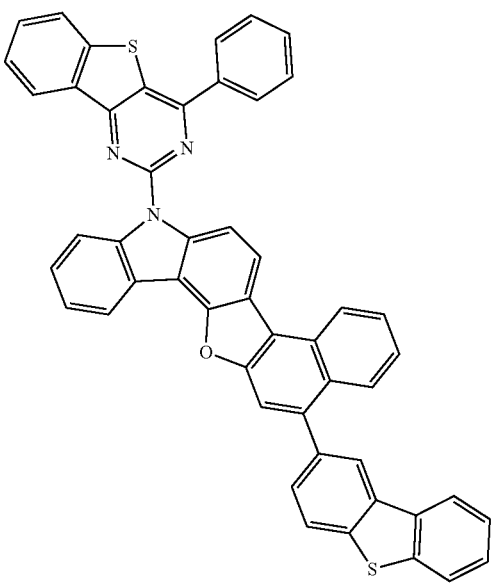
a-98
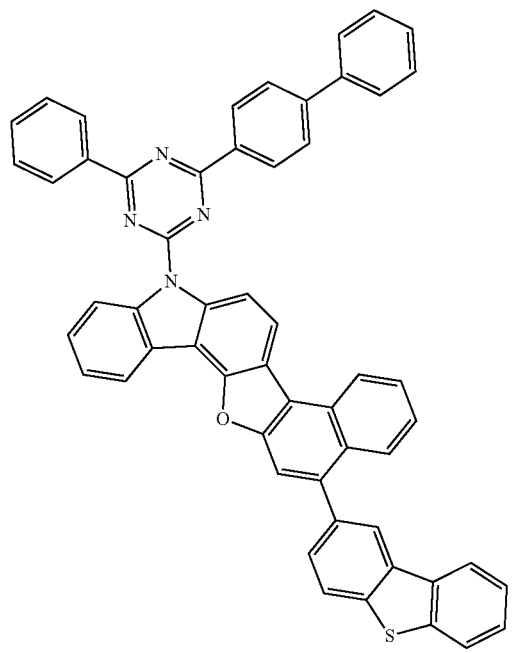
a-100 a-101
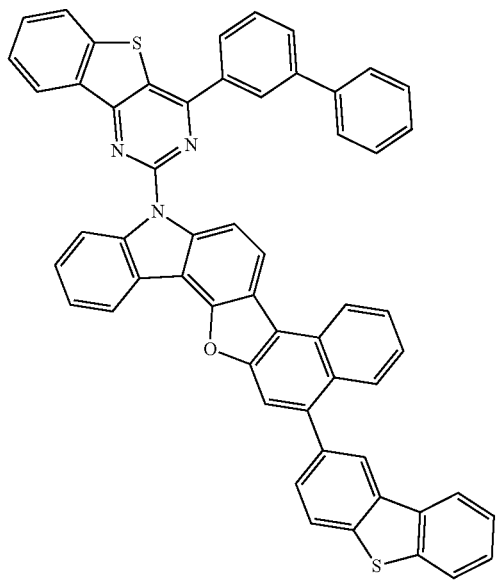
a-102
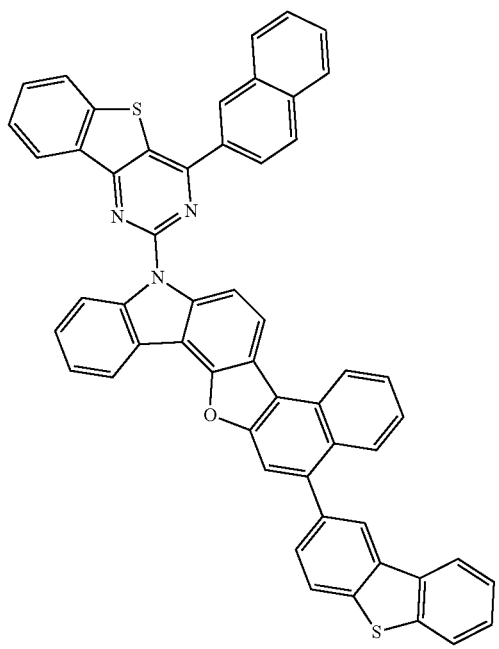
a-103
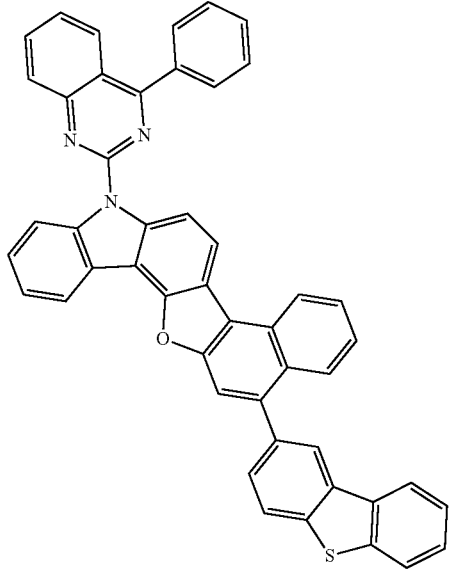
a-104
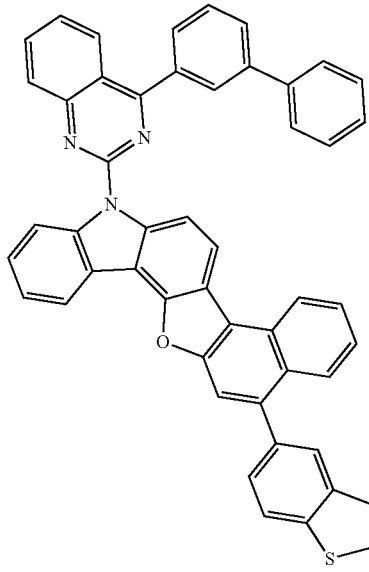

-continued
a-105
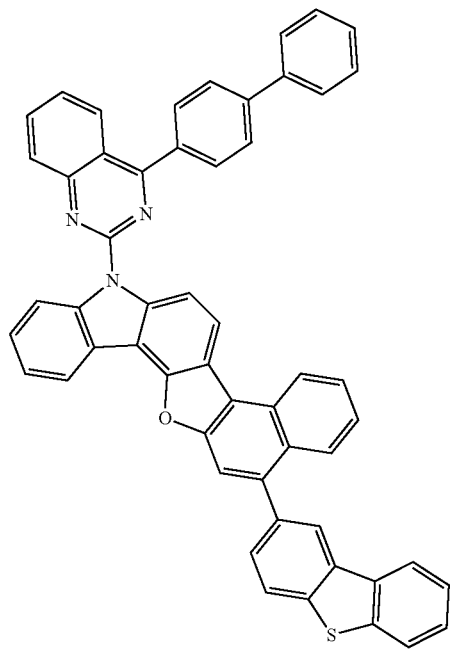
a-106
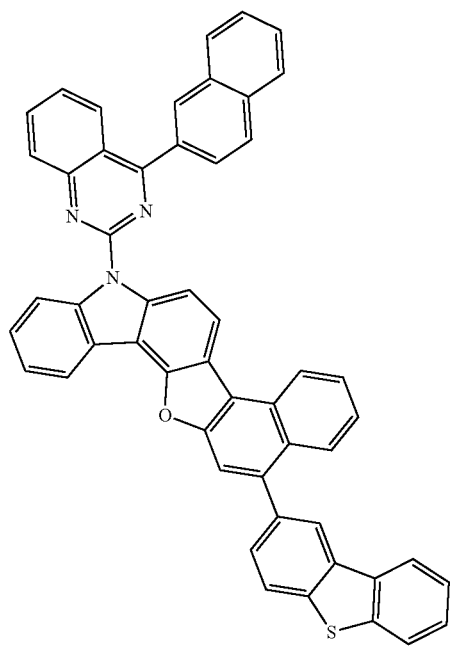
a-107
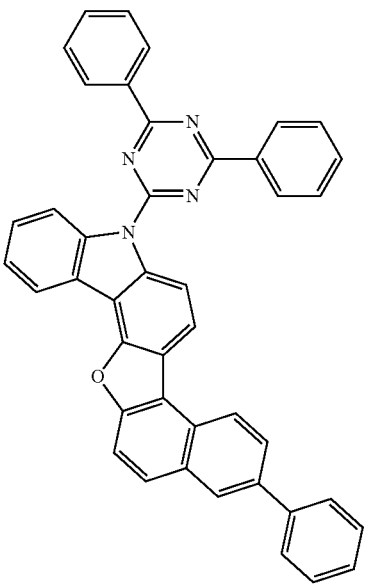
a-108
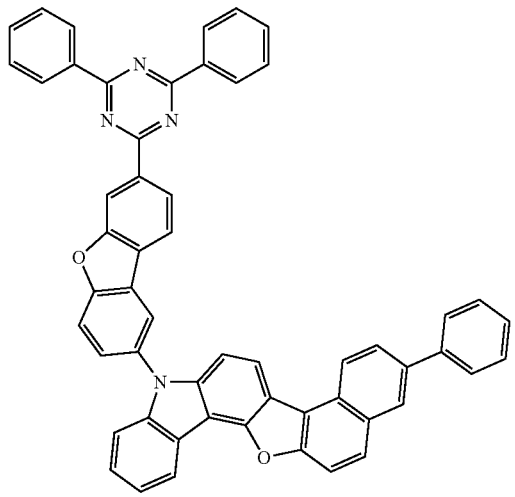

a-109
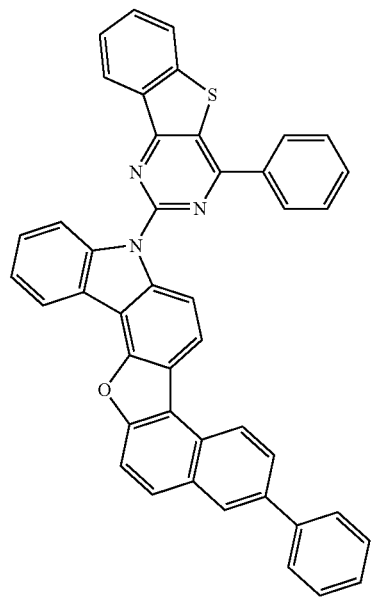
a-111
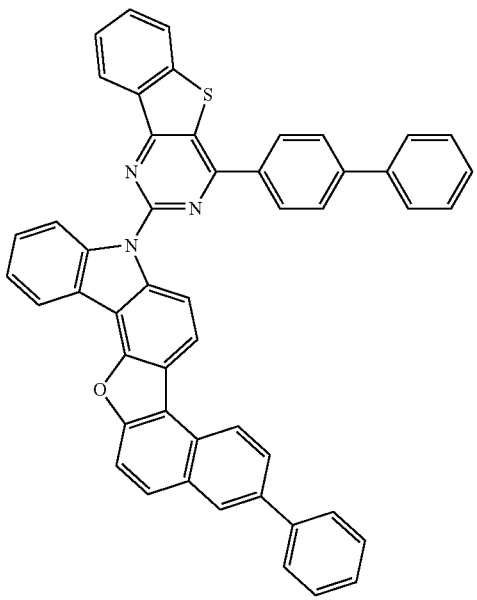
a-110
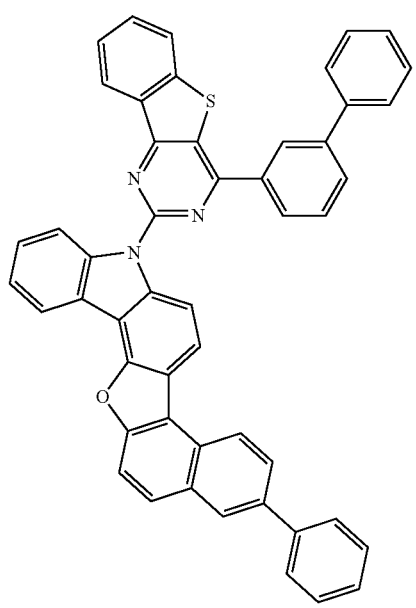
a-112
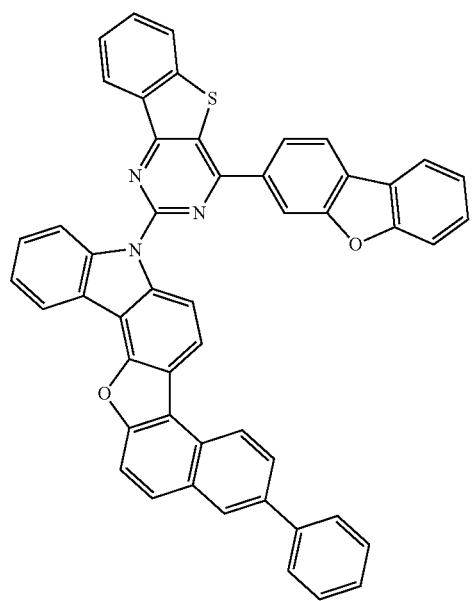

-continued
a-113
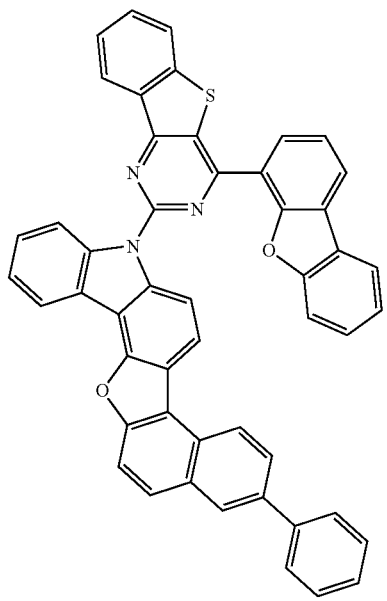
a-114
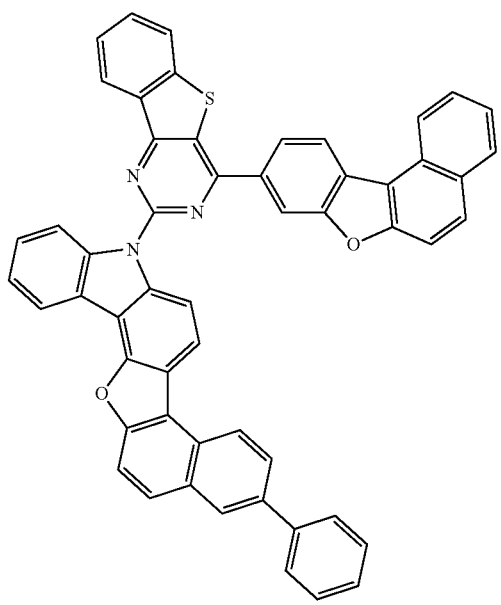
a-115
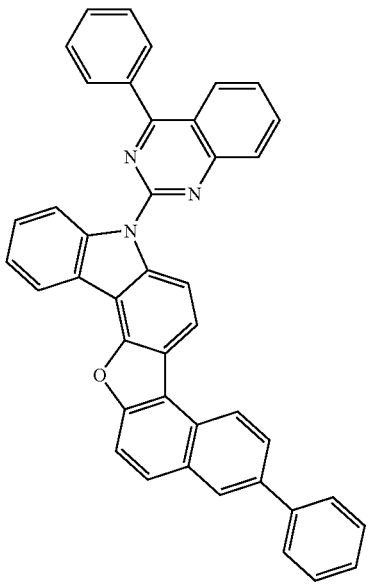
a-116
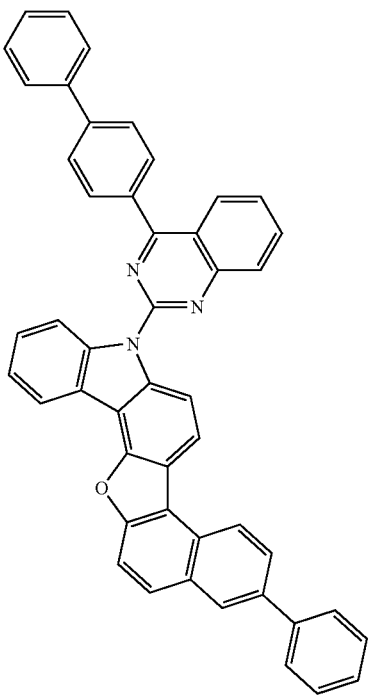

a-117
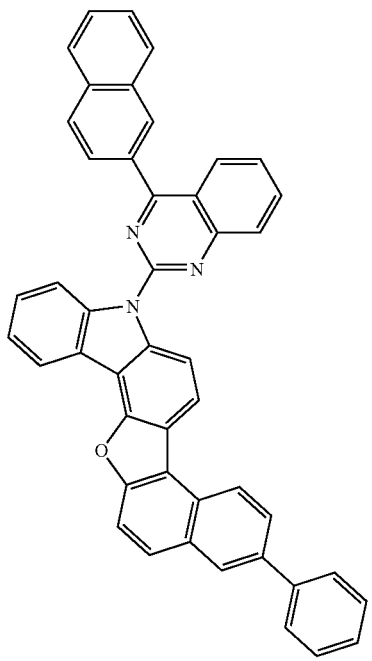
a-118
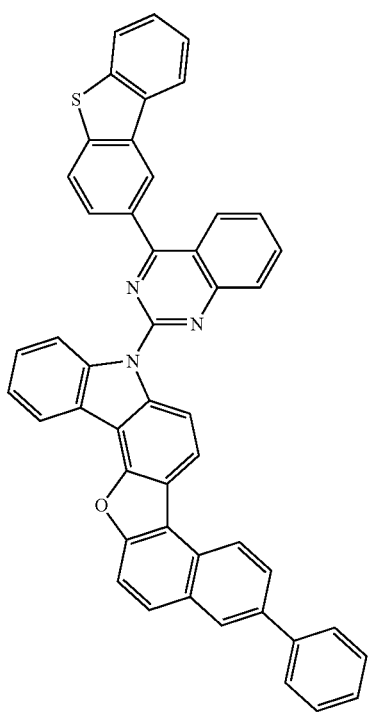
a-119
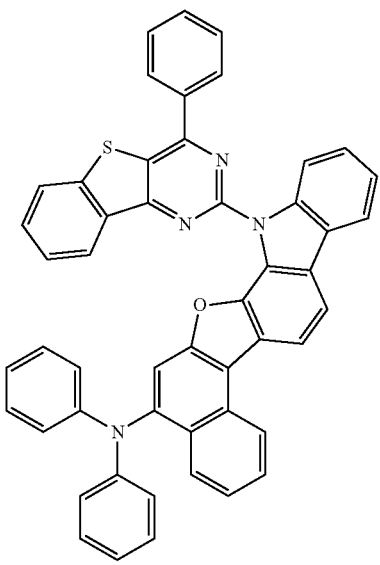
a-120
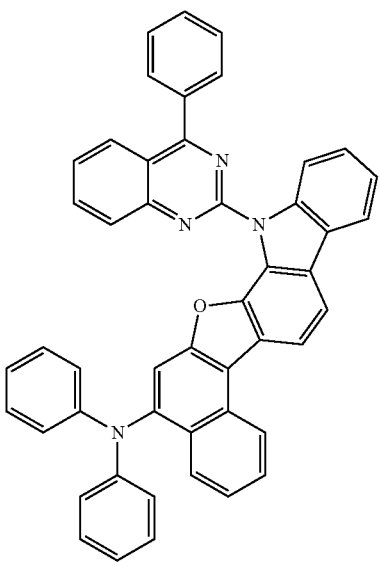

a-121
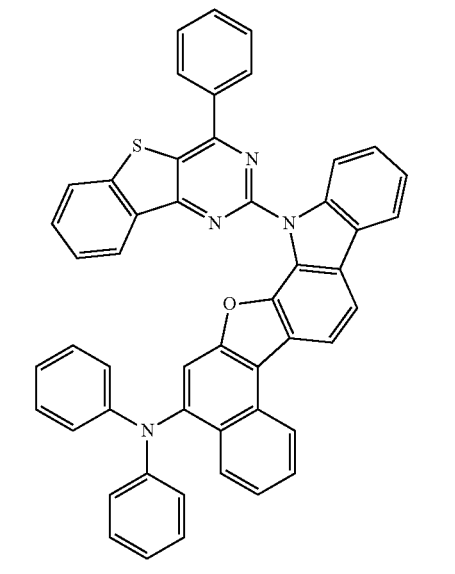
a-122
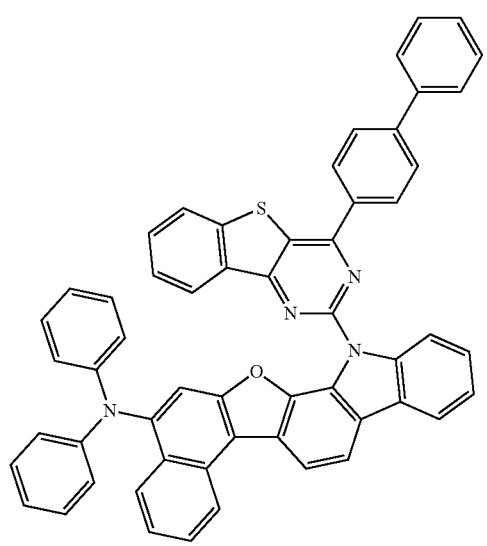
a-123
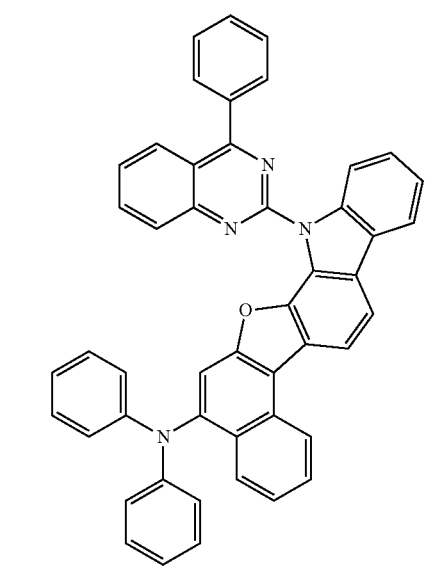
a-124
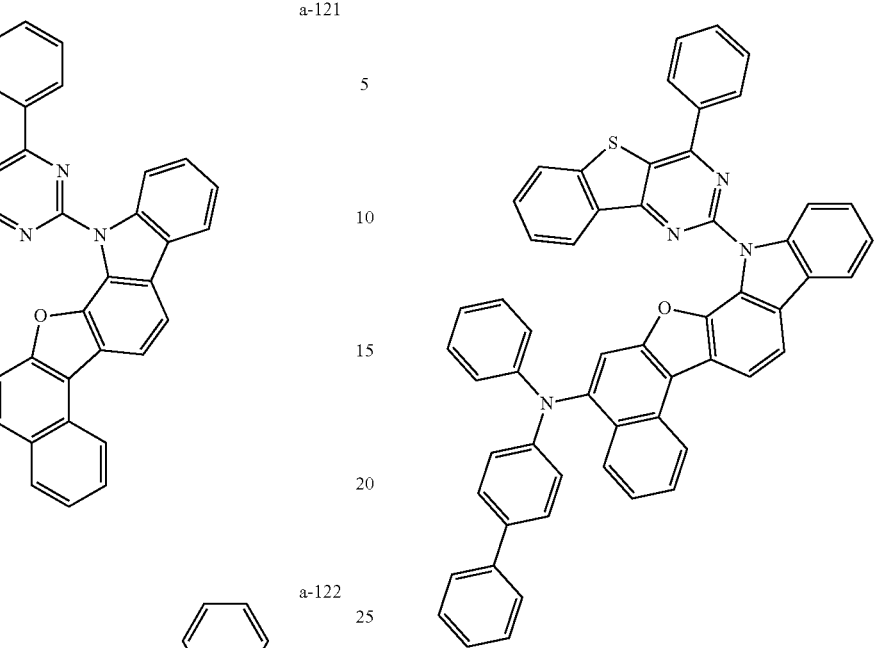
a-125
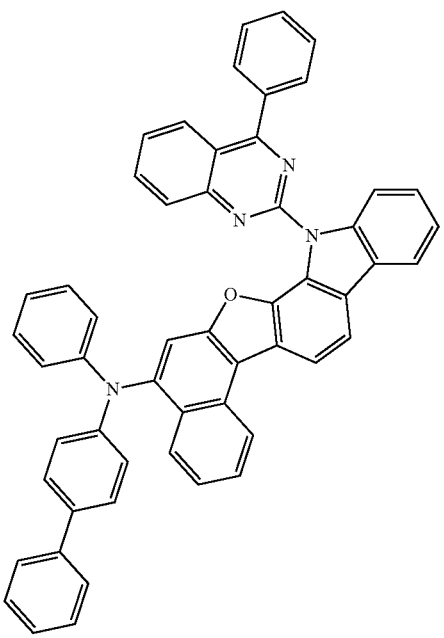

a-126
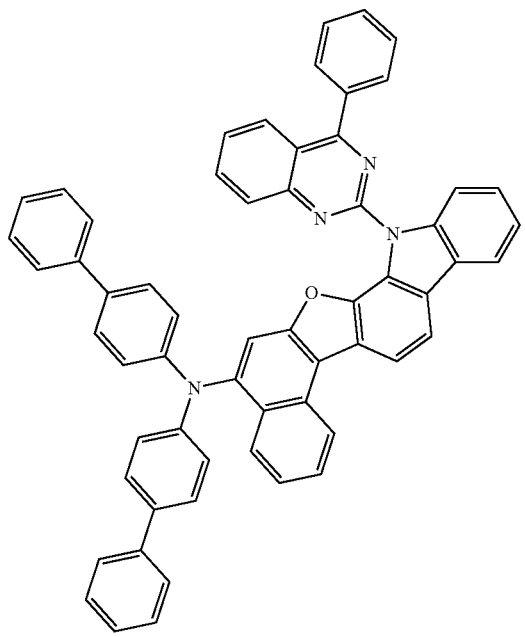
a-128
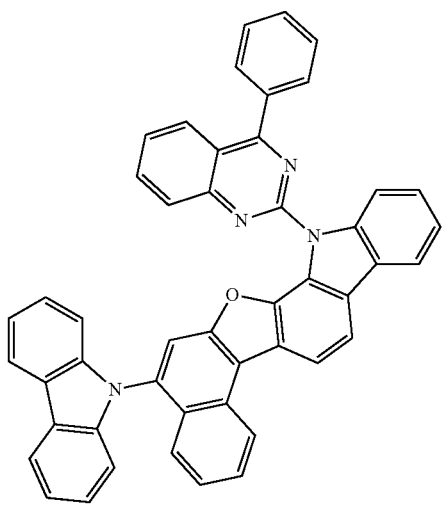
a-127
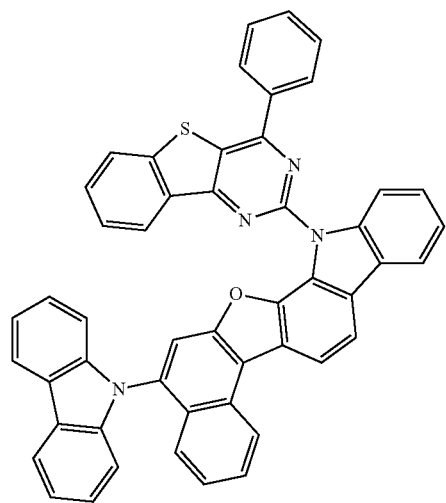
a-129
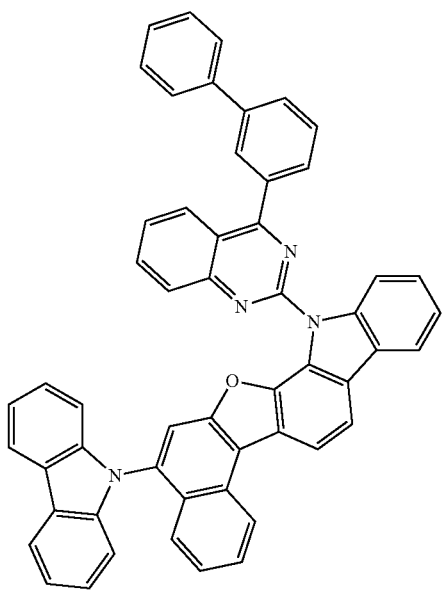

a-130
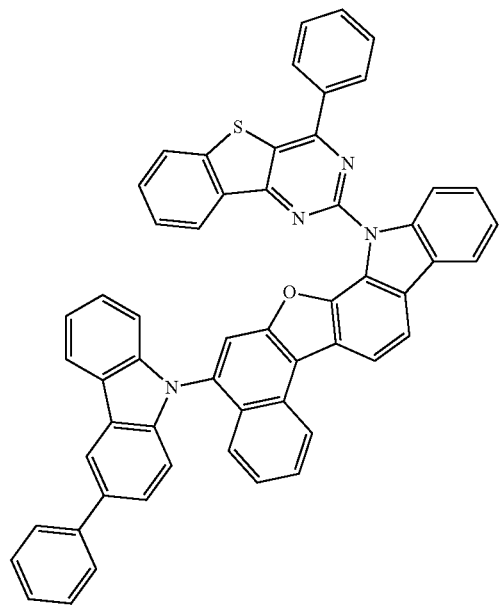
a-131
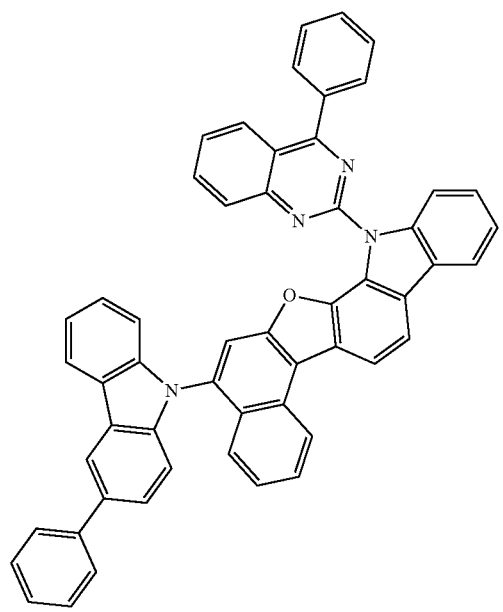
a-132
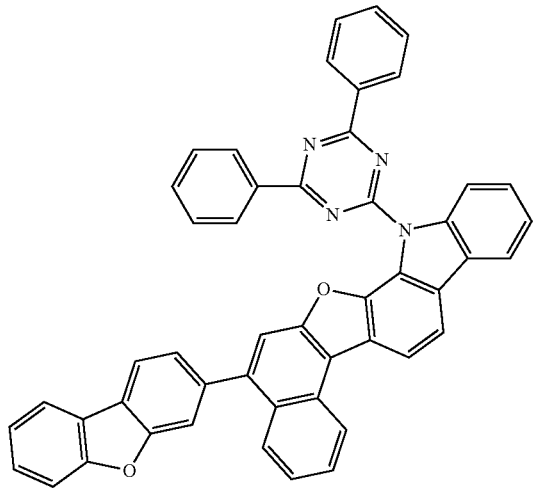
a-133
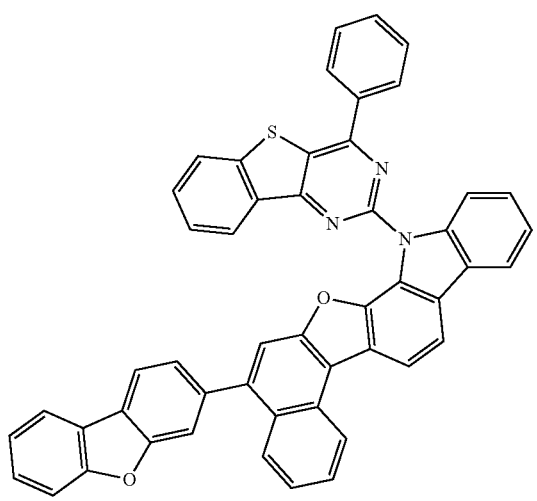
a-134
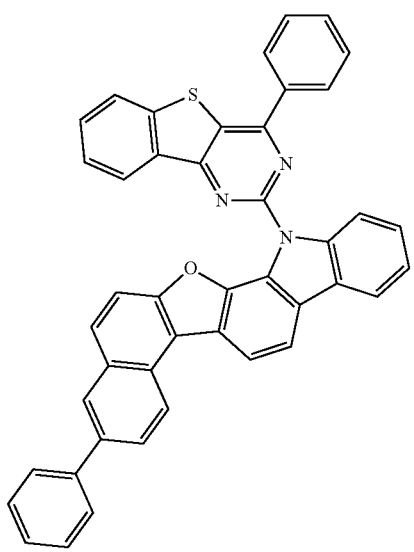

a-125
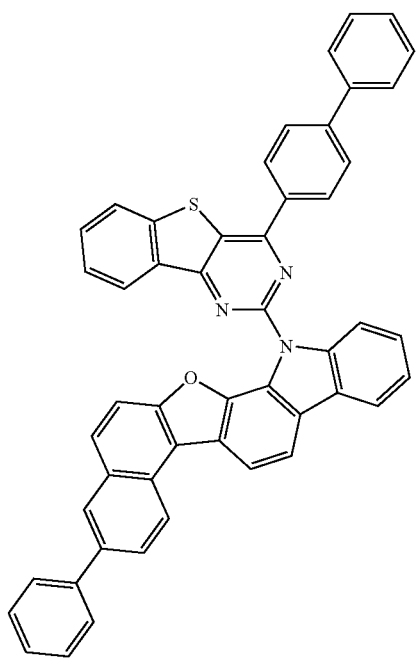
a-137
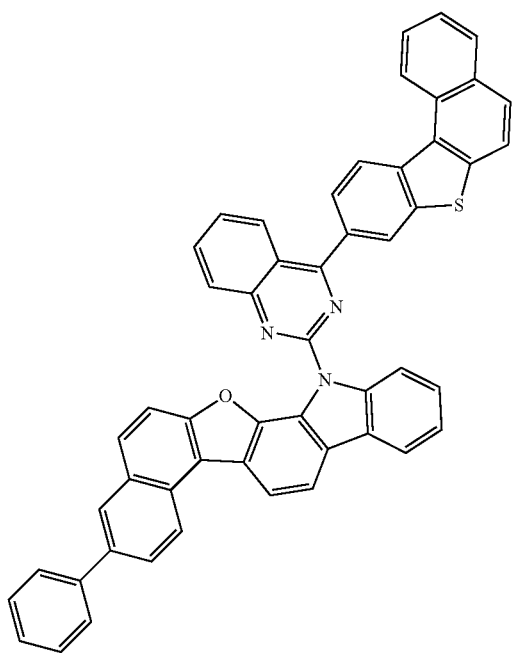
a-138
a-136
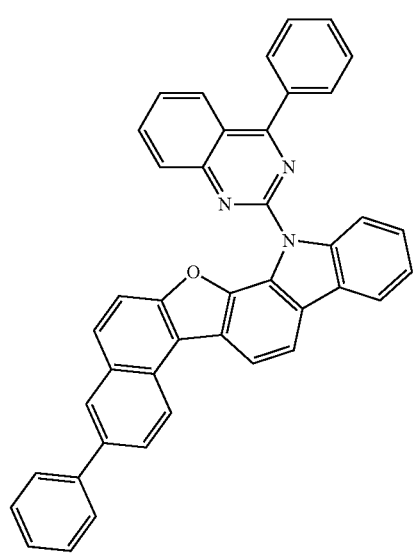
a-139
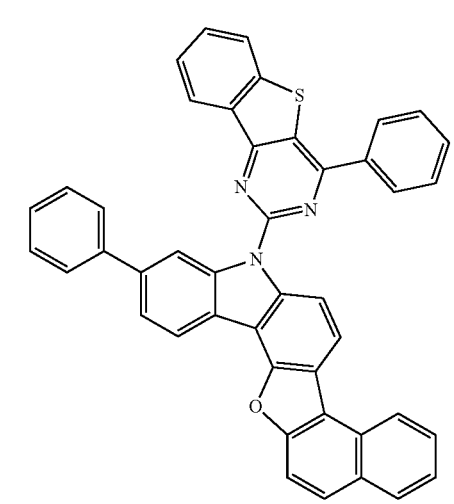

a-140
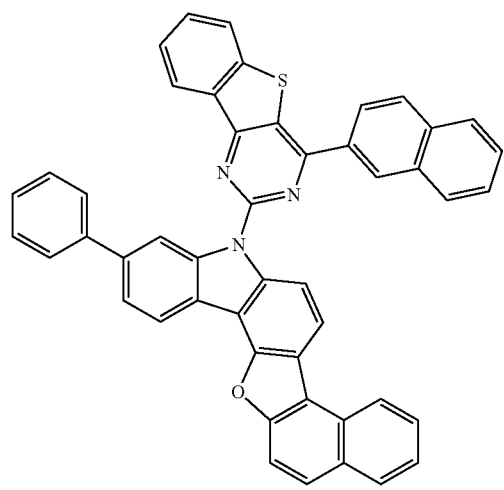
a-141
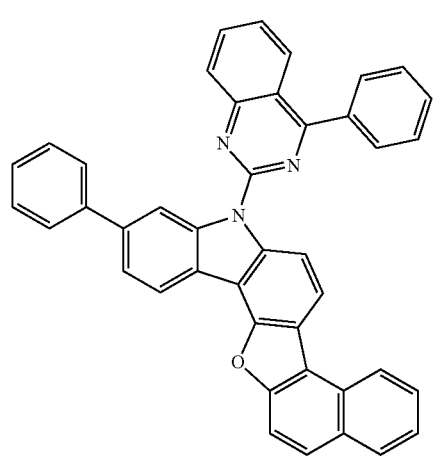
a-142
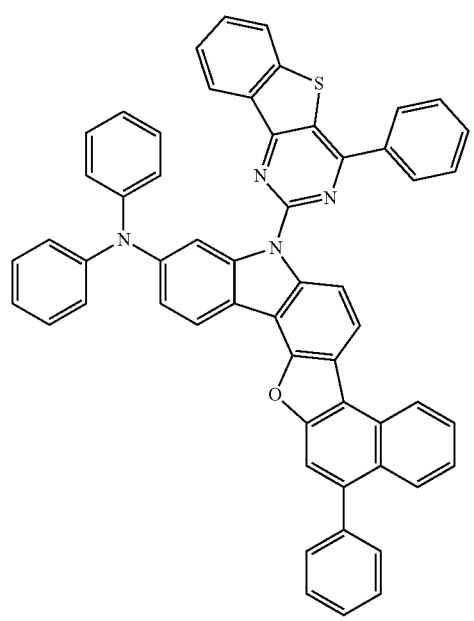
a-143
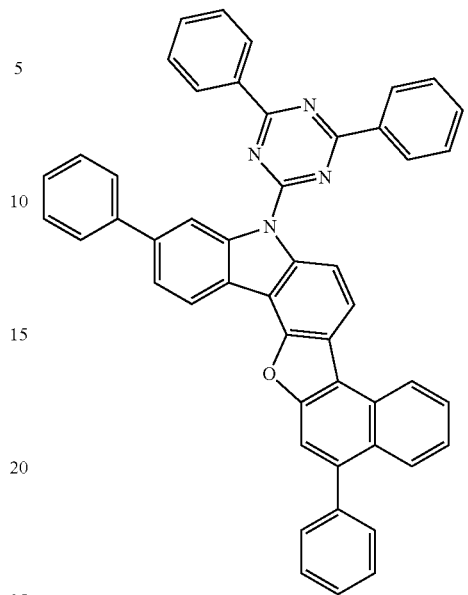
a-144
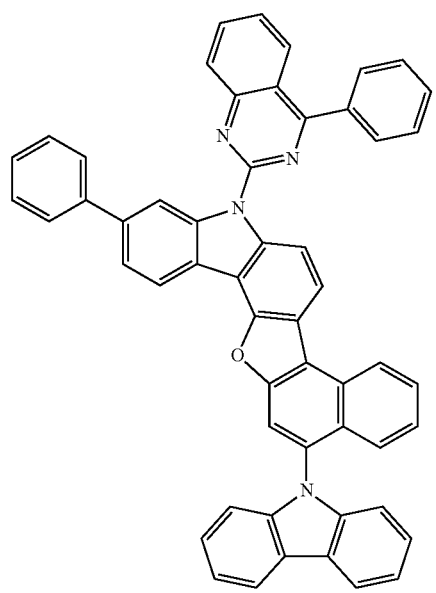

a-145
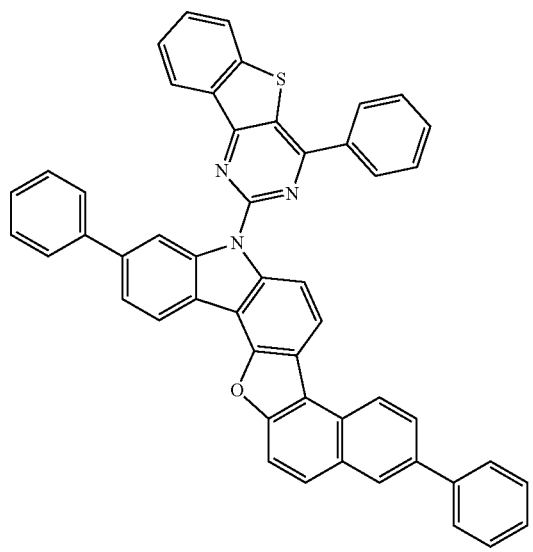
a-146
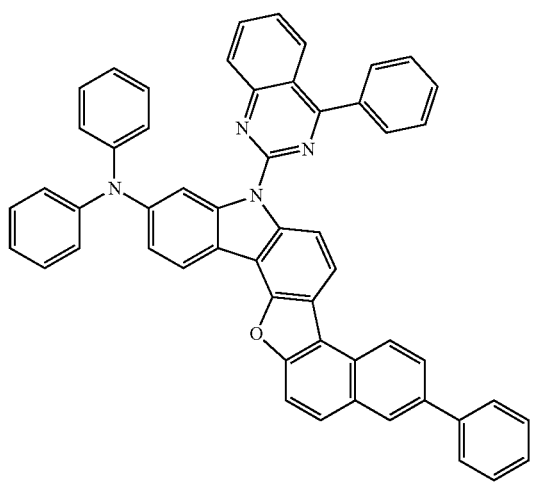
a-147
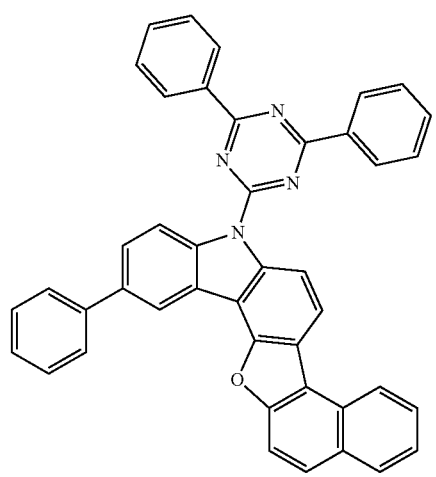
a-148
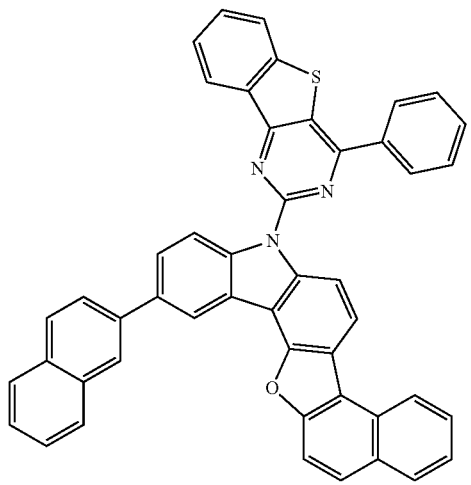
a-149
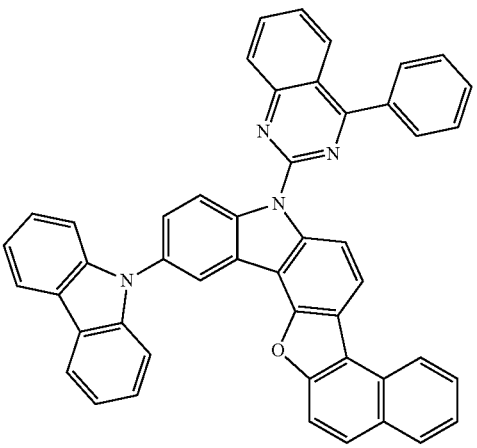
a-150
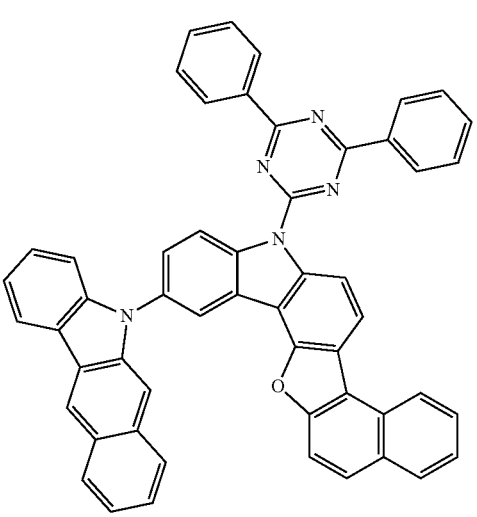

a-151
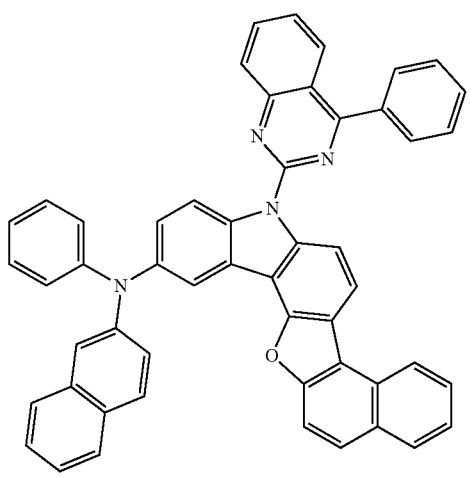
a-152
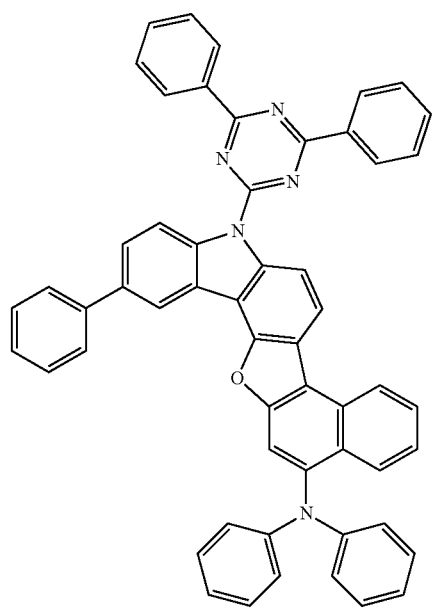
a-153
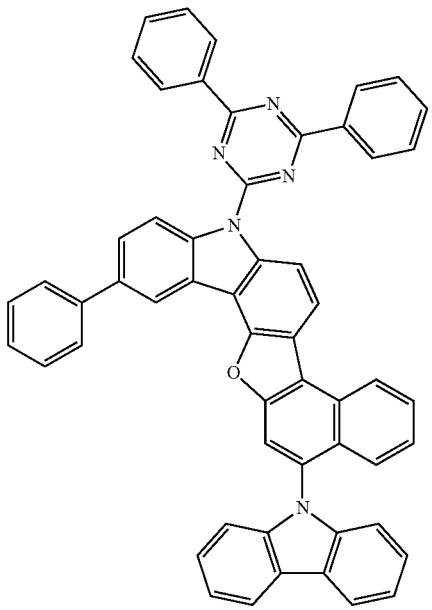
a-154
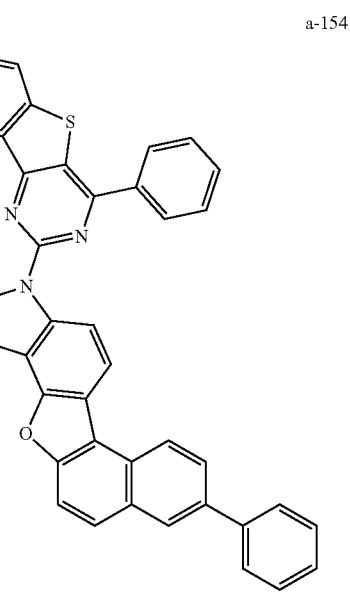

a-155
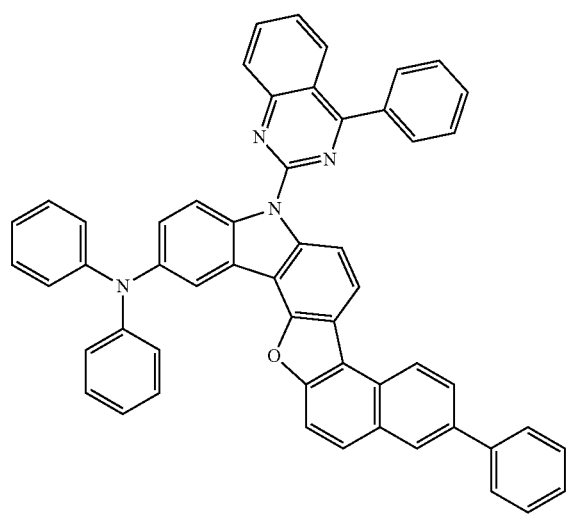
a-156
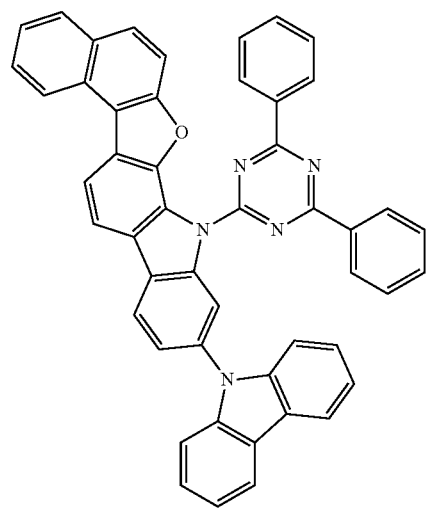
a-157
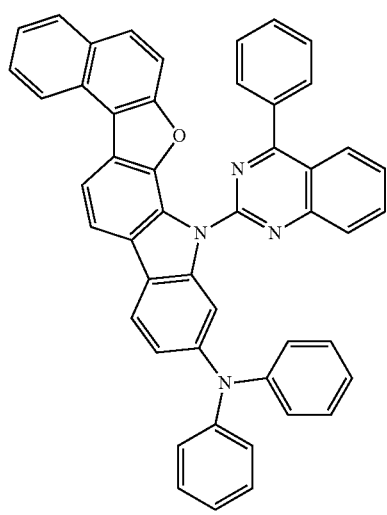
a-158
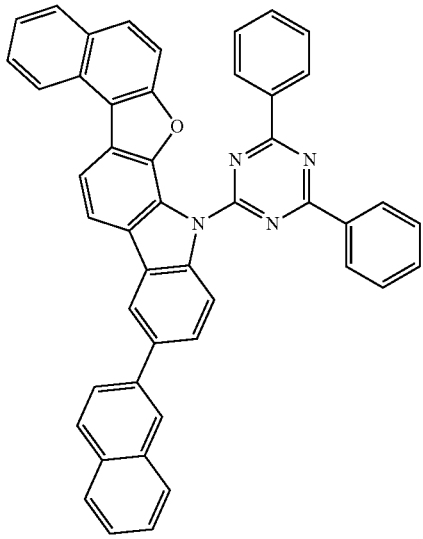
a-159
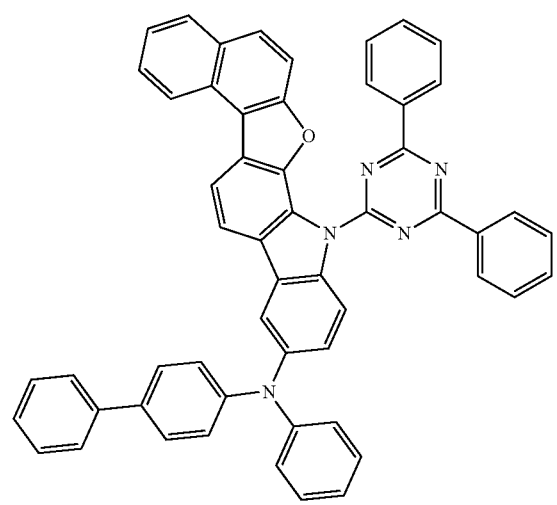
a-160
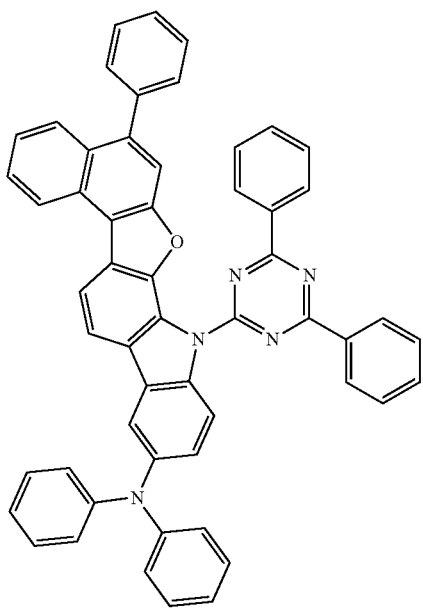

a-161
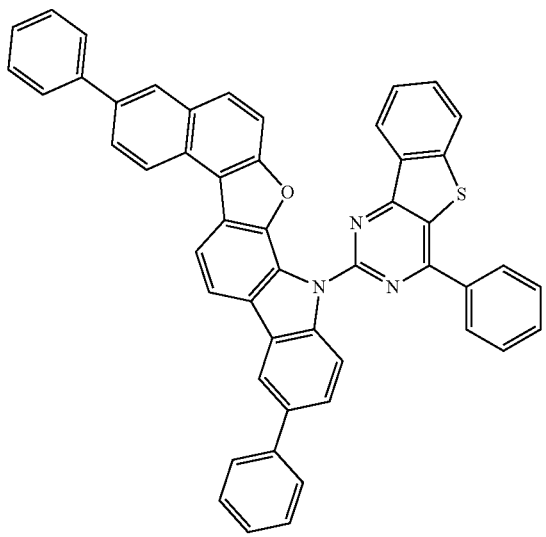
b-1
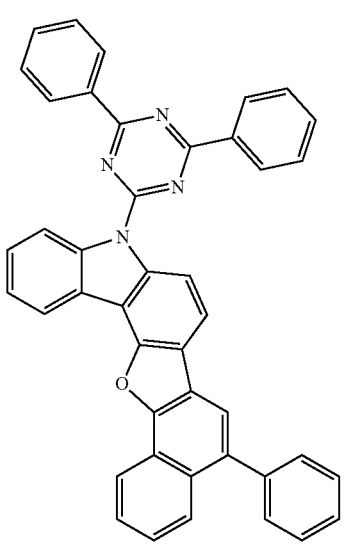
b-2
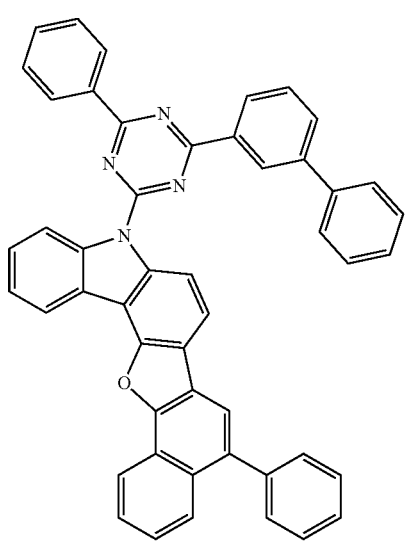
b-3
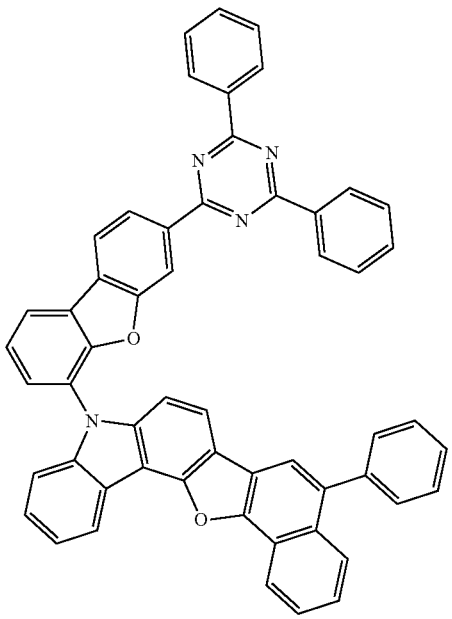
b-4
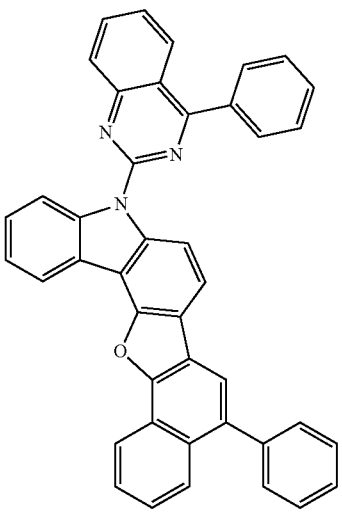
b-5
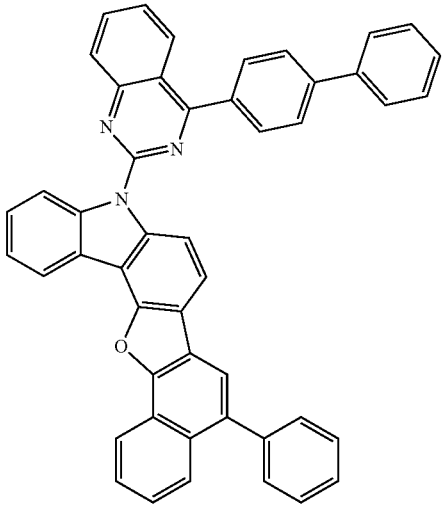

b-6
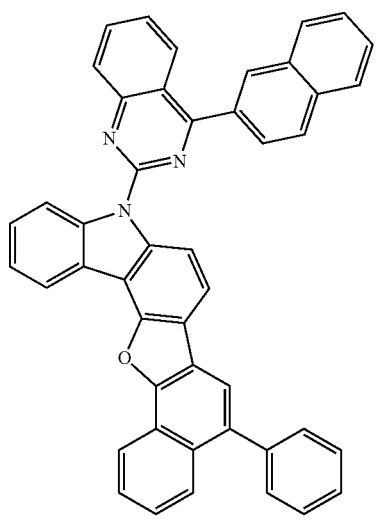
b-7
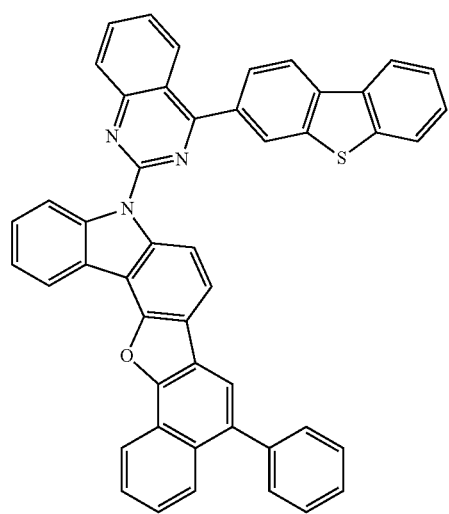
b-8
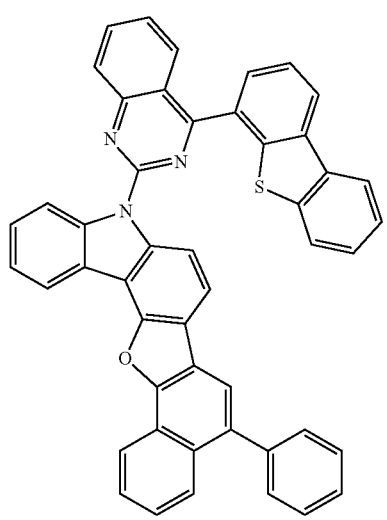
b-9
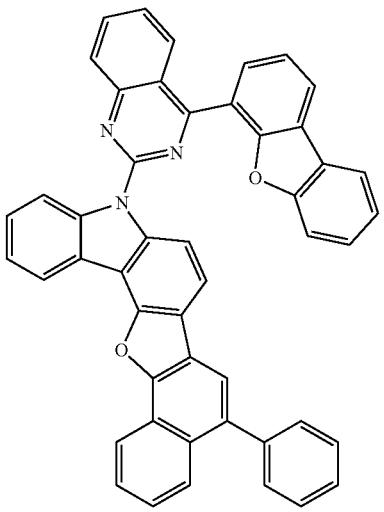
b-10
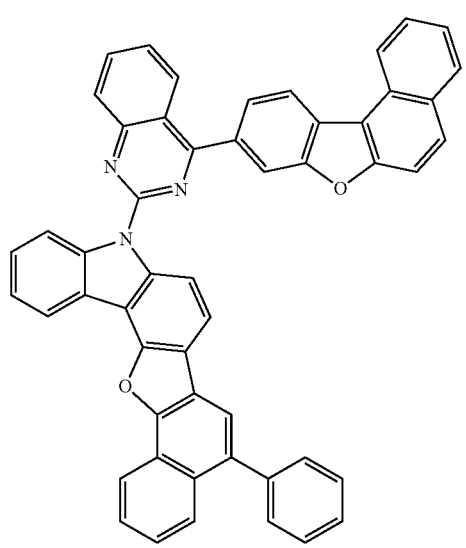
b-11
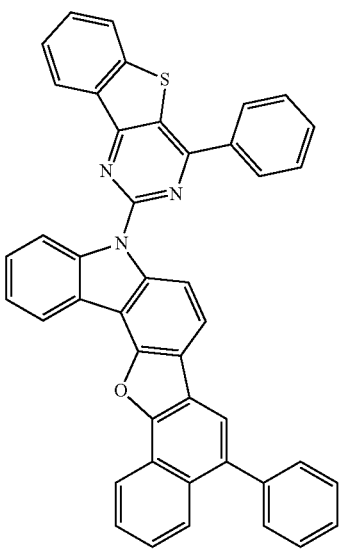

b-12
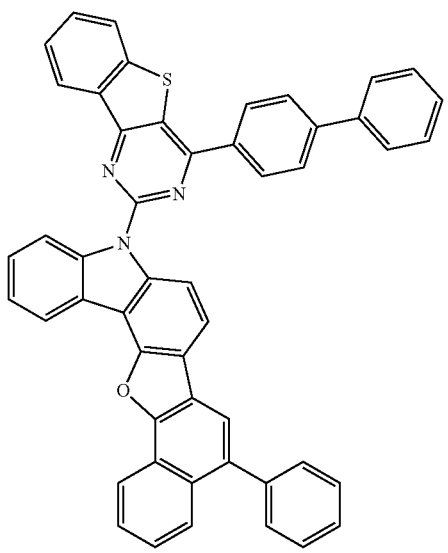
b-14
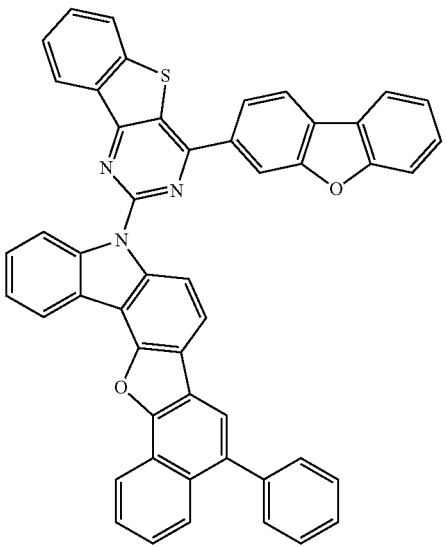
b-15
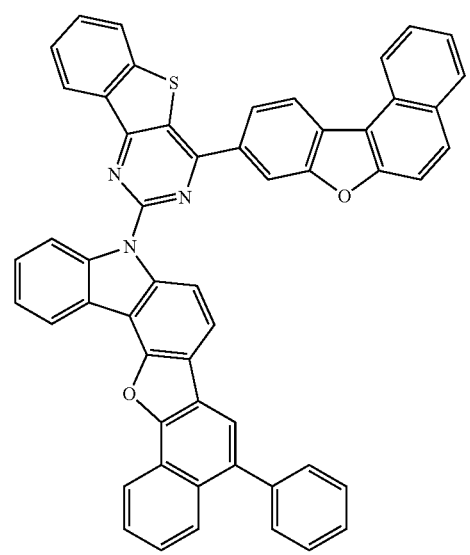
b-13
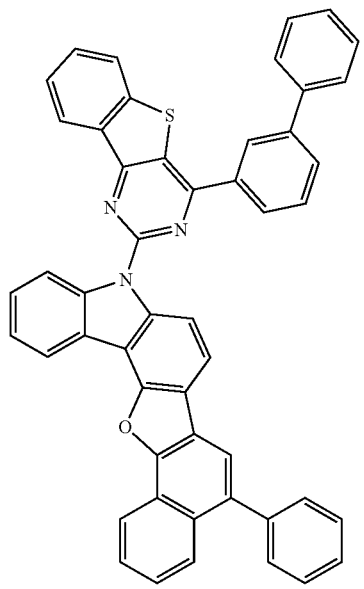
b-16
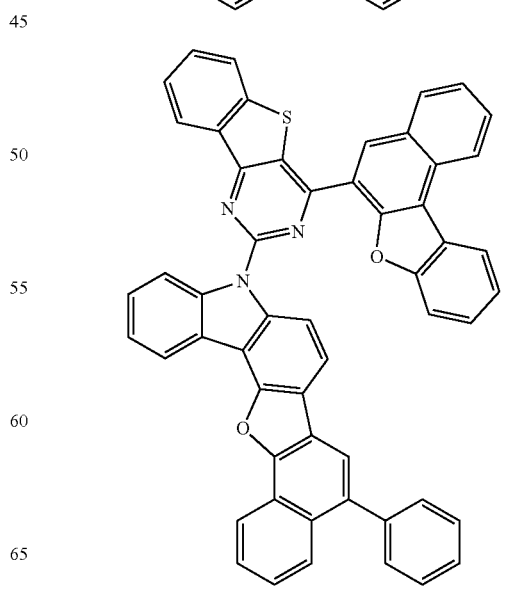

b-17
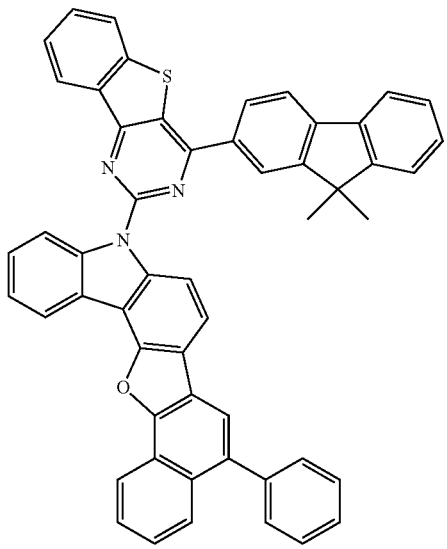
b-18
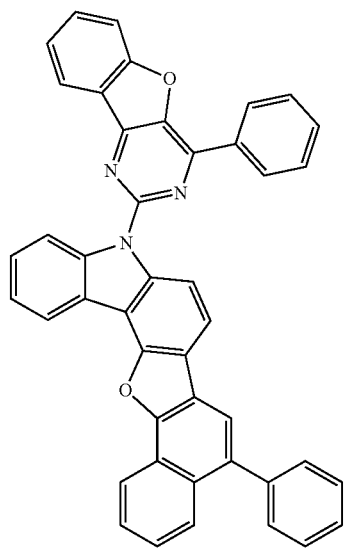
b-19
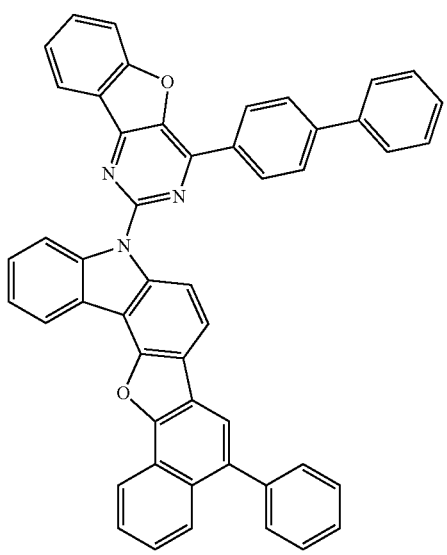
b-20
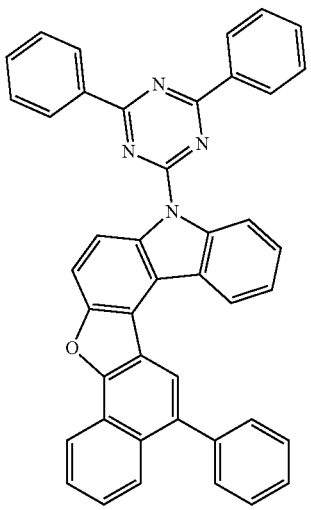
b-21
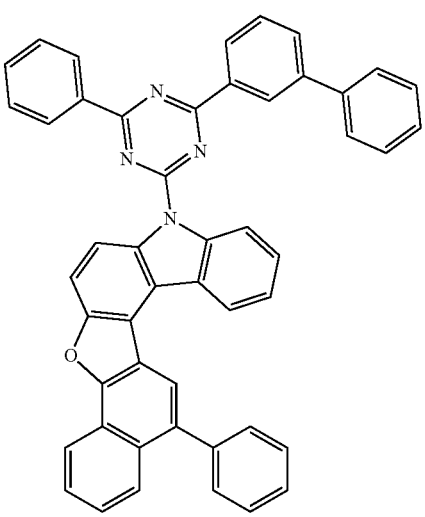
b-22
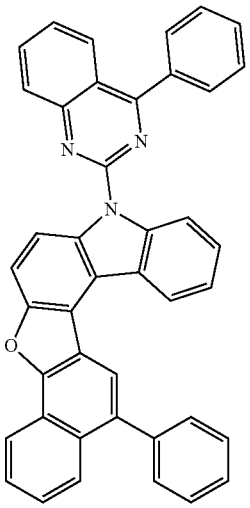

b-23
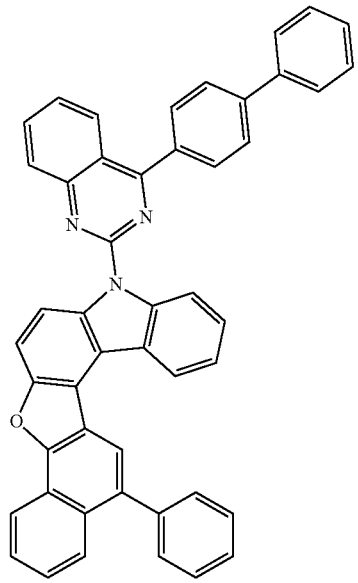
b-24
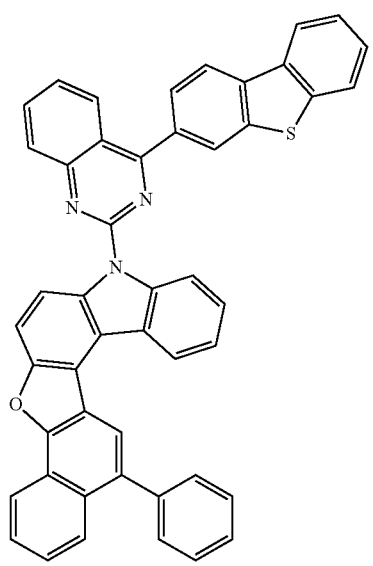
b-25
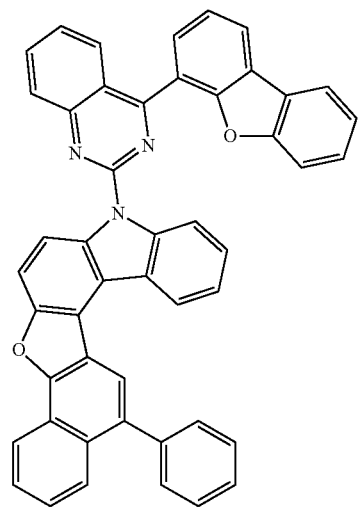
b-26
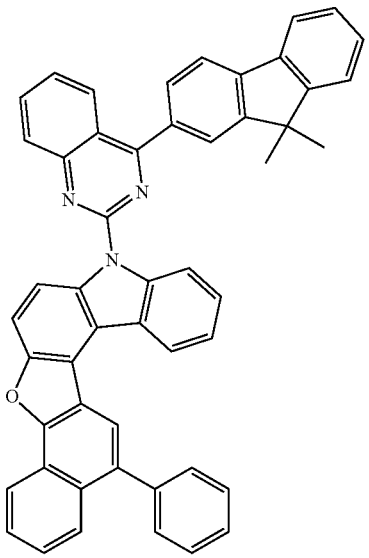
b-27
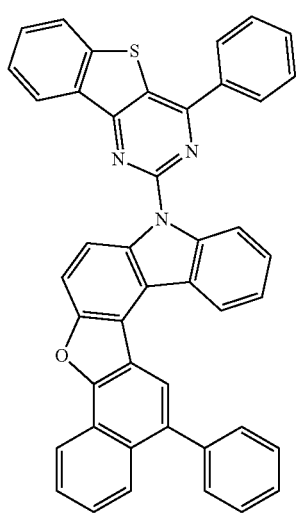
b-28
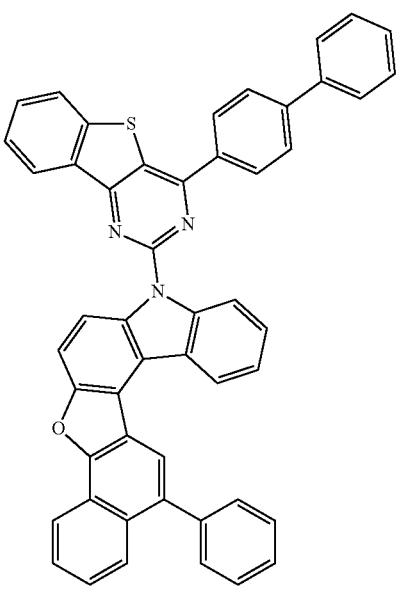

b-29
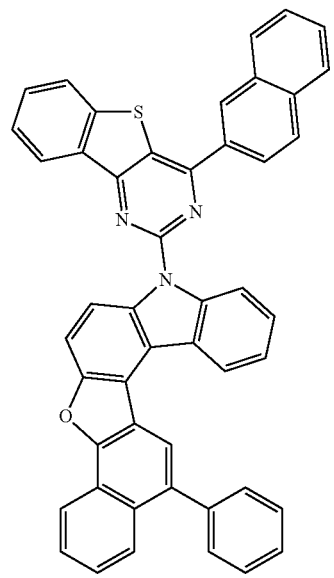
b-30
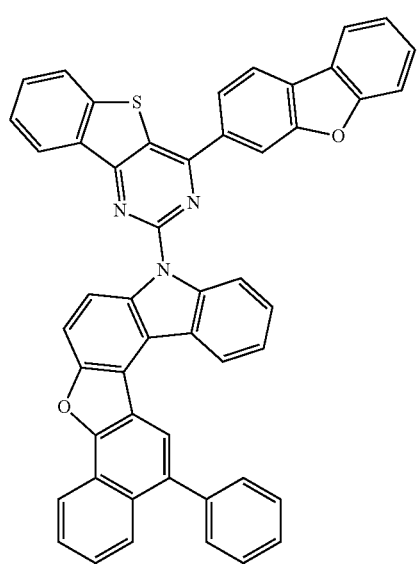
b-31
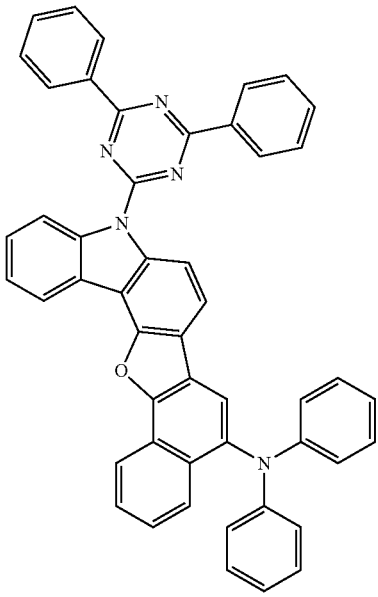
b-32
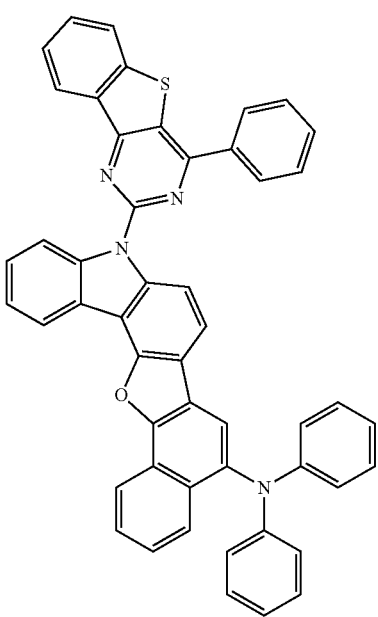

353
-continued
b-33
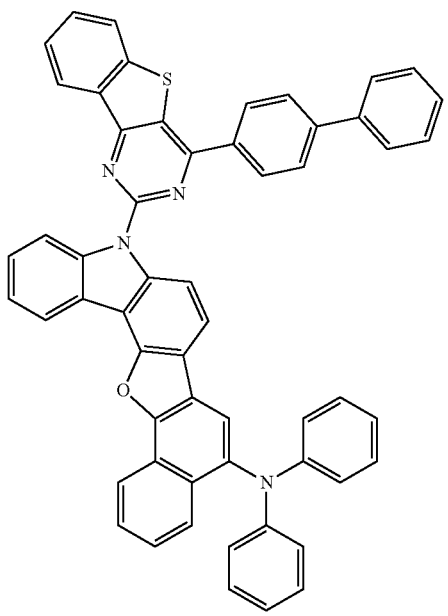
b-34
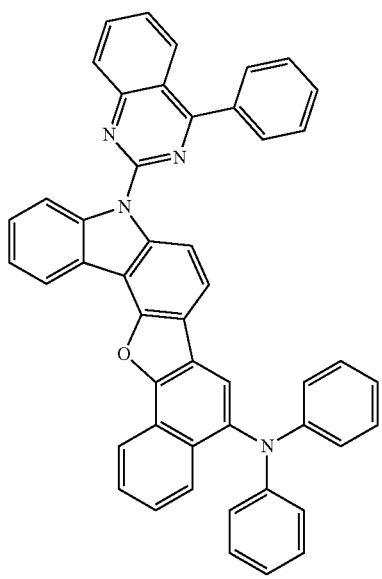
354
-continued
b-35
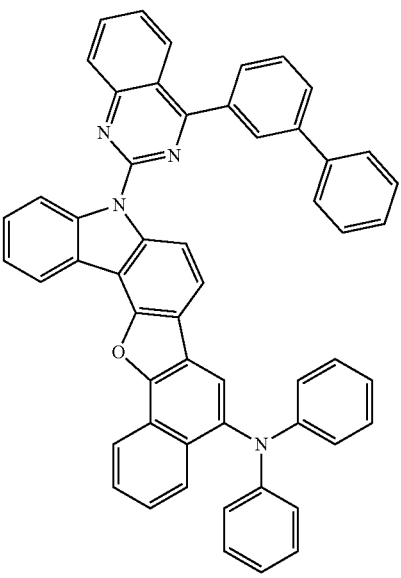
b-36
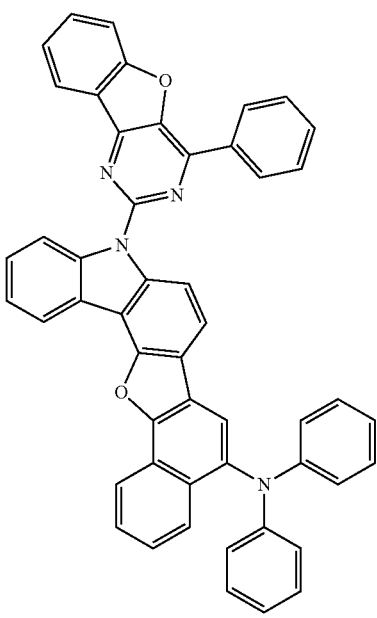

355
-continued
b-37
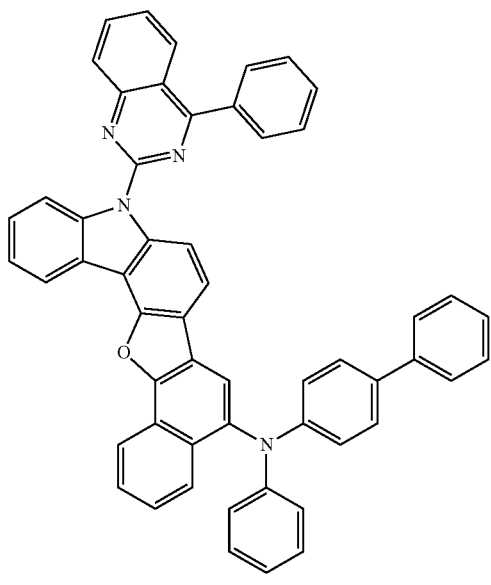
b-38
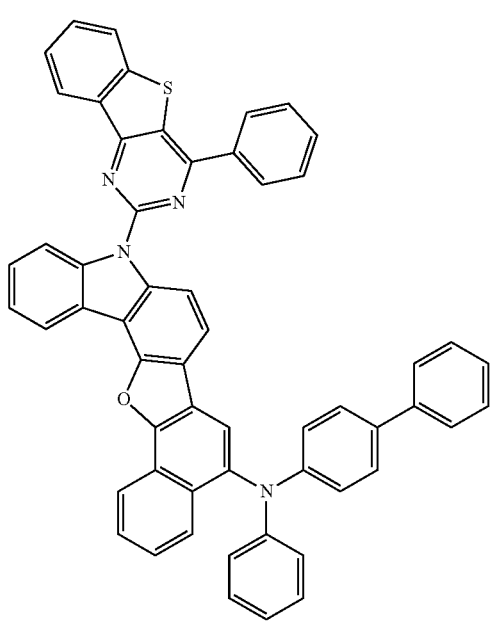
356
-continued
b-39
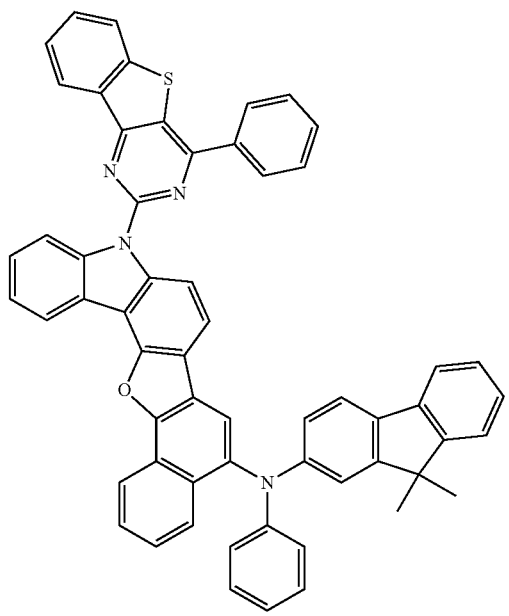
b-40
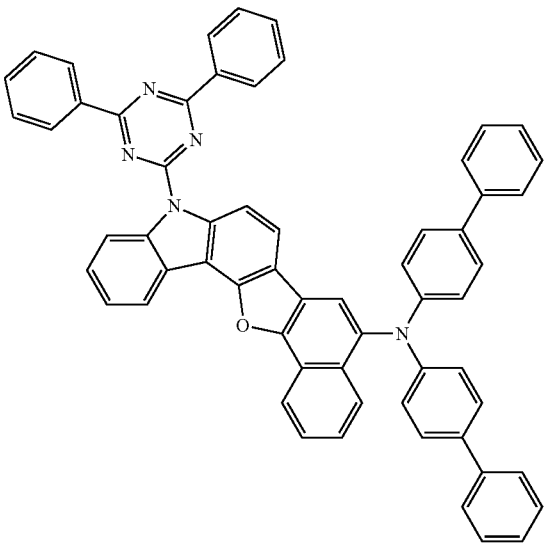

b-41
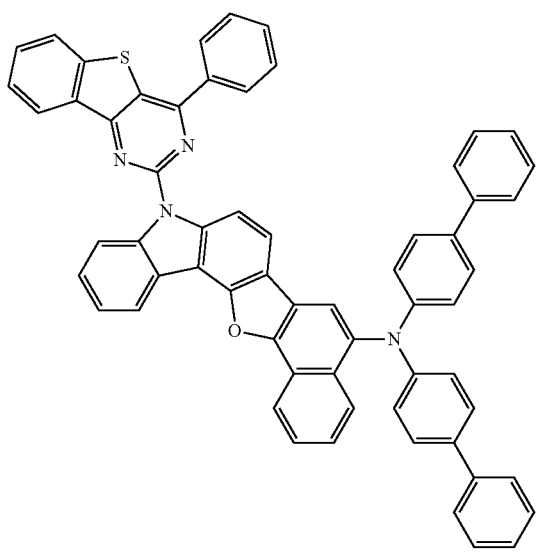
b-43
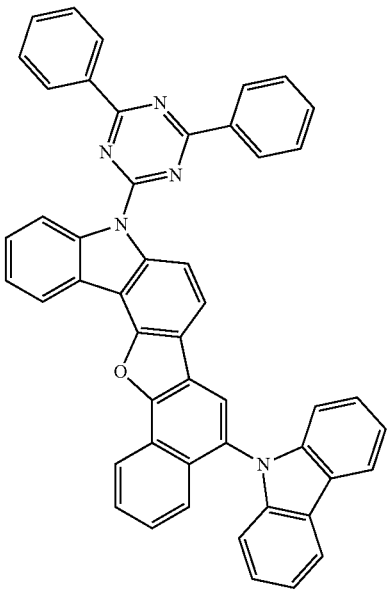
b-42
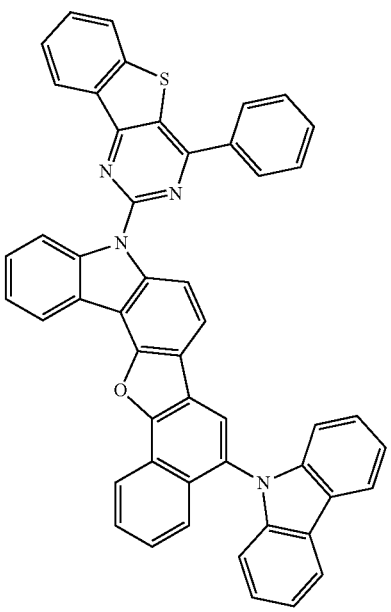
b-44 b-45
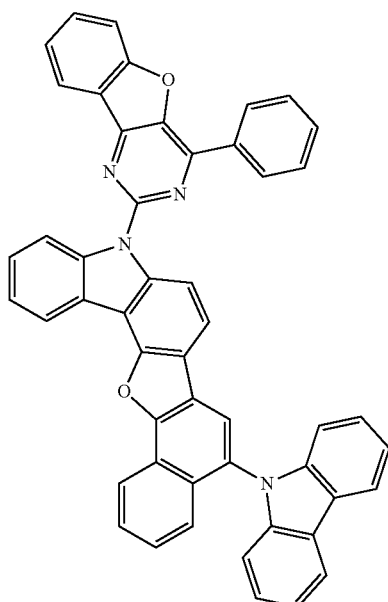
b-46
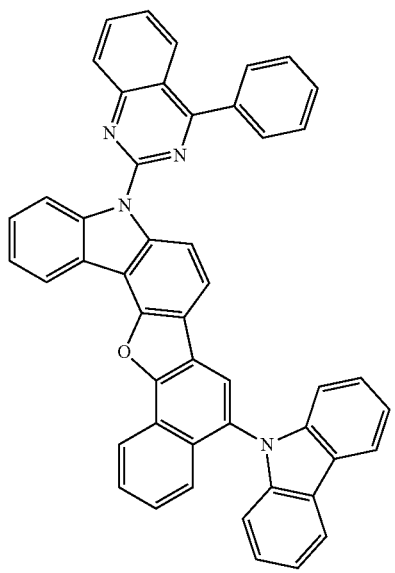
b-47
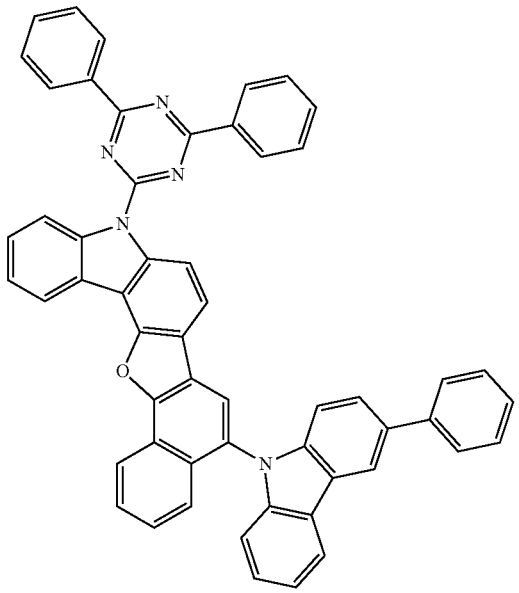
b-48
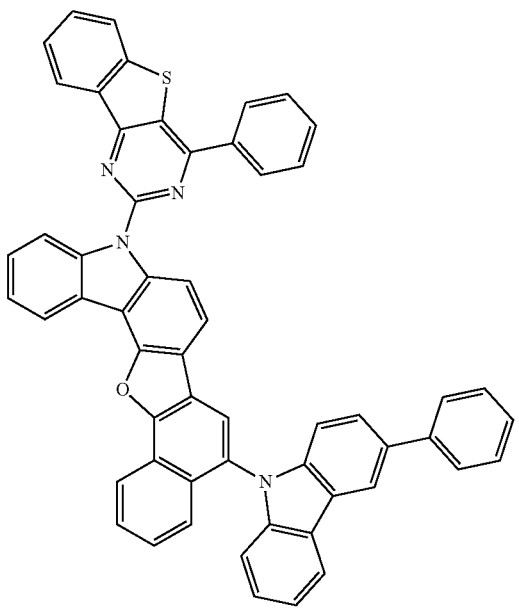

b-49
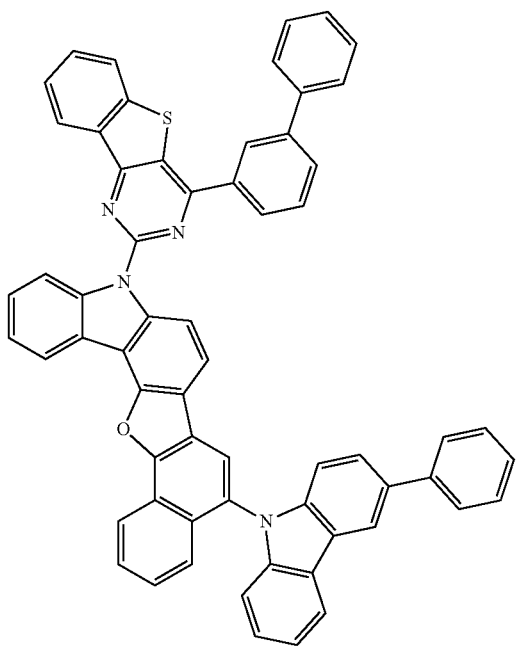
b-51
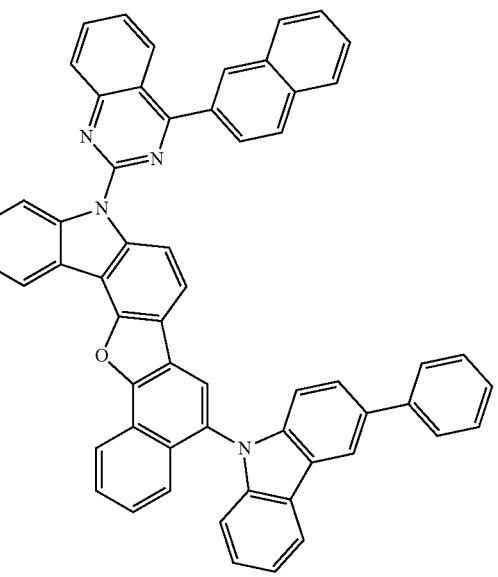
b-50
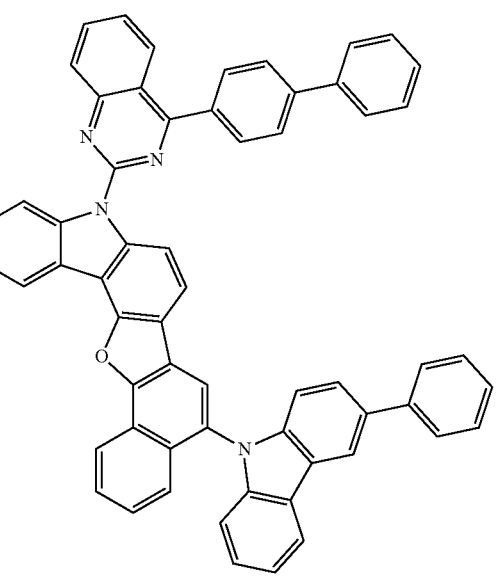
b-52

363
-continued
b-53
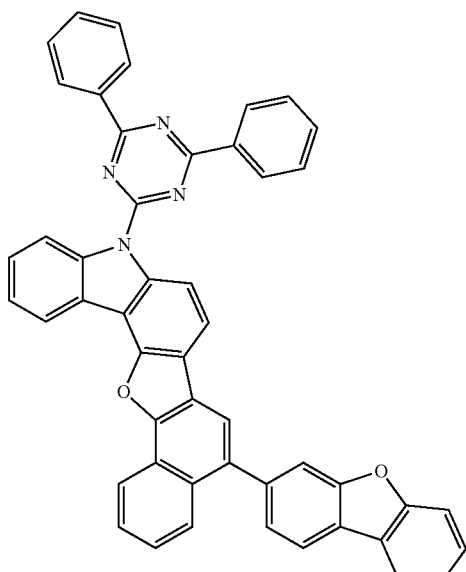
364
-continued
b-55
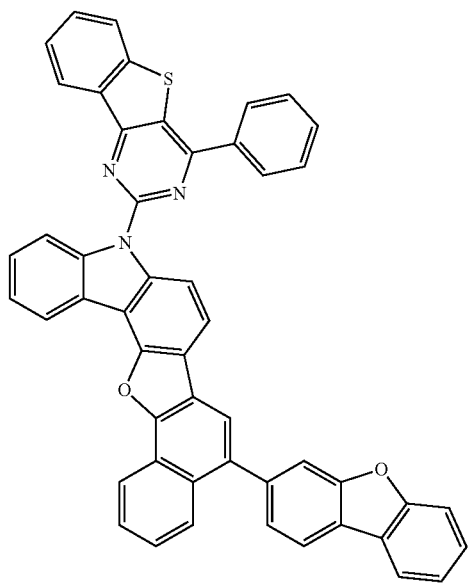
b-54
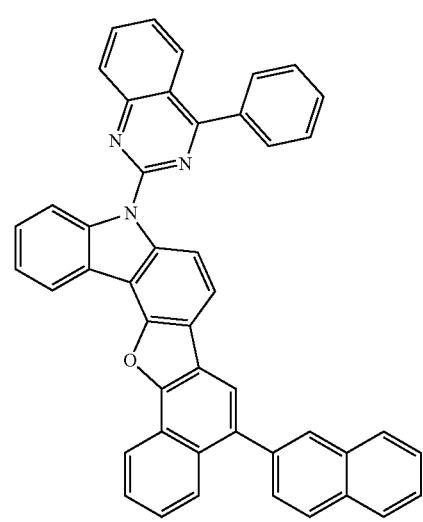
b-56
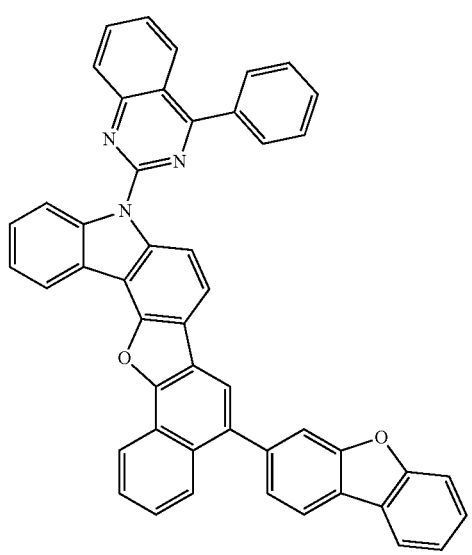

b-57
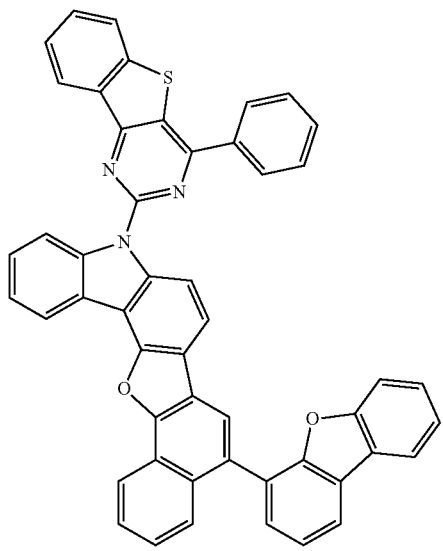
b-58
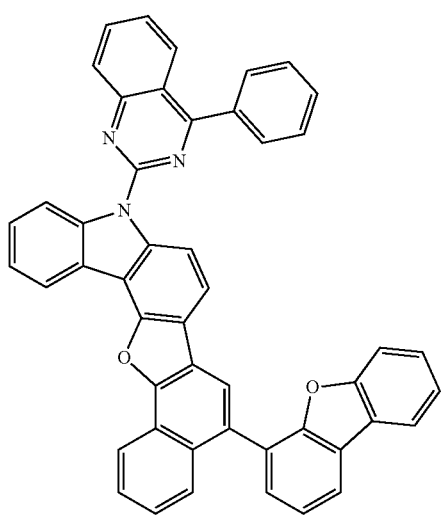
b-59
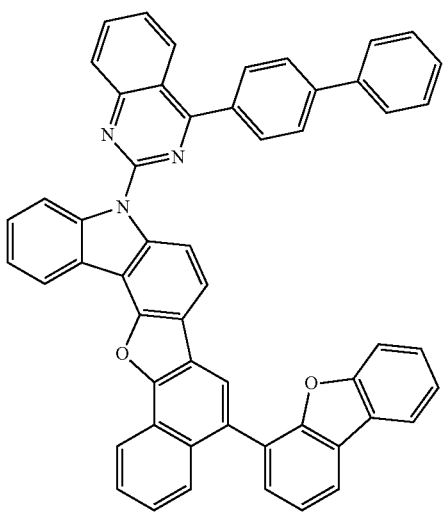
b-60
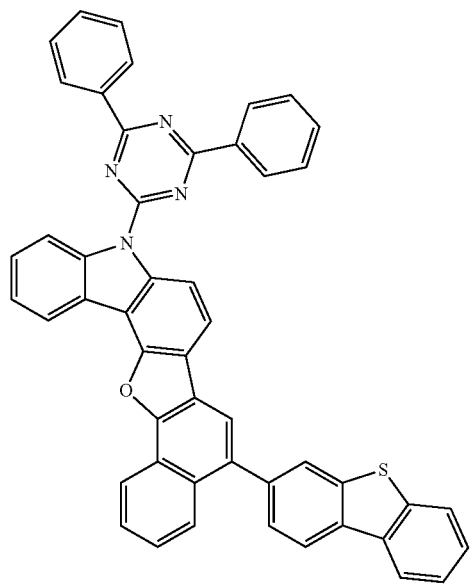
b-61
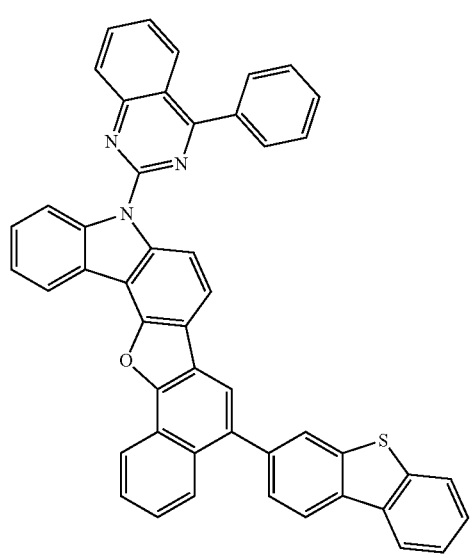

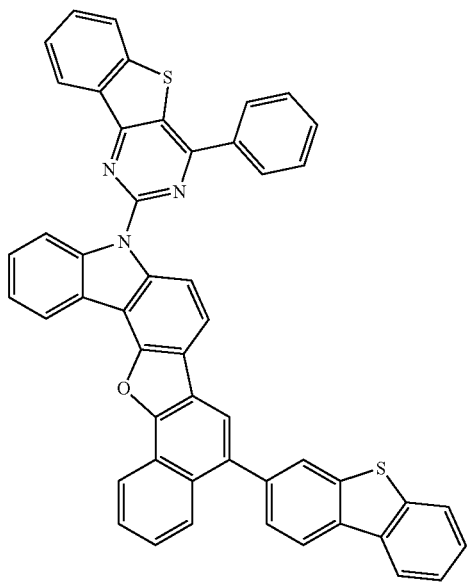
b-62
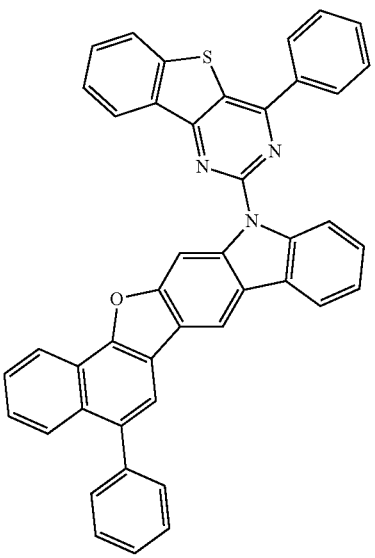
b-64
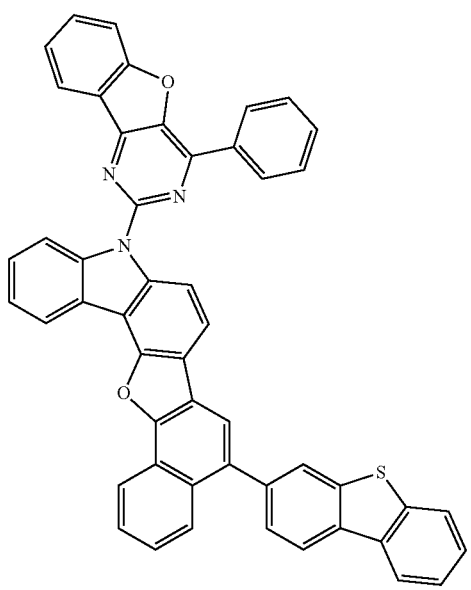
b-63
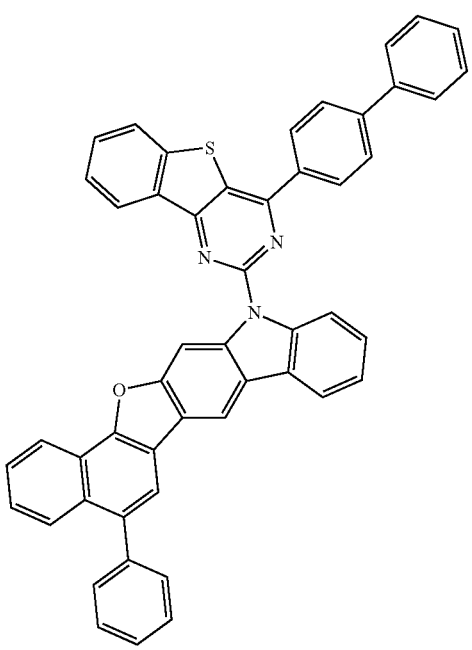
b-65 b-66
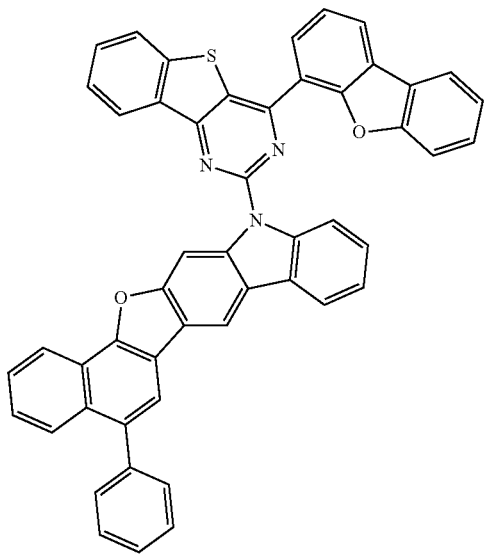
b-68
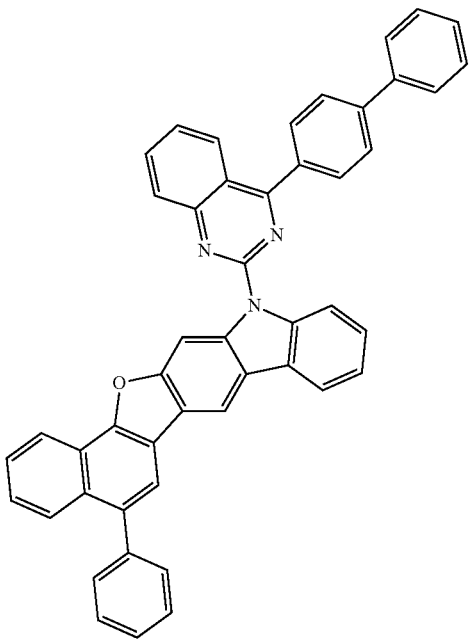
b-67
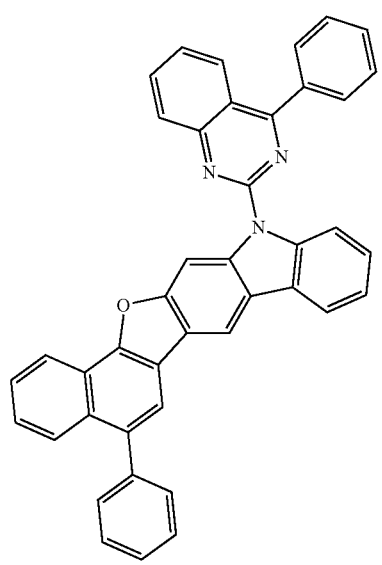
b-69
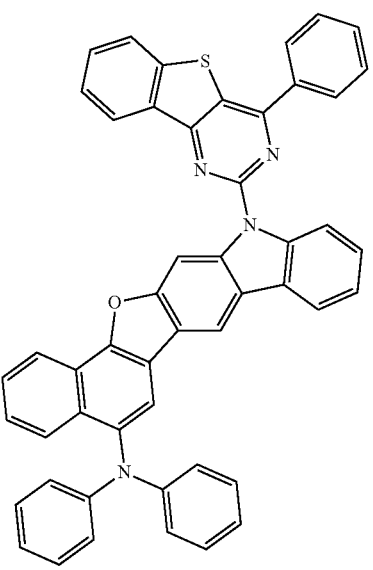

b-70
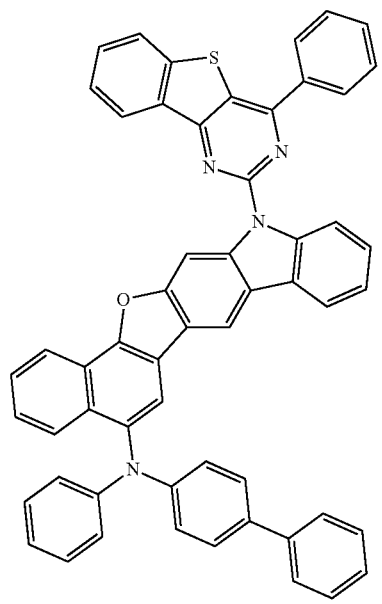
b-71
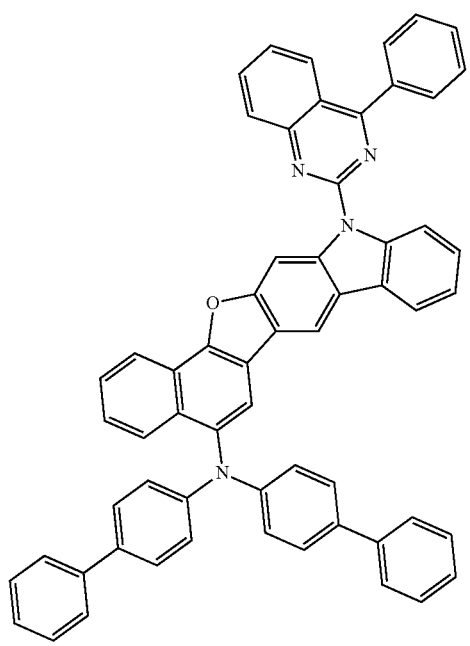
b-72
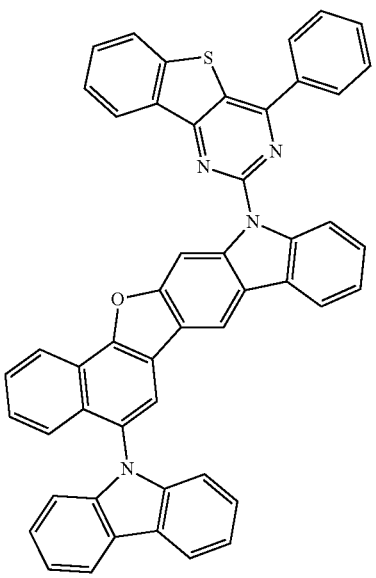
b-73
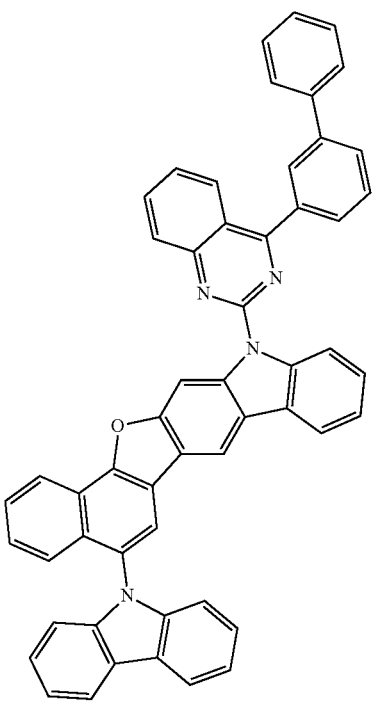

-continued
b-74
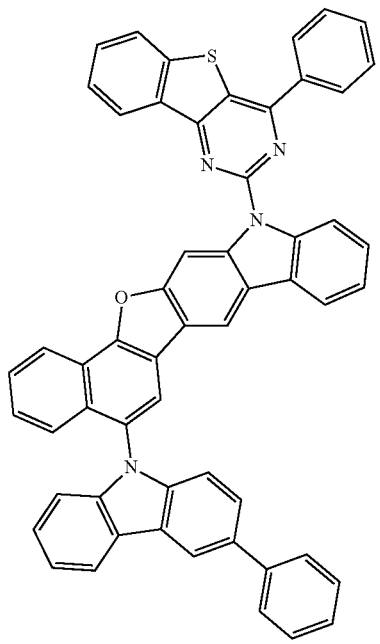
b-75
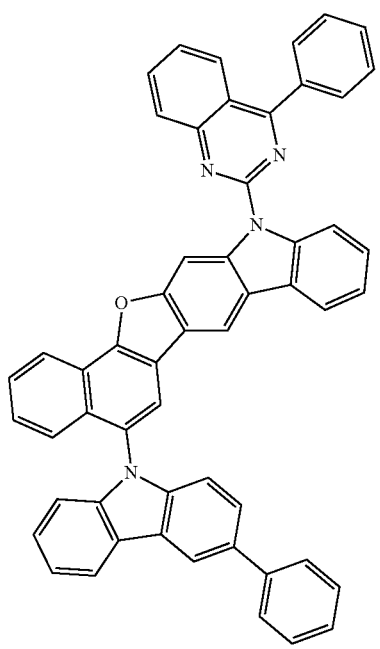
b-76
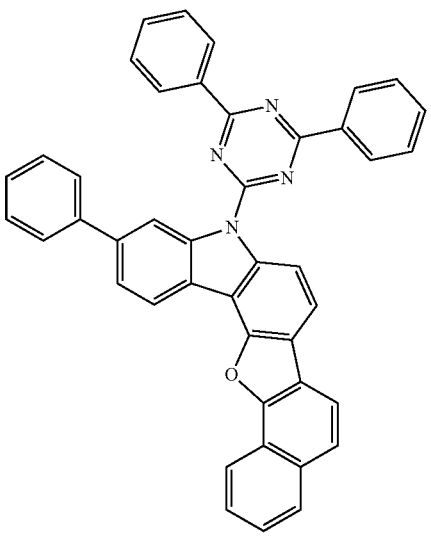
b-77
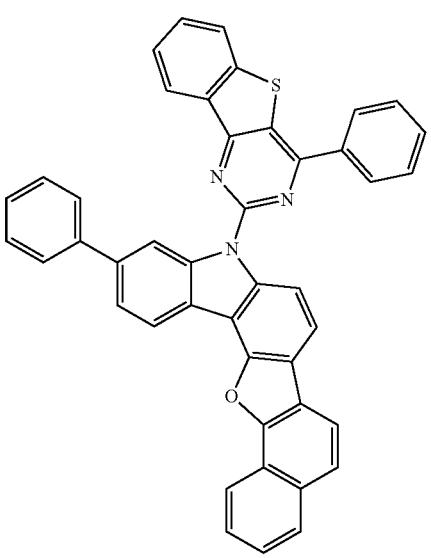
b-78
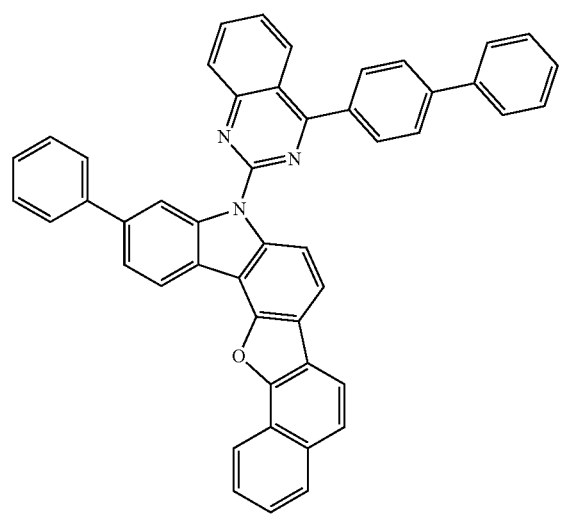

-continued
b-79
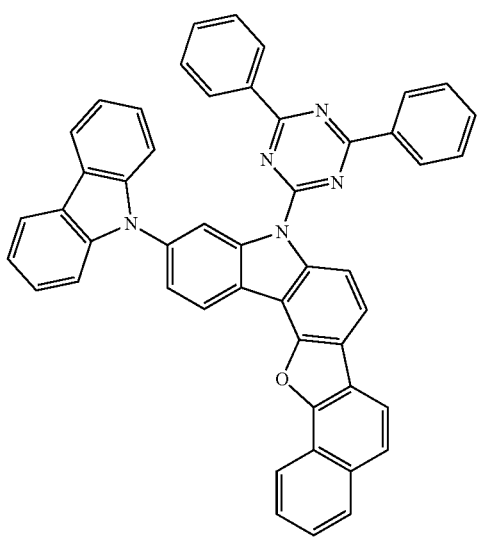
b-80
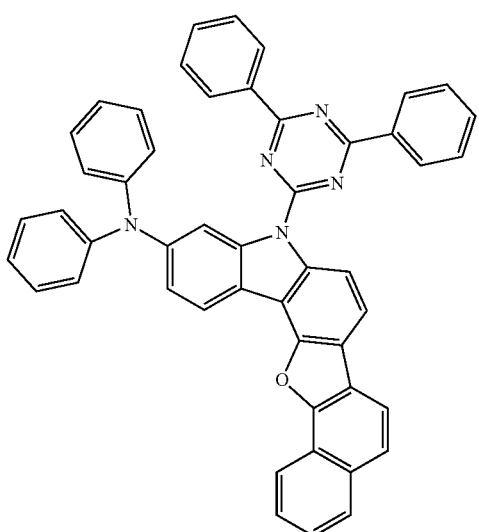
b-81
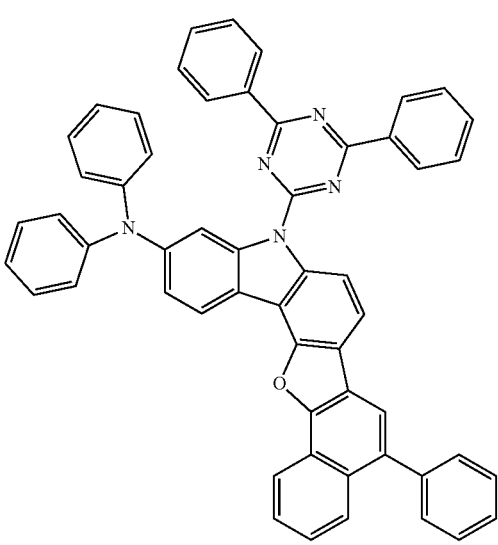
-continued
b-82
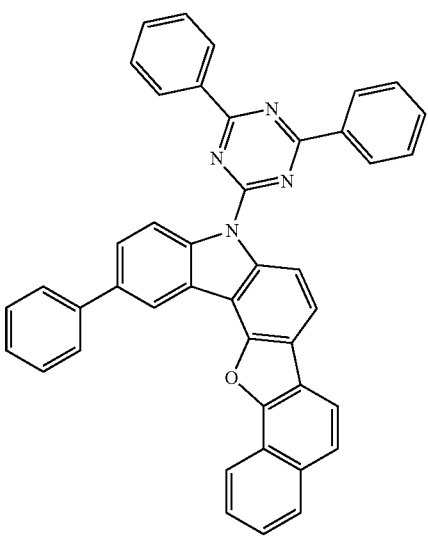
b-83
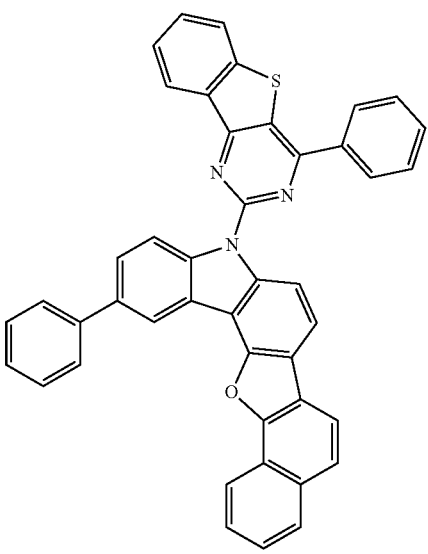
b-84
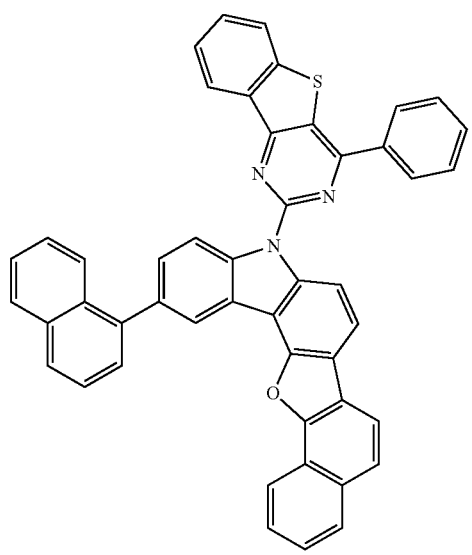

-continued
b-85
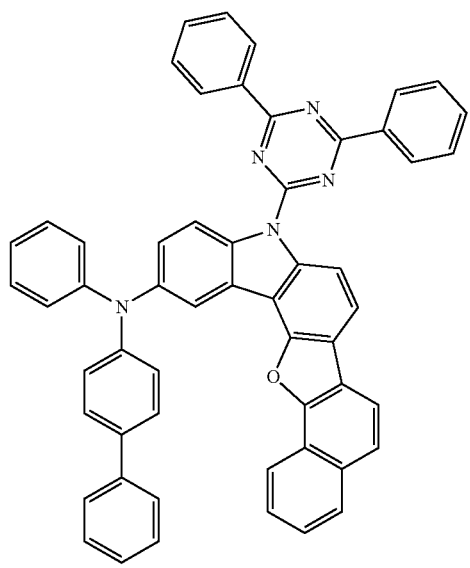
b-86
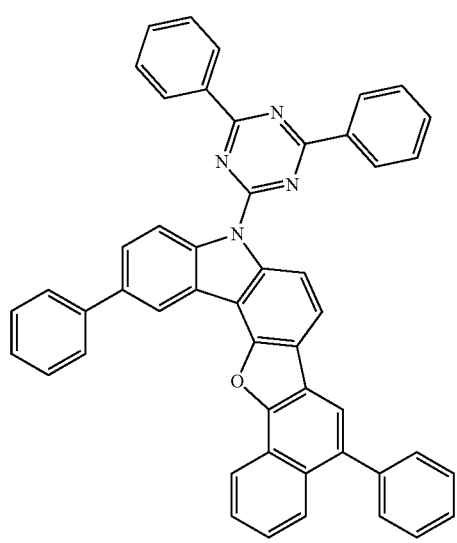
b-87
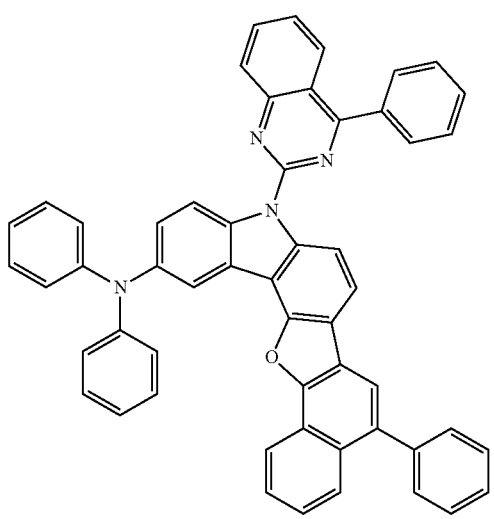
-continued
b-88
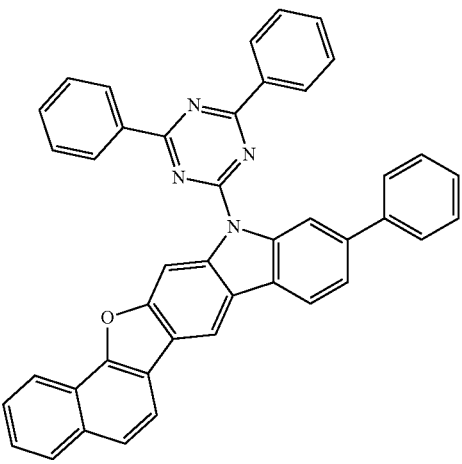
b-89
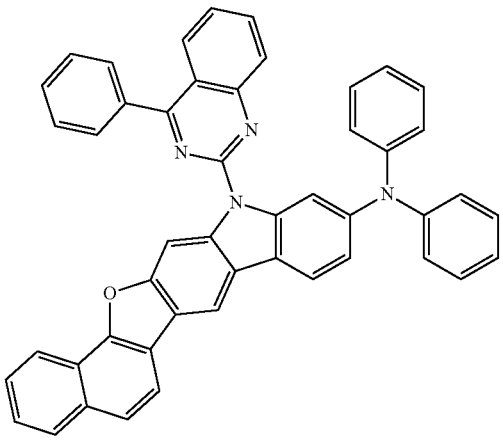
b-90
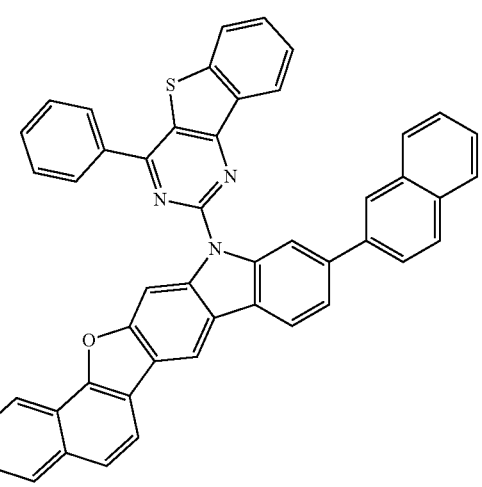

b-91
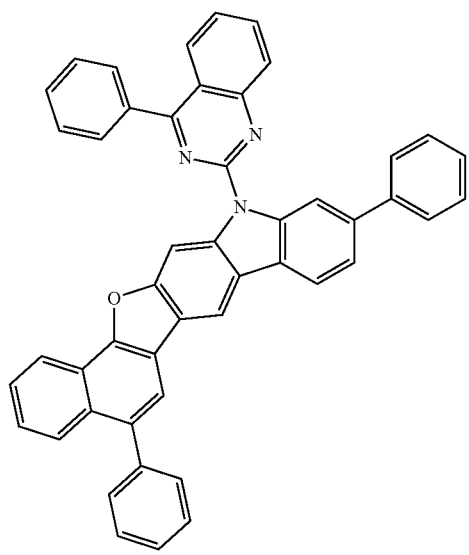
b-92
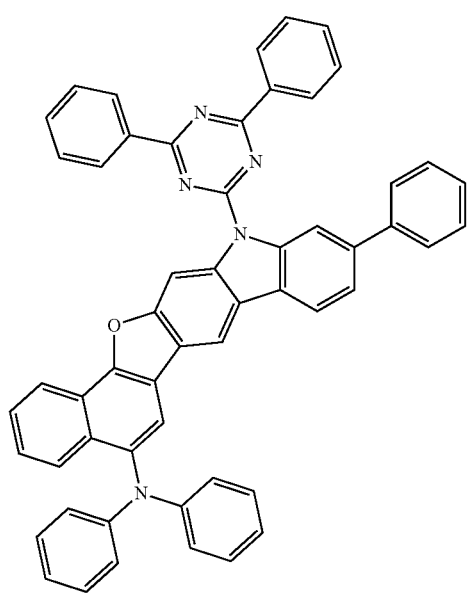
b-93
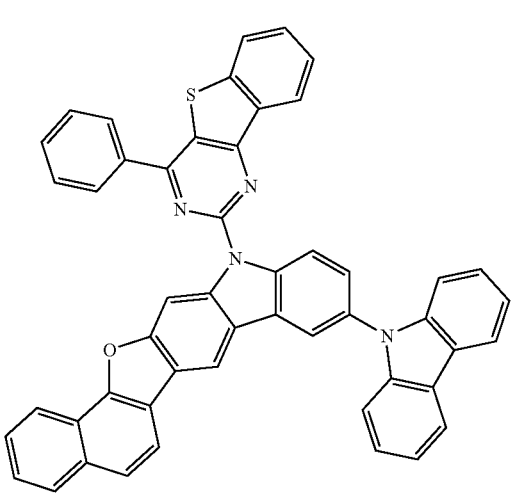
b-94
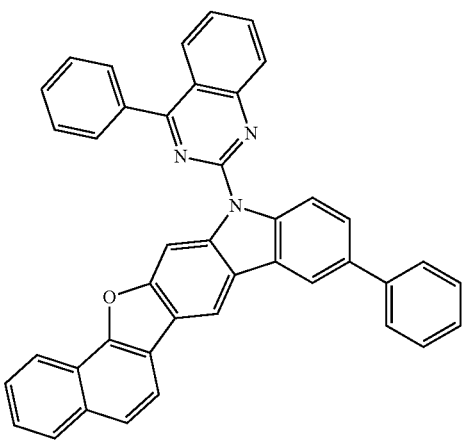
b-95
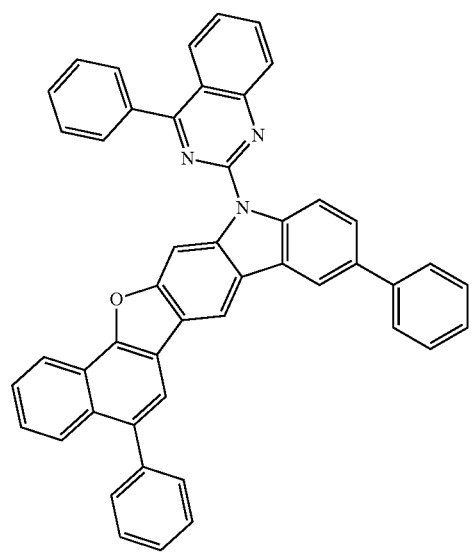
c-1
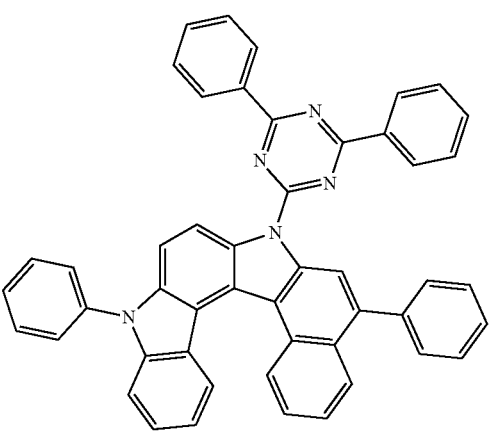

-continued
c-2
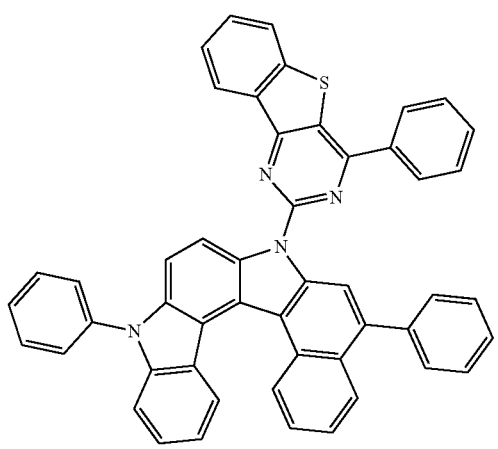
c-3
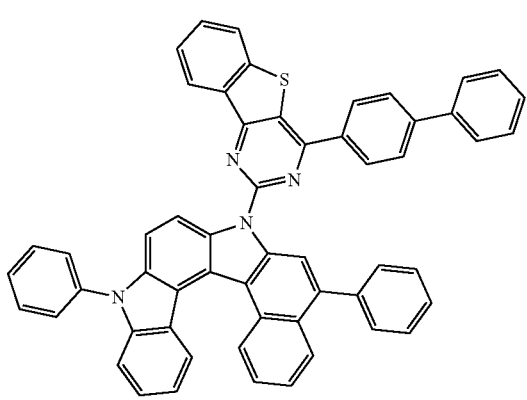
c-4
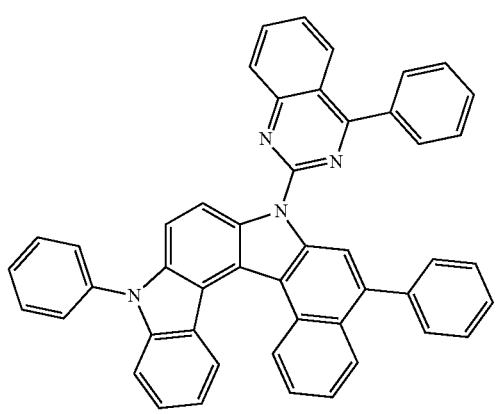
-continued
c-5
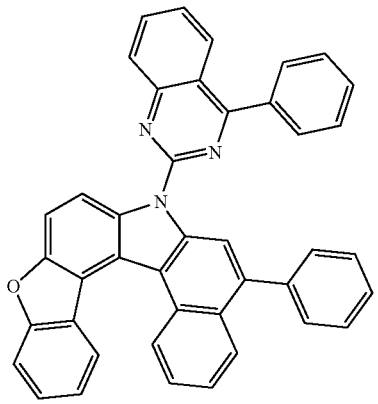
c-6
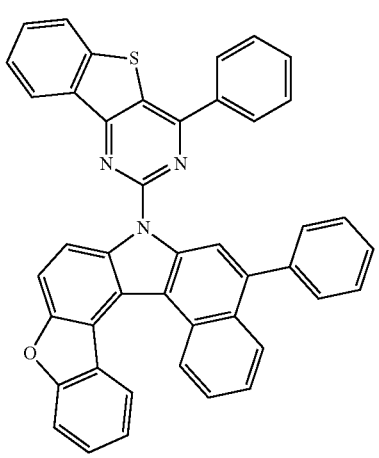
c-7
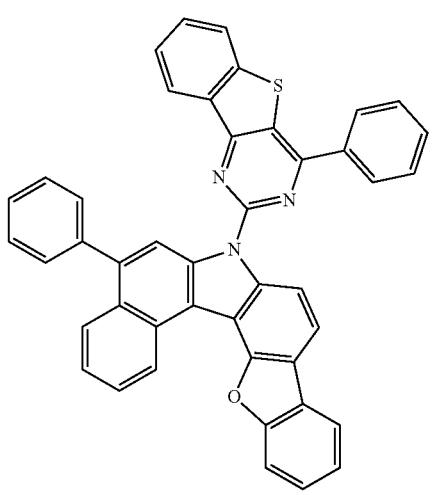

-continued
c-8
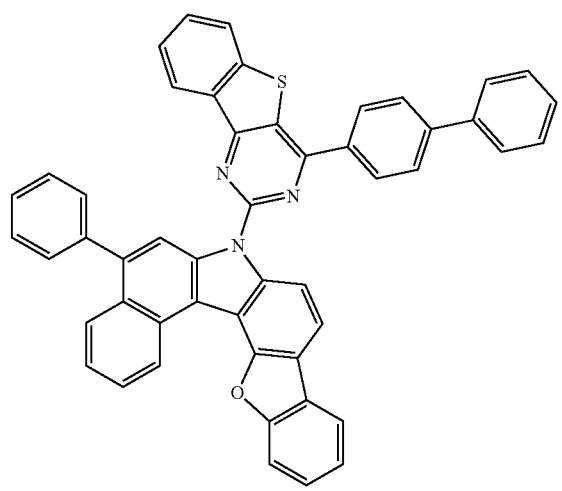
c-9
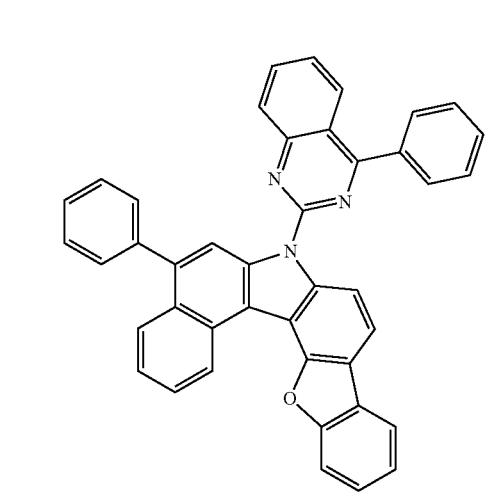
c-10
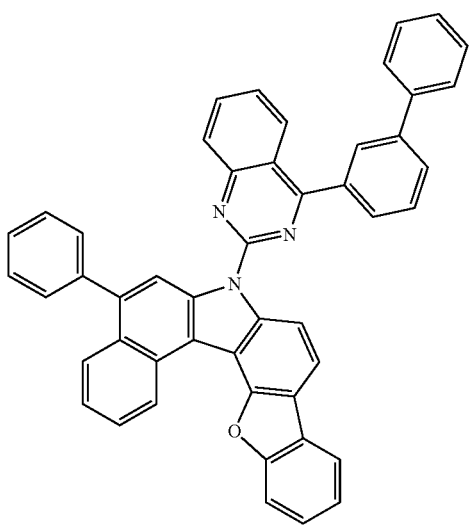
-continued
c-11
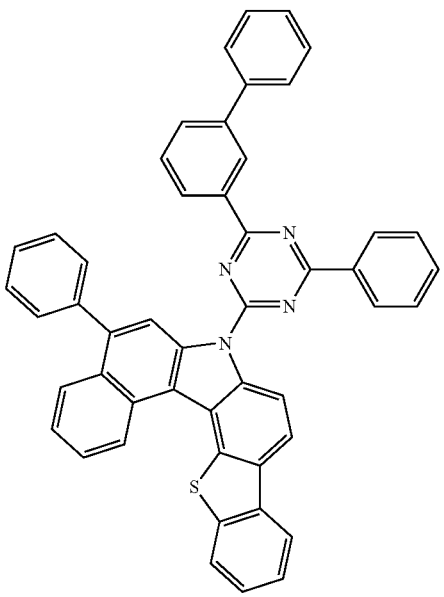
c-12
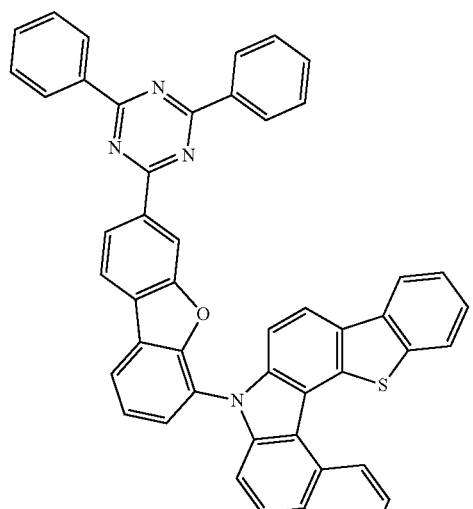
c-13
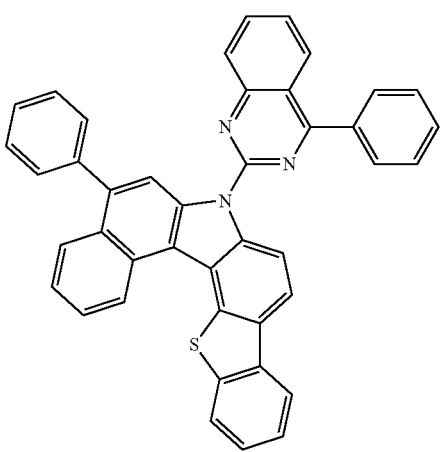

-continued
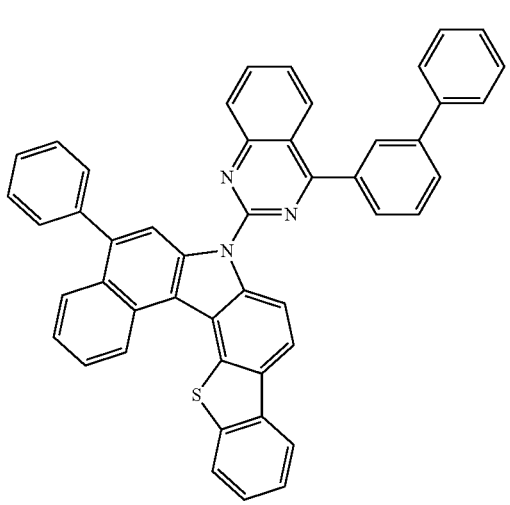
c-14
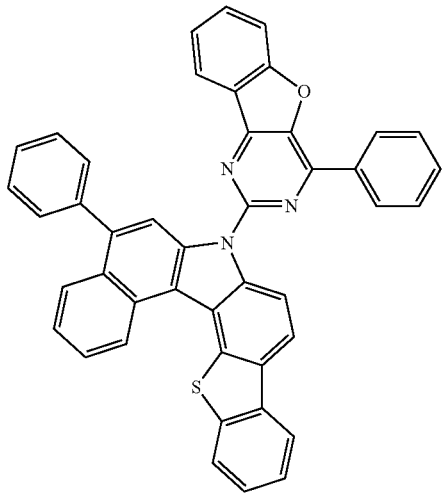
c-17
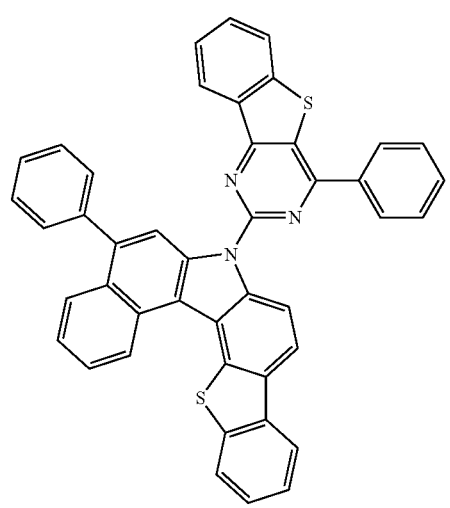
c-15
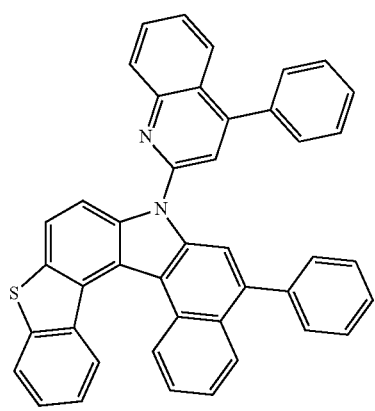
c-18
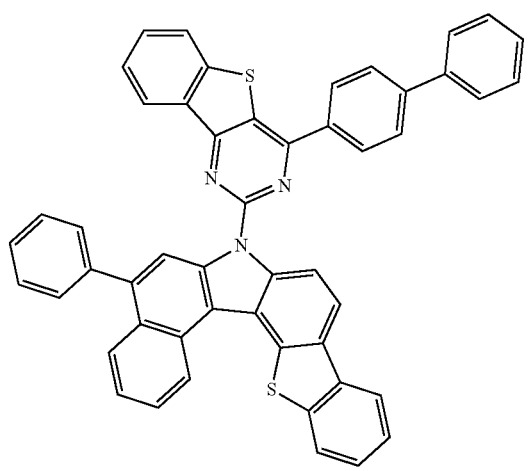
c-16
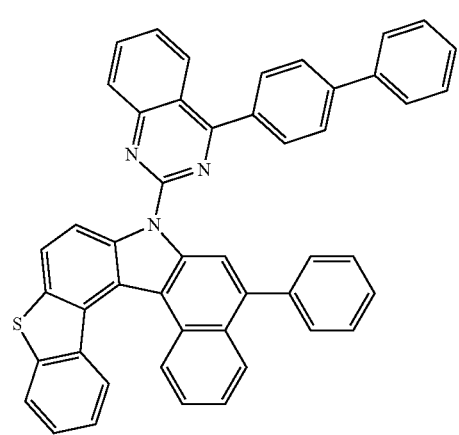
c-19 c-20
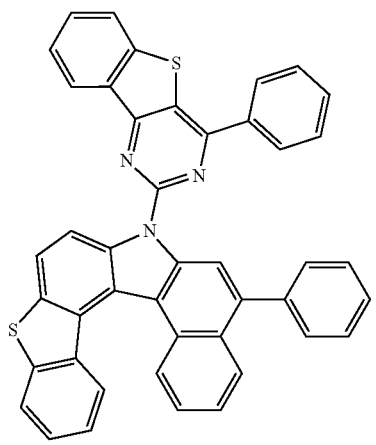
c-21
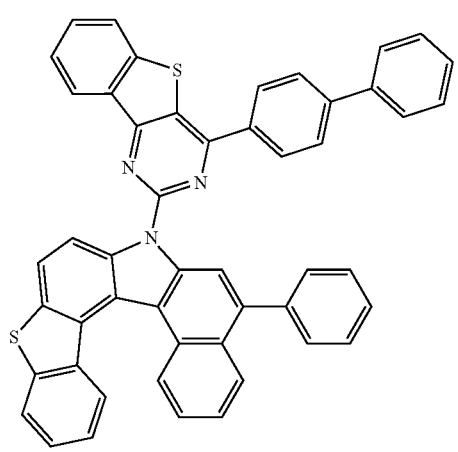
c-22
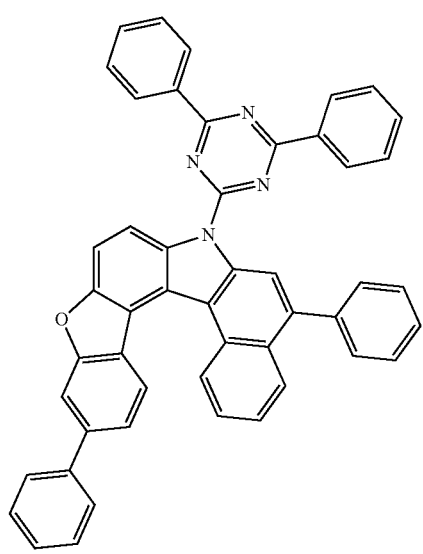
c-23
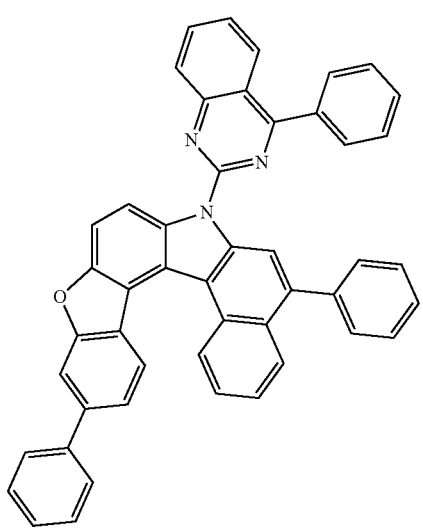
c-24
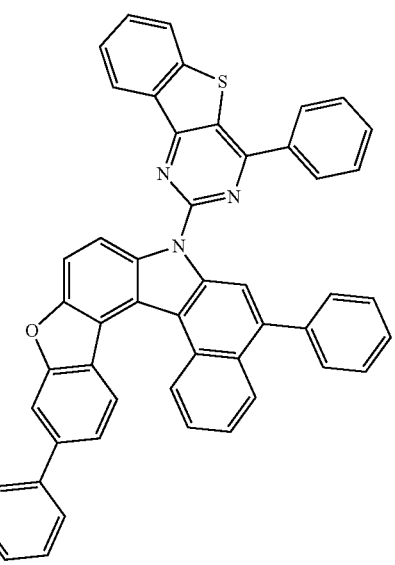
c-25
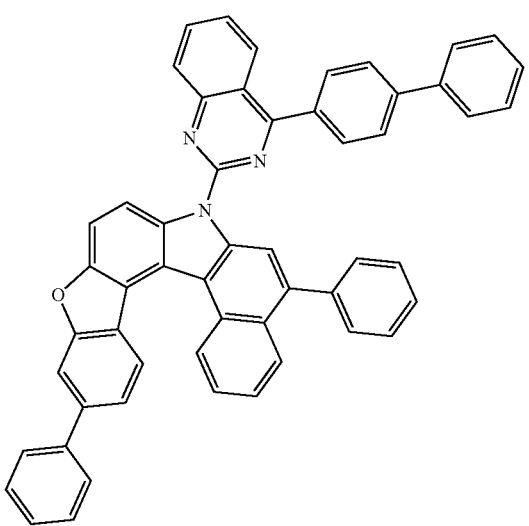

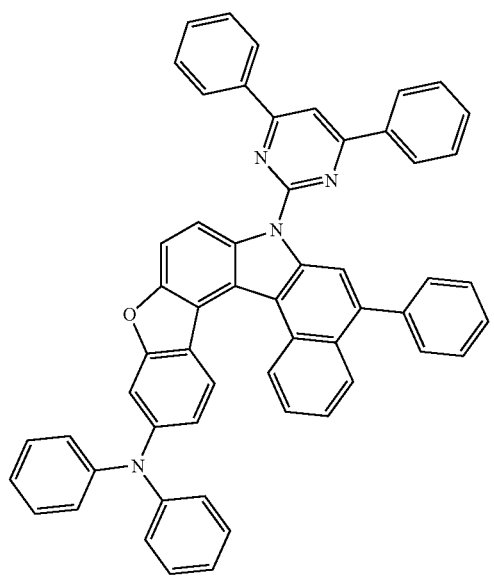
c-26
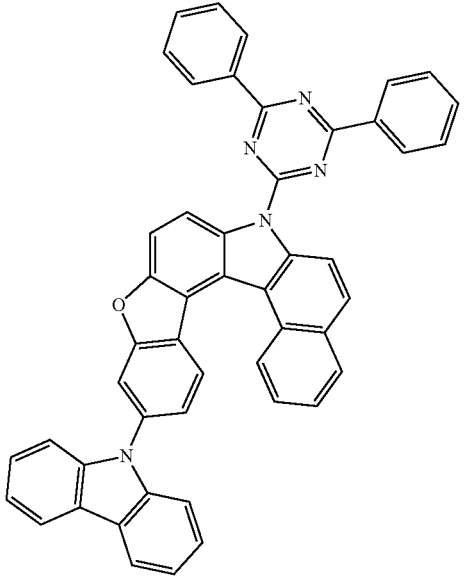
c-28
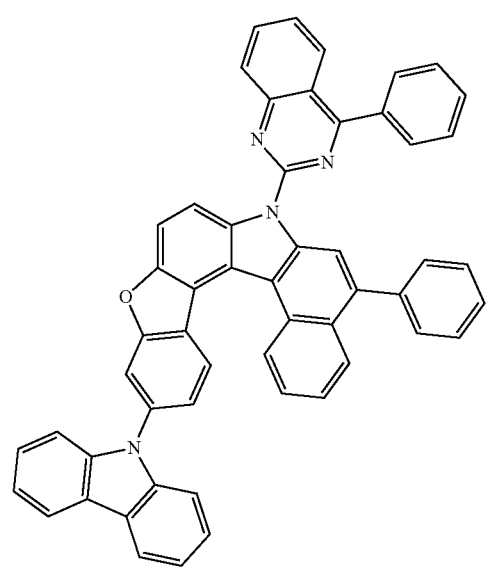
c-27
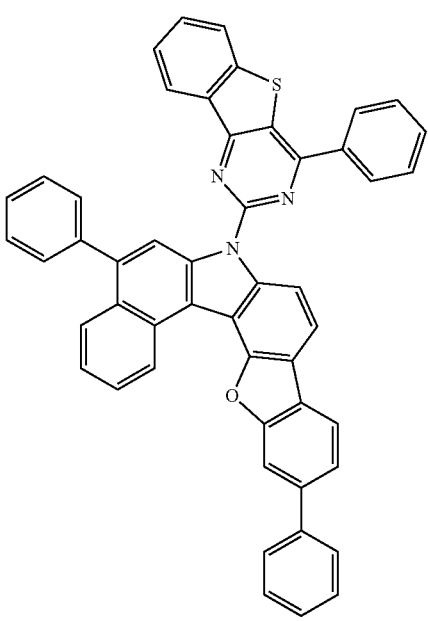
c-29

c-30
c-31
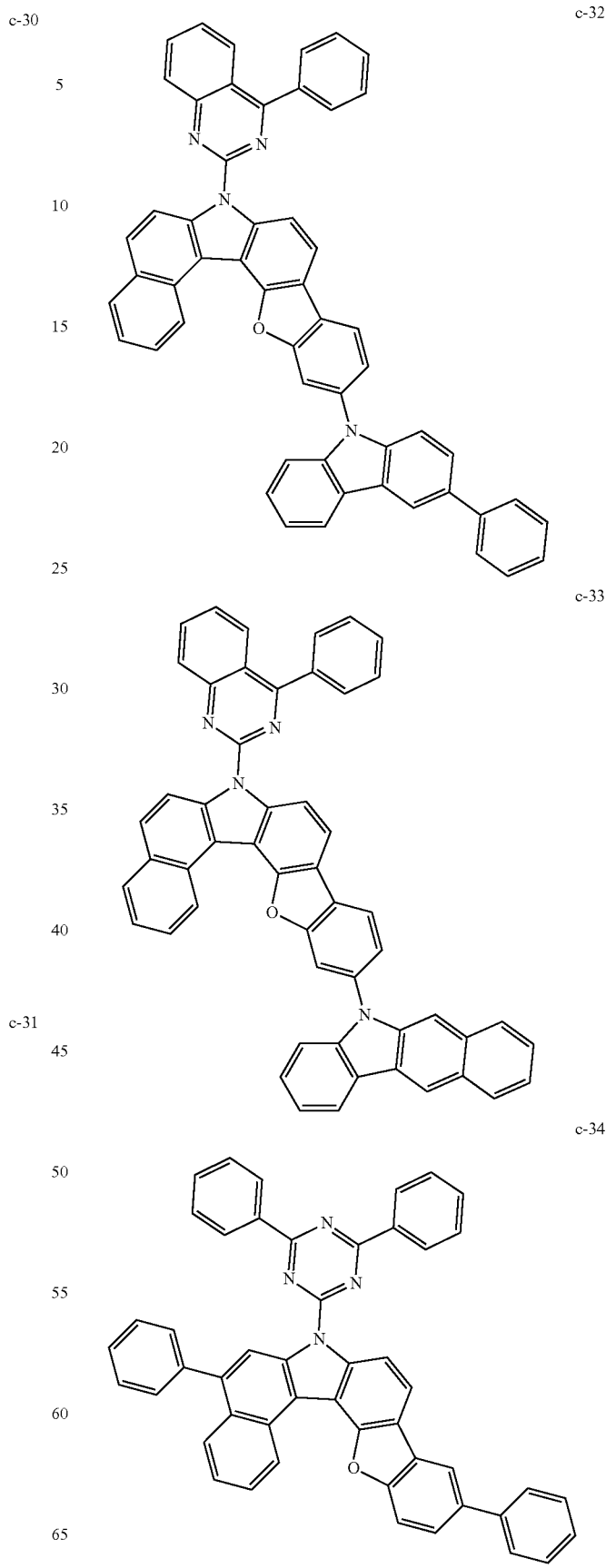
c-32
c-33
c-34 c-35
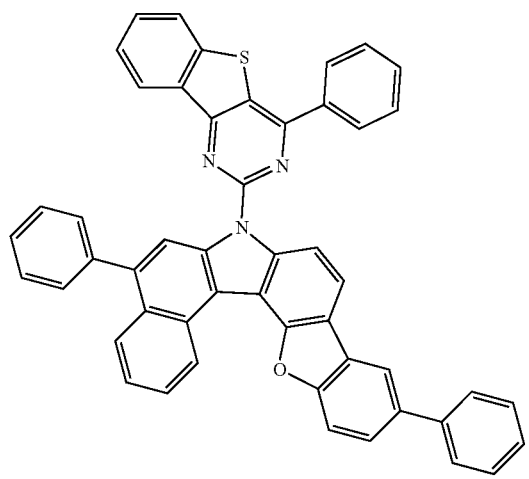
c-36
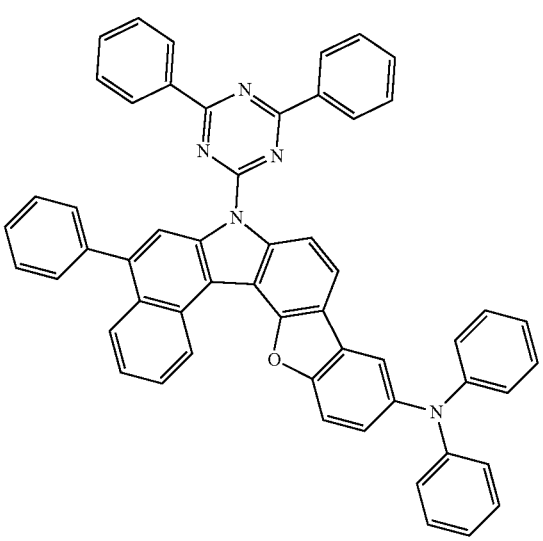
c-37
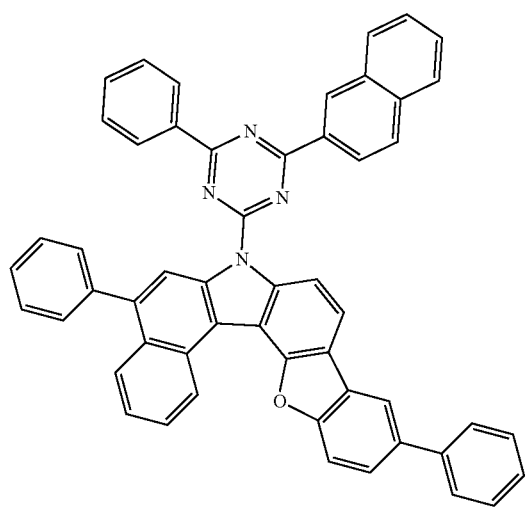
c-38
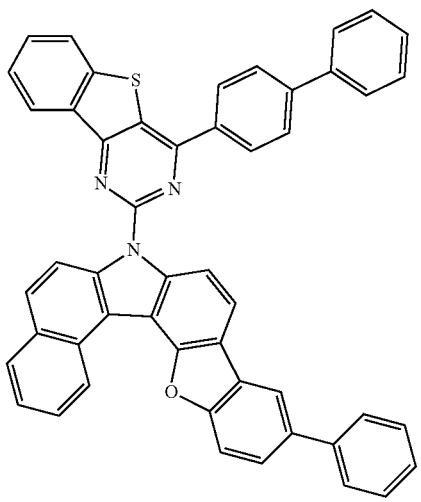
c-39
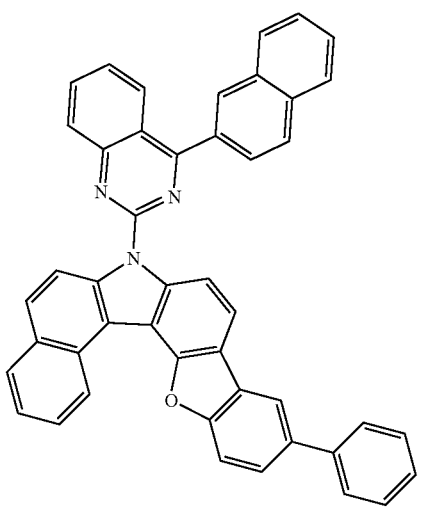
c-40
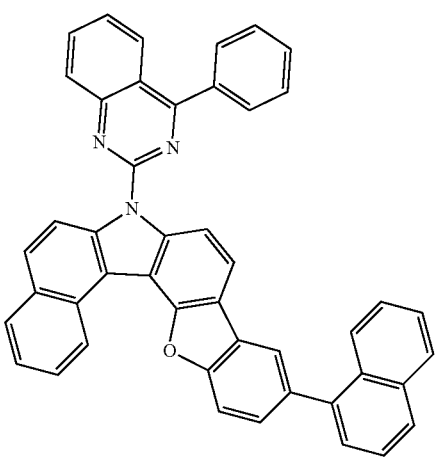

c-41
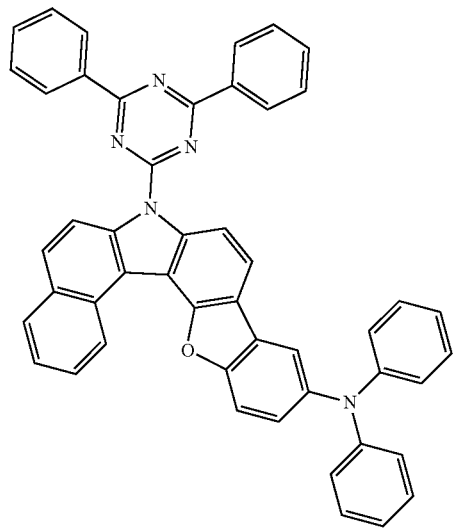
c-42
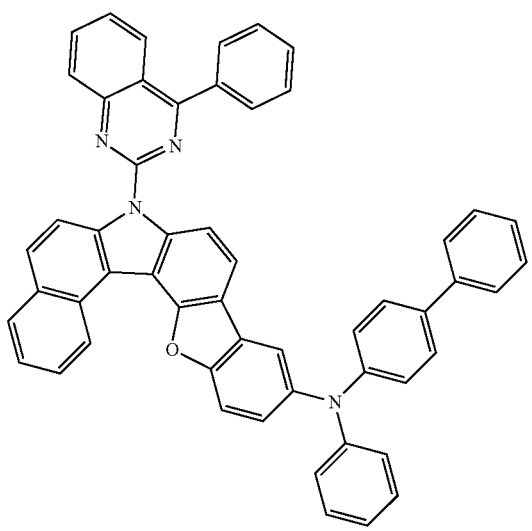
c-43
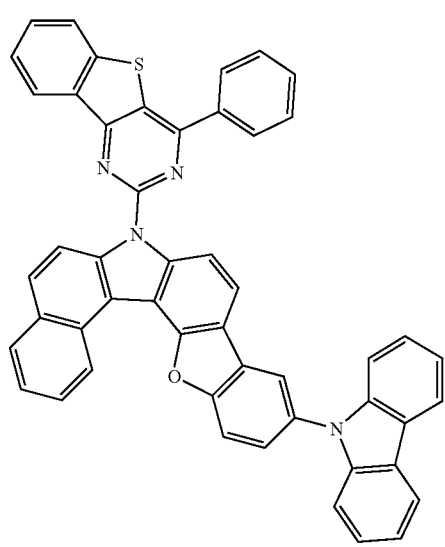
c-44
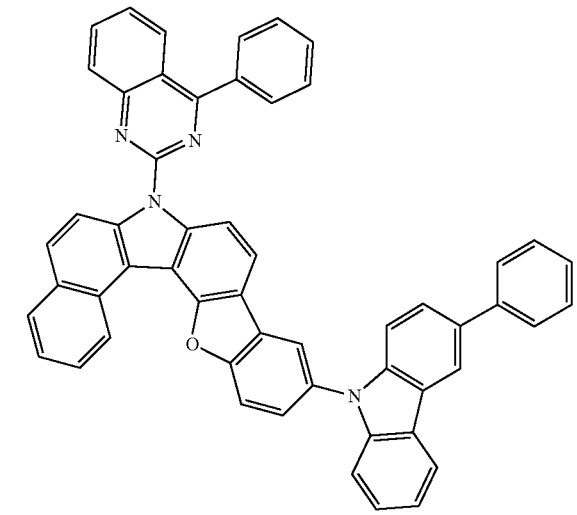
c-45
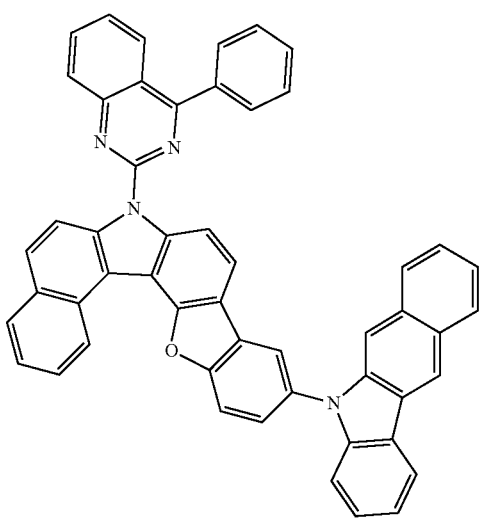
d-1
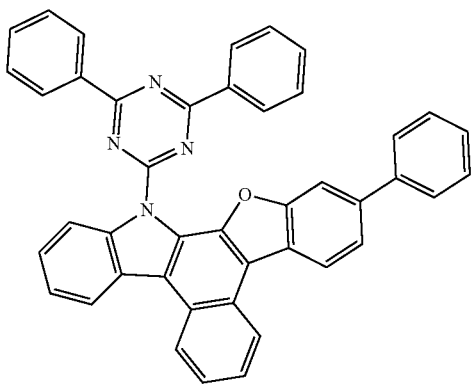

d-2
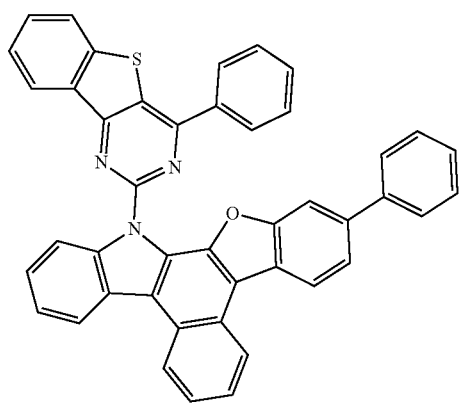
d-3
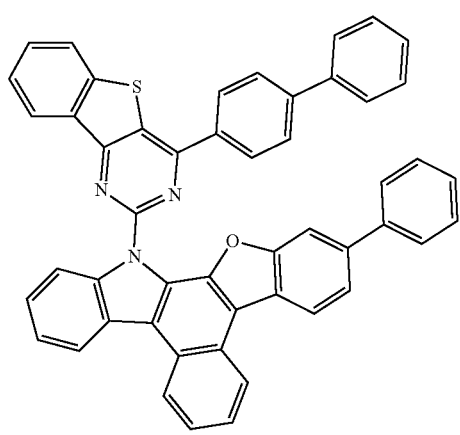
d-4
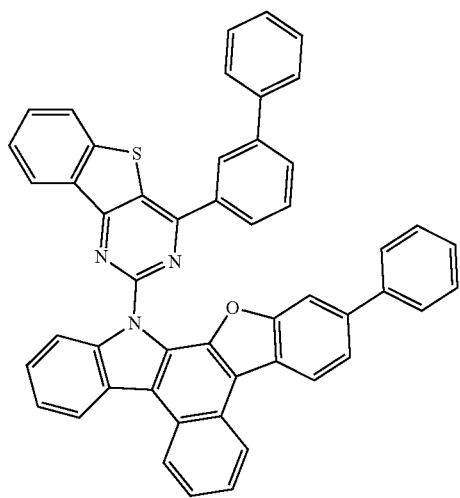
d-5
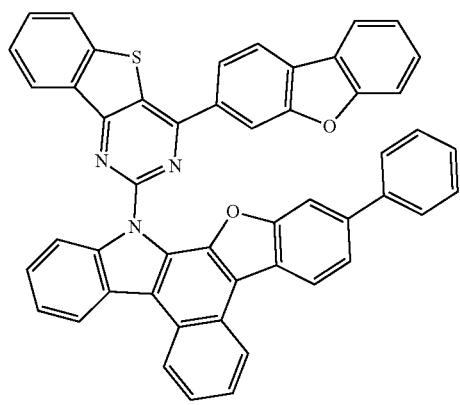
d-6
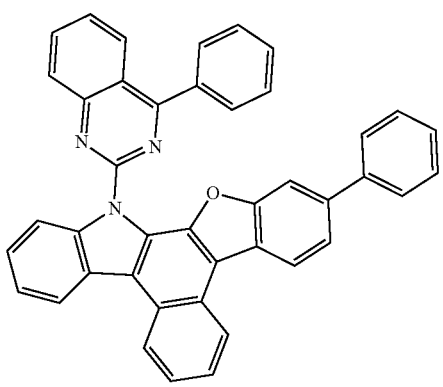
d-7
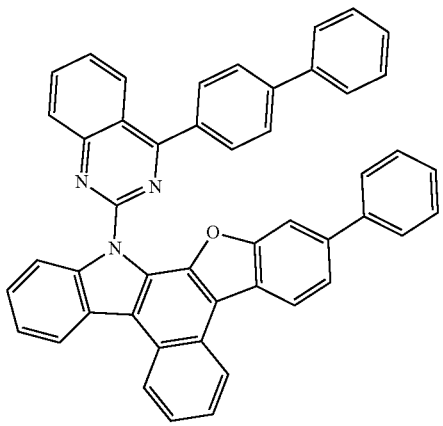

-continued
d-8
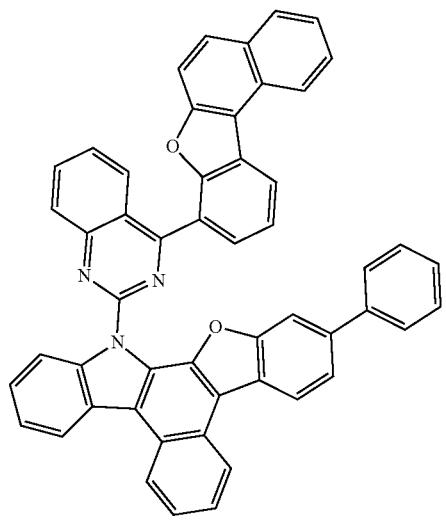
d-9
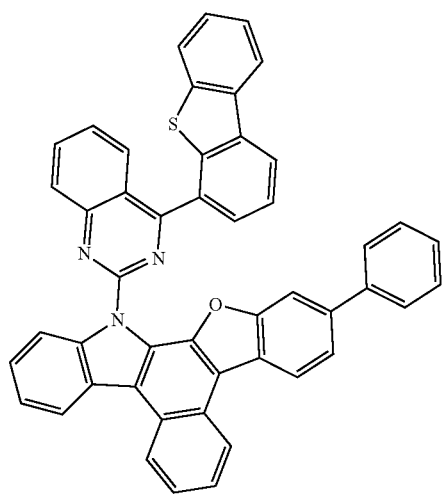
d-10
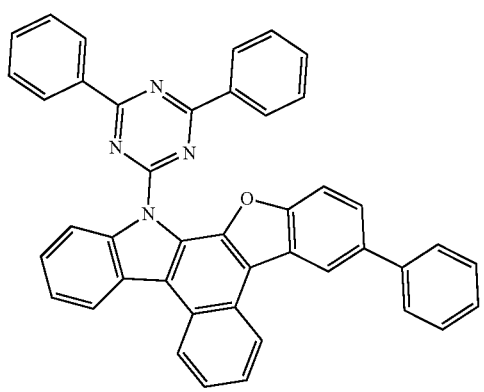
-continued
d-11
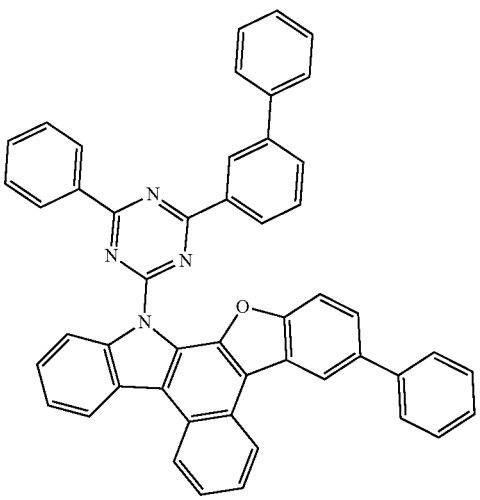
d-12
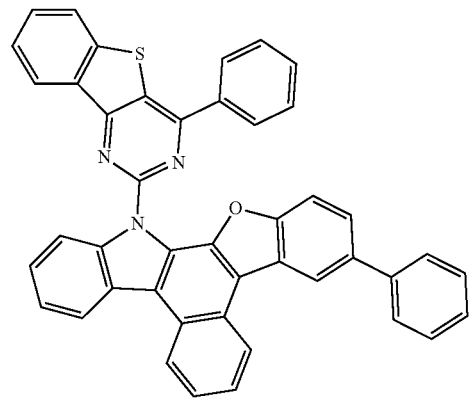
d-13
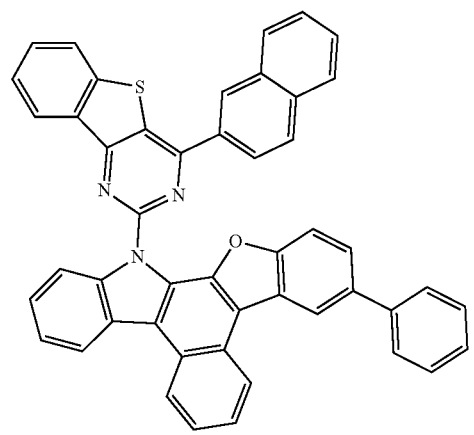

-continued
d-14
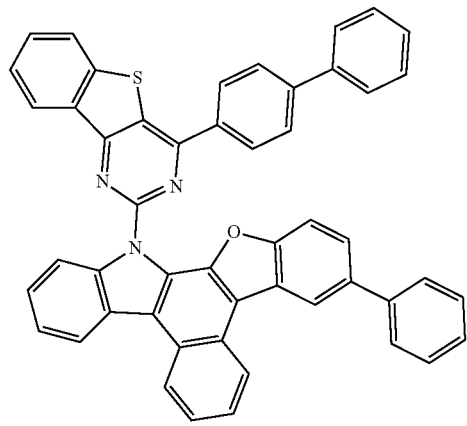
d-15
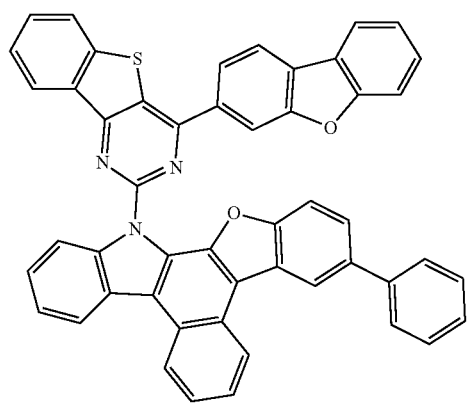
d-16
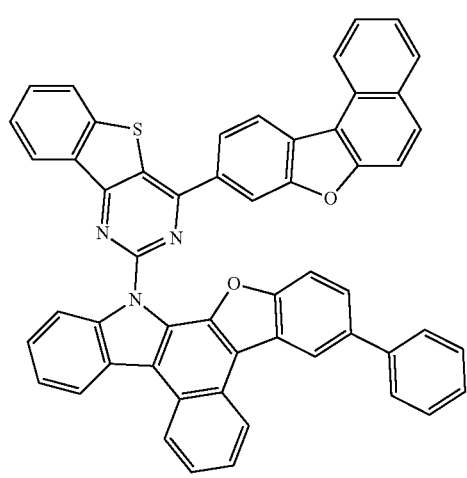
-continued
d-17
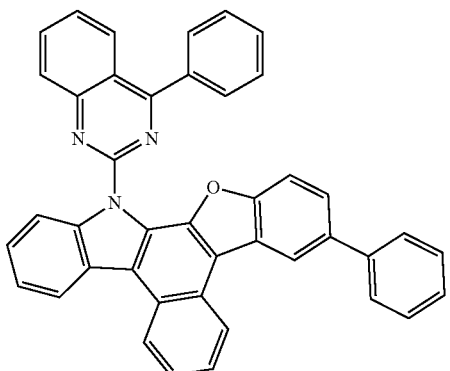
d-18
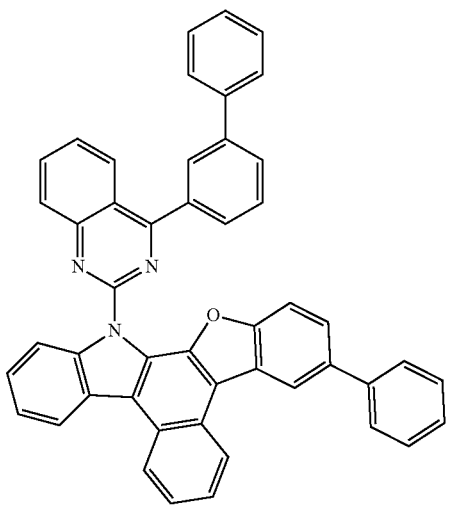
d-19
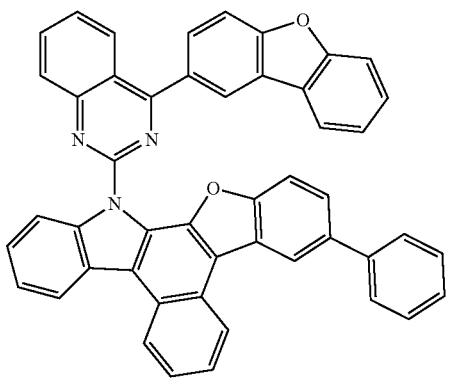
d-20
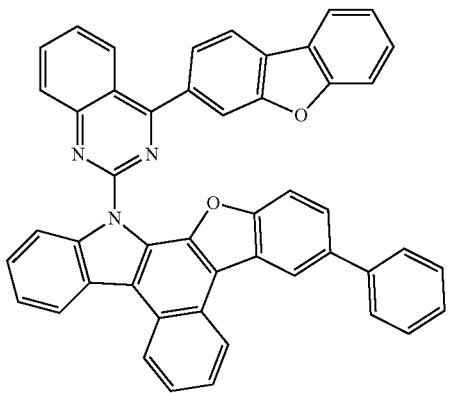

d-21
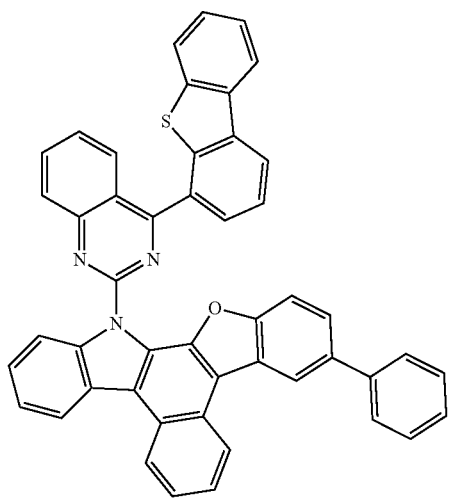
d-22
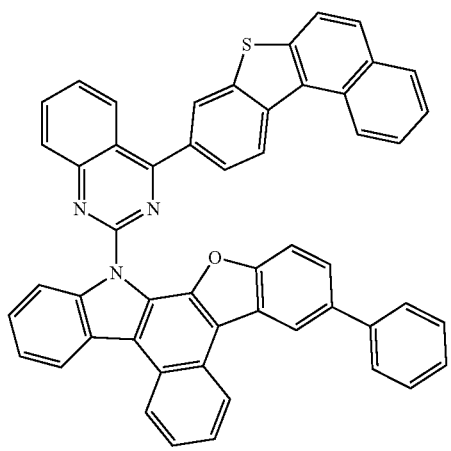
d-23
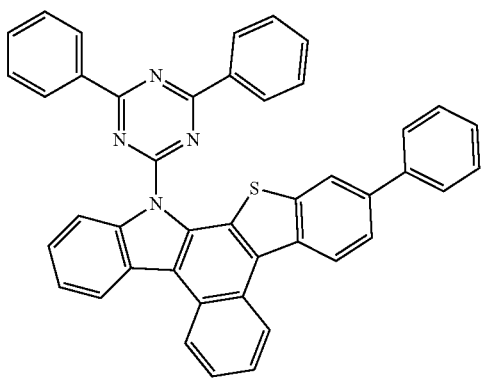
d-24
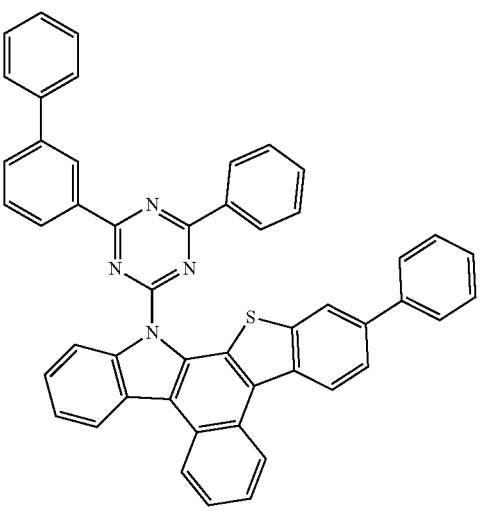
d-26
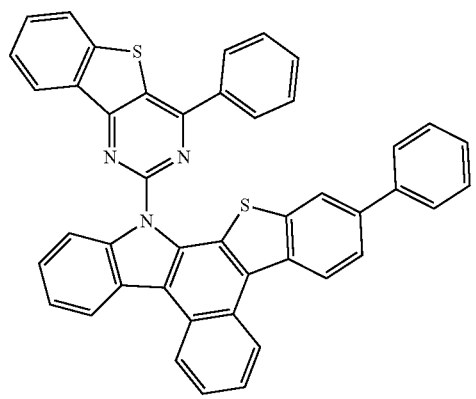
d-27
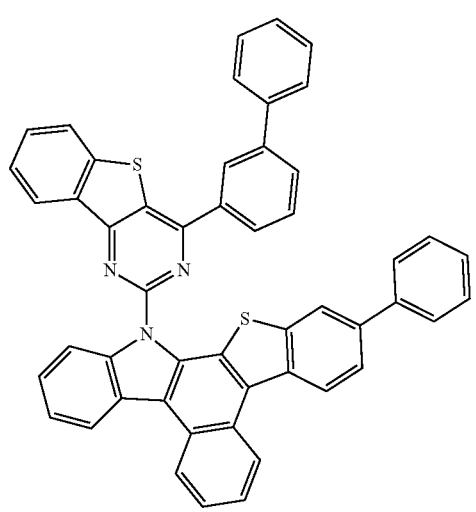

-continued
d-28
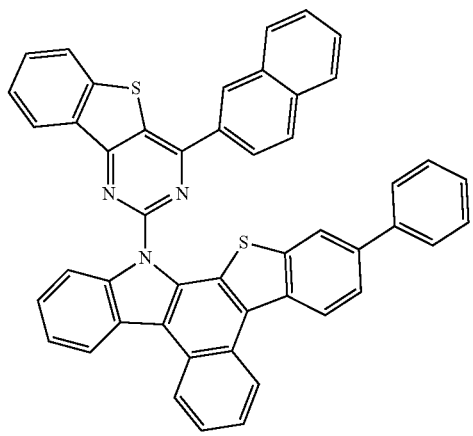
d-29
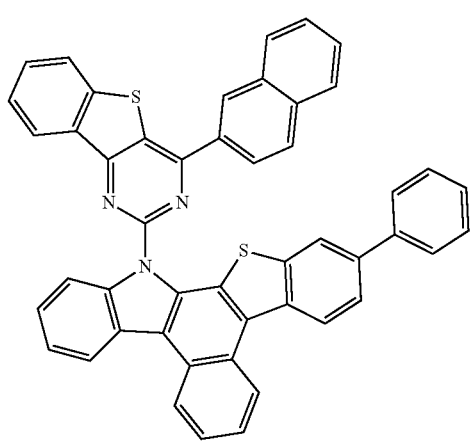
d-30
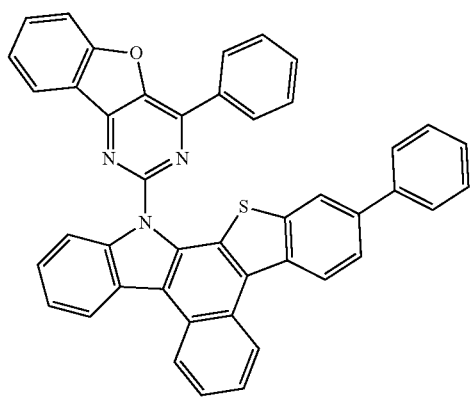
d-31
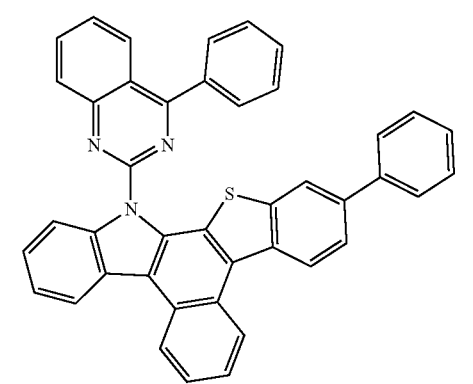
-continued
d-32
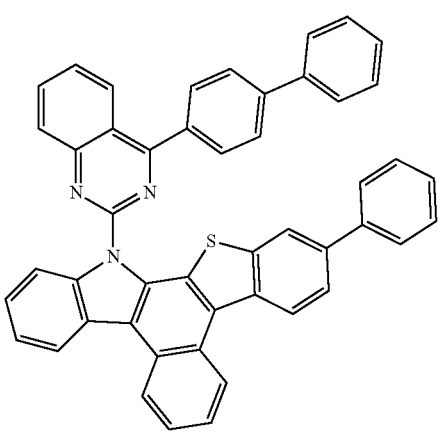
d-33
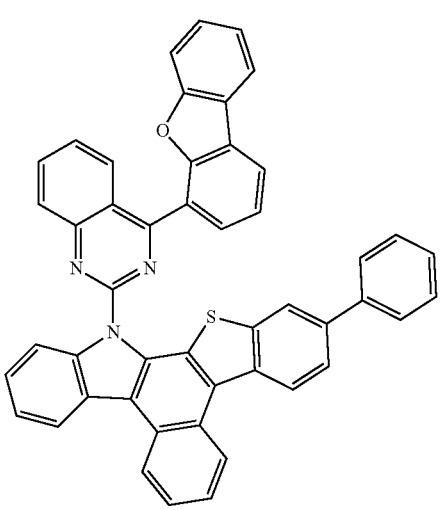
d-34
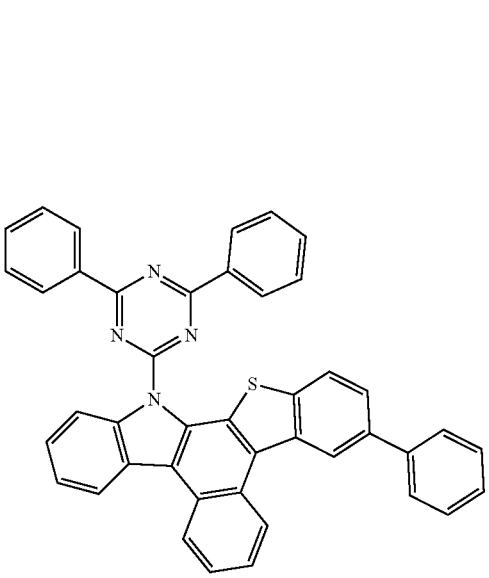

d-35
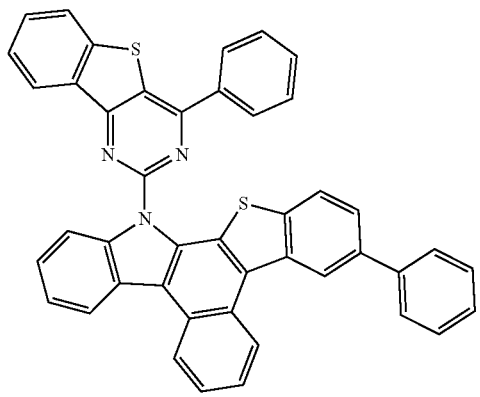
d-36
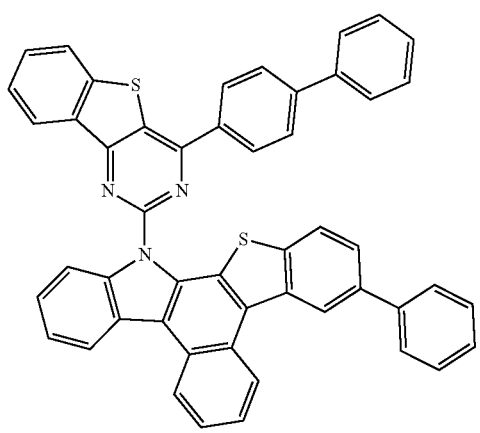
d-37
d-38
d-39
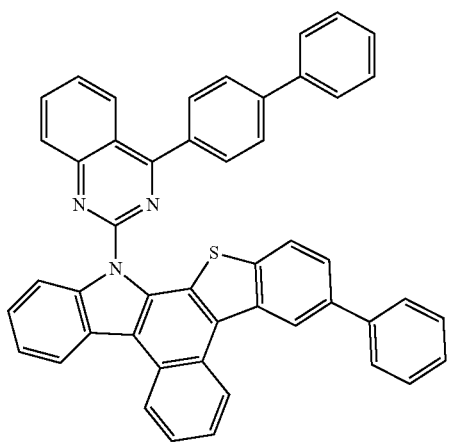
d-40
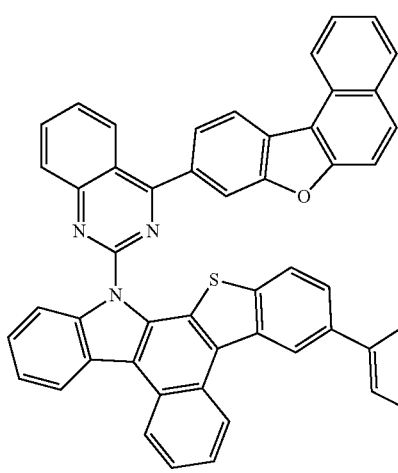
d-41
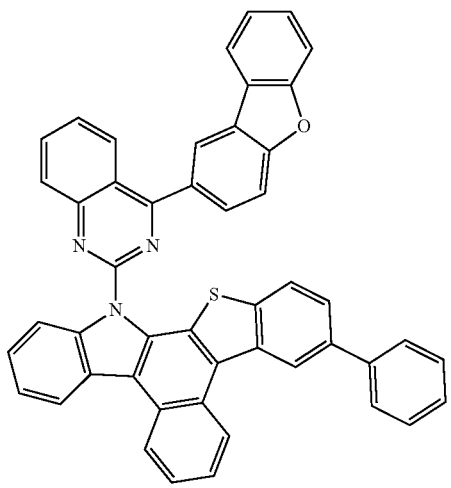

d-42
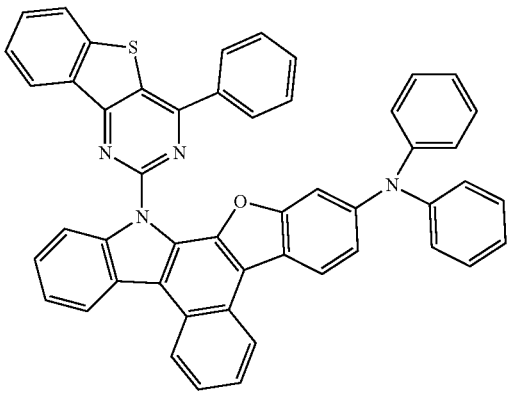
d-43
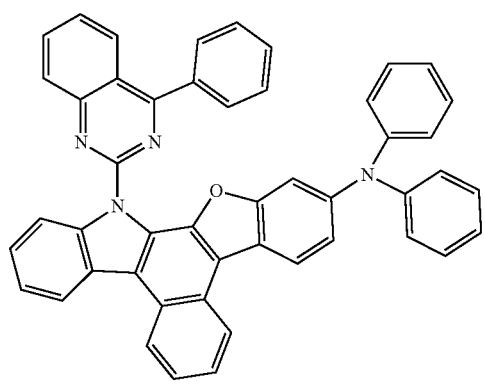
d-44
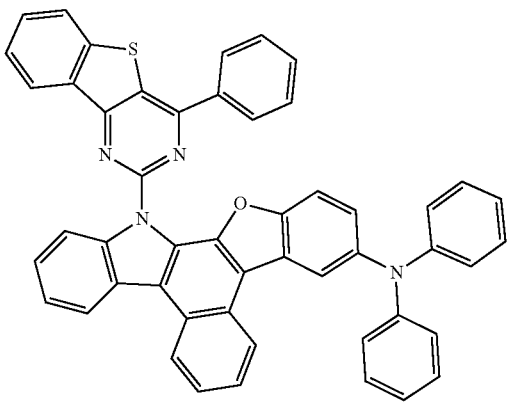
d-45
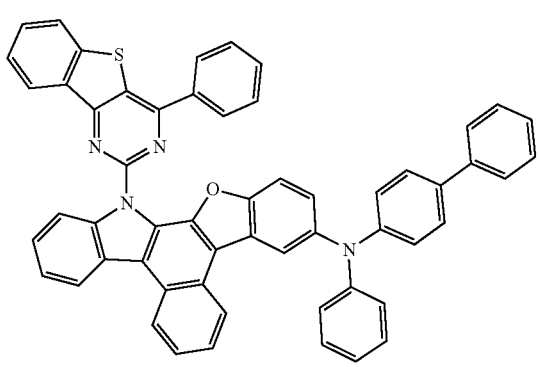
d-46
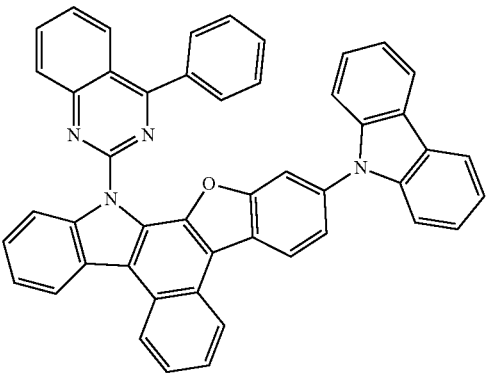
d-47
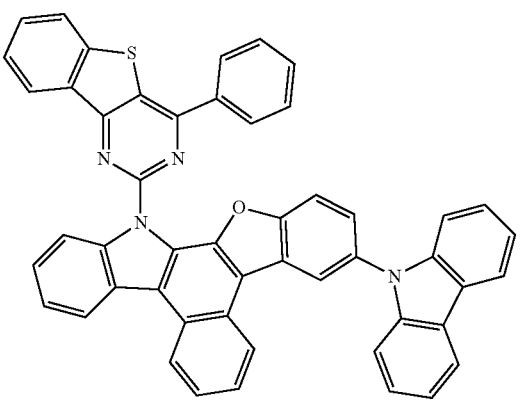
d-48
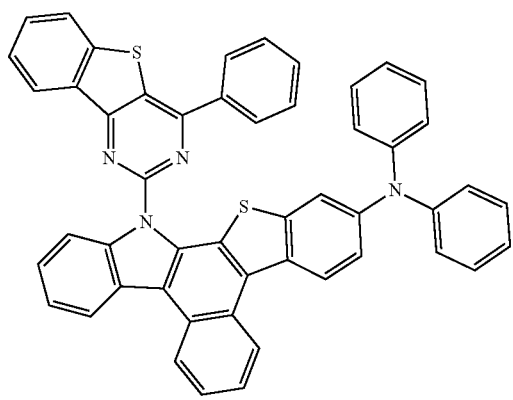
d-49
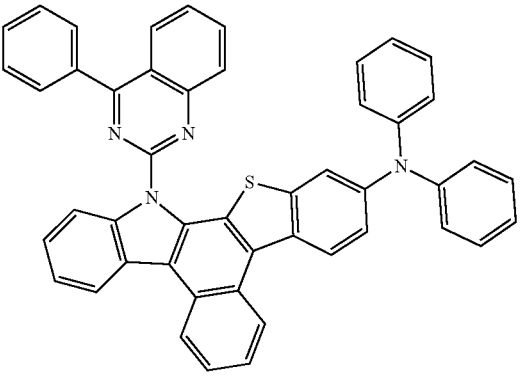

d-50
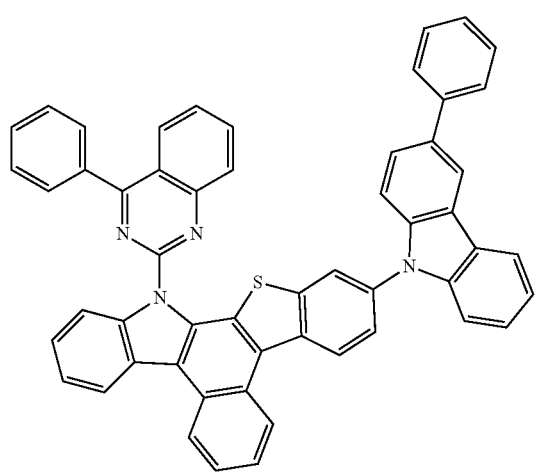
d-51
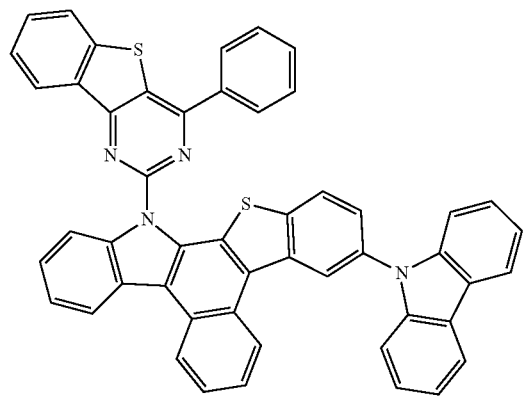
d-52
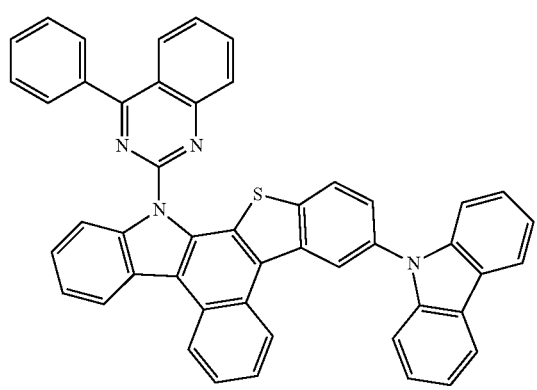
d-53
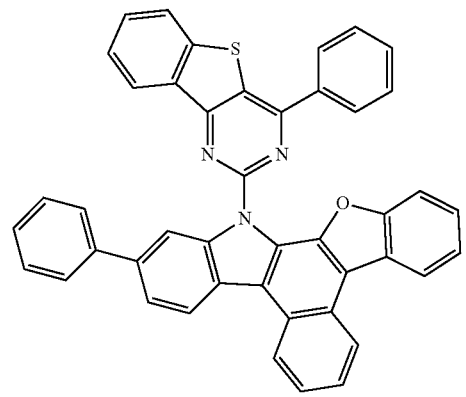
d-54
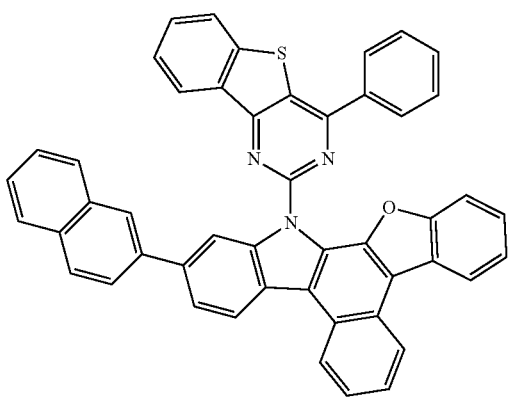
d-55
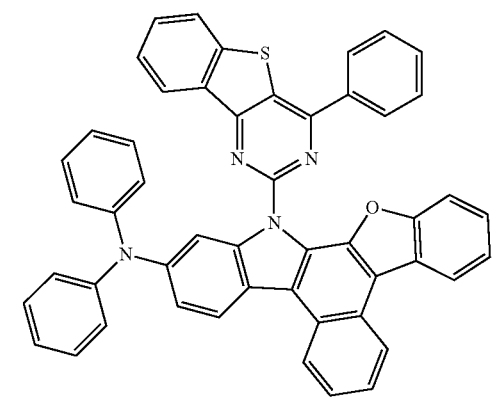
d-56
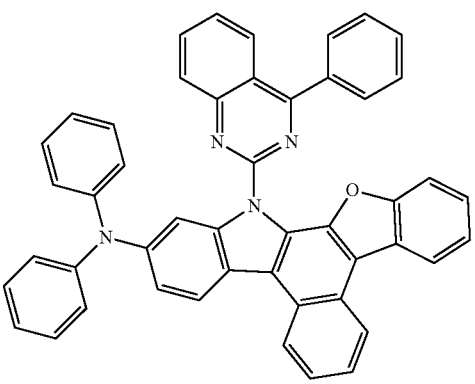

-continued
d-57
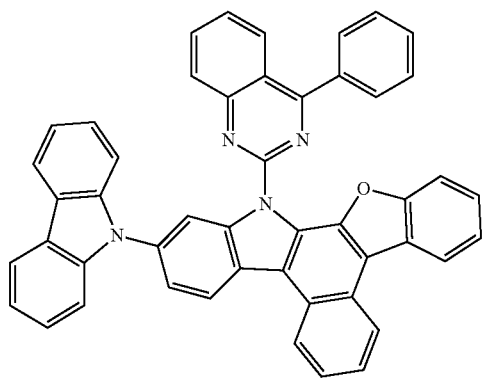
d-58
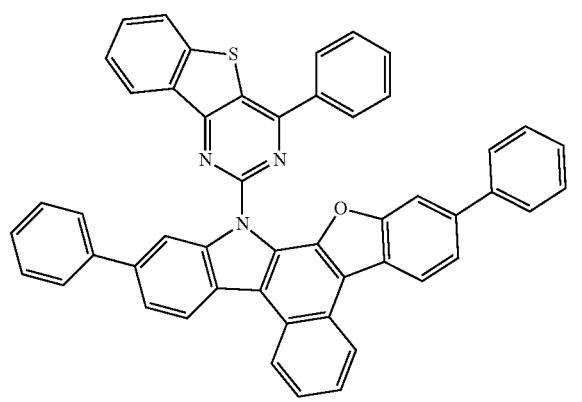
d-59
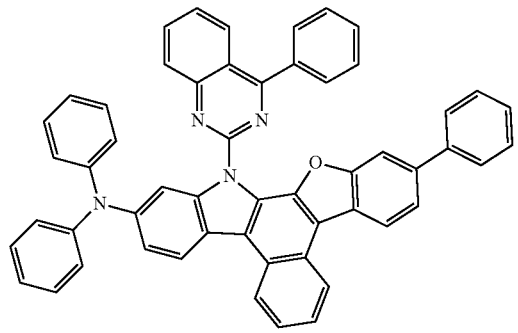
d-60
-continued
d-61
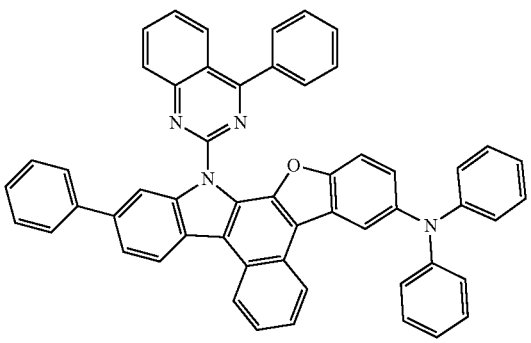
d-62
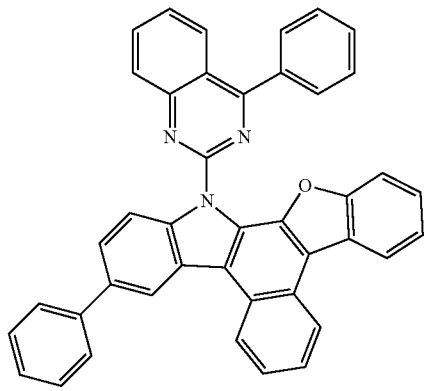
d-63
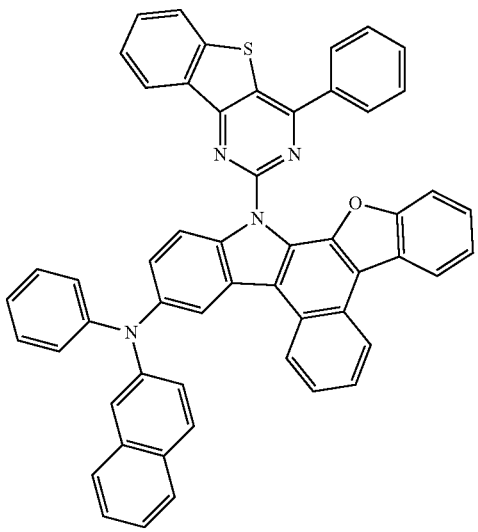

d-64
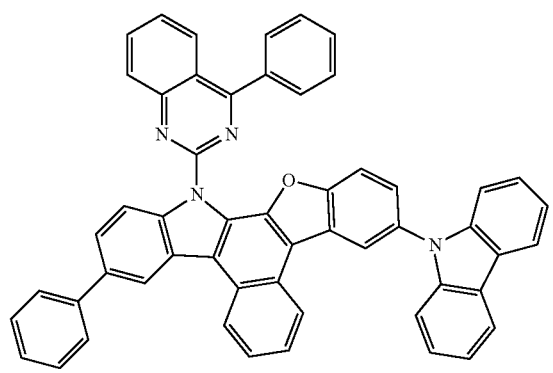
d-68
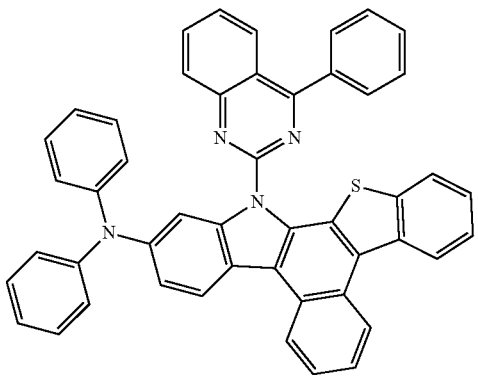
d-65
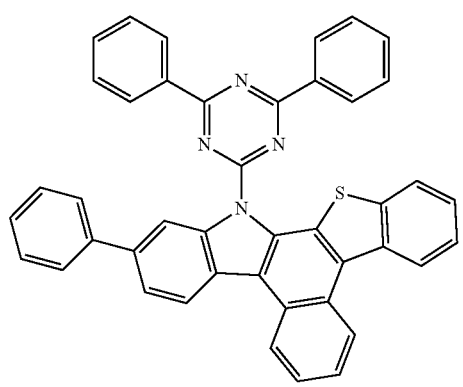
d-69
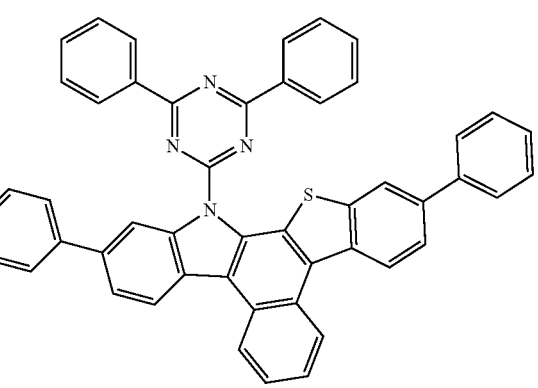
d-66
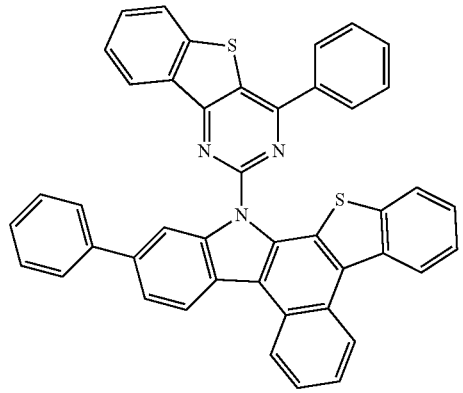
d-70
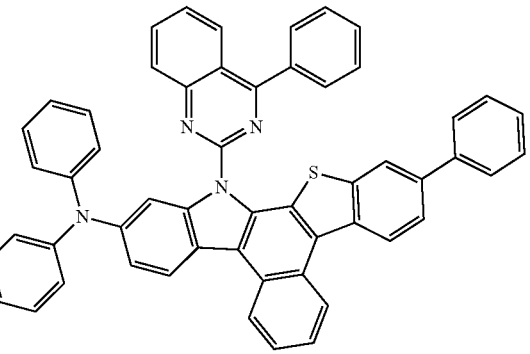
d-67
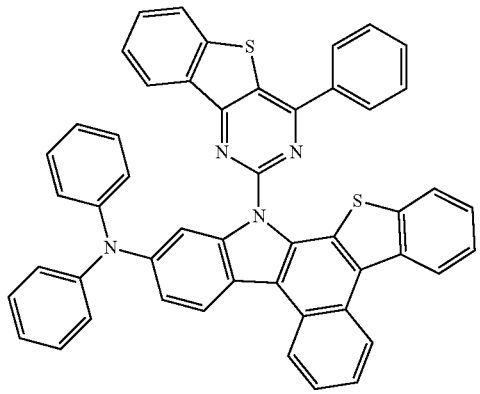
d-71
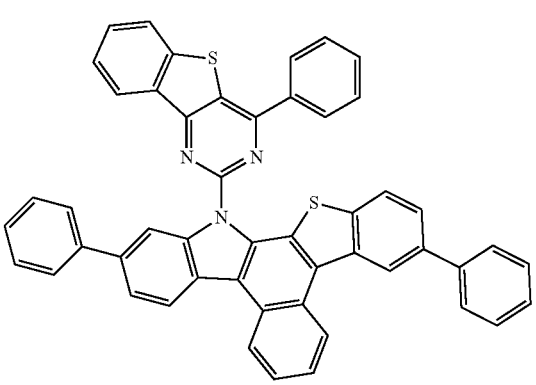

-continued d-72
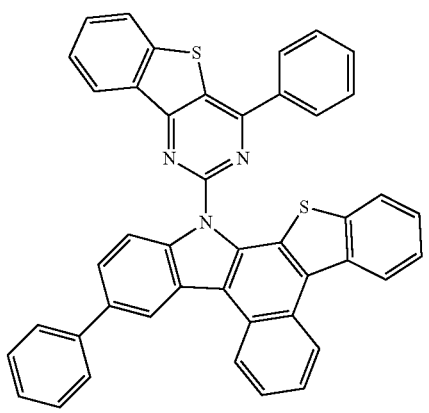

d-73
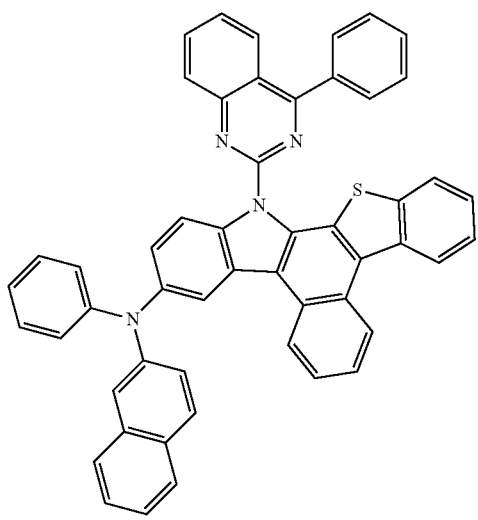

d-74
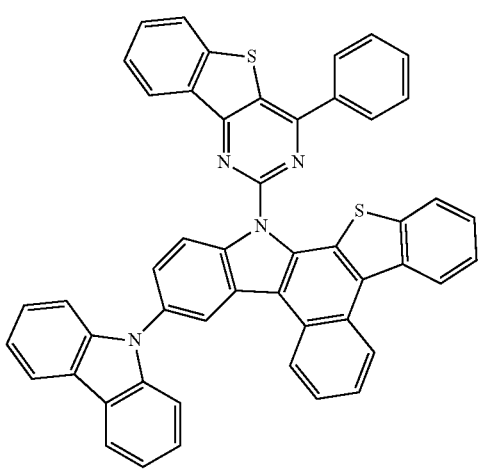

-continued d-75
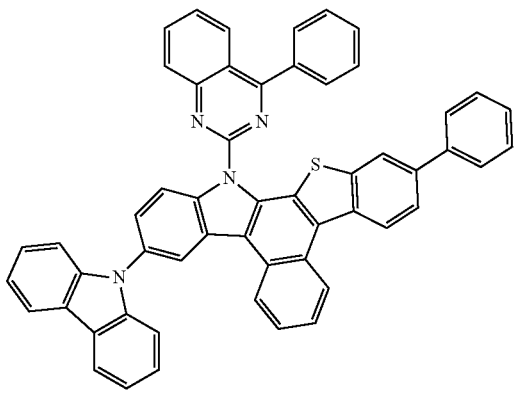

d-76
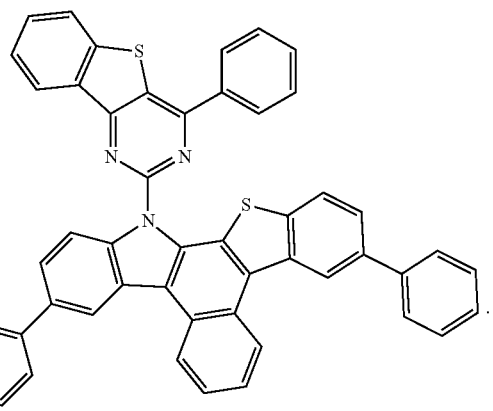

7. An organic light emitting device comprising:
 a first electrode;
 a second electrode; and
 an organic material layer provided between the first electrode and the second electrode, wherein the organic material layer includes one or more types of the heterocyclic compound of claim 1.

8. The organic light emitting device of claim 7, wherein the organic material layer includes a light emitting layer, and the light emitting layer includes one or more types of the heterocyclic compound.

9. The organic light emitting device of claim 8, wherein the light emitting layer includes a host, and the host includes one or more types of the heterocyclic compound.

10. The organic light emitting device of claim 7, wherein the organic material layer further includes a compound of the following Chemical Formula 11:

[Chemical Formula 11]

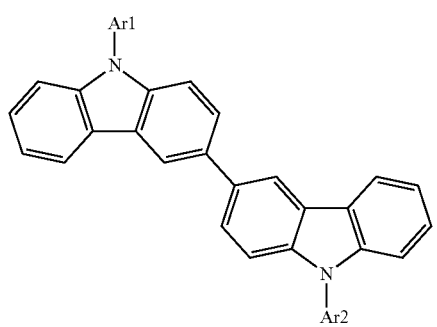

in Chemical Formula 11,

Ar1 and Ar2 are each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group.

11. The organic light emitting device of claim 10, wherein Chemical Formula 11 is represented by any one of the following compounds:

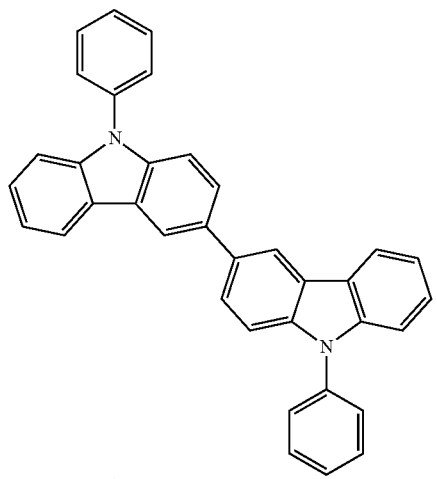

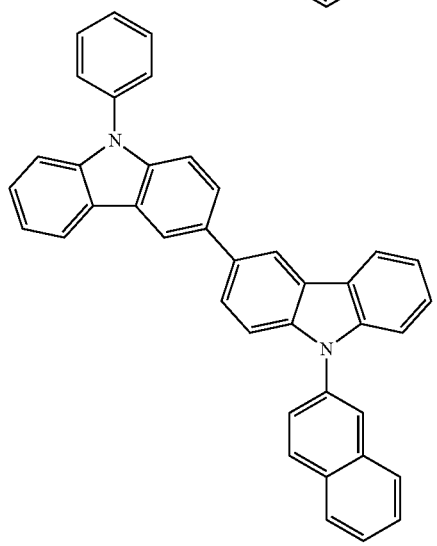

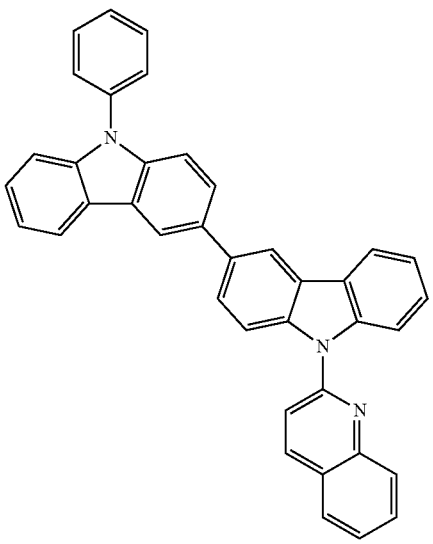

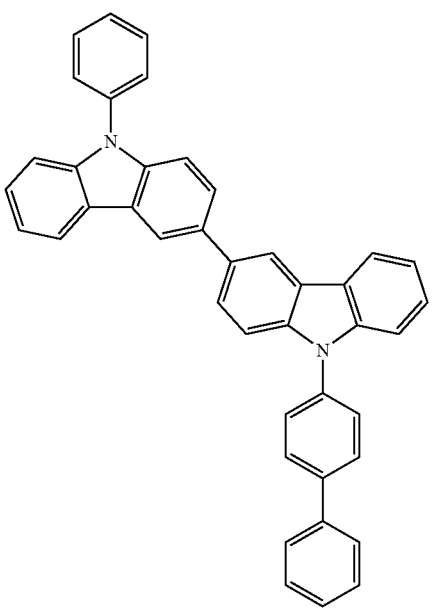

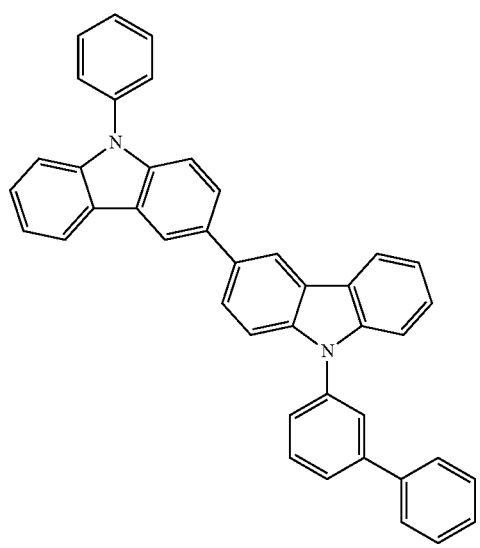

421
-continued
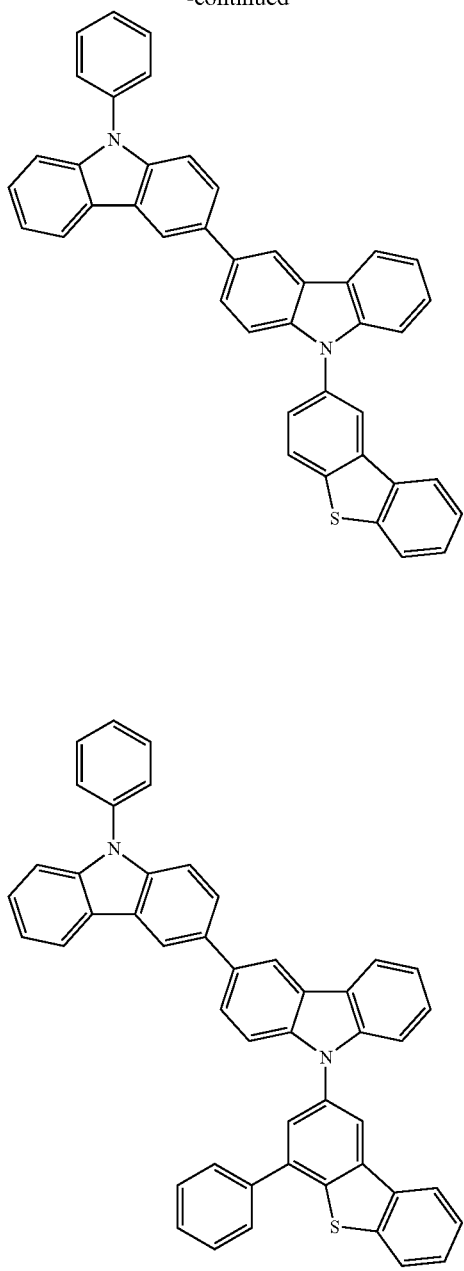
422
-continued
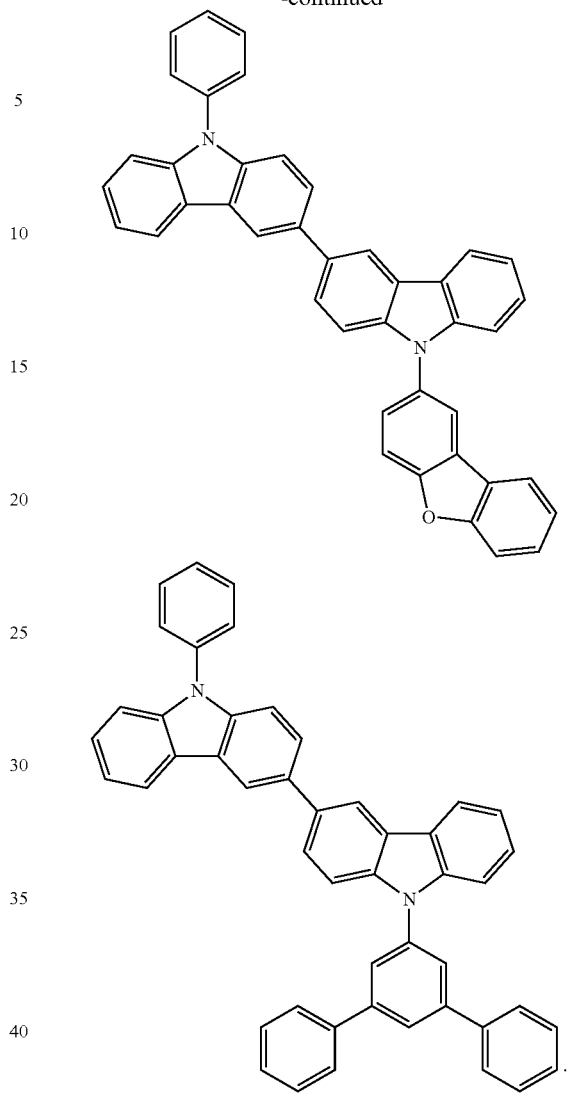
12. The organic light emitting device of claim 7, further comprising one layer selected from the group consisting of a light emitting layer, a hole injection layer, a hole transfer layer, an electron injection layer, an electron transfer layer, an electron blocking layer and a hole blocking layer.
* * * * *